US011932866B2

(12) United States Patent
Stirnweis et al.

(10) Patent No.: US 11,932,866 B2
(45) Date of Patent: Mar. 19, 2024

(54) PATHOGEN RESISTANCE IN CROP PLANTS

(71) Applicant: KWS SAAT SE & Co. KGaA, Einbeck (DE)

(72) Inventors: Daniel Fabian Stirnweis, Gottingen (DE); Dietmar Stahl, Einbeck (DE); Urs Konrad Fischer, Gottingen (DE); Christine Klapprodt, Osterode (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 0 days.

(21) Appl. No.: 17/433,316

(22) PCT Filed: Mar. 1, 2020

(86) PCT No.: PCT/EP2020/055380
§ 371 (c)(1),
(2) Date: Aug. 24, 2021

(87) PCT Pub. No.: WO2020/178215
PCT Pub. Date: Sep. 10, 2020

(65) Prior Publication Data
US 2022/0170040 A1 Jun. 2, 2022

(30) Foreign Application Priority Data
Mar. 1, 2019 (EP) .................................... 19160408

(51) Int. Cl.
C12N 15/82 (2006.01)
(52) U.S. Cl.
CPC .............. C12N 15/8282 (2013.01)
(58) Field of Classification Search
None
See application file for complete search history.

(56) References Cited

FOREIGN PATENT DOCUMENTS

WO 2019/238909 A1 12/2019

OTHER PUBLICATIONS

Jones et al., "The plant immune system", Nature, 2006, vol. 444, No. 7117, pp. 323-329.
Gaudet et al., "Heptose sounds the alarm: Innate sensing of a bacterial sugar stimulates immunity", PLoS pathogens, 2016, vol. 12, No. 9, e1005807, 6 pages.
Manosalva et al., "Conserved nematode signalling molecules elicit plant defenses and pathogen resistance", Nature Communications, 2015, vol. 6, No. 7795, 8 pages.
Macho et al., "Plant PRRs and the activation of nate immune signaling", Molecular Cell, 2014, vol. 54, No. 2, pp. 263-272.
Buratowski, "Progression through the RNA polymerase II CTD cycle", Molecular Cell, 2009, vol. 36, No. 4, pp. 541-546.
Hajheidari et al., "Emerging roles for RNA polymerase II CTD in *Arabidopsis*", Trends in Plant Science, 2013, vol. 18, No. 11, pp. 633-643.
Koiwa et al., "C-terminal domain phosphatase-like family members (AtCPLs) differentially regulate *Arabidopsis thaliana* abiotic stress signaling, growth, and development", PNAS, 2002, vol. 99, No. 16, pp. 10893-10898.
Fukudome et al., "*Arabidopsis* CPL4 is an essential Ser2-specific CTD-phosphatase regulating general and xenobiotic responsive gene expression (617.2)", the FASEB Journal, 2014, vol. 28. Issue S1, Supplement 617.2.
Ueda et al., "The *Arabidopsis thaliana* carboxyl-terminal domain phosphatase-like 2 regulates plant growth, stress and auxin responses", Plant Molecular Biology, 2008, vol. 67, No. 6, pp. 683-697.
Fukudome et al., "Silencing *Arabidopsis* Carboxyl—Terminal Domain Phosphatase—Like 4 induces cytokinin—oversensitive de novo shoot organogenesis", The Plant Journal, 2018, vol. 94, No. 5, pp. 799-812.
Jin et al., "AtCPL5, a novel Ser—2—specific RNA polymerase II C—terminal domain phosphatase, positively regulates ABA and drought responses in *Arabidopsis*", New Phytologist, 2011, vol. 190, No. 1, pp. 57-74.
Perkins et al., "Disease development and yield losses associated with northern leaf blight on corn", Plant Disease, 1987, vol. 71, No. 10, pp. 940-943.
Younis et al., "RNA Interference (RNAi) Induced Gene Silencing: A Promising Approach of Hi-Tech Plant Breeding", Int J Biol Sci., 2014, vol. 10, No. 10, pp. 1150-1158.
Li et al., "Therapeutic targeting of microRNAs: current status and future challenges", Nature Reviews Drug Discovery, 2014, vol. 13, No. 8, pp. 622-638.
Guha et al., "Programmable Genome Editing Tools and their Regulation for Efficient Genome Engineering", Computational and Structural Biotechnology Journal, 2017, vol. 15, pp. 146-160.
Cox et al., "RNA editing with CRISPR-Cas13", Science, 2017, vol. 358, No. 6366, pp. 1019-1027.
Komor et al., Programmable editing of a target base in genomic DNA without double-stranded DNA cleavage, Nature, 2016, vol. 533, No. 7603, pp. 420-424.
Gaudelli et al., "Programmable base editing of A•T to G•C in genomic DNA without DNA cleavage", Nature, 2017, vol. 551, pp. 464-471.
Yuan et al., "A High Throughput Barley Stripe Mosaic Virus Vector for Virus Induced Gene Silencing in Monocots and Dicots", PLoS ONE, 2011, vol. 6, Issue 10, e26468, 16 pages.

(Continued)

Primary Examiner — Medina A Ibrahim
(74) Attorney, Agent, or Firm — Troutman Pepper Hamilton Sanders LLP

(57) ABSTRACT

The present invention relates to the field of plant biotechnology. Specifically, there are provided methods and nucleic acid sequences for obtaining pathogen resistance in plants and for generating resistant plants. In particular, the role of a central molecule in plant immunity is studied. Based on the mechanisms elucidated, the present invention provides strategies to specifically modulate said phosphatase-like protein family member molecule by different transient and/or stable techniques, alone or in combination, to achieve a robust increased of pathogen resistance in different target plants to obtain inherently pathogen resistant plants and plant materials to avoid severe harvest losses as caused by major plant pathogens by biological means instead of herbicide or pesticide treatment.

6 Claims, 31 Drawing Sheets

Specification includes a Sequence Listing.

(56) References Cited

OTHER PUBLICATIONS

Millyard et al., "The ubiquitin conjugating enzyme, TaU4 regulates wheat defence against the phytopathogen Zymoseptoria tritici", Scientific Reports, 2016, vol. 6, 35683, 11 pages.
Schmidt et al., "Suppression of phenylalanine ammonia lyase expression in sugar beet by the fungal pathogen Cercospora beticola is mediated at the core promoter of the gene", Plant Molecular Biology, 2004, vol. 55, No. 6, pp. 835-852.
Oerke, "Crop losses to pests", Journal of Agricultural Science, 2006, vol. 144, No. 1, pp. 31-43.
International Search Report and Written Opinion issued in International Application No. PCT/EP2020/055380 dated Mar. 30, 2020.
Li et al., "Modulation of RNA Polymerase II Phosphorylation Downstream of Pathogen Perception Orchestrates Plant Immunity", Cell Host & Microbe, 2014, vol. 16, No. 6, pp. 748-758.
Database UniProt [Online] Jan. 9, 2013 (Jan. 9, 2013), "SubName: Full=Uncharacterized protein {ECO:0000313:EMBL:KRH01515.I, ECO:0000313:EnsemblPlants:KRH01516};", XP002791456, retrieved from EBI accession No. UNIPROT:K7MV85 Database accession No. K7MV85 sequence.
Schmutz et al., "Genome sequence of the palaeopolyploid soybean", Nature, 2010, vol. 463, No. 7278, pp. 178-183.
Yang et al., "A comprehensive analysis of protein phosphatases in rice and *Arabidopsis*", Plant Systematics and Evolution, 2010, vol. 289, No. 3-4, pp. 111-126.
Tominaga et al., "*Arabidopsis* Caprice-Like MYB 3 (CPL3) controls endoreduplication and flowering development in addition to trichome and root hair formation", Development, 2008, vol. 135, No. 7, pp. 1335-1345.

Figure 1B

| | 1 | 2 | 3 | 4 | 5 | 6 | 7 | 8 | 9 | 10 |
|---|---|---|---|---|---|---|---|---|---|---|
| 1 Arabidopsis thaliana AtCPL3_protein | | | | | | | | | | |
| 2 Glycine max Glyma.18g282300.2_protein | 44.65 | | | | | | | | | |
| 3 Glycine max Glyma.08g257900.1_protein | 44.19 | 92.36 | | | | | | | | |
| 4 Solanum tuberosum PGSC0003DMT400052897_protein | 42.84 | 49.50 | 49.50 | | | | | | | |
| 5 Beta vulgaris g12062.t1_protein | 42.12 | 48.16 | 48.19 | 48.35 | | | | | | |
| 6 Triticum aestivum TaCPL3-B_protein | 36.65 | 37.57 | 37.53 | 38.53 | 36.70 | | | | | |
| 7 Triticum aestivum TaCPL3-D_protein | 36.65 | 37.59 | 37.55 | 38.33 | 36.65 | 97.29 | | | | |
| 8 Triticum aestivum TaCPL3-A_protein | 36.80 | 37.88 | 37.76 | 38.48 | 36.86 | 96.09 | 96.81 | | | |
| 9 Sorghum bicolor Sb05g019010.1_protein | 36.23 | 37.51 | 37.39 | 38.85 | 36.14 | 64.38 | 64.69 | 64.15 | | |
| 10 Zea mays ZmCPL3_protein | 35.71 | 37.10 | 37.05 | 37.59 | 35.67 | 63.19 | 63.50 | 63.11 | 88.33 | |

[Sequence alignment figure showing DNA sequences from positions ~1440 to 1680 for the following taxa/genes:
- Arabidopsis thaliana AtCPL3_CDS
- Glycine max Glyma.18g282300.2_CDS
- Glycine max Glyma.08g257900.1_CDS
- Solanum tuberosum PGSC0003DMT400052897_CDS
- Beta vulgaris g12062.t1_CDS
- Triticum aestivum TaCPL3-B_CDS
- Triticum aestivum TaCPL3-D_CDS
- Triticum aestivum TaCPL3-A_CDS
- Sorghum bicolor Sb05g0190010.1_CDS
- Zea mays ZmCPL3_CDS]

Figure 2A (continued)

| Species | Sequence | |
|---|---|---|
| Arabidopsis thaliana AtCPL3_CDS | CAAGACTAAGGCTTGCCGAAACCTGAT---GCTGCCAATGTAACCATTTATTCGT-----ACTCGTCTGGCCACGCTAGAAAT | 1644 |
| Glycine max Glyma.18g282300.2_CDS | CTAGGCTTCGTTTCGTTAATTCTGAT---GCAAGTGCCGTGGA------TAACCCATCTACATTGATACATAAT | 1668 |
| Glycine max Glyma.08g257900.1_CDS | CCAGGCTTCGTTTCGTTCATTAATTCTGAT---GCAAGTGCTGTGGA------TAACCTGTCTACATTGATAATAAT | 1680 |
| Solanum tuberosum PGSC0003DMT400052897_CDS | CCAGACTCAGACTGGCAATCTTAATCTGAT---GCAGTTGCTCAGAACACGAATAAAATATCTTGCCTATCCAGACATTGAT | 1596 |
| Beta vulgaris g12062.t1_CDS | CTAGGCTTCGGACTTGTTTTGAACCGTGTTAATCCTAAT---TTTGGCTCGTTAGACCTGATGCCGTCCTATGGTTCCCAGTTCA | 1644 |
| Triticum aestivum TaCPL3-B_CDS | CAAGGCTCAGGTTTTTTGAACCGTGGTTAATCCTGAT-TCTGGTGGTCGGTACTCAGATGCAGATAGACATGTAAATTGGCAGAGCCAAATG-- | 1630 |
| Triticum aestivum TaCPL3-D_CDS | CAAGGCTCAGGTTTTTTGAACCGTGGTTAATCCTGAT-TCTGGTGGTCGGTACTCAGATGCAGATAGACATGTAAATTTTGCAGAGCCAAATG-- | 1657 |
| Triticum aestivum TaCPL3-A_CDS | CAAGGCTCAGGTTTTTTGAACCGTGATTCTGAT-TCTGGTGGTCGGTACTCAGATGCAGATAGACATATACACATGTAAATTTGCAGAGCCAAATG-- | 1657 |
| Sorghum bicolor Sb05g019010_CDS | CAAGGCTCAGATTTTTGAACCGTCAGATTCTGATTCGTGATCGGTGCTACAGATGTGAATCGGGCGCAAATTTTCAGAACTGAA---- | 1646 |
| Zea mays ZmCPL3_CDS | CGAGGCTCAGATTTTTGAACCGTCAGATTCTGATTCGTGATCGGTGCTACAGATGTAAATTGGCGTGCAAATTTTCAGAACTGAA---- | 1763 |

| | | |
|---|---|---|
| Arabidopsis thaliana AtCPL3_CDS | CTTTCAAAAGTAGAGCTTTCTGCAGACTTGGTGAACCCAA------GAAAACAAAAAGCCGCTGATGAATTTTTAATTGAT | 1719 |
| Glycine max Glyma.18g282300.2_CDS | ATGCCTAAAAGTGGAATATGTGGAATATTCTGGAACAACAATG---TCAA-----GGAAACAAAAAGGCTGCTGAAGAACCTTCTTTTGGAT | 1740 |
| Glycine max Glyma.08g257900.1_CDS | ATGTCTAAAAGTGGAATATTCTGGAACAACAATC----TCAA-----GGAAACAAAAAGGCTGCTGAAGAACCTACCTACCAGTCTTTGGT | 1752 |
| Solanum tuberosum PGSC0003DMT400052897_CDS | TTGAAATTGGAGGCTTCTTTAGAGATGATTGCT-----TCAA-----AAAAGCAGAACCAGGCACTTGAGGGGCGCCTTCTGAT | 1668 |
| Beta vulgaris g12062.t1_CDS | GCATCTAAATTGGAGCCGCTAGGGAGGGAAATTATGAAATCAA---------AGAAGACCGGAAGCAACTGGCCAACCTCTCACGGAT | 1719 |
| Triticum aestivum TaCPL3-B_CDS | CTTCCAAAGATGGGACTTGGGTGGACCCTTGGGGGGGGGGTGGTGTTGTATCAGATAATAGCCCGGAAGCAACTGGCCAACCTCTCACGGAT | 1710 |
| Triticum aestivum TaCPL3-D_CDS | CTTCCAAAGATGGGACTTGGGTGGACCCTTGGGGGGGGGGTGGTGTTGTATCAGATAATAGCCCGGAAGCAACTGGCCAACCTCTCACGGAT | 1737 |
| Triticum aestivum TaCPL3-A_CDS | CTTCCAAAGATGGGACTTGGGTGGACCCTTGGGGGGGGGGTGGTGTTGTATCAGATAATAGCCCGGAAGCAACTGGCCAATTGATGATCCTCATGGAT | 1737 |
| Sorghum bicolor Sb05g019010_CDS | ------GGATGGGAACTTGGGTGGACGG----TCAGTTGGTAACCGTAAACACAAGCTAAACACGTAAACCGTAACCCGTAACCAGTTGATCATCCTCAGGTGGAT | 1716 |
| Zea mays ZmCPL3_CDS | ------GGATGGGAACTTGGGTGGACGG----TCAGTTGGTAACCGTAAACACAAGCAAAAGCAAAAGCCAGTTGATGATCCTCAGGTGGAT | 1833 |

| | | |
|---|---|---|
| Arabidopsis thaliana AtCPL3_CDS | GGGCCTGCATGGGAAAAGACAAAAGAGT--------GATACGGATGCACCAAAAGC----AGC | 1769 |
| Glycine max Glyma.18g282300.2_CDS | GTTACTGTATCAAAAAAGAAGACAAAAGTCCATTGGAAAATACTGA--GCA---TAATATGAGCGAAGTAAG-------AAC | 1808 |
| Glycine max Glyma.08g257900.1_CDS | GTTACTGTATCAAAAAAGACTAAAAAGTTCTTTGGAAAATACTGA--GCA---TAATATGAGCGAAGTAAG-------AAC | 1820 |
| Solanum tuberosum PGSC0003DMT400052897_CDS | GCTCCATTGCCGAAAGACAAAGAGACAAGAACAAGAACT-------GAACAGACTGA--TTCAATCATTGTGAGTGATGTGCCTCTTGAC | 1739 |
| Beta vulgaris g12062.t1_CDS | GGTCCTACTGCCAAGGAGAGACCAAGAAAGAAATGGCCTGGAAGATATGTCCATGAATGCAAATCAAGTGCTAAAACTCTCCA | 1799 |
| Triticum aestivum TaCPL3-B_CDS | GAAACCGTGTTAAAAAGAAGCTAGGGAG-------AGTACTGGGAATCCCAGAGACATGCAGGT | 1766 |
| Triticum aestivum TaCPL3-D_CDS | GAAACCGTGTTAAAAAGAAGCTAGGGAG-------AGTACTGGGAATCCCAGAGACATGCAGGT | 1793 |
| Triticum aestivum TaCPL3-A_CDS | GAAACCGTGTTAAAAAGAAGCTAGGGGC-------AGTACTGGGAGTCCCAGAGACATTCTGGT | 1793 |
| Sorghum bicolor Sb05g019010_CDS | GAAAATGTGTTAAAAAGATTTAGGGGC--------GGAACTGCAAATCCGAGAGAGACTTGCAA-- | 1770 |
| Zea mays ZmCPL3_CDS | GACAATTGCGTTAAAAAGATTTAGGGGC--------GGAATTGCGAATCAGAGAGAGACATGCAG-- | 1887 |

```
Arabidopsis thaliana AtCPL3_CDS           GAGGATGTGTCAGTTTCAGCAGGATCAGTAACGGCTGGTGCCTGCCACTCGTTCCATGAACAGTTGGGAGATGTGGA 2681
Glycine max Glyma.18g282300.2_CDS         CTGGAGGCTGGCATGGTCATCAGTGTATCAGCTGCTCAGCTGCTCATCGTTCGATCCAGAATACATGGGAGATGTTGA 2729
Glycine max Glyma.08g257900.1_CDS         CTGCAGGCTGACATGGCCATCTGCTGCTTAGCTTGCTGCATCAGTCAGTTACCTCTCGATCCAGTACATGGGAGATGTTGA 2741
Solanum tuberosum PGSC0003DMT400052897_CDS CGGGTGAATGATGCTGGCTTGGCTTGCATTGAGGCCCGAAGAAGGTTGTCTCCTGGTTCATTGCAACCACAGATCTCTTGGGAGATGTTGA 2612
Beta vulgaris g12062.t1_CDS               CAGCGTACTCGTGTCTGCATTGAGGCCCGAAGAAGGTTGTCTCGGGCGGTAGTAAGTTGGGAGATGTTGA 2714
Triticum aestivum TaCPL3-B_CDS             G------ATGCTGCCCCTGCTACAA---CACTTGGTACCAGGCCACCAGCTAACCAGTGGGTGATCTTGA 2669
Triticum aestivum TaCPL3-D_CDS             G------ATGCTGCCCCTGCTACAA---CACTTGGTACCAGGCCACCAGCTAACCAGTGGGTGATCTTGA 2696
Triticum aestivum TaCPL3-A_CDS             A------ATGCTGCCCCTGCTACAA---CACTTGGTACCAGGCCACCAGCTAACCAGTGGGTGATCTTGA 2696
Sorghum bicolor Sb05g019010.1_CDS         GCTGATGCAACAACAACAAATGGTGCTTCTGCAACAG---AACTTGAAGCTACACAGCCTGTTAGCCCATGGCCATGGGGTAATCTTGA 2552
Zea mays ZmCPL3_CDS                       GCTGATGCAACAACAACAAATGGTGCTTCTGCAACAA---CACTTGAAGCTACACAGCCTGTTAGTCCATGGGGTGATGTTGA 2666
                                                                                                                           3280

Arabidopsis thaliana AtCPL3_CDS           ACACCTATTTGAAGGATATGATGACATTCAGAGAGTAGCTATTCAAAGAGAGAGAGAGTTCGTAGGTTAGAGGACAGAATA 2761
Glycine max Glyma.18g282300.2_CDS         GCATCTTTTTGAAGGTTATGATGAGCAGCAGCAACAGCAGCAGCTGCTATACAGCAGAGAGAAGAAGAAGAAGAACAGAATA 2809
Glycine max Glyma.08g257900.1_CDS         GCATCTATTTGAAGGTTATGACGGCTACAGCAGGATCAGGATGATATCCAGAGACAGCAGGGAGGATTGAAGAACAGAATA 2821
Solanum tuberosum PGSC0003DMT400052897_CDS GCATCTCTATTTGAGGGTACAGCAGCATGATGATATCAGCAGCACCAACAGCAGGCAGCAGGGTAGGAGGCTTGAGGAACAGAAAA 2692
Beta vulgaris g12062.t1_CDS               GCATCTCTTTGACGGATATGATGATGATGATGACCAGGATCAGGATCAGGATCAGAACAGCAGGAAGCAGAGAGGAAGAGAGGCTTGATGAGGAACACA 2794
Triticum aestivum TaCPL3-B_CDS             TGATCCTCCTCAAACGGTTATGATGACGGTTATGATGATGACCAGGATCAGGATCAGGATCAGAACAGCAGGAAGCAGGAAGGGCAAGACGGATCATGAACAACACA 2749
Triticum aestivum TaCPL3-D_CDS             TGATCCTCCTCAAACGGTTATGATGACGGTTATGATGACCAGGATCAGGATCAGGATCAGAACAGCAGGAAGCAGGAAGGGCAAGACGGATCATGAACAACACA 2776
Triticum aestivum TaCPL3-A_CDS             TGATCCTCCTTAACGGTTATGATGATGATGATGATGATGACCAGGATCAGGATCAGAATAAGCAGCAGGAAGCAAGGGCAAGACGGATCATGAACGAACACA 2776
Sorghum bicolor Sb05g019010.1_CDS         TCATCTCCTTGATGGATATGGATATGGATGATGATGACCAAGATCAGGATCAGAACGAATAAACAGAACAACACA 2632
Zea mays ZmCPL3_CDS                       TCATCTCCTTGATGGATATGGATATGGATGATGATGACCAAGATCAGGATCAGAACGAATAAACAGAACAACACA 2746
                                                                                                                           3360

Arabidopsis thaliana AtCPL3_CDS           AAATGTTTGCATCTCAAAAGCTCTCAAATTCAGCTAAGTTTAATGAGTT 2841
Glycine max Glyma.18g282300.2_CDS         AAATGTTTGCTGCTCGAAATTGTGCCTTGTTAGTGCTTTAATTCTGCTAAGTTTGTGGAAGTT 2889
Glycine max Glyma.08g257900.1_CDS         AAATGTTTGCTGCTCGAAATTGCTGCCTTGTATTGGACCTAGATCACACCTAATTCTGCCAAGTTTGTGGAAGTT 2901
Solanum tuberosum PGSC0003DMT400052897_CDS AAATGTTTTTCTGCTCGTTCGGAAGCTCGTCGTTGCTCGTCGTTGCTCTTGGACCTTGGACCTTGAATTCAGCAGCAAAGTTGTTGAAATC 2772
Beta vulgaris g12062.t1_CDS               AAATGTTTGCTGCTCGATCGGCAAGTTGTCTTGTCGTGTCTTGCTAGTCCTTAGTGCTTGGATCGGATCTGATTGGAATTCAGCAGCAAAGTTTCAGAGGTA 2874
Triticum aestivum TaCPL3-B_CDS             CGATGTTTTCATCGAGGAGGAAACTTTGTTAGTGCTAGTTGATTGGATCGTCAATTCTGCGAAGTTTCGAGAGGAAGTG 2829
Triticum aestivum TaCPL3-D_CDS             CGATGTTTTCATCGAGGAGGAAACTTTGTTAGTGCTAGTTGATTGGATCGTCAATTCTGCGAAGTTTCGAGAGGAAGTG 2856
Triticum aestivum TaCPL3-A_CDS             CGATGTTTTCATCGAGGAGGAAGCTAGTTGATTGGATCGTCAATTCTGCGAAGTTTCGAGAGGAAGTG 2856
Sorghum bicolor Sb05g019010.1_CDS         AAATGTTTCTCAGCGCCGCACACGGCAGCTATGCTTGGTGCTGGTTGGATTTGGATCACACCCCTTCTTAATTCTGCAAAGTTTATAGAAGTG 2712
Zea mays ZmCPL3_CDS                       AAATGTTTCTCAGCGGCGGAAGCTATGCTTGGTGCTGGTTGGATTTGGATCACACCCCTTCTTAATTCTGCAAAGTTTATAGAAGTG 2826
```

Figure 2A (continued)

```
                                              3620                3640                3660                3680
Arabidopsis thaliana AtCPL3_CDS           GT------------------------------------CATATCGAAAGGAGATGATGGAGATCCTCTTGATGGAGACGAACGAGTACCTAAGAG 3140
Glycine max Glyma.18g282300.2_CDS         GT------------------------TATCTCTAGAGGTGATGATGATACTGATTGATTCAGTTCAGTTGATGGTGAGGAGAGGCTCCCAAAAG 3188
Glycine max Glyma.08g257900.1_CDS         GT------------------------TATCTCTAGAGGTGATGATGATGATGATGATTGATTCAGTTCAGTTGATGGTGAGGAGAGGGTTCCCAAAAG 3200
Solanum tuberosum PGSC0003DMT400052897_CDS GT------------GATCTCCAGGGTGGACATGATGGAGATCCATTTGATGGGGATGAAAGGGTTCCTAAGAG 3071
Beta vulgaris g12062.t1_CDS               GT------------TATCTCACGGGTGATGATGGGGATCGTGATGATGATTTGATTGATGAGGGGATGTGATGAGAGAGACCTATACAAAAAG 3173
Triticum aestivum TaCPL3-B_CDS             GTCATCTCAAGAGGTGGTGATGGCCATCTCAAGAGGTGTGATGGTGATACATTTGACAGGATGATGACCGTGTACCAAAAG 3149
Triticum aestivum TaCPL3-D_CDS             GTCATCTCAAGAGGTGGTGATGGCCATCTCAAGAGGTGTGATGGTGATACATTTGACAGGATGATGACCGTGTACCAAAAG 3176
Triticum aestivum TaCPL3-A_CDS             GTAATCTCAAGGGGTGGTGATGGTATCTCAAGAGGTGTGACGGTGATCATTTGACACGATGATGACGTGTACCAAAAG 3176
Sorghum bicolor Sb05g019010.1_CDS         GT---------------CATATCAAGAGGTGATGATGGTGATCCTTTGACAGTGATGAACCAGTGCCGAAAAG 3011
Zea mays ZmCPL3_CDS                       GT---------------CATATCAAGAGGTGATGATGGTGATCCTTTGACAGTGATGAACCAGTGCCAAAAAG 3125
                                              3700                3720                3740                3760
Arabidopsis thaliana AtCPL3_CDS           CAAAGATTTAGAAGGAGTTATGGGTATGGGTATCGTCTGTGGTGATCATAGATGACTCTCCGAGTGTGCCTCAACACA 3220
Glycine max Glyma.18g282300.2_CDS         CAAAGATTTGGAAGGCCGTTTGGGTTTTGGGCATGGGATGTTATGGGATGTTATGGGATGAATCATTATAGATGATTATAACA 3268
Glycine max Glyma.08g257900.1_CDS         CAAAGATTTGGAAGGCGTTTGGGTTTTGGGCATGGGATGTATGGGATGTTATGGGATGAATCATTATAGATGATTCATAACA 3280
Solanum tuberosum PGSC0003DMT400052897_CDS TAAGGACTTGGAGGGACTGTTTATGGGTATGGGTATTGGGATGTTTGGCAGAGTCTGCAGAGTCTGACACATAACA 3151
Beta vulgaris g12062.t1_CDS               CAAGGATTTAGAGGGTGATCTTGATTATGGGGATGGGGATGGGTATTGGGATGTTTGGGATGATCGACGACTCTGTCTGACGACAACA 3253
Triticum aestivum TaCPL3-B_CDS             TAAAGATTTGGAGGGCTTGATGATGATGATGATGGGATTGGGATGTATGGGATGATCGACGATTCGACGACTCGATGAGTCGATGAGAACAACA 3229
Triticum aestivum TaCPL3-D_CDS             TAAAGATTCTTGAGGGCTTGATGATGATGATGATGGGATTGGGATGTATGGGATGATCGACGATTCGACGACTCGATGAGTCGATGAGAACAACA 3256
Triticum aestivum TaCPL3-A_CDS             TAAAGATTCTTGAGGGCTTGATGATGATGATGATGGGATTGGGATGTATGGGATGATCGACGATTCGACGACTCGATGAGTCGATGAGAACAACA 3256
Sorghum bicolor Sb05g019010.1_CDS         TAAAGATTTGGAGGGCTACTGGGTATGGGTATGGGTATGTTGTGATCGATGATTCGATGAGTAAGAGTCTGTAAGAGTCATAACA 3091
Zea mays ZmCPL3_CDS                       TAAAGATTTGGATGGGCTACTGGGTATGGGTATGGGTATGTTGTGATCGATGATTCGATGATGAGAGAGATTCGATAACA 3205
                                              3780                3800                3820                3840
Arabidopsis thaliana AtCPL3_CDS           AAATGAATTTAATAGCTGTGTTGAAAGATATCTTTATTTCCCTTGTAGTAGACGGCAATTTGGGCTTCCTTGGTCCTTCTCTT 3300
Glycine max Glyma.18g282300.2_CDS         AACTGAACCTGATAGTGGTGATAGTGTTCTTGTTGACATACATACTCTCCCCTGTAGTAGACGTGAGTCAGTTGGACTTCAGTTGGCCTTGGCCCTTCCCTT 3348
Glycine max Glyma.08g257900.1_CDS         AACTGAACCTGATAGTGGTGATAGTGTTCTTGTTGTAGATACATACATACTCCCCCTGTAGTAGACGTGAGTCAGTTGGACGTCAGTTGGCCTTGGCCCTTCCCTT 3360
Solanum tuberosum PGSC0003DMT400052897_CDS AGCTAAACTTGATAGTCGTGTAGATAGAGGTATATTTACTTTCCTTGCAGTGAGTAGACGTGAGACGTGGACGTGAGCAATTTGGTCTGCCCCTGGTCCTTCTCTT 3231
Beta vulgaris g12062.t1_CDS               AGCTAAACTTGATAGTCGTGTAGATAGAGGTATATTTACTTTCCTTGCAGTGAGTAGACGTGAGACGTGGACGTGAGCAATTTGGTCTGCCCCTGGTCCTTCTCTT 3333
Triticum aestivum TaCPL3-B_CDS             AAAACAATATGATCATTGATCATTGTAGAGAGAGAGAGATACACCCTATTCCCCTTATTCCCCTGTGCAGCAGCAGCAATTTGGCCTTCCTTGGACCATCACTT 3309
Triticum aestivum TaCPL3-D_CDS             AAAACAATATGATCATTGATCATTGTAGAGAGAGAGATACACCTATTCCCCTTATTCCCCTATTCCCCTGTGCAGCAGCAGCAATTTGGCCTTCCTTGGACCATCACTT 3336
Triticum aestivum TaCPL3-A_CDS             AAAACAATATGATCATTGATCATTGTAGAGAGAGAGATACACCTATTCCCCTATTCCCCTATTCCCCTGTGCAGCAGCAGCAATTTGGCCTTCCTTGGACCATCACTT 3336
Sorghum bicolor Sb05g019010.1_CDS         GGCACAATTTGATAGTTGTAGAGAGAGATACACCTATTTCCCCCTATTCCCCTGCAGACACTACACCCTGCAGACAGGCGTCAATTGGCCTTCCTTGGACCATCACTT 3171
Zea mays ZmCPL3_CDS                       GGCACAATTTGATAGTCGTCAATTGTAGAGAGAGATACACCTATTCCCCCTATTCCCCTGCAGACACTACACCCTGCAGACAGCGGCGTCAATTTGGCCTTCCTTGGACCATCACTT 3285
```

Figure 2B

| | 1 | 2 | 3 | 4 | 5 | 6 | 7 | 8 | 9 | 10 |
|---|---|---|---|---|---|---|---|---|---|---|
| 1 Arabidopsis thaliana AtCPL3_CDS | | 52,85 | 52,28 | 50,72 | 49,37 | 45,35 | 45,34 | 45,62 | 45,61 | 44,18 |
| 2 Glycine max Glyma.18g282300.2_CDS | | | 93,93 | 57,55 | 56,14 | 46,27 | 46,49 | 46,73 | 46,49 | 45,36 |
| 3 Glycine max Glyma.08g257900.1_CDS | | | | 58,23 | 56,69 | 45,74 | 45,96 | 46,16 | 46,45 | 45,50 |
| 4 Solanum tuberosum PGSC0003DMT400052897_CDS | | | | | 54,52 | 44,87 | 45,12 | 45,14 | 44,58 | 43,85 |
| 5 Beta vulgaris g12062.t1_CDS | | | | | | 43,89 | 44,11 | 44,24 | 44,51 | 43,40 |
| 6 Triticum aestivum TaCPL3-B_CDS | | | | | | | 97,87 | 97,02 | 69,76 | 69,04 |
| 7 Triticum aestivum TaCPL3-D_CDS | | | | | | | | 97,85 | 70,28 | 69,56 |
| 8 Triticum aestivum TaCPL3-A_CDS | | | | | | | | | 70,12 | 69,45 |
| 9 Sorghum bicolor Sb05g019010.1_CDS | | | | | | | | | | 89,69 |
| 10 Zea mays ZmCPL3_CDS | | | | | | | | | | |

| | Empty vector | Mock | Untreated | Silencing sequence TaCPL3_fragA | Silencing sequence TaCPL3_fragB |
|---|---|---|---|---|---|
| Pycnidia ± SD ANOVA | 15,6 ± 10,9 a[1] | 18,6 ± 10,5 a | 20,1 ± 9,6 ab | 4,9 ± 2,2 bc | 3,4 ± 1,3 c |
| Spores ± SD ANOVA | 45,3 ± 15,6 a | 70,5 ± 11,9 a | 75,3 ± 12,8 b | 18,8 ± 4 c | 12,8 ± 3,4 c |

Figure 5A:

| Line | Plant number | Disease score (0-100%) 5 + 6. leaf | Fungal biomass[2] ± SD | Gene expression[3] qRT-PCR relative to ntg segregant |
|---|---|---|---|---|
| A188 | 33 | 52,4 ± 20,3 | 165 ± 96,6 | |
| MTR0374-T-038 | 8 | 40,6 ± 14 | 149,6 ± 74,8 | 39 |
| MTR0374-T-038 ntg[1] | 5 | 54 ± 5,8 | 199,3 ± 23,3 | 100 |
| MTR0374-T-053 | 12 | 53 ± 14,3 | 153,6 | 50 |
| MTR0374-T-053 ntg[1] | 8 | 48 ± 12,9 | 213,3 | 100 |

Figure 5B:

| Line | Plant number | Mean plant size [3] (cm) | Mean leaf width (cm) | Disease score (0-100%) 5 + 6. leaf |
|---|---|---|---|---|
| A188 | 36 | 61,1 | 3,9 | 52,1 a[1] |
| MTR0374-T2-038 | 24 | 62,1 | 3,8 | 41,3 bc |
| MTR0374-T2-038 ntg[2] | 24 | 62,6 | 4,0 | 49,3 ab |
| MTR0374-T2-053 | 24 | 59,9 | 4,0 | 35,8 c |
| MTR0374-T2-053 ntg[2] | 24 | 58,9 | 3,9 | 48 ab |

PATHOGEN RESISTANCE IN CROP PLANTS

CROSS-REFERENCE TO RELATED APPLICATIONS

This application is a U.S. National Phase of International Patent Application No. PCT/EP2020/055380, filed on Mar. 1, 2020, which claims priority to European Application No. 19160408.1, filed Mar. 1, 2019. The entire contents of these applications are incorporated herein by reference in their entirety.

TECHNICAL FIELD

The present invention relates to the field of plant biotechnology. Specifically, there are provided methods and nucleic acid sequences for obtaining pathogen resistance in plants and for generating resistant plants. In particular, the role of a central molecule in plant immunity is studied. Based on the mechanisms elucidated, the present invention provides strategies to specifically modulate a phosphatase-like protein family member molecule or the expression of said phosphatase-like protein family member molecule by different transient and/or stable techniques, alone or in combination, to achieve a robust increase of pathogen resistance in different target plants to obtain inherently pathogen resistant plants and plant materials to avoid severe harvest losses as caused by major plant pathogens by biological means instead of herbicide or pesticide treatment.

BACKGROUND OF THE INVENTION

Plant, unlike mammals, lack an immune system relying on mobile circulating defending cells and do not possess mechanisms like an adaptive immune system. Still, plants possess a highly efficient, two-layered innate immune system that allows them to respond to infections, e.g., by microbial pathogens (Jones and Dangl, (2006). The plant immune system. *Nature,* 444(7117), 323). The first layer of defense relies on the recognition of evolutionary conserved pathogen- or microbial-associated molecular patterns (PAMPs or MAMPs) by the so-called pattern recognition receptors (PRRs). PAMPs or MAMPs are invariant structures broadly represented among microbial taxa and have essential roles in microbial physiology. Only an extremely selective group of molecules have been found to function as PAMPs (Gaudet and Gray-Owen, (2016). Heptose sounds the alarm: Innate sensing of a bacterial sugar stimulates immunity. *PLoS pathogens,* 12(9), e1005807). It was also found that conserved molecules from nematodes can elicit plant defenses and pathogen resistance (Manosalva et al., (2015). Conserved nematode signaling molecules elicit plant defenses and pathogen resistance. *Nature communications,* 6, 7795.). Accordingly, such molecules were defined as nematode-associated molecular patterns (NAMPs).

Besides molecular patterns originating from the pathogen, plants can also sense molecular patterns associated with cell wall destruction or cell damage, the so-called danger/damage-associated molecular patterns (DAMPs).

PRRs are generally plasma membrane receptors which are often coupled to intracellular kinase domains or require a co-receptor to provide signaling function. Depending on the presence of the signaling transduction domain the plant PRRs are classified either as receptor-like kinases (RLKs) or as receptor-like proteins (RLPs) as described by Macho and Zipfel ((2014). Plant PRRs and the activation of innate immune signaling. *Molecular cell,* 54(2), 263-272.). Recognition of PAMPs, MAMPs, NAMPs or DAMPs in the apoplast by pattern recognition receptors (PPRs) initiates a complex signaling cascades from the receptor in the plasma membrane to the nucleus leading to PRR-triggered immunity (PTI). As an evolutionary adaption, pathogens compete with the defense system and may be able to suppress the first defense layer through the secretion of effector proteins that interfere with the signaling (Jones and Dangl, 2006).

The second layer of plant defense, the effector triggered immunity (ETI), largely takes place inside a plant cell. ETI relies on the specific recognition of disease resistance effectors on a pathogen, wherein the disease resistance effector, as it is understood to date, usually are recognized by plant recognition proteins comprising polymorphic nucleotide binding (NB) and leucine rich repeat (LRR) domains. This recognition leads to a strong defense response which is often associated with a local programmed cell death, the hypersensitive reaction. Since pathogenic effectors are often species or isolate specific, this second layer of immunity is only efficient against isolates that carry the recognized effector, which is then called an avirulence gene.

Whether a potential pathogen is able to overcome the first layer of defense, the PTI, and to reproduce effectively, depends on its intrinsic ability to suppress PTI responses of the plant. But it also depends on the plants ability to efficiently and quickly induce and, if required, to maintain defense responses above a certain threshold for effective resistance (Jones and Dangl, 2006). PTI responses are generally conserved and include the activation of mitogen-activated protein kinases (MAPKs), the generation of reactive oxygen species, the activation of salicylic acid (SA)- and jasmonic acid (JA)-signaling pathways and the enhanced expression of plant defense genes, like pathogenesis-related genes.

Transcriptional activation as induced by a PTI or ETI mechanism can be measured very fast, typically within minutes or hours after infection and it is reduced after effective defense response. Transcription of protein-coding genes in eukaryotes is intricately orchestrated by RNA polymerase II (RNAPII), general transcription factors, mediators, and gene-specific transcription factors. The multi-subunit RNAPII complex is evolutionary conserved from yeast to human. Its largest subunit Rpb1 contains a carboxyl-terminal domain (CTD) consisting of conserved heptapeptide repeats with the consensus sequence $Y_1S_2P_3T_4S_5P_6S_7$ (Buratowski, (2009). Progression through the RNA polymerase II CTD cycle. *Molecular cell,* 36(4), 541-546.). The number of repeats varies from 26 in yeast, 34 in *Arabidopsis,* and 52 in mammals (Hajheidari et al., (2013). Emerging roles for RNA polymerase II CTD in *Arabidopsis. Trends in plant science,* 18(11), 633-643.). The combinatorial complexity of CTD posttranslational modifications constitutes the so-called "CTD-code" which is read by CTD-binding proteins to regulate the transcription cycle, modify chromatin structure, and modulate RNA capping, splicing and polyadenylation. In particular, the CTD undergoes waves of SER phosphorylation and dephosphorylation events regulated by various CTD kinases, often members of cyclin-dependent kinases (CDKs), and phosphatases during transcription initiation, elongation and termination. The interplay between different CTD kinases and phosphatases provides means for coupling and coordinating specific stages of transcription by recruiting other factors required for proper gene expression (Buratowski, 2009).

In Arabidospis, so far five members of the CTD phosphatase-like proteins family (CPL1-5) have been described (Koiwa et al. (2002). C-terminal domain phosphatase-like family members (AtCPLs) differentially regulate *Arabidopsis thaliana* abiotic stress signaling, growth, and development. *Proceedings of the National Academy of Sciences,* 99(16), 10893-10898.; and Fukudome et al. (2014). *Arabidopsis* CPL4 is an essential Ser2-specific CTD-phosphatase regulating general and xenobiotic responsive gene expression (617.2). *The FASEB Journal,* 28(1_supplement), 617-2.). They were shown to possess preferences for different phosphorylated serines in the heptapeptide repeats and to be involved in different biological processes. *Arabidopsis* AtCPL1 was shown to be a negative regulator of stress-responsive gene expression under various stress conditions (cold, abscisic acid (BA), salt treatment and iron deficiency) (Koiwa et al., 2002) and negatively regulates wound-induced JA-biosynthesis genes. *Arabidopsis* AtCPL2 was described to be involved in the regulation of osmotic stress and auxin responses and influences plant development (Ueda et al., (2008). The *Arabidopsis thaliana* carboxyl-terminal domain phosphatase-like 2 regulates plant growth, stress and auxin responses. *Plant molecular biology,* 67(6), 683.). *Arabidopsis* AtCPL3 was shown to be a negative regulator of BABA-induced gene expression (Koiwa et al., 2002). A complete knockout of AtCPL3 by T-DNA insertion or early-stop-codon mutations resulted in reduced growth and early flowering (Koiwa et al., 2002). *Arabidopsis* AtCPL4 was described as an essential gene involved in the regulation of xenobiotic stress responses (Fukudome et al., 2014), lateral root development and its silencing induces cytokinin-oversensitive de novo shoot organogenesis (Fukudome et al., (2018). Silencing *Arabidopsis* CARBOXYL-TERMINAL DOMAIN PHOSPHATASE-LIKE 4 induces cytokinin-oversensitive de novo shoot organogenesis. *The Plant Journal,* 94(5), 799-812.). *Arabidopsis* AtCPL5 was reported to encode a unique CPL family protein that positively regulates ABA-mediated development and drought responses in *Arabidopsis* (Jin et al., (2011). AtCPL5, a novel Ser-2-specific RNA polymerase II C-terminal domain phosphatase, positively regulates ABA and drought responses in *Arabidopsis. New Phytologist,* 190(1), 57-74.). At date, certain CPL family members of genes/proteins has been identified in *Arabidopsis*, but further work on the specific function of said proteins, in particular in the context of the complex network of plant immunity, has to be accomplished.

Presently, there is thus an increasing understanding of plant immunity. In particular, certain aspects of PRR signaling and ETI responses in plants have been elucidated, yet only very few is known about the complex interplay between plants and pathogens seeking to subvert the plant immune system in a co-evolutionary manner. Notably, depending on its life cycle and mode of infection, each pathogen will have an individual defense strategy so that individual defense mechanisms are needed for sessile plants to combat infection.

Infections and infestations of crop plants by pathogens encompassing viruses, bacteria, fungi, nematodes and insects and the resulting damages cause significant yield losses of cultivated plants. In maize or corn (*Zea mays*), said terms being used interchangeably herein, as one of the major crop plants worldwide there are a large number of fungal pathogens which cause leaf diseases. The fungus which can cause by far the most damage under tropical and also under temperate climatic conditions, such as those in large parts of Europe and North America as well as in Africa and India, is known as *Helminthosporium turcicum* or synonymously as *Exserohilum turcicum* (teleomorph: *Setosphaeria turcica*). *H. turcicum/E. turcicum* is the cause of the leaf spot disease known as "Northern Corn Leaf Blight" (NCLB), which can occur in epidemic proportions during wet years, attacking vulnerable maize varieties and causing a great deal of damage and considerable losses of yield of 30% and more over wide areas (Perkins & Pedersen, 1987. Disease development and yield losses associated with northern leaf blight on corn. *Plant Disease,* 71(10), 940-943.; Raymundo & Hooker, 1981. Effect of gene HtN on the development of northern corn leaf blight epidemics. *Plant disease.*). Since the 1970s, natural resistance in genetic material has been sought. Of course, it is not only fungi that cause plant diseases. There are also bacteria, viruses, nematode worms (e.g., eel worms), aphids and insects to name relevant further plant pathogens. Serious plant diseases are caused by all these other pests, but fungi probably cause the most severe losses for major crop plants worldwide. Crop protection measures include weed control, which can be managed mechanically or chemically, and the control of animal pests or diseases, which relies heavily on synthetic chemicals. Herbicide use has enabled farmers to modify production systems to increase crop productivity while still maintaining some measure of control over the damaging effect of pests. Unfortunately, despite large increases in pesticide use, crop losses have not significantly decreased during the last 40 years.

The race for defining and establishing new resistance strategies against pathogens for major crop plants is more and more accelerated due to the increasing resistance breaking characteristics of pathogens, i.e., the evolutionary strategy of pathogens to adapt to and survive pressure of plant protective agents and/or to subvert the endogenous plant immunity defence mechanisms introduced above.

So far, there is thus a great need to transfer the basic knowledge about plant defense mechanisms and plant immunity elucidated in model plants like *Arabidopsis thaliana* to major crop plants. It was therefore an intention of the present invention to identify new genes specifically present in crop plants that could be associated with pathogen resistance. It was another object of the present invention to transfer the knowledge about conserved signaling mechanisms in plant immunity to a more specific level to identify specific interactions and to present new strategies to establish broad pathogen resistance in a variety of crop plants based on biological means, i.e., disease control strategies relying on establishing and growing resistant cultivars for providing more effective and environmentally sound disease control, wherein obtaining plant varieties with greater pathogen resistance is central to this.

It was thus a further object of the present invention to investigate the functional basis of resistance to pathogens, including fungal pathogens as well as further kinds of plant pathogens, to provide new strategies to combat pathogen infection or infestation based on exploiting plant-endogenous defense mechanisms as source of resistance or tolerance against pathogens. Instead of relying on anti-fungal chemicals, it was an aim to establish new urgently needed resistance strategies for a variety of important crop plants by characterizing the molecular players involved in disease resistance in a plant and in turn to modulate said plant-endogenous resistance pathways in a targeted manner, in particular to obtain increased pathogen resistance whilst maintaining normal growth in a plant in view of the fact that modulating central effectors of the plant immune system without a proper understanding of the regulatory mechanisms is usually accomplished with severe side effects, e.g., reduced plant development or growth which should be avoided according to the present invention.

SUMMARY OF THE INVENTION

The above object was achieved by identifying the molecular role of CPL genes, in particular CPL3, in pathogen resistance and further by studying the effect of targeted mutations or modulations of said genes or gene products or their expression or translation, which has advantageous effects in comparison to the generation of full knock-out lines.

In a first aspect, there is provided a plant having pathogen resistance, wherein pathogen resistance is conferred or increased by modulation of a nucleotide sequence encoding an endogenous C-terminal domain phosphatase-like 3 (CPL3) protein or a regulatory sequence thereof, or by modulation of the transcription of an endogenous CPL3 protein, wherein modulation is achieved by (i) one or more mutation(s) of the nucleotide sequence encoding a CPL3 protein, preferably wherein the one or more mutation(s) has/have a dominant negative effect, preferably wherein the one or more mutation(s) cause(s) an alteration of the amino acid sequence of the conserved catalytic domain of the CPL3 protein comprising the DXDXT/V motif; and/or (ii) one or more silencing construct(s) directed to one or more endogenous nucleotide sequence(s) encoding a CPL3 protein, preferably directed to all endogenous nucleotide sequences encoding a CPL3 protein; and/or (iii) a modification of the native regulatory sequence(s) of one or more nucleotide sequence(s) encoding an endogenous CPL3 protein, preferably of all native regulatory sequence(s) of the nucleotide sequences encoding an endogenous CPL3 protein, wherein the modification causes a reduced expression rate of the one or more nucleotide sequence(s) encoding an endogenous CPL3 protein.

In a further aspect, there is provided a cell, tissue, organ, seed or material of the plant having pathogen resistance, wherein pathogen resistance is conferred or increased by modulation of a nucleotide sequence encoding an endogenous C-terminal domain phosphatase-like 3 (CPL3) protein or a regulatory sequence thereof, or by modulation of the transcription of an endogenous CPL3 protein as detailed in the above first aspect.

In a second aspect, there is provided a nucleic acid molecule comprising a nucleotide sequence encoding for a C-terminal domain phosphatase-like 3 (CPL3) protein, wherein the nucleotide sequence is selected from the group consisting of: (a) a nucleotide sequence set forth in SEQ ID NOs: 2-10 or a homologous, orthologous or paralogous sequence thereof; (b) a nucleotide sequence having at least 80%, at least 85%, at least 90%, at least 92%, at least 94%, at least 95%, at least 96%, at least 97%, at least 98% or at least 99% identity to one of the nucleotide sequences set forth in SEQ ID NOs: 2-10, (c) a nucleotide sequence encoding for the amino acid sequence set forth in SEQ ID NOs: 11-19; (d) a nucleotide sequence encoding for an amino acid sequence having at least 80%, at least 85%, at least 90%, at least 92%, at least 94%, at least 95%, at least 96%, at least 97%, at least 98% or at least 99% identity to one of the sequences set forth in SEQ ID NOs: 11-19, or (e) a nucleotide sequence hybridizing with a nucleotide sequence complementary to the nucleotide sequence as defined in (a)-(d) under stringent conditions, wherein the nucleotide sequence comprises at least one mutation capable of conferring or increasing resistance to a pathogen in plant in which the nucleic acid molecule is expressed, wherein the pathogen is at least one of a fungal pathogen, an oomycete pathogen, a bacterial pathogen, a virus, a nematode pathogen, or an insect, preferably wherein the pathogen is a hemibiotrophic fungus, more preferably the pathogen is a hemibiotrophic fungus selected from the group consisting of: *Zymoseptoria tritici*, *Setosphaeria turcica*, *Fusarium* spp. *Fusarium graminearum*, *Colletotrichum* spp. such as *Colletotrichum graminicola*, *Magnaporthe grisea*, *Magnaporthe oryzae*, *Phytophthora infestans*, or preferably wherein the pathogen is a fungus selected from *Cercospora* spp., preferably *Cercospora beticola* or *Cercospora zeae-mayidis*.

In yet another aspect, there is provided a method of conferring or enhancing the pathogen resistance in a plant or of generating a plant having pathogen resistance or a plant cell, tissue, organ, seed, or plant material thereof, comprising the steps of: (i) providing one or more silencing construct(s), or one or more sequences encoding the same; (ii) modifying a plant cell, tissue, organ, plant, seed, or plant material by introducing the one or more silencing construct(s) or the sequence encoding the same of (i), into the genome of said plant cell, tissue, organ, plant, seed, or plant material; and (iii) obtaining the modified plant cell, tissue, organ, plant, seed or plant material, (iv) optionally, regenerating a plant from the plant cell, tissue, organ or plant material or growing a seed on a plant obtained in (iii), wherein the plant cell, tissue, organ, plant, seed or plant material obtained in (iii), the plant regenerated in (iv) or the seed grown in (iv) comprise the introduced one or more silencing construct(s) or the sequence encoding the same and thereby has pathogen resistance.

In another aspect, there is provided a method of conferring or enhancing the pathogen resistance in a plant or of generating a plant having pathogen resistance or a plant cell, tissue, organ, seed, or plant material thereof, comprising the steps of: (i) providing at least one site-directed DNA modifying enzyme, or a sequence encoding the same, and optionally at least one DNA repair template, wherein the at least one site-directed DNA modifying enzyme and optionally the at least one DNA repair template: (a) is/are directed or targeted to the nucleotide sequence encoding the CPL3 protein; or (b) is/are directed or targeted to regulatory sequence of at least one CPL3 protein encoding nucleotide sequence; (ii) introducing the at least one site-directed DNA modifying enzyme or a sequence encoding the same, and optionally the at least one DNA repair template into the plant cell, tissue, organ, plant, or plant material; (iii) mutating or modifying the nucleotide sequence encoding the CPL3 protein or the regulatory sequence thereof in the genome of the plant cell, tissue, organ, plant, or plant material and obtaining a mutant or modified population of plant cells, tissues, organs, plants, or plant materials; (iv) optionally: screening the population for a dominant negative mutation, thereby conferring or increasing pathogen resistance, or screening the population for a mutation or modification in the nucleotide sequence encoding the CPL3 protein or the regulatory sequence thereof; (v) identifying and thereby obtaining a plant cell, tissue, organ, plant, or plant material having pathogen resistance.

In another aspect, there is provided a method of conferring or enhancing the pathogen resistance in a plant or of generating a plant having pathogen resistance or a plant cell, tissue, organ, seed, or plant material thereof, comprising the steps of: (i) subjecting the plant cell, tissue, organ, plant, or plant material, preferably seeds of a plant, to an efficient amount of a mutagenic agent, preferably ethylmethane sulfonate, N-ethyl-N-nitrosourea, or radiation, (ii) obtaining a mutagenized population of plant cells, tissues, organs, plants, or plant materials, optionally by growing plants from the mutagenized population; (iii) screening the mutagenized population for pathogen resistance, optionally by isolating and analyzing genomic DNA from the plants having pathogen resistance; (iv) identifying and obtaining a modified plant cell, tissue, organ, plant, or plant material having pathogen resistance.

In yet another aspect, there is provided a method of conferring or enhancing the pathogen resistance in a plant or of generating a plant having pathogen resistance or a plant cell, tissue, organ, seed, or plant material thereof, comprising the steps of: (i) transforming at least one plant cell with at least one nucleic acid molecule as defined in the second aspect above; and (ii) regenerating and thus obtaining a plant cell, tissue, organ, plant, or plant material having pathogen resistance.

In a further aspect there is provided a method for identifying a plant having pathogen resistance or a plant cell, tissue, organ, seed, or plant material thereof, comprising the steps of: (i) isolating DNA from at least one cell of the plant or of tissue, organ, seed, or plant material thereof, and (ii) detecting at least one nucleic acid molecule as defined in the second aspect above, and optionally (iii) selecting a plant comprising at least one nucleic acid molecule as defined in the second aspect above based on the detection in step (ii), and optionally (iv) breeding progeny having pathogen resistance through crossing of the plant selected in step (iii) with another plant, preferably of the same species, and thereby introducing the at least one nucleic acid molecule detecting in step (ii) in to the genome of the progeny.

Another aspects provides the use of the nucleic acid molecule as defined in the second aspect above, or the use of a silencing construct as defined in the first aspect above, for the generation of a plant cell, tissue, organ, whole plant, or plant material having pathogen resistance, or for conferring or increasing pathogen resistance of in a plant, plant cell, tissue, organ, whole plant, or plant material.

DEFINITIONS

An "allele" or "allelic variant" as used herein refers to a variant form of a given gene. As most multicellular organisms have two sets of chromosomes; that is, they are diploid (or, if more chromosome sets are present, they are polyploidy), these chromosomes are referred to as homologous chromosomes. If both alleles at a gene (or locus) on the homologous chromosomes are the same, they and the organism are homozygous with respect to that gene (or locus). If the alleles are different, they and the organism are heterozygous with respect to that gene. Alleles can result in the same, or a different observable phenotype. The term "allele" thus refers to one or two or more nucleotide sequences at a specific locus in the genome. A first allele is on a chromosome, a second on a second chromosome at the same position. If the two alleles are different, they are heterozygous, and if they are the same, they are homozygous. Various alleles of a gene (gene alleles) differ in at least one SNP (single nucleotide polymorphism). Additionally, ploidy gives the number of complete sets of chromosomes in a cell, and hence the number of possible alleles. The generic term polyploid is used to describe cells with three or more chromosome sets. For example, about half of all known plant genera contain polyploid species, and about two third of all grasses are polyploid.

The term "anamorph" or "anamorphs" as used herein in the context of mycology refers to an asexual reproductive stage (morph), often mold-like of a fungus. When a single fungus produces multiple morphologically distinct anamorphs, these are called synanamorphs. The "teleomorph" form of the fungus represents the sexual reproductive stage (morph), typically a fruiting body. A "holomorph" means the whole fungus, i.e., including anamorphs and teleomorph.

The term "catalytically active fragment" or "functional fragment" as used herein referring to amino acid sequences denotes the core sequence derived from a given template amino acid sequence, or a nucleic acid sequence encoding the same, comprising all or part of the active site of the template sequence with the proviso that the resulting catalytically active fragment still possesses the activity characterizing the template sequence, for which the active site of the native enzyme or a variant thereof is responsible. Said modifications are suitable to generate less bulky amino acid sequences still having the same activity as a template sequence making the catalytically active fragment a more versatile or more stable tool being sterically less demanding. For amino acid sequences not representing enzymes, the term "functional fragment" can also imply that part or domain of the amino acid sequence involved in interaction with another molecule, and/or involved in any structural function within the cell.

"Complementary" or "complementarity" as used herein describes the relationship between two DNA, two RNA, or, regarding hybrid sequences according to the present invention, between an RNA and a DNA nucleic acid region. Defined by the nucleobases of the DNA or RNA, two nucleic acid regions can hybridize to each other in accordance with the lock-and-key model. To this end the principles of Watson-Crick base pairing have the basis adenine and thymine/uracil as well as guanine and cytosine, respectively, as complementary bases apply. Furthermore, also non-Watson-Crick pairing, like reverse-Watson-Crick, Hoogsteen, reverse-Hoogsteen and Wobble pairing are comprised by the term "complementary" as used herein as long as the respective base pairs can build hydrogen bonding to each other, i.e., two different nucleic acid strands can hybridize to each other based on said complementarity.

The term "construct", "recombinant construct" or expression construct, especially also "silencing construct", refers to a recombinant construct or expression construct and, as used herein, refers to a construct comprising, inter alia, plasmids or plasmid vectors, and may comprise an expression cassette, isolated single-stranded or double-stranded nucleic acid sequences, comprising DNA and/or RNA sequences, or amino acid sequences, viral vectors, including modified viruses, and a combination or a mixture thereof, for introduction or transformation, transfection or transduction into a target cell or plant, plant cell, tissue, organ or material according to the present disclosure.

The term "delivery construct" or "delivery vector" as used herein refers to any biological or chemical means used as a cargo for transporting a nucleic acid, comprising RNA and/or DNA, and/or an amino acid sequence of interest into a target cell, preferably a eukaryotic cell. The term delivery construct or vector as used herein thus refers to a means of transport to deliver a genetic or a recombinant construct according to the present disclosure into a target cell, tissue, organ or an organism. A vector can thus comprise nucleic acid sequences, optionally comprising sequences like regulatory sequences or localization sequences for delivery, either directly or indirectly, into a target cell of interest or into a plant target structure in the desired cellular compartment of a plant. A vector can also be used to introduce an amino acid sequence or a ribonucleo-molecular complex into a target cell or target structure. Usually, a vector as used herein can be a plasmid vector. Furthermore, a direct introduction of a construct or sequence or complex of interest can be conducted, e.g., by chemical means of transfection. The term "introduction" in this context shall imply both a direct and an indirect introduction. Direct introduction implies that the desired target cell or target structure containing a DNA target sequence to be modified according to the present disclosure is directly transformed or transduced or transfected into the specific target cell of interest, where the material delivered with the delivery vector will exert its effect. The term indirect introduction implies that the introduction is achieved into a structure, for example, cells of leaves or cells of organs or tissues, which do not themselves represent the actual target cell or structure of interest to be transformed, but those structures serve as basis for the systemic spread and transfer of the vector or construct to the actual target structure. In case the term vector is used in the context of transfecting amino acid sequences and/or nucleic sequences into a target cell the term vector implies suitable agents for peptide or protein transfection, like for example ionic lipid mixtures, cell penetrating peptides (CPPs), or particle bombardment. In the context of the introduction of nucleic acid material, the term vector cannot only imply plasmid vectors but also suitable carrier materials which can serve as basis for the introduction of nucleic acid and/or amino acid sequence delivery into a target cell of interest, for example by means of particle bombardment. Said carrier material comprises, inter alia, gold or tungsten particles. Viral vectors, as further detailed below, and bacterial vectors, like for example *Agrobacterium* spp., like for example *Agrobacterium tumefaciens* vectors can be used, e.g., binary and superbinary vectors. Finally, the term vector also implies suitable chemical transport agents for introducing linear nucleic acid sequences (single- or double-stranded), or amino sequences, or a combination thereof into a target cell combined with a physical introduction method, including polymeric or lipid-based delivery constructs. Suitable "delivery constructs" or "vectors" thus comprise biological means for delivering nucleotide and/or amino acid sequences into a target cell, including viral vectors, *Agrobacterium* spp., or chemical delivery constructs, including nanoparticles, e.g., mesoporous silica nanoparticles (MSNPs), cationic polymers, including PEI (polyethylenimine) polymer based approaches or polymers like DEAE-dextran, or non-covalent surface attachment of PEI to generate cationic surfaces, lipid or polymeric vesicles, or combinations thereof. Lipid or polymeric vesicles may be selected, for example, from lipids, liposomes, lipid encapsulation systems, nanoparticles, small nucleic acid-lipid particle formulations, polymers, and polymersomes.

The term "derivative" or "descendant" or "progeny" as used herein according to the present disclosure relates to the descendants of such a cell or material which result from natural reproductive propagation including sexual and asexual propagation. It is well known to the person having skill in the art that said propagation can lead to the introduction of mutations into the genome of an organism resulting from natural phenomena which results in a descendant or progeny, which is genomically different to the parental organism or cell, however, still belongs to the same genus/species and possesses mostly the same characteristics as the parental recombinant host cell. Such derivatives or descendants or progeny resulting from natural phenomena during reproduction or regeneration are thus comprised by the term of the present disclosure.

Furthermore, the terms "derived", "derived from", or "derivative" as used herein in the context of an isolated biological sequence (nucleic acid or amino acid) or a molecule or a complex—rather than referring to a whole cell or organism—may imply that the respective sequence is based on a reference sequence, for example from the sequence listing, or a database accession number, or the respective scaffold structure, i.e., originating from said sequence, whereas the reference sequence can comprise more sequences, e.g., the whole genome or a full polyprotein encoding sequence, of a virus, whereas the sequence "derived from" the native sequence, i.e. a sequence as naturally occurring in a cell or organism, may only comprise one isolated fragment thereof, or a coherent fragment thereof. In this context, a cDNA molecule or a RNA can be said to be "derived from" a DNA sequence serving as molecular template. The skilled person can thus easily define a sequence "derived from" a reference sequence, which will, by sequence alignment on DNA or amino acid level, have a high identity to the respective reference sequence and which will have coherent stretches of DNA/amino acids in common with the respective reference sequence (>75% query identity for a given length of the molecule aligned provided that the derived sequence is the query and the reference sequence represents the subject during a sequence alignment). The skilled person can thus clone the respective sequences based on the disclosure provided herein by means of polymerase chain reactions and the like into a suitable vector system of interest, or use a sequence as vector scaffold. The term "derived from" is thus no arbitrary sequence, but a sequence corresponding to a reference sequence it is derived from, whereas certain differences, e.g., certain mutations naturally occurring during replication of a recombinant construct within a host cell, cannot be excluded and are thus comprised by the term "derived from". Furthermore, several sequence stretches from a parent sequence can be concatenated in a sequence derived from the parent. The different stretches will have high or even 100% identity to the parent sequence.

The term an "endogenous" in the context of nucleic acid and/or amino acid sequences refers to the nucleic acid and/or amino acid as found and/or expressed in a plant genome in its natural form as DNA/RNA or protein. As it is known to the skilled person, several variants, e.g., allelic variants, of a gene nucleic acid sequence may exist in a given population of plants.

A "fungus" or "fungal pathogen" as used herein means any plant pathogenic fungus in any developmental stage, including spores, or any part of such a fungus, which can interact with a plant or plant part or cell to induce a response in said plant or plant part or cell.

As used herein, "fusion", e.g., in the context of a base editor or a CRISPR/Cas system, can refer to a protein and/or nucleic acid comprising one or more non-native sequences (e.g., moieties). A fusion can be at the N-terminal or C-terminal end of the modified protein, or both, or within the molecule as separate domain. For nucleic acid molecules, the fusion molecule can be attached at the 5' or 3' end, or at any suitable position in between. A fusion can be a transcriptional and/or translational fusion. A fusion can comprise one or more of the same non-native sequences. A fusion can comprise one 10 or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the site-specific effector or base editor (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify. A fusion can be a small molecule such as biotin or a dye such as alexa fluor dyes, Cyanine3 dye, Cyanine5 dye. The fusion can provide for increased or decreased stability. In some embodiments, a fusion can comprise a detectable label, including a moiety that can provide a detectable signal. Suitable detectable labels and/or moieties that can provide a detectable signal can include, but are not limited to, an enzyme, a radioisotope, a member of a specific binding pair; a fluorophore; a fluorescent reporter or fluorescent protein; a quantum dot; and the like. A fusion can comprise a member of a FRET pair, or a fluorophore/quantum dot donor/acceptor pair. A fusion can comprise an enzyme. Suitable enzymes can include, but are not limited to, horse radish peroxidase, luciferase, beta-galactosidase, and the like. A fusion can comprise a fluorescent protein. Suitable fluorescent proteins can include, but are not limited to, a green fluorescent protein (GFP), (e.g., a GFP from *Aequoria victoria*, fluorescent proteins from *Anguilla japonica*, or a mutant or derivative thereof), a red fluorescent protein, a yellow fluorescent protein, a yellow-green fluorescent protein (e.g., mNeonGreen derived from a tetrameric fluorescent protein from the cephalochordate *Branchiostoma lanceolatum*) any of a variety of fluorescent and colored proteins. A fusion can comprise a nanoparticle. Suitable nanoparticles can include fluorescent or luminescent nanoparticles, and magnetic nanoparticles, or nanodiamonds, optionally linked to a nanoparticle. Any optical or magnetic property or characteristic of the nanoparticle(s) can be detected. A fusion can comprise a helicase, a nuclease (e.g., FokI), an endonuclease, an exonuclease (e.g., a 5' exonuclease and/or 3' exonuclease), a ligase, a nickase, a nuclease-helicase (e.g., Cas3), a DNA methyltransferase (e.g., Dam), or DNA demethylase, a histone methyltransferase, a histone demethylase, an acetylase (including for example and not limitation, a histone acetylase), a deacetylase (including for example and not limitation, a histone deacetylase), a phosphatase, a kinase, a transcription (co-) activator, a transcription (co-) factor, an RNA polymerase subunit, a transcription repressor, a DNA binding protein, a DNA structuring protein, a long non-coding RNA, a DNA repair protein (e.g., a protein involved in repair of either single- and/or double-stranded breaks, e.g., proteins involved in base excision repair, nucleotide excision repair, mismatch repair, NHEJ, HR, microhomology-mediated end joining (MMEJ), and/or alternative non-homologous end-joining (ANHEJ), such as for example and not limitation, HR regulators and HR complex assembly signals), a marker protein, a reporter protein, a fluorescent protein, a ligand binding protein (e.g., mCherry or a heavy metal binding protein), a signal peptide (e.g., Tat-signal sequence), a targeting protein or peptide, a subcellular localization sequence (e.g., nuclear localization sequence, a chloroplast localization sequence), and/or an antibody epitope, or any combination thereof.

The term "modification" or "genetic modification" is used in a broad sense herein and means any modification of a nucleic acid sequence or an amino acid sequence, a target cell, tissue, organ or organism, which is accomplished by human intervention, either directly or indirectly, to influence the endogenous genetic material or the transcriptome or the proteome of a target cell, tissue, organ or organism to modify it in a purposive way so that it differs from its state as found without human intervention. The human intervention can either take place in vitro or in vivo/in planta, or also both. Further modifications can be included, for example, one or more point mutation(s), e.g., for targeted protein engineering or for codon optimization, deletion(s), and one or more insertion(s) or deletion(s) of at least one nucleic acid or amino acid molecule (including also homologous recombination), modification of a nucleic acid or an amino acid sequence, or a combination thereof. The terms shall also comprise a nucleic acid molecule or an amino acid molecule or a host cell or an organism, including a plant or a plant material thereof which is/are similar to a comparable sequence, organism or material as occurring in nature, but which have been constructed by at least one step of purposive manipulation. The modification can be effected in a transient way, or in a stable, inheritable manner.

The term "genome" refers to the entire complement of genetic material, including genes and non-coding sequences, the nuclear and optionally present further genomes, e.g., the genome of organelles, that is present in each cell of an organism, or organelle, and/or a complete set of chromosomes inherited as a (haploid) unit from one parent, or that encodes a virus. The genome thus also defines the "genotype" being the part of the genetic makeup of a given cell, and therefore of an organism or individual, which determines a specific characteristic (phenotype) of that cell/organism/individual.

The terms "genome editing", "genome engineering", or "gene editing/engineering" are used interchangeably herein and refer to strategies and techniques for the targeted, specific modification of any genetic information or genome of a living organism. As such, the terms comprise gene editing, but also the editing of regions other than gene encoding regions of a genome. It further comprises the editing or engineering of the nuclear (if present) as well as other genetic information (e.g., the RNA transcriptome) of a cell. Furthermore, the terms "genome editing" and "genome engineering" also comprise an epigenetic editing or engineering, i.e., the targeted modification of, e.g., methylation, histone modification or of non-coding RNAs possibly causing heritable changes in gene expression.

"Germplasm", as used herein, is a term used to describe the genetic resources, or more precisely the DNA of an organism and collections of that material. In breeding technology, the term germplasm is used to indicate the collection of genetic material from which a new plant or plant variety can be created.

The terms "guide RNA", "gRNA" or "single guide RNA" or "sgRNA" are used interchangeably herein and either refer to a synthetic fusion of a CRISPR RNA (crRNA) and a trans-activating crRNA (tracrRNA), or the term refers to a single RNA molecule consisting only of a crRNA and/or a tracrRNA, or the term refers to a gRNA individually comprising a crRNA or a tracrRNA moiety. The tracr and the crRNA moiety thus do not necessarily have to be present on one covalently attached RNA molecule, yet they can also be comprised by two individual RNA molecules, which can associate or can be associated by non-covalent or covalent interaction to provide a gRNA according to the present disclosure. The terms "gDNA" or "sgDNA" or "guide DNA" are used interchangeably herein and either refer to a nucleic acid molecule interacting with an Argonaute nuclease. Both, the gRNAs and gDNAs as disclosed herein are termed "guiding nucleic acids" or "guide nucleic acids" due to their capacity to interacting with a site-specific nuclease and to assist in targeting said site-specific nuclease to a genomic target site.

The term "hemibiotroph" or "hembibiotrophic" refers to an organism that is in part (hemi) parasitic in living tissue for some time and thus relies on an initial biotrophic phase. This phase is followed by a necrotrophic phase, i.e., the organism can induce host cell death and/or can persist in dead tissue without the need for a living host or host cell.

The term "hybridization" as used herein refers to the pairing of complementary nucleic acids, i.e., DNA and/or RNA, using any process by which a strand of nucleic acid joins with a complementary strand through base pairing to form a hybridized complex. Hybridization and the strength of hybridization (i.e., the strength of the association between the nucleic acids) is impacted by such factors as the degree and length of complementarity between the nucleic acids, stringency of the conditions involved, the Tm of the formed hybrid, and the G:C ratio within the nucleic acids. The term hybridized complex refers to a complex formed between two nucleic acid sequences by virtue of the formation of hydrogen bounds between complementary G and C bases and between complementary A and T/U bases. A hybridized complex or a corresponding hybrid construct can be formed between two DNA nucleic acid molecules, between two RNA nucleic acid molecules or between a DNA and an RNA nucleic acid molecule. For all constellations, the nucleic acid molecules can be naturally occurring nucleic acid molecules generated in vitro or in vivo and/or artificial or synthetic nucleic acid molecules. Hybridization as detailed above, e.g., Watson-Crick base pairs, which can form between DNA, RNA and DNA/RNA sequences, are dictated by a specific hydrogen bonding pattern, which thus represents a non-covalent attachment form according to the present invention. In the context of hybridization, the term "stringent (hybridization) conditions" should be understood to mean those conditions under which a hybridization takes place primarily only between homologous nucleic acid molecules. The term "hybridization conditions" in this respect refers not only to the actual conditions prevailing during actual agglomeration of the nucleic acids, but also to the conditions prevailing during the subsequent washing steps. Examples of stringent hybridization conditions are conditions under which primarily only those nucleic acid molecules that have at least 70%, preferably at least 75%, at least 80%, at least 85%, at least 90% or at least 95% sequence identity undergo hybridization. Stringent hybridization conditions are, for example: 4×SSC at 65° C. and subsequent multiple washes in 0.1×SSC at 65° C. for approximately 1 hour. The term "stringent hybridization conditions" as used herein may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization takes place under stringent conditions.

As used herein, the term "mutation" is used to refer to a deletion, insertion, addition, substitution, edit, strand break, and/or introduction of an adduct in the context of nucleic acid manipulation in vivo or in vitro. A deletion is defined as a change in a nucleic acid sequence in which one or more nucleotides is absent. An insertion or addition is that change in a nucleic acid sequence which has resulted in the addition of one or more nucleotides. A "substitution" or "edit" results from the replacement of one or more nucleotides by a molecule which is a different molecule from the replaced one or more nucleotides. For example, a nucleic acid may be replaced by a different nucleic acid as exemplified by replacement of a thymine by a cytosine, adenine, guanine, or uridine. Pyrimidine to pyrimidine (e.g., C to T or T to C nucleotide substitutions) or purine to purine (e.g., G to A or A to G nucleotide substitutions) are termed transitions, whereas pyrimidine to purine or purine to pyrimidine (e.g., G to T or G to C or A to T or A to C) are termed transversions. Alternatively, a nucleic acid may be replaced by a modified nucleic acid as exemplified by replacement of a thymine by thymine glycol. Mutations may result in a mismatch. The term mismatch refers to a non-covalent interaction between two nucleic acids, each nucleic acid residing on a different nucleotide sequence or nucleic acid molecule, which does not follow the base-pairing rules. For example, for the partially complementary sequences 5'-AGT-3' and 5'-AAT-3', a G-A mismatch (a transition) is present. A mutation may have a dominant negative effect, i.e., the resulting gene product, even when present in the heterozygous state, can effect certain cellular functions despite the presence of the wild-type copy, for example, in case the product of the dominant negative mutation can still interact with the same elements as the product encoded by the wild-type gene, but block some aspect of its function.

The terms "nucleotide" and "nucleic acid" with reference to a sequence or a molecule are used interchangeably herein and refer to a single- or double-stranded DNA or RNA of natural or synthetic origin. The term nucleotide sequence is thus used for any DNA or RNA sequence independent of its length, so that the term comprises any nucleotide sequence comprising at least one nucleotide, but also any kind of larger oligonucleotide or polynucleotide. The term(s) thus refer to natural and/or synthetic deoxyribonucleic acids (DNA) and/or ribonucleic acid (RNA) sequences, which can optionally comprise synthetic nucleic acid analoga. A nucleic acid according to the present disclosure can optionally be codon optimized. "Codon optimization" implies that the codon usage of a DNA or RNA is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism. As used herein, "nucleotide" can thus generally refer to a base-sugar-phosphate combination. A nucleotide can comprise a synthetic nucleotide. A nucleotide can comprise a synthetic nucleotide analog. Nucleotides can be monomeric units of a nucleic acid sequence (e.g., deoxyribonucleic acid (DNA) and ribonucleic acid (RNA)).

The term "ortholog" or "orthologues" defines a pair of genes that derives from the same ancestral gene by speciation in the course of evolution. Normally, orthologs retain the same function in the course of evolution.

The term "paralog" or "paralogues" defines a pair of genes that derives from the same ancestral gene by duplication within a genome, wherein the genes in a given cell reside at different locations within the same genome.

The term "particle bombardment" as used herein, also named "biolistic transfection" or "microparticle-mediated gene transfer", refers to a physical delivery method for transferring a coated microparticle or nanoparticle comprising a nucleic acid or a genetic construct of interest into a target cell or tissue. The micro or nanoparticle functions as projectile and is fired on the target structure of interest under high pressure using a suitable device, often called gene-gun. The transformation via particle bombardment uses a microprojectile of metal covered with the gene of interest, which is then shot onto the target cells using an equipment known as "gene gun" at high velocity fast enough (1500 km/h) to penetrate the cell wall of a target tissue, but not harsh enough to cause cell death. For protoplasts, which have their cell wall entirely removed, the conditions are different logically.

The precipitated nucleic acid or the genetic construct on the at least one microprojectile is released into the cell after bombardment, and integrated into the genome. The acceleration of microprojectiles is accomplished by a high voltage electrical discharge or compressed gas (helium). Concerning the metal particles used it is mandatory that they are non-toxic, non-reactive, and that they have a lower diameter than the target cell. The most commonly used are gold or tungsten. There is plenty of information publicly available from the manufacturers and providers of gene-guns and associated system concerning their general use.

A "pathogen" as used herein refers to an organism or virus which can infect a plant, or which can cause a disease in a plant, or which can harm a plant. Pathogens showing at least one intracellular or biotrophic phase which can infect a plant, or which can cause a disease in a plant, include fungi, oomycetes, bacteria, viruses, viroids, virus-like organisms, phytoplasmas, protozoa, nematodes and parasitic plants. Plant parasites can cause damage by feeding on a plant and can be selected from ectoparasites like insects, comprising aphids and other sap-sucking insect, mites, and vertebrates. Further included are, for example, necrotrophic fungi secreting toxins and enzymes that kill host cells and then take up nutrients released from the dead cells or tissue.

The term "plant" as used herein is to be construed broadly and refers to a whole plant organism, a plant organ, differentiated and undifferentiated plant tissues, plant cells, seeds, and derivatives and progeny thereof. "Plant cells" include without limitation, for example, cells from seeds, from mature and immature embryos, meristematic tissues, seedlings, callus tissues in different differentiation states, leaves, flowers, roots, shoots, gametophytes, grains, kernels, sporophytes, pollen and microspores, protoplasts, macroalgae and microalgae. The different plant cells can either be haploid, diploid or multiploid. The term "plant organ" refers to plant tissue or a group of tissues that constitute a morphologically and functionally distinct part of a plant. Typically, the term "grain" is used to describe the mature kernel produced by a plant grower for purposes other than growing or reproducing the species, and "seed" means the mature kernel used for growing or reproducing the species. For the purposes of the present invention, "grain", "seed", and "kernel", will be used interchangeably.

A "plant material" as used herein refers to any material which can be obtained from a plant during any developmental stage. The plant material can be obtained either in planta or from an in vitro culture of the plant or a plant tissue or organ thereof. The term thus comprises plant cells, tissues and organs as well as developed plant structures as well as sub-cellular components like nucleic acids, polypeptides and all chemical plant substances or metabolites which can be found within a plant cell or compartment and/or which can be produced by the plant, or which can be obtained from an extract of any plant cell, tissue or a plant in any developmental stage. The term also comprises a derivative of the plant material, e.g., a protoplast, derived from at least one plant cell comprised by the plant material. The term therefore also comprises meristematic cells or a meristematic tissue of a plant.

"Progeny" comprises any subsequent generation of a plant, plant cell, plant tissue, or plant organ.

The terms "protein", "amino acid" or "polypeptide" are used interchangeably herein and refer to an amino acid sequence having a catalytic enzymatic function or a structural or a functional effect. The term "amino acid" or "amino acid sequence" or "amino acid molecule" comprises any natural or chemically synthesized protein, peptide, polypeptide and enzyme or a modified protein, peptide, polypeptide and enzyme, wherein the term "modified" comprises any chemical or enzymatic modification of the protein, peptide, polypeptide and enzyme, including truncations of a wild-type sequence to a shorter, yet still active portion. In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & SJ. Higgins eds. (1985); *Transcription and Translation* (B. D. Hames & S. J. Higgins, eds. (1984); *Animal Cell Culture* (RI. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

The term "regulatory region" as used herein refers to a nucleic acid sequence, which can direct and/or influence the transcription and/or translation and/or modification of a nucleic acid sequence of interest. A regulatory sequence may comprise at least one of a core promoter sequence, a proximal promoter sequence, a cis regulatory sequence, a trans regulatory sequence, a locus control sequence, an insulator sequence, a silencer sequence, an enhancer sequence, a terminator sequence, and/or any combination thereof. In addition to a nucleic acid sequence "regulatory sequence" or "regulatory region", there may be "regulatory domains" or "regulatory proteins/enzymes". These amino acid sequences regulate, for example, transcription, RNA capping, splicing, polyadenylation, chromatin structure, signaling events, post-translational modifications and the like by (i) binding to, or (ii) by catalyzing a relevant reaction, e.g., by (i) blocking signaling by binding to a signaling domain, or regulating transcription as transcription factor acting on a nucleic acid sequence in trans, or (ii) by (de)phosphorylation events, e.g., as it is the case for many kinases.

The terms "site-directed/specific DNA modifying enzyme", "site-specific effector", or "site-specific nuclease" are used interchangeably herein and refer to a protein or a functional fragment thereof which is able to introduced a modification such as a double-stranded DNA break (DSB) or single-strand DNA break at a target site of a genomic sequence in a site-specific manner, either alone, or in combination with further molecules in a molecular complex. A "base editor" or "base editor complex" comprises at least one site-directed/specific DNA modifying enzyme which is able to induce a targeted base exchange at a target site of a genomic sequence.

The term "TILLING" as used herein is an abbreviation for "Targeting Induced Local Lesions in Genomes" and describes a well-known reverse genetics technique originally designed to detect unknown SNPs (single nucleotide polymorphisms) in genes of interest using an enzymatic digestion and is widely employed in plant and animal genomics. The technique allows for the high-throughput identification of an allelic series of mutants with a range of modified functions for a particular gene. TILLING combines mutagenesis (e.g., chemical or via UV-light) with a sensitive DNA screening-technique that identifies single base mutations.

The terms "transgene" or "transgenic" as used herein refer to at least one nucleic acid sequence that is taken from the genome of one organism, or produced synthetically, and which is then introduced into a host cell or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (comprising at least one of DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation and thus inheritance of the respective at least one molecule introduced into the genome of a cell.

The term "transient introduction" as used herein thus refers to the transient introduction of at least one nucleic acid and/or amino acid sequence according to the present disclosure, preferably incorporated into a delivery vector or into a recombinant construct, with or without the help of a delivery vector, into a target structure, for example, a plant cell, wherein the at least one nucleic acid sequence is introduced under suitable reaction conditions so that no integration of the at least one nucleic acid sequence into the endogenous nucleic acid material of a target structure, the genome as a whole, occurs, so that the at least one nucleic acid sequence will not be integrated into the endogenous DNA of the target cell. As a consequence, in the case of transient introduction, the introduced genetic construct will not be inherited to a progeny of the target structure, for example a prokaryotic, an animal or a plant cell. The at least one nucleic acid and/or amino acid sequence or the products resulting from transcription, translation, processing, post-translational modifications or complex building thereof are only present temporarily, i.e., in a transient way, in constitutive or inducible form, and thus can only be active in the target cell for exerting their effect for a limited time. Therefore, the at least one sequence or effector introduced via transient introduction will not be heritable to the progeny of a cell. The effect mediated by at least one sequence or effector introduced in a transient way can, however, potentially be inherited to the progeny of the target cell.

A "variant" in the context of a nucleic acid or amino acid sequence protein means a nucleic acid or amino acid sequence derived from the native nucleic acid or amino acid sequence, or another starting sequence, by deletion (so-called truncation) or addition of one or more sequences to the 5'/N-terminal and/or 3'/C-terminal end of the native nucleic acid or amino acid sequence; deletion or addition of one or more nucleic acid or amino acid sequence at one or more sites in the native nucleic acid or amino acid sequence; or substitution of one or more nucleic acid or amino acid sequence at one or more sites in the native protein. Variant proteins encompassed by the present invention are biologically active, that is they continue to possess all or some of the activity of the native proteins of the invention as described herein. Such variants may result from, for example, genetic polymorphism or from human manipulation.

Whenever the present disclosure relates to the percentage of the homology or identity of nucleic acid or amino acid sequences these values define those as obtained by using the EMBOSS Water Pairwise Sequence Alignments (nucleotide) programme (www.ebi.ac.uk/Tools/psa/emboss water/nucleotide) nucleic acids or the EMBOSS Water Pairwise Sequence Alignments (protein) programme (www.ebi.ac.uk/Tools/psa/emboss water/) for amino acid sequences, preferably over the entire length of the sequence, i.e., any percentage value provided means the % homology or % identity as measured over the whole length of a subject or starting sequence in comparison to an identical or variant further sequence. Those tools provided by the European Molecular Biology Laboratory (EMBL) European Bioinformatics Institute (EBI) for local sequence alignments use a modified Smith-Waterman algorithm (see www.ebi.ac.uk/Tools/psa/ and Smith, T. F. & Waterman, M. S. "Identification of common molecular subsequences" Journal of Molecular Biology, 1981 147 (1):195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5. Furthermore, bioinformatics tools for multiple sequence alignments for nucleic acid and amino acid sequences are readily available to the skilled person and can, for example, be obtained from EMBL/EBI, including Clustal Omega, Kalign, MAFFT, MUSCLE, MView, T-Coffee, or WebPRANK.

6 and 16) resulted in reduced pycnidia and spore formation of *Zyoseptoria tritici* infected wheat leaved from cultivar Taifun. Pycnidia: n=10 plants with 2 analyzed leaves of each plant. Spores: spores of 5 leaves were washed and counted (n=8). [1]: numbers with different capitals are statistically different according to ANOVA.

Figure 1A:
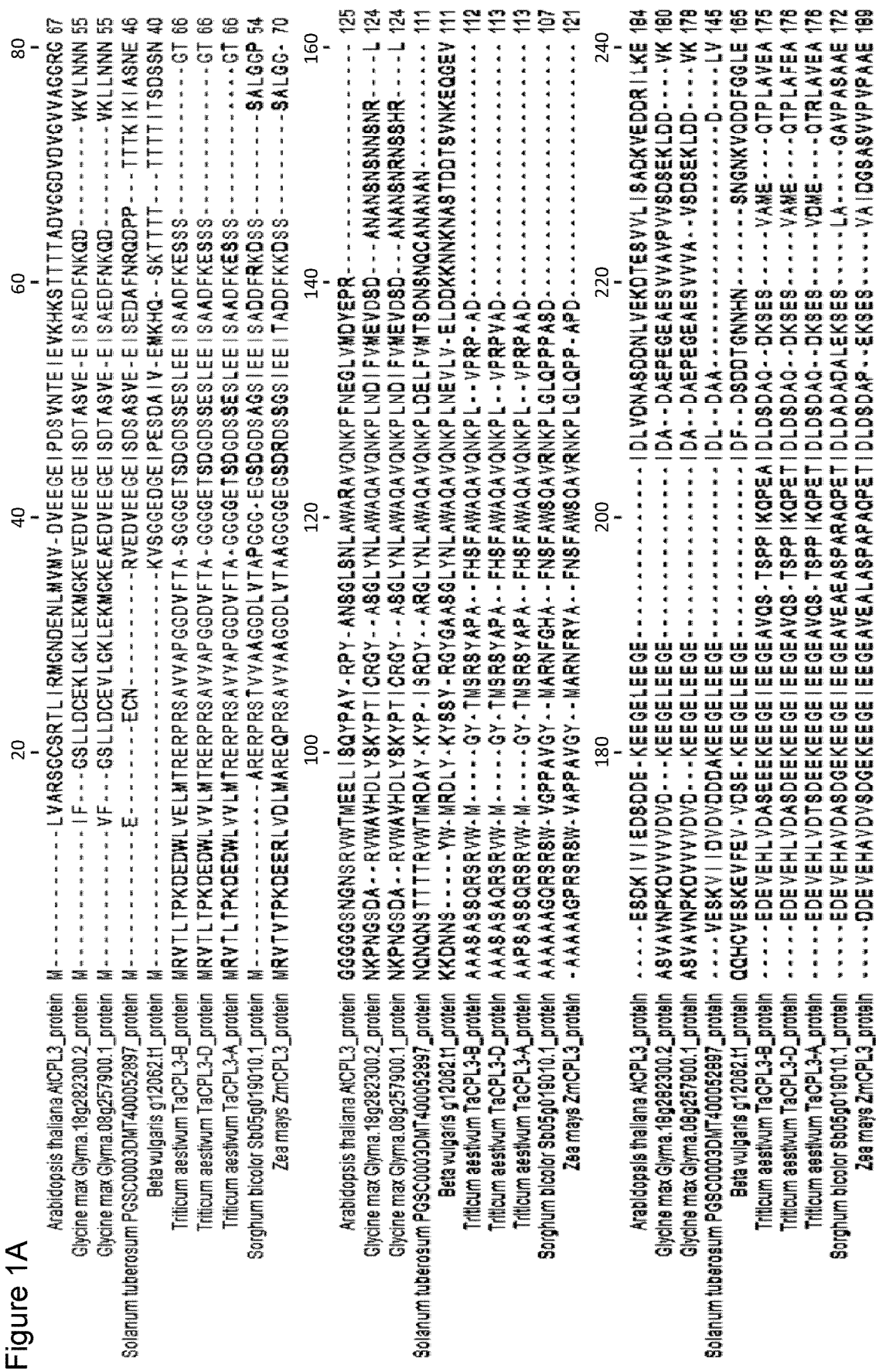
FIG. 1 shows identities between the different protein sequences (SEQ ID NOs: 11 to 19) of the CPL3 genes and comparison to the *Arabidopsis* AtCPL3 protein sequence (reference sequence: SEQ ID NO: 20). A: Sequence Alignments of amino acid sequences encoded by the CPL3 genes of six different crops compared to the *Arabidopsis thaliana* reference sequence; B: shows percent identities determined from the alignment. As evident when performing a sequence alignment of the respective protein sequences, said sequences significantly vary in the different plants (*Arabidopsis thaliana, Glycine max, Solanum tuberosum, Triticum aestivum, Sorghum bicolor, Beta vulgaris* and *Zea mays*, respectively), i.e., sequence identities of between 36% and 45% in comparison to the *Arabidopsis* reference sequence were observed.
Figure 1A:
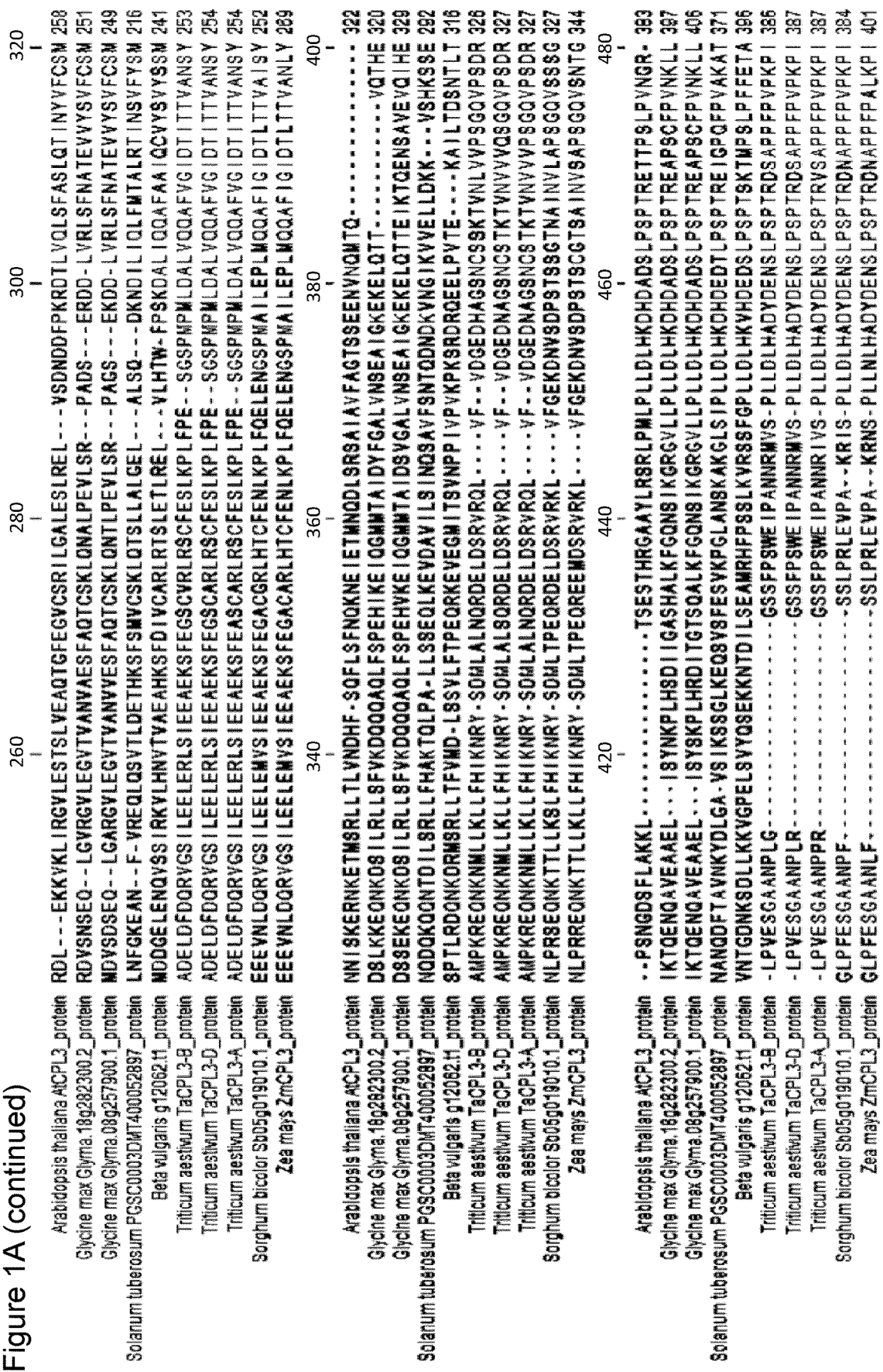
Figure 1A:
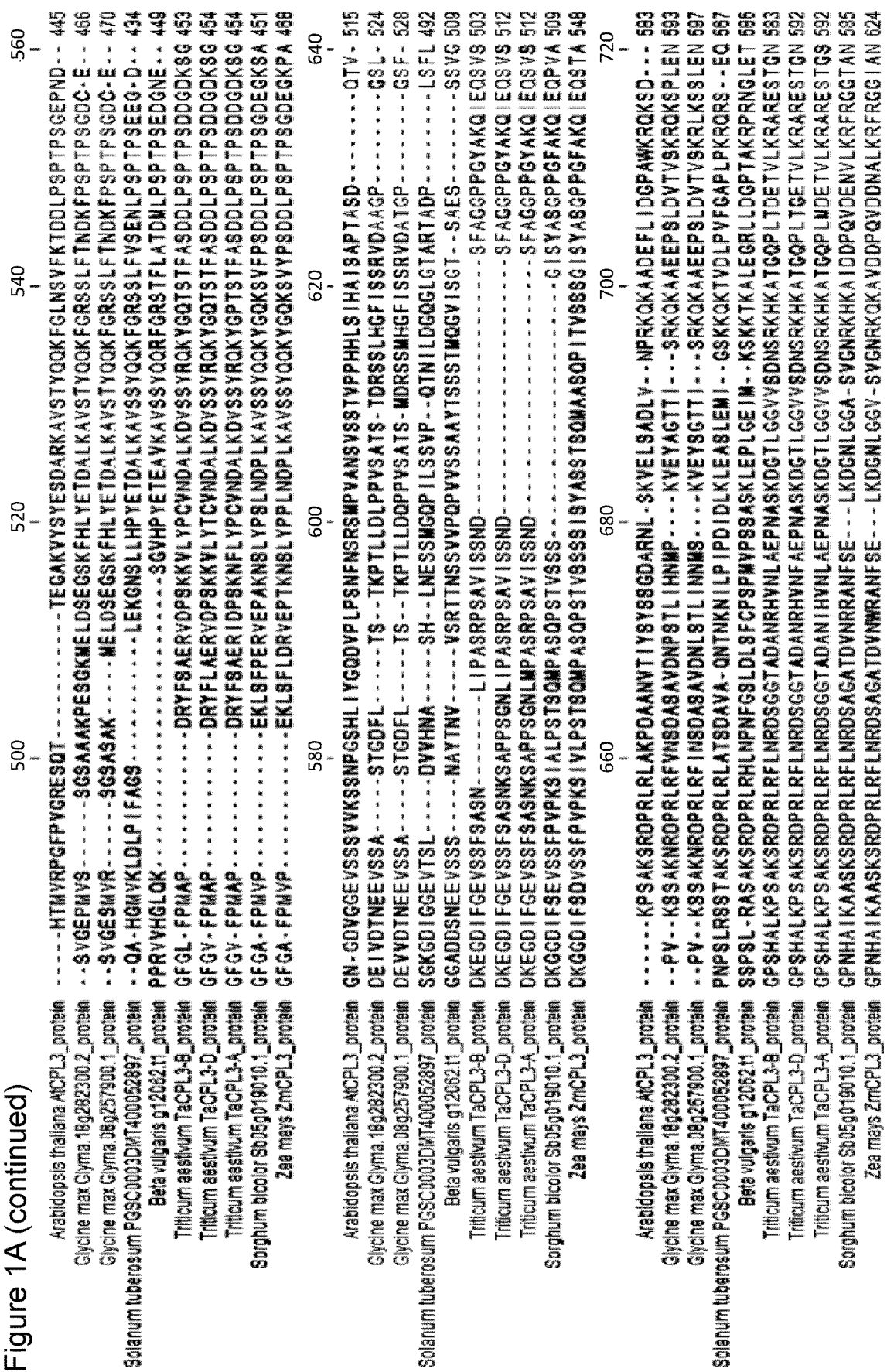
Figure 1A:
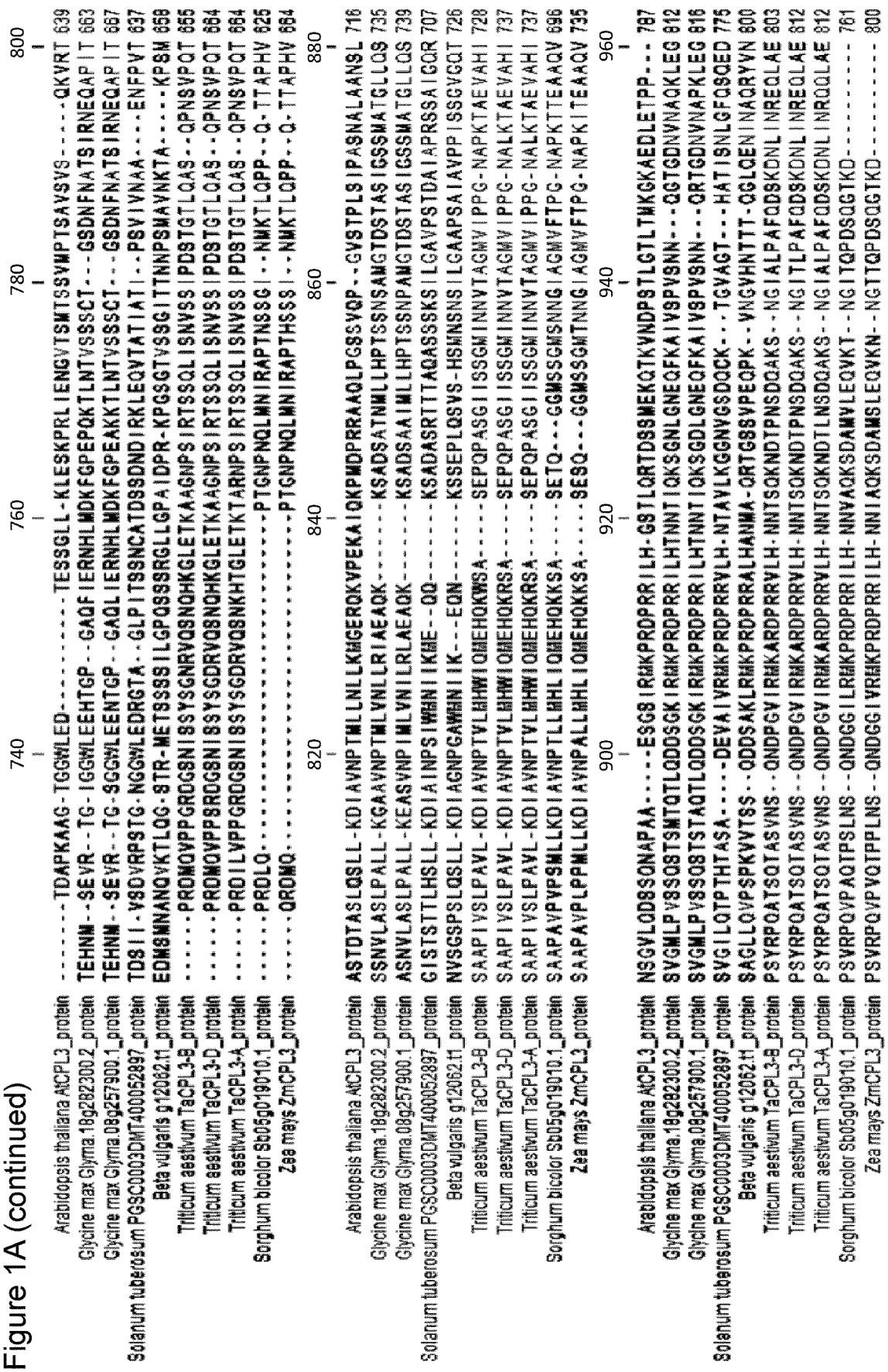
Figure 1A:
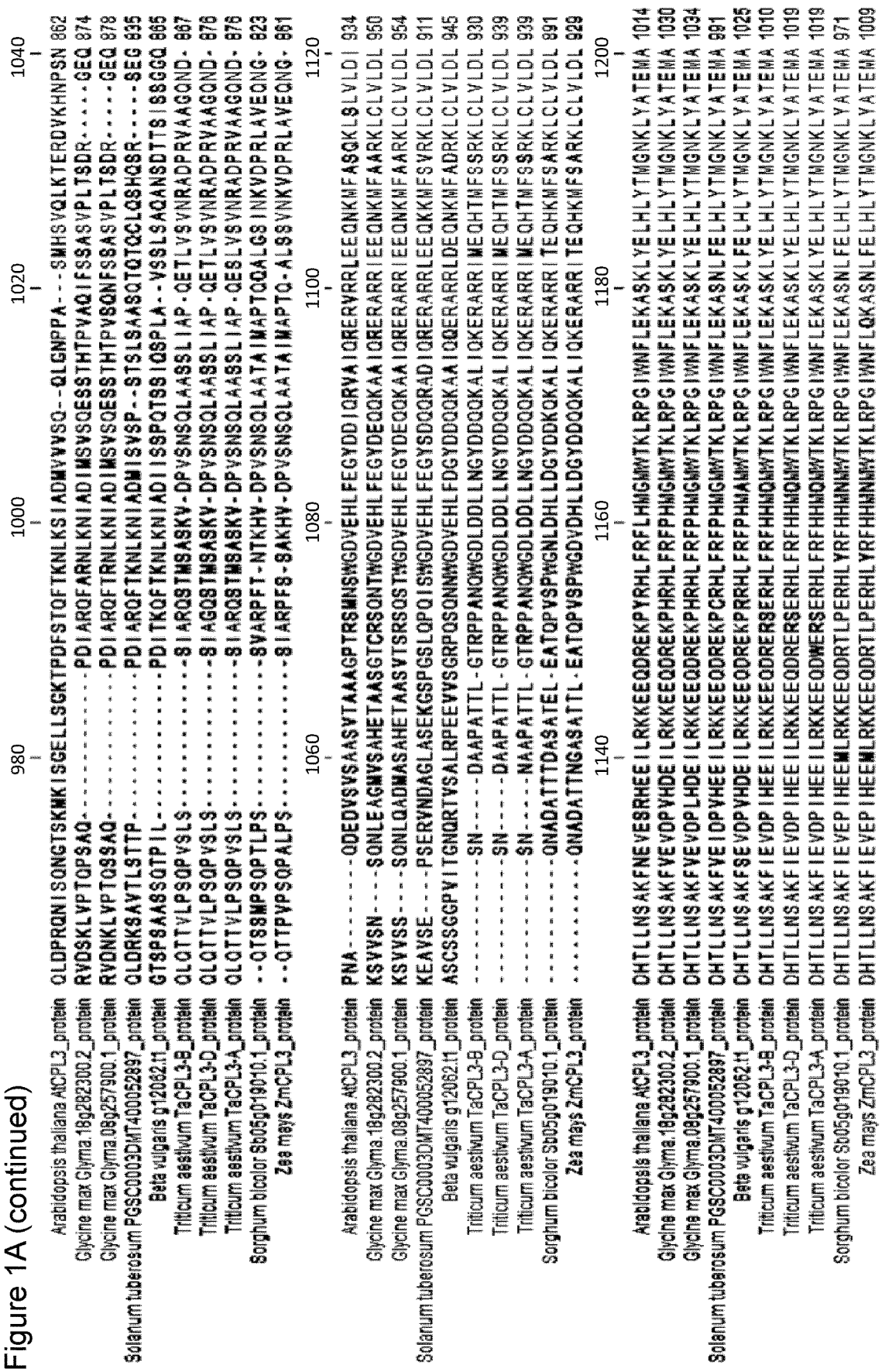
Figure 1A:
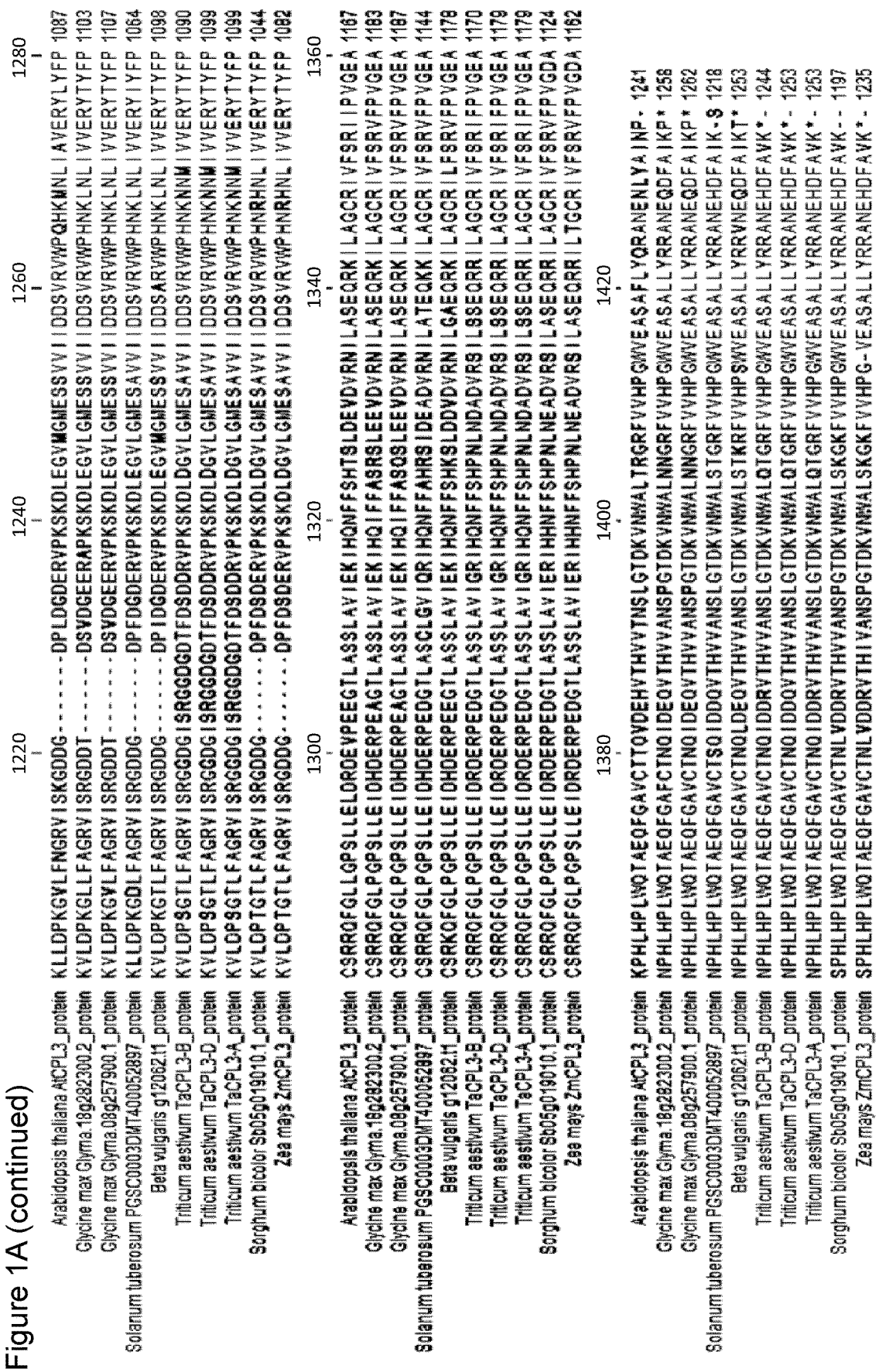
Figure 2A:
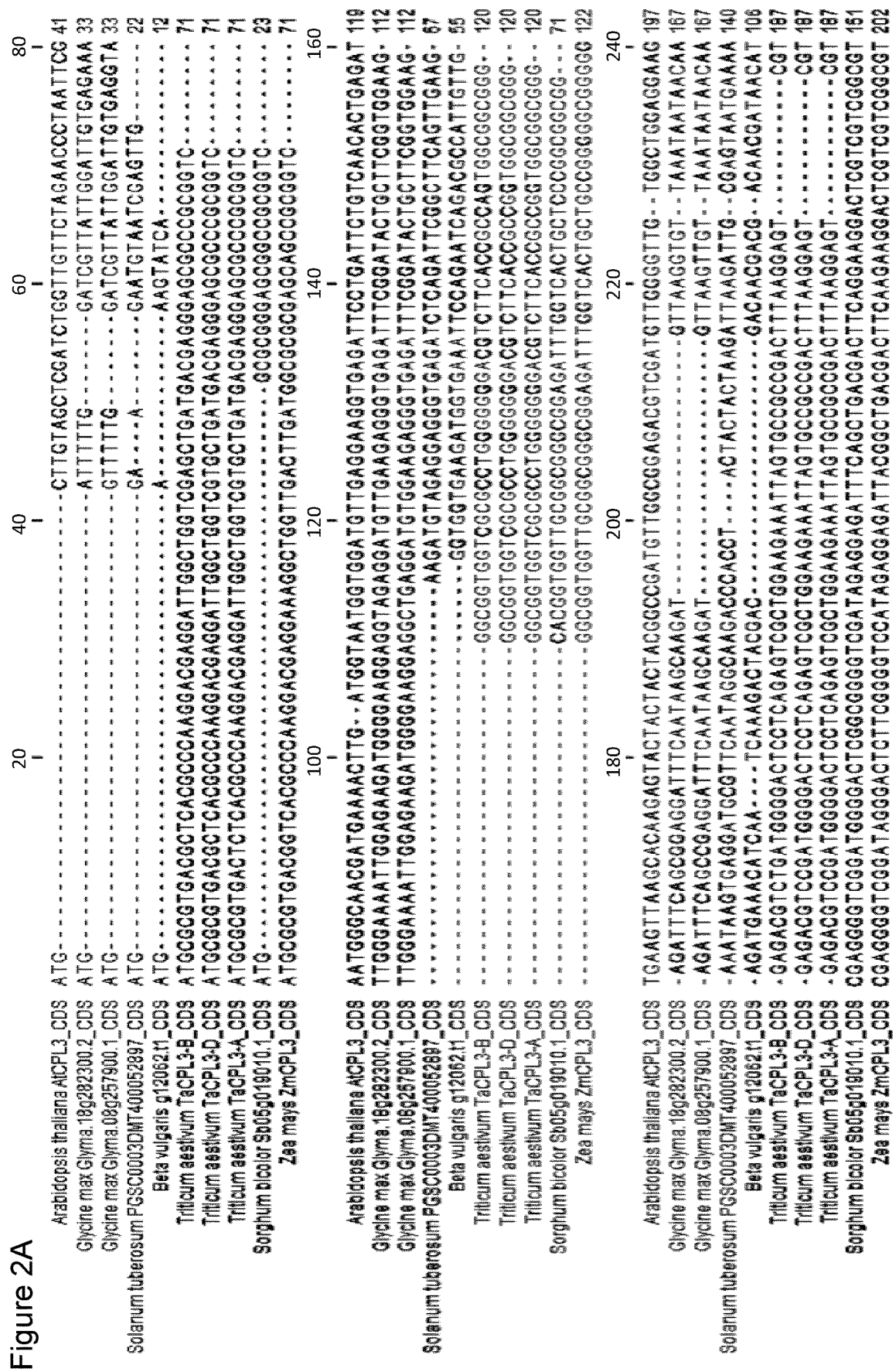
FIG. 2 shows identities between the different coding sequences of the CPL3 genes (SEQ ID NOs: 2 to 10) in comparison to the *Arabidopsis* AtCPL3 coding sequence as reference sequence (reference sequence: SEQ ID NO: 1). A: Sequence Alignments of coding sequences of the CPL3 genes of six different crops compared to the *Arabidopsis thaliana* reference sequence; B: shows percent identities determined from the alignment. As evident when performing a sequence alignment of the respective gene sequences, said sequences significantly vary in the different plants (*Arabidopsis thaliana, Glycine max, Solanum tuberosum, Triticum aestivum, Sorghum bicolor, Beta vulgaris* and *Zea mays*, respectively), i.e., sequence identities of between 44% and 53% in comparison to the *Arabidopsis* reference sequence were observed.
Figure 2A:
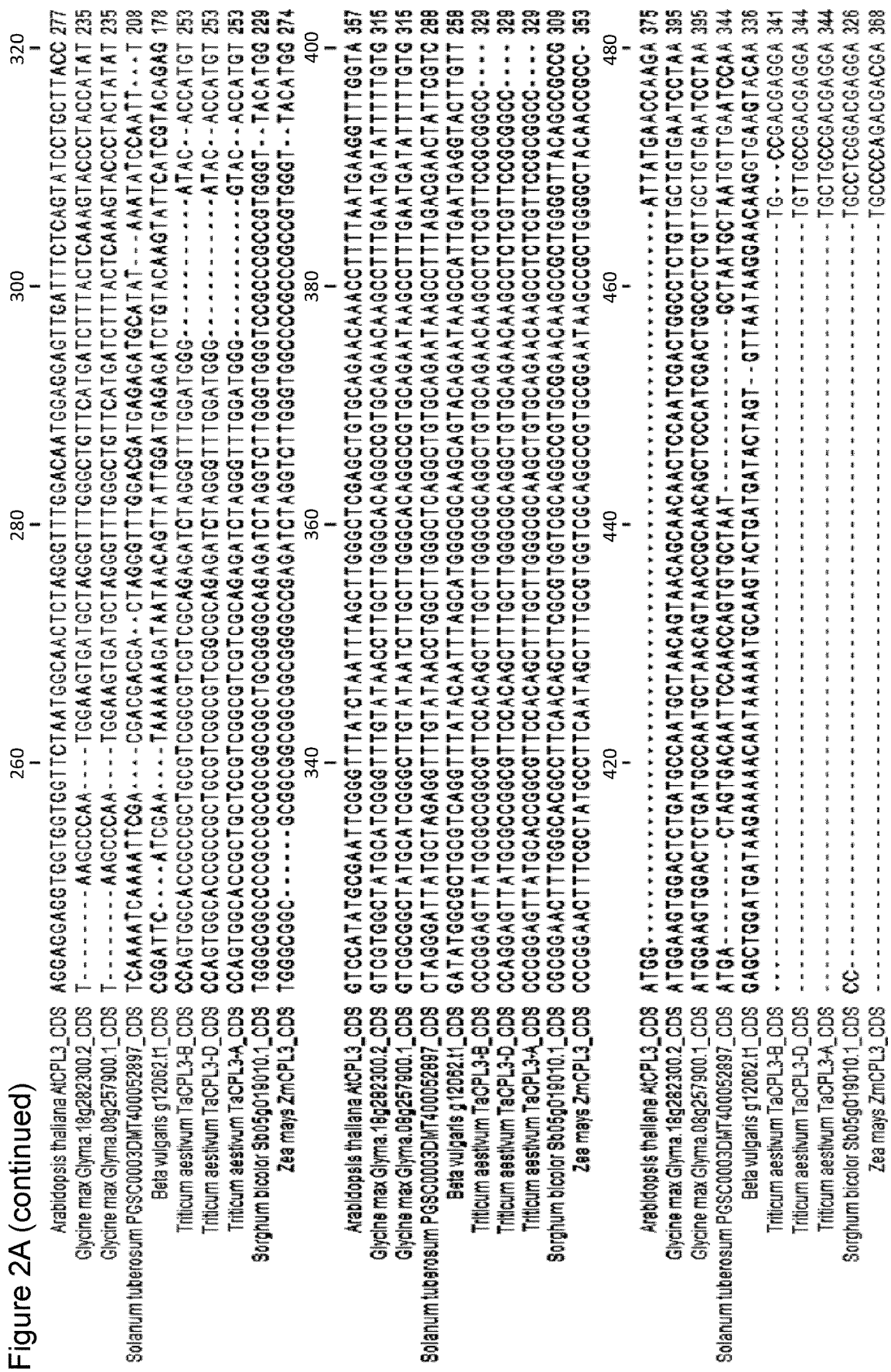
Figure 2A:
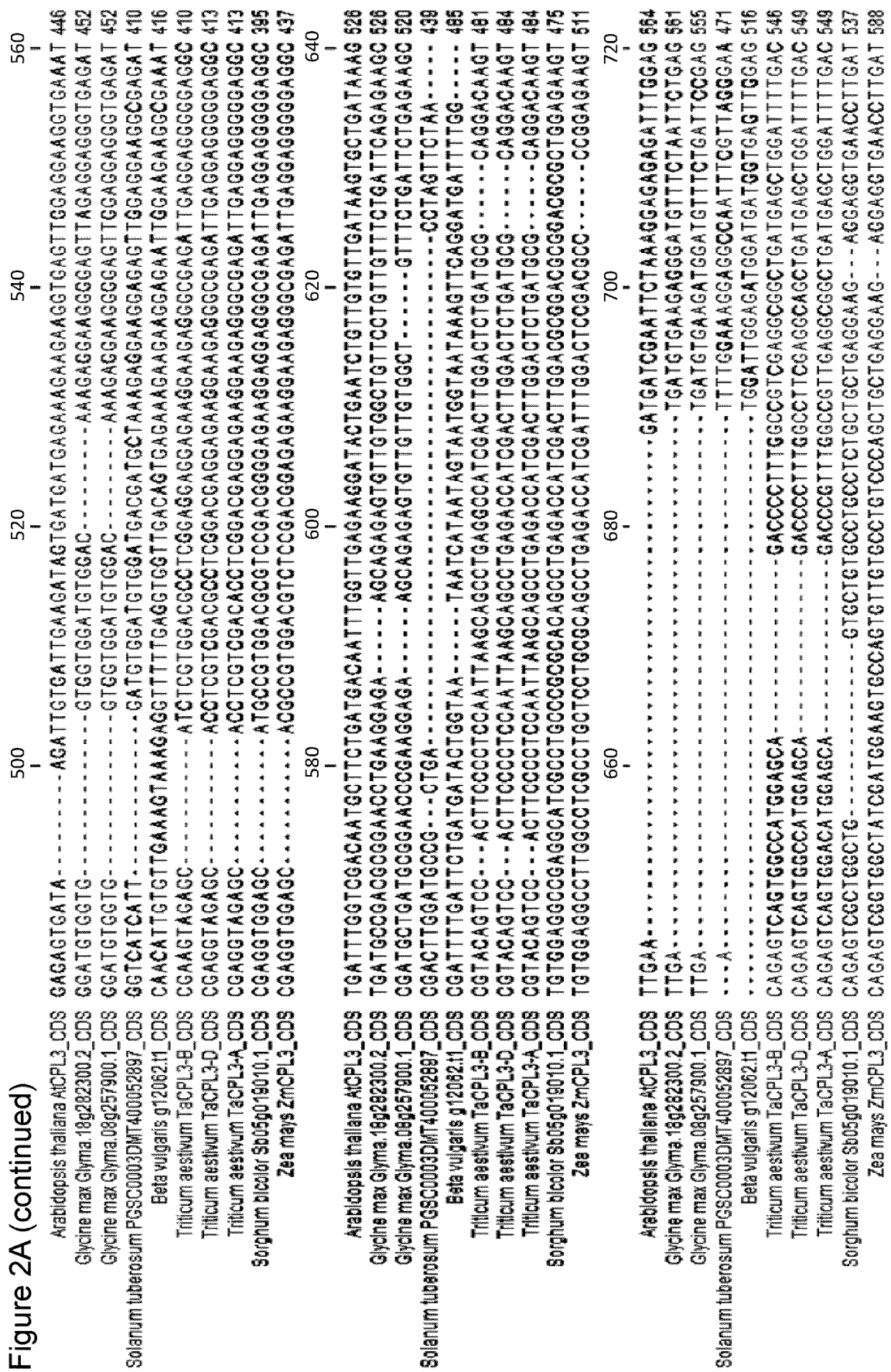
Figure 2A:
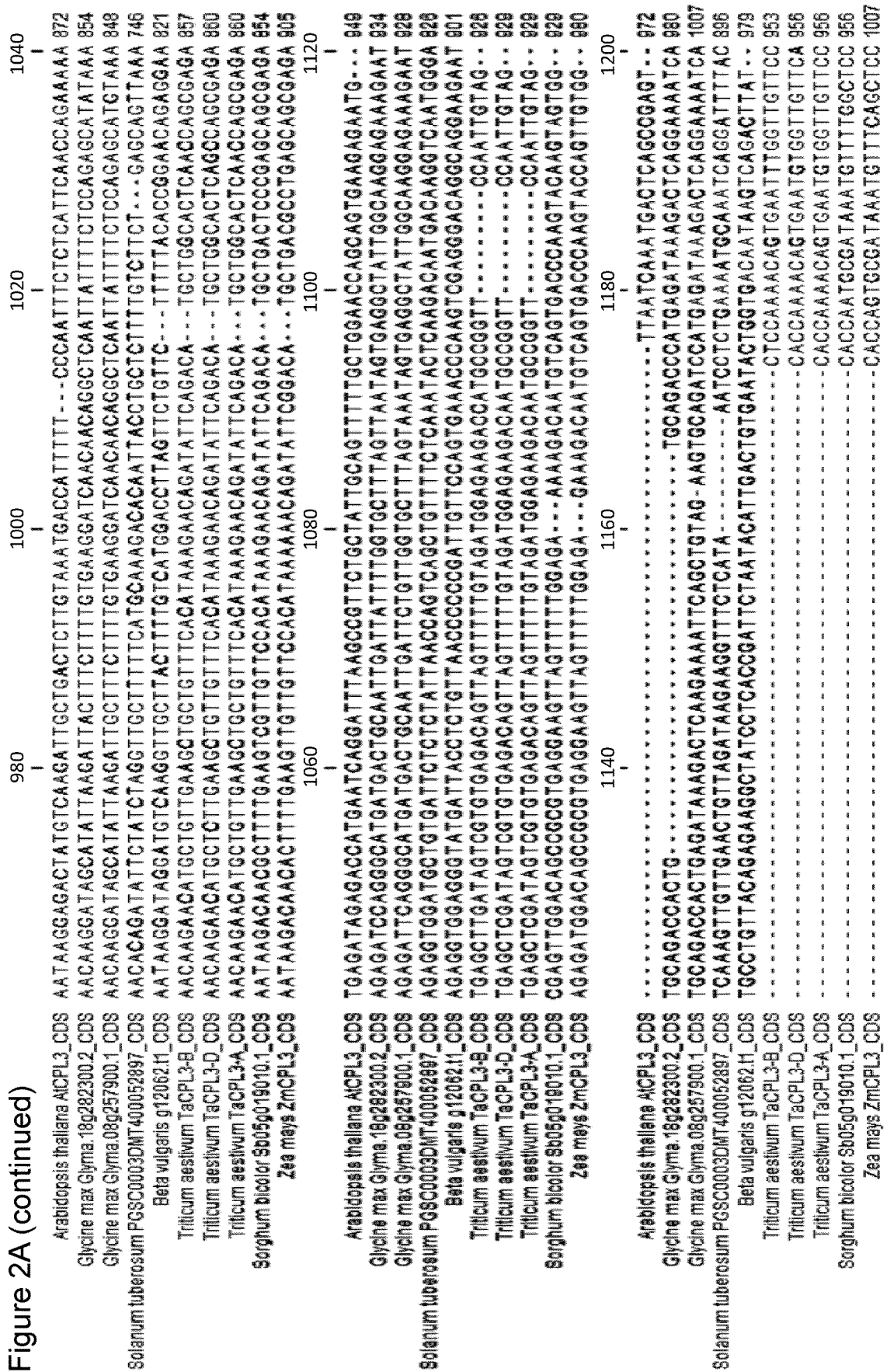
Figure 2A:
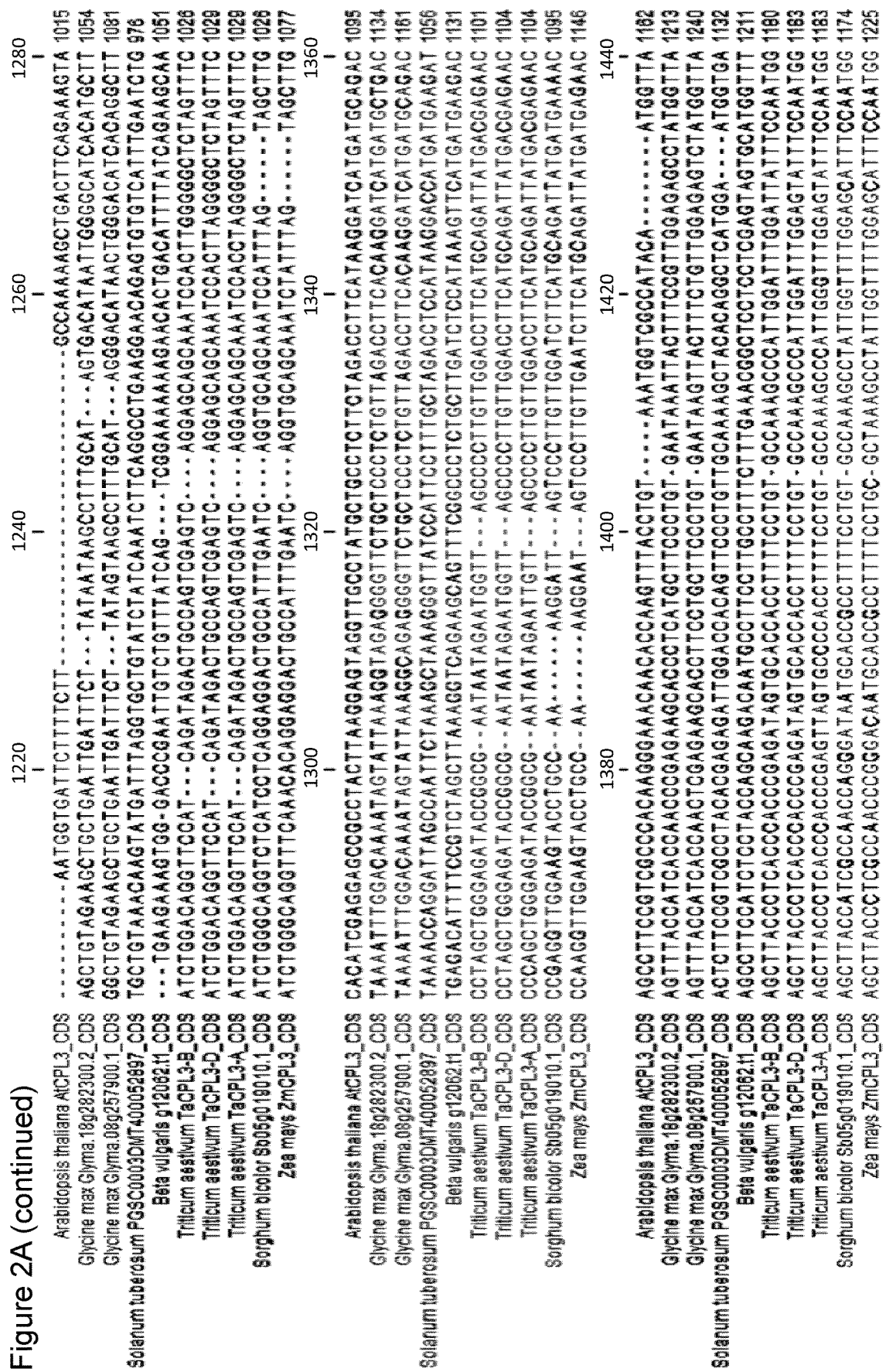
Figure 2A:
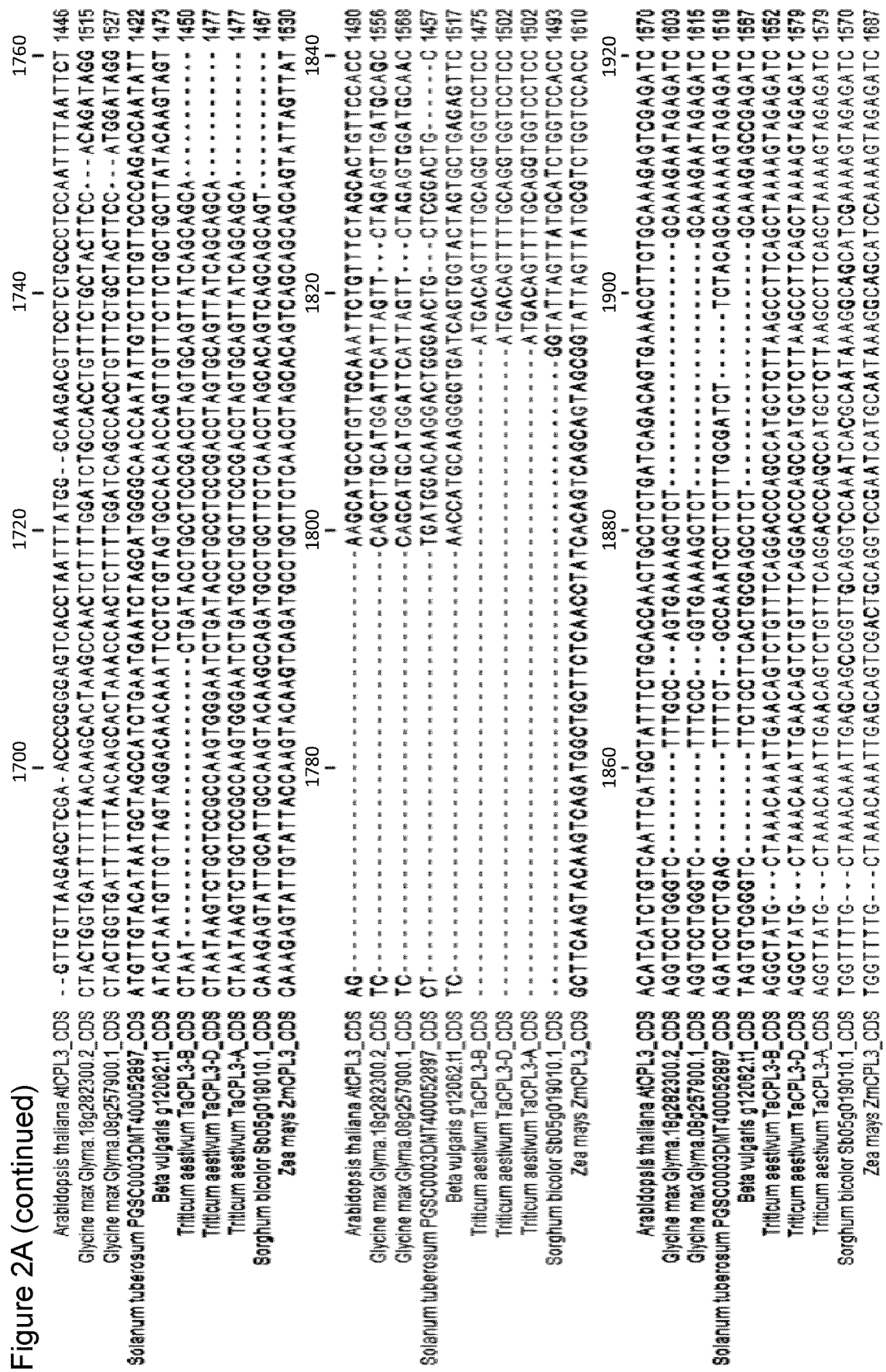
Figure 2A:
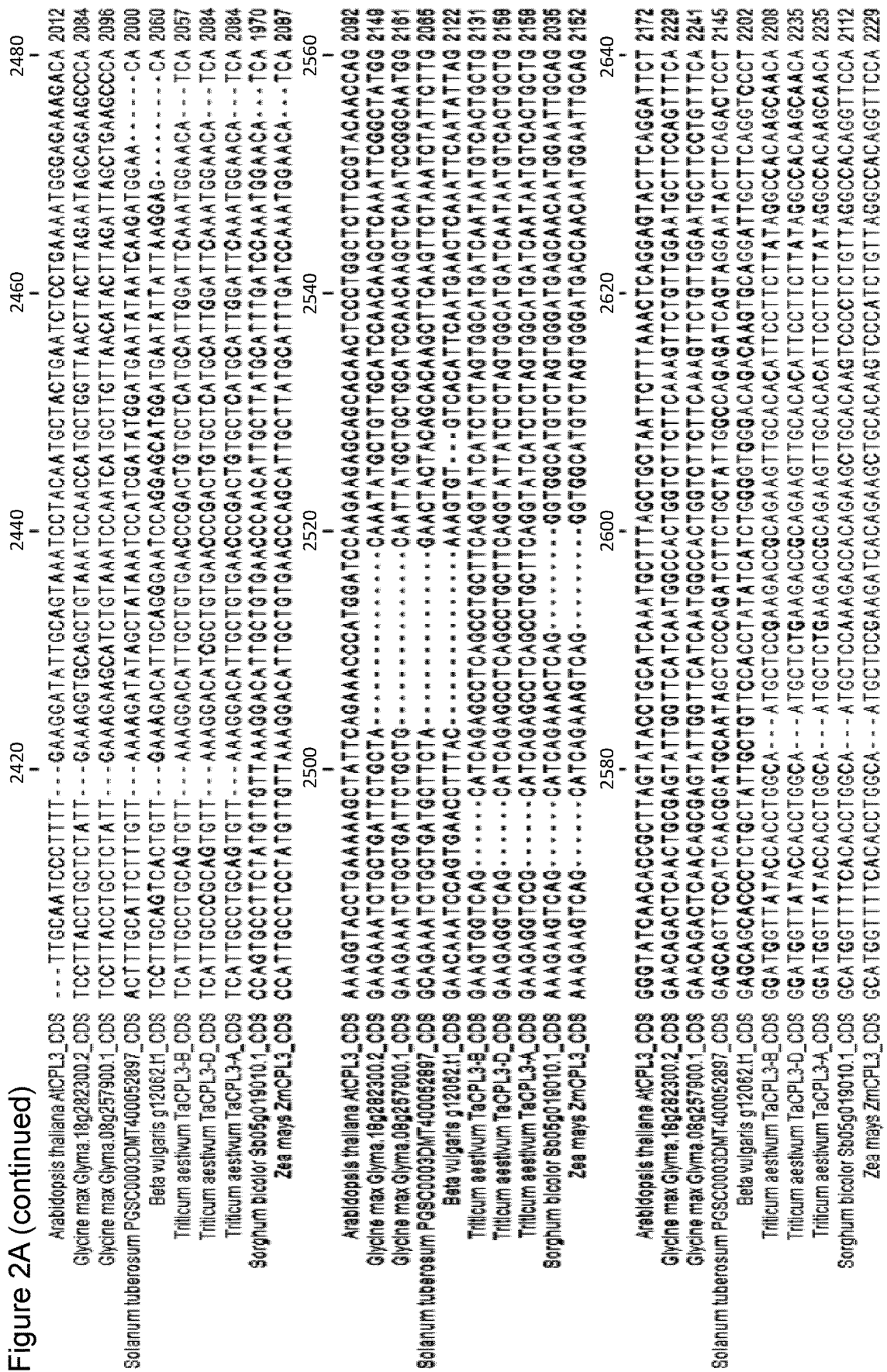
Figure 2A:
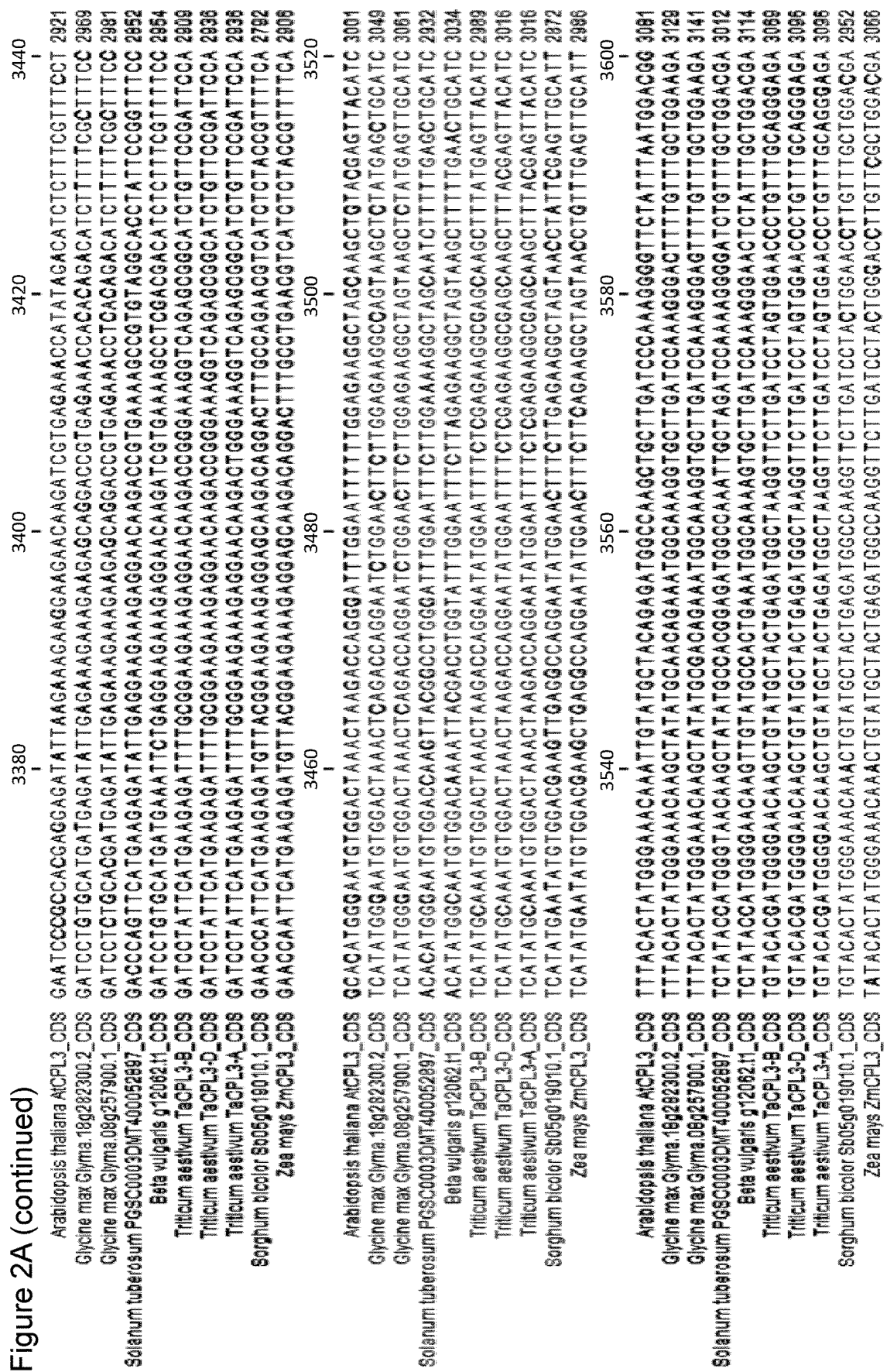
Figure 2A:
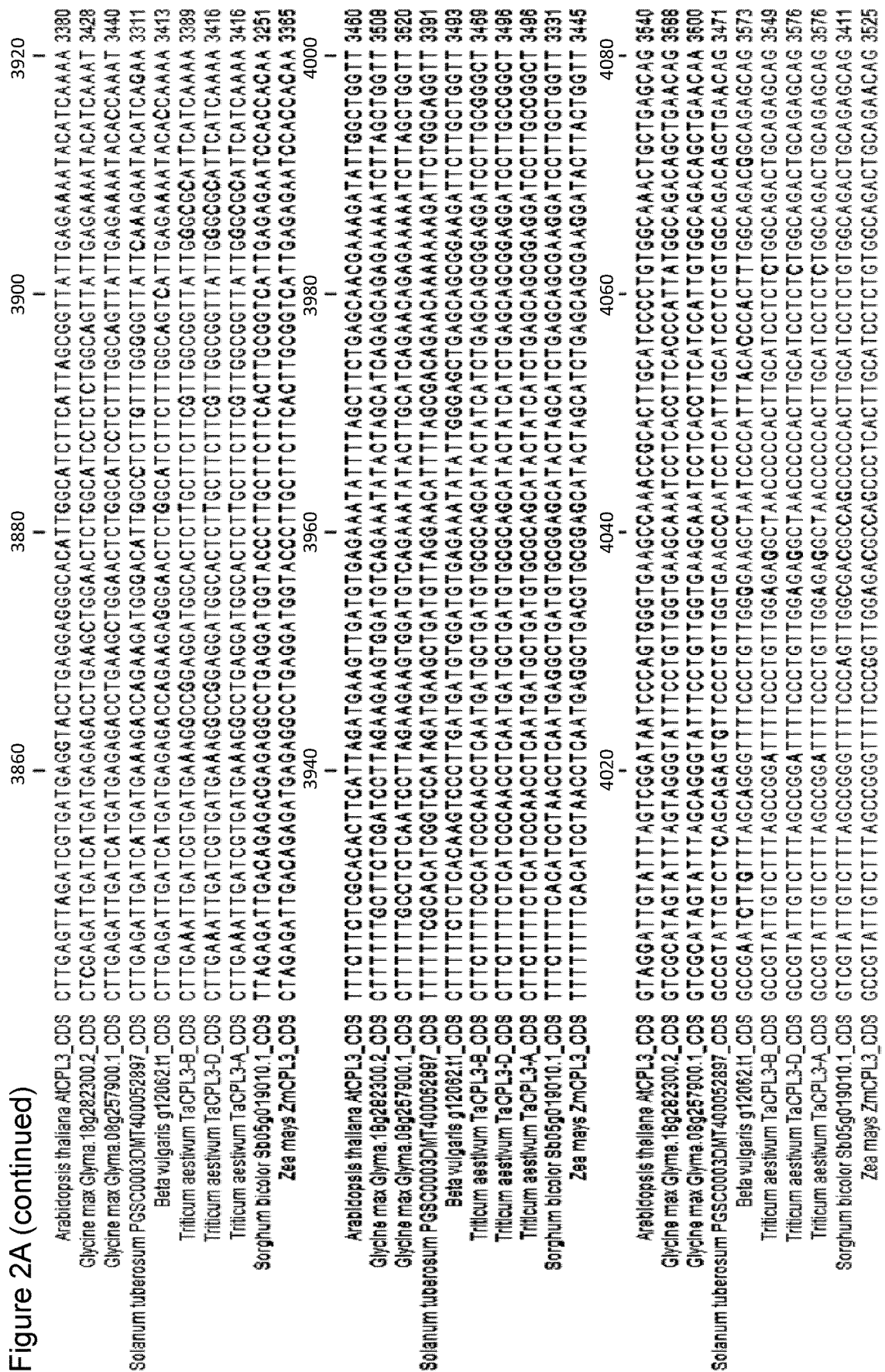
Figure 2A:
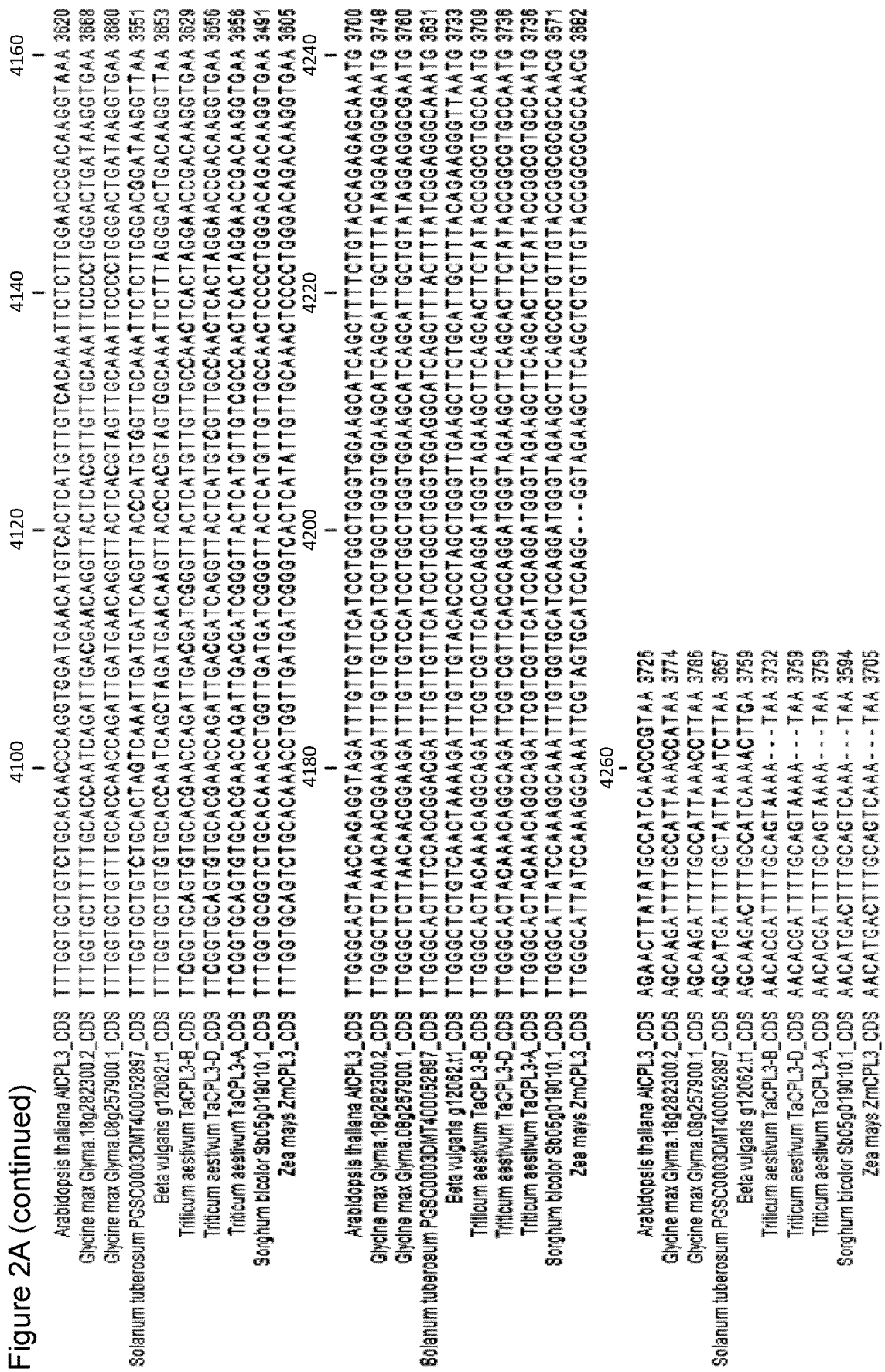
Figures 3, 4:
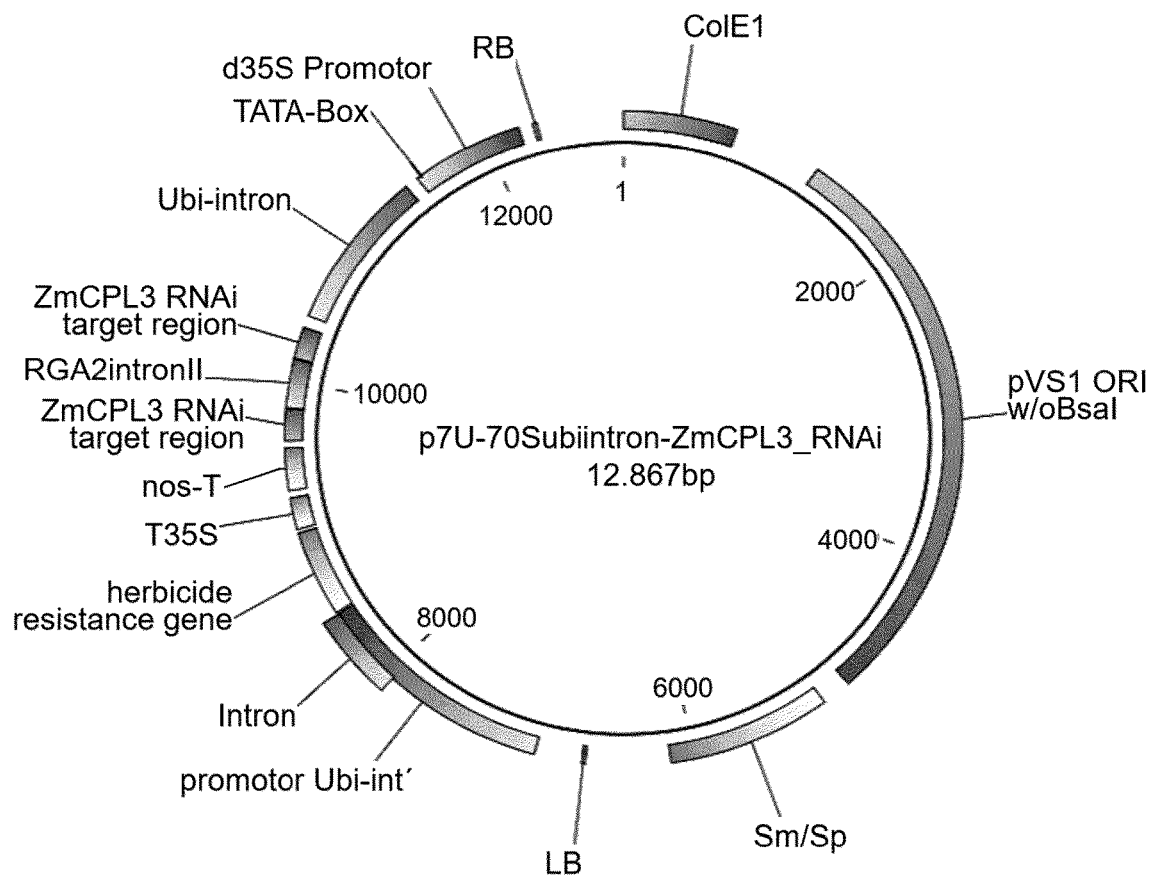
FIG. 3 shows the results of TaCPL3-virus induced gene silencing (VIGS) experiment further detailed below in Example 1. VIGS of all TaCPL3 homeologues by Barley Stripe Mosaic Virus (BSMV) with the silencing sequence TaCPL3_fragA also called TaCPL3-A (SEQ ID NO: 5 and 15) or TaCPL2_fragB also called TaCPL3-B (SEQ ID NO.

FIG. 4 shows a vector map of the plasmid construct used for maize transformation to silence ZmCPL3 (Example 2 and SEQ ID NO: 24).

FIG. 5 shows the results of *Setosphaeria turcica* resistance assay: A: assay with segregating T1 plants of ZmCPL3_RNAi transformation events MTR0374-T-038 and MTR0374-T-053 as further illustrated in Example 2. [1]: ntg=non-transgenic segregant (azygous line). [2]: Fungal biomass was determined by quantitative PCR on DNA extracted from infected leaves after the resistance assay. Quantitative PCR with maize DNA-specific primers was used for data normalization. [3]: Gene expression for the different lines was determined by ZmCPL3-specific quantitative reverse transcription PCR. Data is normalized to the expression of the housekeeping gene ZmEF1. Data was generated with plants that were not infected; B: assay with T2 lines and the respective azygous sisterlines (null segregants) as further illustrated in Example 2. [1]: number with different capitals are statistically according to ANOVA. [2]: ntg=non-transgenic segregant (azygous line). [3]: measured before plant inoculation.

Figure 6:
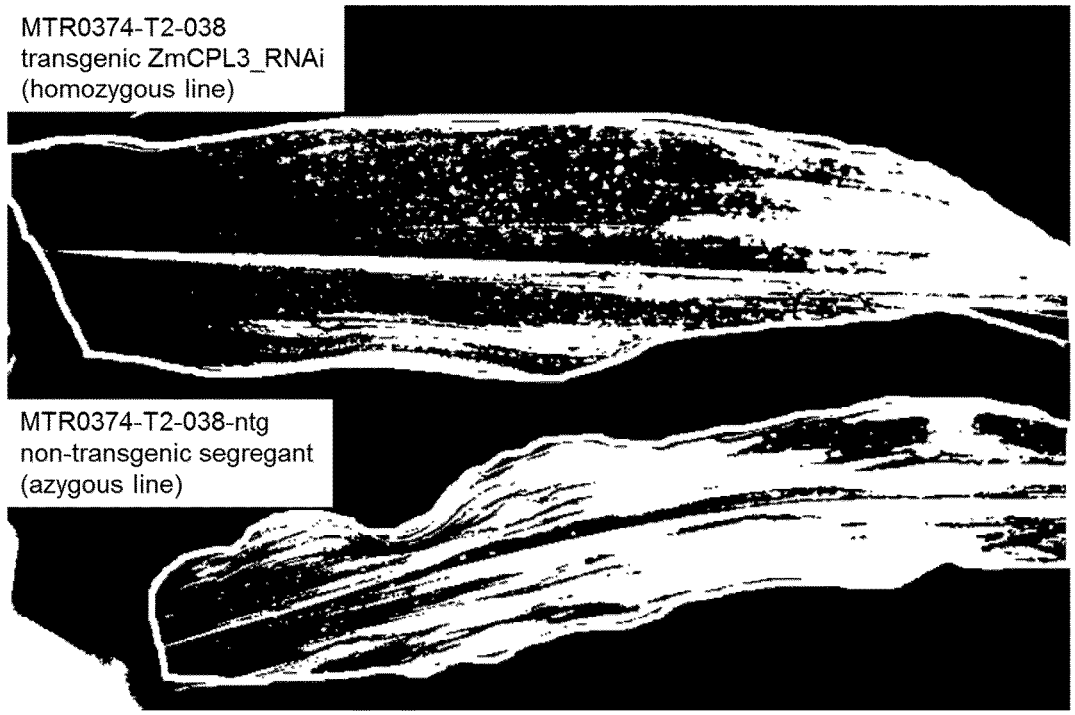

FIG. 6 shows a representative picture of the results of infected leaves for *Setosphaeria turcica* resistance assay with homozygous T2 lines and the respective azygous sisterlines (null segregants). ZmCPL3_RNAi experiments (T2 plants) as further illustrated in Example 2.

Figure 7:
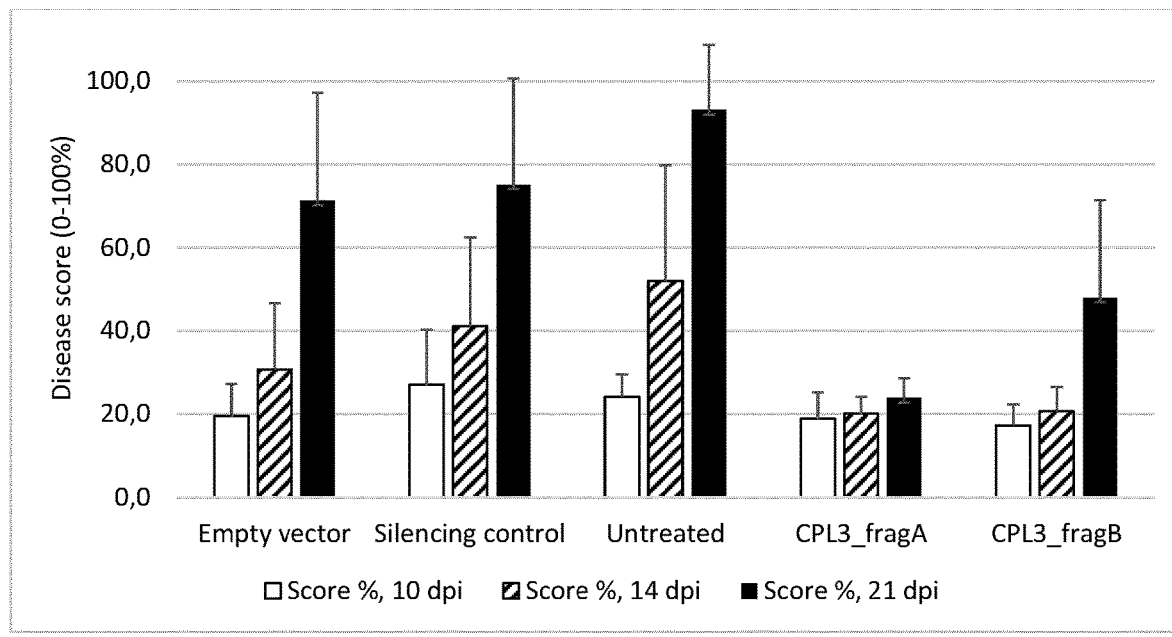

FIG. 7 shows enhanced *Fusarium* resistance of Taifun after VIGS mediated silencing of CPL3 (see also Table 8).

Figure 8:

FIG. 8 shows wheat plant heads after *Fusarium graminearum* infection. a. transformed with empty vector, b. untreated, c. silencing control, d. VIGS-silenced CPL3.

Figure 9:
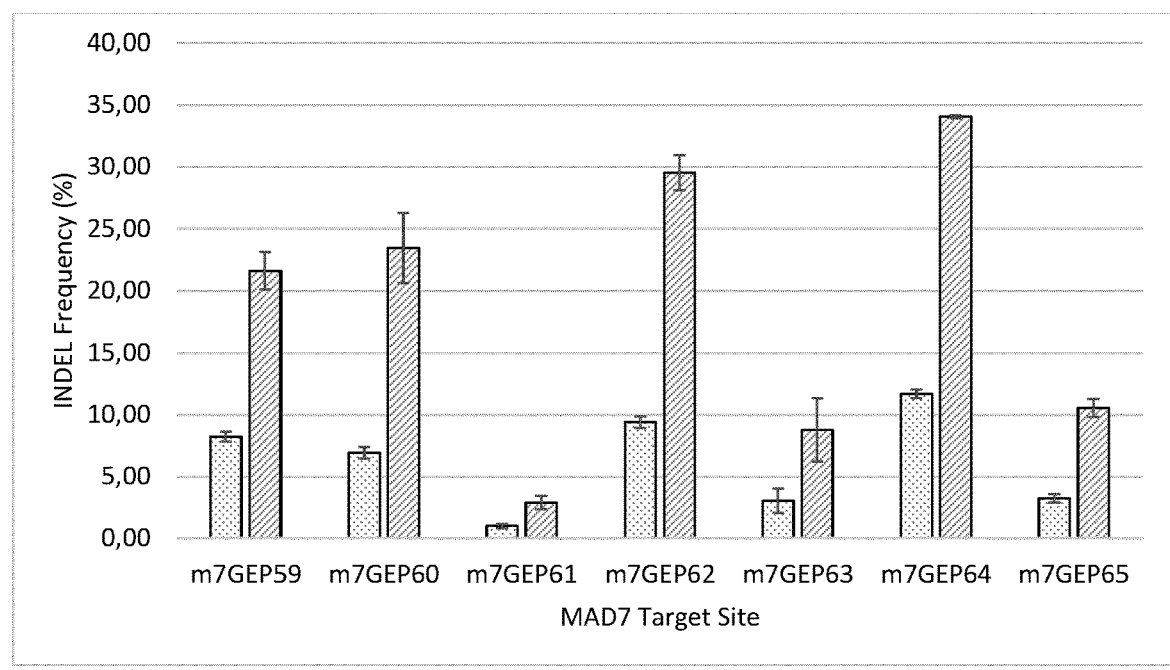

FIG. 9 shows MAD7 nuclease activity at multiple Zm-CPL3 target sites in maize protoplasts. Maize line A188 protoplasts were independently co-transfected with constructs that express the MAD7 nuclease protein gene and one of a variety of crRNA sequences to specific sites in the gene. Although target sites were pre-selected based on the same criteria, there were differences observed in the INDEL frequencies. Stippled bars show the raw data from protoplast treatments while the striped set are based on extrapolated values based on 100% protoplast transfection.

Figure 10:
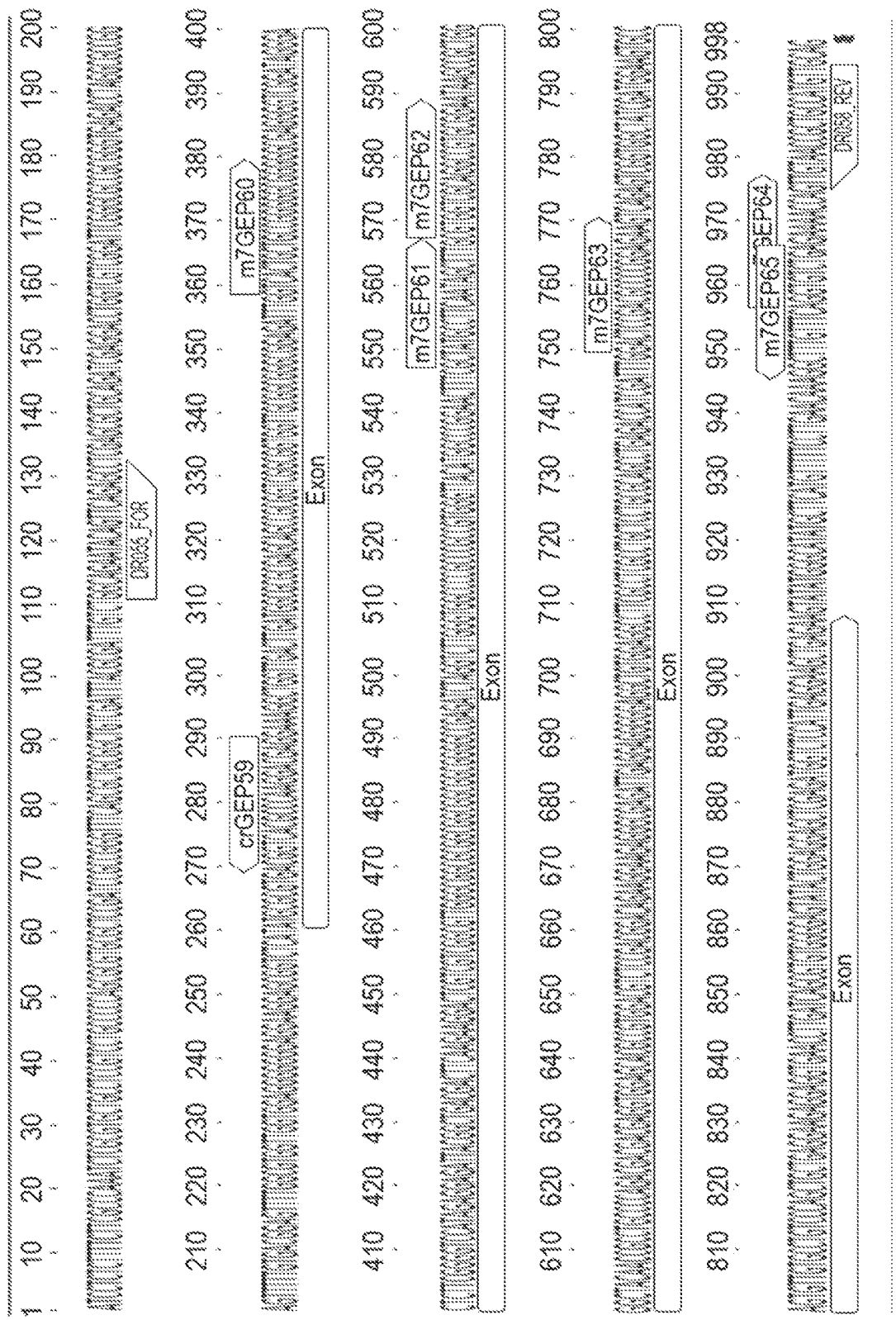

FIG. 10 shows graphical sequence representation for Zm-CPL3 exon 1 showing the positions of tested target sites. CPL3 exon 1 is shown in yellow and the crRNA sequences are labelled in grey to demonstrate the position of potential double stranded breaks from each target sequence or construct. In addition, the green markers are indicating the primers used for PCR to generate the amplicon for Sanger sequence analysis and DRIVE.

DETAILED DESCRIPTION

The present invention is based on the identification of CPL3 homologues in a large variety of different plant species, including major crop plants, which were functionally characterized and which were shown to be crucial for plant immunity leading to increased pathogen resistance, importantly also towards hemibiotrophic fungal pathogens. The findings of the present invention indicate that the desired effect of pathogen resistance can be achieved by a targeted modulation of the CPL3 gene making a complete knock out unnecessary, which knock-out might be associated with undesired effects like impaired plant growth or undesired signaling functions due to the lack of an CPL effector. The findings of the present invention indicate that the desired effect of pathogen resistance can be achieved by a simple knock-down of the CPL3 gene, or by introducing a targeted mutation into a CPL3 gene, or a regulatory sequence thereof, including also combinations of these strategies, making a complete knock-out unnecessary as modulation of the CPL3 function is mediated based on the understanding of the functional interplay of CPL3 with other effectors in plant immunity to achieve pathogen resistance, preferably also resistance against hemibiotrophic pathogens, which are known for their complex lifestyles associated with severe problems in causing plant diseases leading to crop losses. Furthermore, downregulation of CPL3 genes by silencing constructs, or as achieved by RNA editing, or by creating and providing dominant negative mutant alleles avoids the negative effect on plant growth reported by e.g., Koiwa et al. (2002) and potential further side effects associated with a manipulation of a central molecule in plant immunity. Finally, CPL3 downregulation can thus also be achieved by the introduction of a dominant-negative allele of CPL3, for example, by the introduction of a targeted point mutation which leads to dominant CPL3-based resistance.

In a first aspect, a plant having pathogen resistance, wherein pathogen resistance is conferred or increased by modulation of a nucleotide sequence encoding an endogenous C-terminal domain phosphatase-like 3 (CPL3) protein or a regulatory sequence thereof, or by modulation of the transcription of an endogenous CPL3 protein, wherein modulation is achieved by (i) one or more mutation(s) of the nucleotide sequence encoding a CPL3 protein, preferably wherein the one or more mutation(s) has/have a dominant negative effect, preferably wherein the one or more mutation(s) cause(s) an alteration of the amino acid sequence of the conserved catalytic domain of the CPL3 protein comprising the DXDXT/V motif; and/or (ii) one or more silencing construct(s) directed to one or more endogenous nucleotide sequence(s) encoding a CPL3 protein, preferably directed to all endogenous nucleotide sequences encoding a CPL3 protein; and/or (iii) a modification of the native regulatory sequence(s) of one or more nucleotide sequence(s) encoding an endogenous CPL3 protein, preferably all nucleotide sequences encoding an endogenous CPL3 protein, wherein the modification causes a reduced expression rate of the one or more nucleotide sequence(s) encoding an endogenous CPL3 protein may be provided. The above aspect thus covers three different modes (i) to (iii) for a targeted modulation, which may be used alone or in combination to obtain a pathogen resistant plant.

Using homology searches based on an *Arabidopsis* model gene sequence characterized for plant immunity only as negative regulator of BABA-induced gene expression (Koiwa et al., 2002) so far and in a complete knock-out scenario (SEQ ID NO: 1), several new CPL3 coding genes (SEQ ID NO: 2-10) in multiple crop plants not specifically associated with plant immunity at date were identified, characterized and modulated in a targeted way. As shown in FIGS. 1 and 2, the identities to of the discovered CPL3 proteins (SEQ ID NO: 11-19) to the *Arabidopsis* AtCPL3 protein (SEQ ID NO: 20) are between 36% and 45% at amino acid level.

Likewise, the identities of the coding sequence (CDS) of the discovered CPL3 genes (SEQ ID NO: 2-10) to the *Arabidopsis* coding sequence (SEQ ID NO: 1) range from 44% to 53% at the nucleotide level. Furthermore, it was discovered that soybean (*Glycine max*) contains two paralogous CPL3 sequences. Based on this degree of relationship, it was not obvious at first glance whether the identified genes would have favorable functional features so that a deeper mechanistic analysis and mutational and knock-down studies were necessary.

Surprisingly, it was identified that modulation of at least one, preferably all, new CPL3 alleles, or a regulatory sequence thereof is correlated with increased pathogen resistance in a plant carrying the respective CPL3 alleles as endogenous genes/alleles. Several strategies could thus be identified to modify the DNA or RNA sequence of a CPL3 gene, or also the regulatory sequence like a promoter, alone or in combination, which turned out to be superior to creating a full knock-out of a CPL3 gene, probably due to the relevant function CPL gene products fulfill in their natural context in plant immunity.

In one embodiment, the plant having pathogen resistance may comprise a nucleotide sequence, wherein the nucleotide sequence encodes a CPL3 protein modified in a targeted way to optimize pathogen resistance, wherein the CPL3 sequence may be selected from the group consisting of: (a) a nucleotide sequence set forth in SEQ ID NOs: 2-10 or a homologous, orthologous or paralogous sequence thereof; (b) a nucleotide sequence having at least 80%, at least 85%, at least 90%, at least 92%, at least 94%, at least 95%, at least 96%, at least 97%, at least 98% or at least 99% identity to a nucleotide sequence as defined in (a); (c) a nucleotide sequence encoding for an amino acid sequence set forth in SEQ ID NOs: 11-19 or for an amino acid sequence which have at least 80%, at least 85%, at least 90%, at least 92%, at least 94%, at least 95%, at least 96%, at least 97%, at least 98% or at least 99% identity to the one sequence as set forth in SEQ ID NOs: 11-19; (d) a nucleotide sequence encoding for an amino acid sequence having at least 80%, at least 85%, at least 90%, at least 92%, at least 94%, at least 95%, at least 96%, at least 97%, at least 98% or at least 99% identity to one of the sequences set forth in SEQ ID NOs: 11-19, or (e) a nucleotide sequence hybridizing with a nucleotide sequence complementary to the nucleotide sequence as defined in (a)-(d) under stringent conditions.

In one embodiment, the pathogen against which an increased resistance of a plant is desired may be at least one of a fungal pathogen, an oomycete pathogen, a bacterial pathogen, a virus, a nematode pathogen, or an insect. Although weeds are the major cause of crop loss on a global scale, major losses are suffered by agricultural crops due to insect damage feeding on the plant as pathogen and other plant diseases caused by various plant pathogens. In rounded (approximate) figures, the world-wide annual production tonnage % lost to various pests at the start of the 21st century have been estimated as follows: losses due to animal pests, 18%; microbial diseases, 16% (and 70-80% of these losses were caused by fungi); weeds, 34%; making a grand total of 68% average annual loss of crop production tonnage (data from Oerke, 2006. Crop losses to pests. *The Journal of Agricultural Science*, 144(1), 31-43.). Plant pathogens are often divided into biotrophs, necrotrophs, and hemibiotrophs according to their lifestyles. The definitions of these terms are as follows: biotrophs derive energy from living cells. They are found on (e.g., also insects feeding on a plant) or in living plants and can have very complex nutrient requirements. Further, they do not kill host plants rapidly. Necrotrophs derive energy from killed cells. They invade and kill plant tissue rapidly and then live saprotrophically on the dead remains. Finally, hemibiotrophs have an initial period of biotrophy followed by necrotrophy.

In another embodiment, the pathogen against which an increased resistance of a plant is desired, may thus be a biotrophic, necrotrophic or hemibiotrophic fungus, preferably selected from the group consisting of: *Zymoseptoria tritici*, *Setosphaeria turcica*, *Fusarium* spp. *Fusarium graminearum*, *Colletotrichum* spp. such as *Colletotrichum graminicola*, *Magnaporthe grisea*, *Magnaporthe oryzae*, *Phytophthora infestans*, *Cercospora* spp., preferably *Cercospora beticola* or *Cercospora zeae-mayidis*.

Plant pathogens can have a broad host range, for example in the case of insects feeding in different plant species with the same preference, or they may have a rather narrow host range, e.g., in the case of plant viruses. A plant pathogen according to the present invention may thus include any plant pathogen against which resistance can be increased by modulation of a CPL3 gene sequence, a regulatory sequence thereof, a transcript thereof or a protein product thereof.

In certain embodiments, the pathogen against which an increased resistance may be obtained may be a wheat or maize pathogen as represented in the following Tables 1 to 7:

TABLE 1

Fungal diseases and corresponding pathogens of *Triticum* spp.

| Pathogen | Disease | Pathogen type | Disease type |
| --- | --- | --- | --- |
| *Blumeria graminis* f. sp. *tritici* | Powdery mildew | Fungus | Foliar disease |
| *Drechslera tritici-repentis* | Tan spot | Fungus | Foliar disease |
| *Fusarium culmorum* | Fusarium head blight | Fungus | Head disease |
| *Fusarium graminearum* | Fusarium head blight | Fungus | Head disease |
| *Gaeumannomyces graminis* var. *tritici* | Various diseases | Fungus | Root disease |
| *Magnaporthe olyzae* | Wheat blast | Fungus | Head disease |
| *Pseudocercosporella herpotrichoides* | Eyespot | Fungus | Stem disease |
| *Puccinia graminis* f. sp. *tritici* | Black rust | Fungus | Foliar and stem disease |
| *Puccinia striiformis* f. sp. *tritici* | Yellow rust | Fungus | Foliar disease |
| *Puccinia triticina* f. sp. *tritici* | Brown rust | Fungus | Foliar disease |
| *Zymoseptoria tritici* | Septoria leaf blotch | Fungus | Foliar disease |
| *Stagonospora nodorum* | Stagonospora nodorum blotch | Fungus | Foliar and head disease |

TABLE 2

Fungal diseases and corresponding pathogens of *Zea mays*

| Pathogen | Disease | Pathogen type | Disease type |
|---|---|---|---|
| *Aspergillus flavus* | Aspergillus ear rot | Fungus | Ear disease |
| *Aspergillus parasiticus* | Aspergillus ear rot | Fungus | Ear disease |
| *Aureobasidium zeae* | Eyespot | Fungus | Foliar disease |
| *Bipolaris maydis* | Southern corn leaf blight | Fungus | Foliar, stalk and ear disease |
| *Bipolaris zeicola* | Northern corn leaf spot | Fungus | Foliar and ear disease |
| *Cercospora zeae-maydis* | Gray leaf spot | Fungus | Foliar disease |
| *Colletotrichum graminicola* | Anthracnose leaf blight Anthracnose stalk rot Anthracnose ear rot | Fungus | Foliar, stalk and ear disease |
| *Fusarium graminearum* | Gibberella crown and stalk rot Gibberella ear rot | Fungus | Crown, stalk and ear disease |
| *Fusarium proliferatum* | Fusarium stalk and ear rot | Fungus | Stalk and ear disease |
| *Fusarium subglutinans* | Fusarium stalk and ear rot | Fungus | Stalk and ear disease |
| *Fusarium temperatum* | Fusarium stalk and ear rot | Fungus | Stalk and ear disease |
| *Fusarium verticillioides* | Fusarium ear rot | Fungus | Ear disease |
| *Macrophomina phaseolina* | Charcoal rot | Fungus | Stalk disease |
| *Penicillium* species | Penicillium ear rot | Fungus | Ear disease |
| *Phaeospaeria maydis* | Phaeospaeria leaf spot | Fungus | Foliar disease |
| *Phoma terrestris*, *Phytium* species and *Fusarium* species | Red root rot | Fungus | Root and stalk disease |
| *Physoderma maydis* | Physoderma brown spot and stalk rot | Fungus | Foliar and stalk disease |
| *Puccinia polysora* | Southern rust | Fungus | Foliar disease |
| *Puccinia sorghi* | Common rust | Fungus | Foliar disease |
| *Rhizoctonia solani* | Rhizoctonia crown and brace root rot | Fungus | Seedling and root disease |
| *Rhizoctonia solani* f. sp. *sasakii* | Banded leaf and sheath blight | Fungus | Foliar disease |
| *Setosphaeria turcia* | Northern corn leaf blight | Fungus | Foliar disease |
| *Sphacelotheca reiliana* | Head smut | Fungus | Ear disease |
| *Stenocarpella macrospora* | Diplodia leaf streak | Fungus | Foliar disease |
| *Stenocarpella maydis* | Diplodia stalk rot Diplodia ear rot | Fungus | Stalk and ear disease |
| *Trichoderma viride* | Trichoderma ear rot | Fungus | Ear disease |
| *Ustilago maydis* | Common smut | Fungus | Foliar disease |

TABLE 3

Oomycete diseases of *Zea mays*

| Pathogen | Disease | Pathogen type | Disease type |
|---|---|---|---|
| *Peronosclerospora sorghi* | Sorghum downy mildew | Oomycete | Foliar disease |
| *Phytium aphanidermatum* | Phytium stalk rot | Oomycete | Stalk disease |
| *Phytium* species | Pythium seedling blight and root rot | Oomycete | Seedling and root |
| *Sclerophthora macrospora* | Crazy top | Oomycete | Foliar disease |

TABLE 4

Bacterial diseases of *Zea mays*

| Pathogen | Disease | Pathogen type | Disease type |
|---|---|---|---|
| *Clavibacter michiganensis* | Goss's wilt | Bacterium | Foliar disease |
| *Erwinia* species | Bacterial stalk rot | Bacterium | Stalk disease |
| *Pantoea stewartii* | Stewart's disease | Bacterium | Foliar and stalk disease |
| *Pseudomonas syringae* pv. *syringae* | Holcus leaf spot | Bacterium | Foliar disease |

TABLE 5

Viral diseases of *Zea mays*

| Pathogen | Disease | Pathogen type | Disease type |
|---|---|---|---|
| Maize dwarf mosaic virus | Maize dwarf mosaiv | Virus | Foliar disease |
| Maize chlorotic dwarf virus | Maize chlorotic dwarf | Virus | Foliar disease |
| Maize rough dwarf virus | Maize rough dwarf | Virus | Foliar disease |
| Maize streak virus | Maize Streak | Virus | Foliar disease |

TABLE 6

Nematode diseases of Zea mays

| Pathogen | Disease | Pathogen type | Disease type |
| --- | --- | --- | --- |
| Belonolaimus and Longidorus species | Sting and needle neamtodes | Nematode | Root disease |
| Meloidogyne species | Root-knot nematode | Nematode | Root disease |
| Paratrichodorus specis | Stubby-root nematode | Nematode | Root disease |
| Pratylenchus species | Root-lesion nematode | Nematode | Root disease |

TABLE 7

Insect diseases of Zea mays

| Pathogen | Disease | Pathogen type | Disease type |
| --- | --- | --- | --- |
| Agrotis ipsilon | Cutworm | Insect | Leaf disease |
| Ostrinia nubilalis | European corn borer | Insect | Stalk and ear disease |
| Pseudaletia unipuncta | Armyworm | Insect | Leaf and ear disease |
| Rhopalosiphum maidis | Corn leaf aphid | Insect | Leaf disease |

The terms "resistance" or "resistant" as used herein refers to the capacity of a plant to resist to the phenotype as caused by infestation with a pathogen, preferably a fungal pathogen to a certain degree, i.e., the prevention, reduction or delay of an infection or harm caused by the pathogen. "Resistance", therefore, does not exclusively refer to a "black or white" phenotype, but is intended to mean any improvement of infection or infestation symptoms as observed for a plant having an endogenous CPL3 protein activity in comparison to a plant having a specifically modified CPL3 activity according to the various aspects of the present disclosure. Resistance to a given pathogen can thus range from a slightly increased resistance to an absolute resistance towards a given pathogen always comparing the modified plant, plant cell, tissue, organ or material to a naturally occurring non modified plant, plant cell, tissue, organ or material, respectively.

In one embodiment, the pathogen resistance may be a fungal resistance, more preferably a hemibiotrophic fungal resistance. Generally, there is a great need to identify new anti-fungal strategies. Hemibiotrophic pathogens cover some of the most relevant pathogens for crop plants, e.g., wheat (Triticum aestivum), soybean (Glycine max), corn (Zea mays) etc. The hemibiotrophic fungal pathogen Exserohilum turcicum (anamorph form of the fungus; teleomorph: Setosphaeria turcica) causing NCLB, for example, is found in humid climates wherever corn is grown and has bipartite life cycle hampering the establishment of efficient anti-fungal agents protecting plants. E. turcicum survives in debris of Zea mays and builds up over time in high-residue and continuous corn cropping systems. High humidity and moderate temperatures favor the persistence of the E. turcicum fungus causing tremendous yield losses, e.g., due to decreased photosynthesis resulting in limited ear fill, or harvest losses if secondary stalk rot infection and stalk lodging accompany loss of leaf area. Due to their complicated life cycle, hembibiotrophic pathogens are hard to combat and represent a huge threat in agriculture as these fungi can often evade the plant immune system. Therefore, strategies, preferably other than relying on fungicides, are needed for providing relevant crop plants having an endogenous resistance to selected pathogens like fungal pathogens.

In one embodiment, the one or more mutation(s) to be introduced into a CPL3 encoding gene, or a regulatory sequence thereof, may have a dominant negative effect and may be present in the heterozygous state in the plant. In another embodiment, the mutation may be present in the homozygous state. Depending on the amount of different CPL3 alleles in a germplasm, and further depending on the function outcome, a homozygous or a heterozygous state may be preferably to obtain an optimum balance between increased fungal resistance and a maintenance of normal cellular functions.

After discovery of the CPL3 homologues and the tests on favorable mutations, the possibility was tested whether downregulation of CPL3 gene expression leads to improved pathogen resistance. Therefore, maize (Zea mays) ZmCPL3 (SEQ ID NO: 9 and 19) and wheat (Triticum aestivum) TaCPL3-A (SEQ ID NO: 5 and 15), TaCPL3-B (SEQ ID NO: 6 and 16) and TaCPL3-D (SEQ ID NO: 7 and 17) genes were selected for pathogen resistance tests to obtain functional data for relevant crop plants based on the genes identified.

It was surprisingly observed that the specific modulation of a CPL3 protein or a nucleic acid sequence encoding the same or encoding the regulatory sequence for a cpl3 gene resulted in a plant cell, tissue, organ, whole plant, or plant material showing overall normal growth and/or proliferation, either for the settings using a dominant negative mutation, a modification of a regulatory sequence, or an incomplete down-regulation of a CPL3 transcript. "Normal growth and proliferation" is meant to imply that a plant cell or organism modulated according to the present disclosure substantially shows the same growth and proliferation characteristics as a not modulated plant or plant cell on a phenotypic level. For example, the modulated plant does not show detectable symptoms associated with growth, cell division, or cell death in direct comparison to a non-modulated material of same origin and with the same genetic background. In view of the fact that CPL3 proteins are important enzymes in cell signaling, this finding was not expected and is likely associated with the way the CPL3 signaling is modulated in a rather specific way according to the present invention relying on specific mutations and/or specific downregulation of expression of CPL3 instead of providing a full knock out of the respective genes in a heterozygous or homozygous state. In particular, it was observed as significant advantage of the present invention that an incomplete down-regulation or a targeted mutation of a CPL3 gene sequence or a regulatory sequence thereof besides the desired effect of achieving pathogen resistance does not disturb normal plant growth and/or development.

The term "modulation" or "modulating" is used herein as a superordinate term for a targeted control or modification of a naturally occurring DNA, RNA, or protein sequence, including the control or modification of transcription, translation or post-translational events. According to the various aspects of the present disclosure, a "mutation" can be understood as specific form of a modulation acting on DNA as target nucleic acid sequence to establish a potentially inheritable modulation. A mutation can be introduced in a targeted way, e.g., by relying on a site-directed DNA modifying enzyme, or a mutation can be introduced in a random manner followed by specific screening, e.g., by TILLING, the latter method allowing a higher throughput, but demanding more screening for identifying desired mutations.

In one embodiment, there may be provided a plant having increased pathogen resistance, wherein the one or more mutation(s) of the nucleotide sequence encoding a CPL3 protein may cause the substitution of Asp by Ala at position 928 referenced to SEQ ID NO: 19, at position 944 referenced to SEQ ID NO: 14, at position 949 referenced to SEQ ID NO: 11, at position 944 referenced to SEQ ID NO: 14, at position 949 referenced to SEQ ID NO: 11, at position 953 referenced to SEQ ID NO: 12, at position 910 referenced to SEQ ID NO: 13, at position 890 referenced to SEQ ID NO: 18, at position 938 referenced to SEQ ID NO: 15, at position 929 referenced to SEQ ID NO: 16, at position 938 referenced to SEQ ID NO: 17.

In another embodiment, the plant having pathogen resistance can be obtain by using one or more silencing construct(s) comprising (I.) an RNAi molecule directed against, targeting, or hybridizing with the nucleotide sequence encoding the CPL3 protein, or a polynucleotide sequence encoding said RNAi molecule; or (II.) an RNA-specific CRISPR/Cas system directed against or targeting the nucleotide sequence encoding the CPL3 protein, or a polynucleotide sequence encoding said RNA-specific CRISPR/Cas system, preferably wherein the RNAi molecule is selected from a dsRNA molecule, a shRNA molecule, a miRNA molecule or a siRNA molecule which comprises at least 15, 16, 17, 18, 19, 20, 21, 22, 23, 24, 25, 26, 27, 28, 29, 30, 31, 32, 33, 34, 35, 36, 37, 38, 39, 40, 45 or 50 contiguous nucleotides of the coding nucleotide sequence of the CPL3 protein or the complementary sequence thereof in sense or antisense direction, more preferably wherein the RNAi molecule is selected from a sequence of SEQ ID NOs: 21 to 24, or a sequence having at least 95%, 96%, 97%, 98% or 99% sequence identity thereto.

In a preferred embodiment, the RNAi molecule or a sequence comprised by a silencing construct does preferably not share substantial sequence identity with other genomic regions in the genome of the plant. "Substantial sequence identity" implies that a RNAi molecule, or a silencing construct encoding or comprising the same, would have identity to a sequence other than the target sequence in the genome or transcriptome of a plant or plant cell. Based on the disclosure herein and further based on the genomic data of relevant crop plants, the skilled person can thus create silencing constructs or RNAi molecules for knock-down experiments of CPL3 transcripts which will be highly specific for a CPL3 target sequence to allow an otherwise normal cellular function.

There are multiple ways to downregulate the expression of a gene. Among them are the expression of RNAi or microRNA constructs or the modification of the promoter or other regulatory elements of a gene. In one embodiment for downregulation of CPL3 genes, in accordance with the second aspect of the modes of modulation according to the present disclosure, a dominant negative allele of CPL3 may be expressed. Fukudome et al. (2014) reported that the point mutation D128A in the conserved DXDT motif of the catalytic phosphatase domain resulted in in a dominant-negative form, at least for the *Arabidopsis* protein AtCPL4 that is involved in normal growth and plant development. Overexpression of the dominant allele AtCPL4_D128A in *Arabidopsis*, however, was lethal and resembled the phenotype of AtCPL4 knock out lines that are homozygous lethal. *Arabidopsis* plants with AtCPL4 RNAi constructs were viable with mild toxicity phenotype. This shows that strong overexpression of a dominant negative AtCPL4 allele resembles a complete knock out of AtCPL4.

To achieve a fine-tuned modulation according to the first aspect of the modes of modulation according to the present disclosure, a dominant negative allele may be provided by introducing at least one targeted mutation into at least one CPL3 protein encoding sequence, wherein the at least one mutation results in a dominant negative CPL3 allele, preferably wherein the mutation causes an alteration of the amino acid sequence of a conserved DXDXT domain of a CPL3 protein. According to one embodiment, the mutant variant of the respective CPL3 variant may then be put under the control of a weak promoter, e.g., an endogenous promoter, optionally an inducible promoter according to the various methods of generating a plant cell, tissue, organ, whole plant, or plant material to achieve pathogen resistance, preferably fungal resistance, by simultaneously avoiding potentially lethal side effects of a strong expression of the variant.

In one embodiment, the promoter may be an endogenous or native promoter.

Therefore, one embodiment covers a dominant negative allele of the CPL3 gene under the control of a native promoter which confers pathogen resistance, preferably resistance against hemibiotrophic pathogens. To gain dominant negative alleles of the discovered CPL3 genes, mutations for example in the DXDXT motif similar to D128A in AtCPL4 may be used. Further preferred point mutations that lead to a dominant negative allele are selected from the group consisting of D928A in ZmCPL3 (SEQ ID NO: 19), D944A in BvCPL3 (SEQ ID NO: 14), D949A in GmCPL3_1 (SEQ ID NO: 11), D953A in GmCPL3_2 (SEQ ID NO: 12), D910A in StCPL3 (SEQ ID NO: 13), D890A in SbCPL3 (SEQ ID NO: 18), D938A in TaCPL3-A (SEQ ID NO: 15), D929A in TaCPL3-B (SEQ ID NO: 16), and D938A in TaCPL3-D (SEQ ID NO: 17). Based on the present disclosure, comparable mutations can be inserted at comparable positions in the conserved DXDXT motif of further CPL gene variants in further plants, preferably crop plants.

In another embodiment, a non-native promoter may be inserted to further control the expression of the CPL3 gene of interest in a target plant of interest.

In a further embodiment, downregulation of at least one CPL3 gene can be achieved by introducing a point mutation into at least one native CPL3 gene by means and techniques further disclosed below that leads to a dominant-negative allele and to keep this mutation in a heterozygous state. The resistance effect of a dominant-negative allele of CPL3 would be genetically dominant which has benefits in breeding of resistant hybrid crops as compared to recessive mutations in the promoter, for example, that would need to be present in both parents of the hybrid.

For plants or plant cells, where paralogs of CPL3 genes are present, like in soybean (*Glycine max*), embodiments using a dominant-negative CPL3 allele for engineering pathogen resistant plants may be preferred as this strategy potentially requires less effort than, for example, downregulating all CPL3 paralogs by promoter modifications or by silencing constructs as disclosed herein at the same time.

In the context of the present disclosure, the terms "RNA interference" or "RNAi" refer to a gene down-regulation mechanism meanwhile demonstrated to exist in all eukaryotes. The mechanism was first recognized in plants where it was called "post-transcriptional gene silencing" or "PTGS". In RNAi, small RNAs (of about 21-24 nucleotides) function to guide specific effector proteins (e.g., members of the Argonaute protein family) to a target nucleotide sequence by complementary base pairing. The effector protein complex then down-regulates the expression of the targeted RNA or DNA. Small RNA-directed gene regulation systems were independently discovered (and named) in plants, fungi, worms, flies, and mammalian cells. Collectively, PTGS, RNA silencing, and co-suppression (in plants); quelling (in fungi and algae); and RNAi (in *Caenorhabditis elegans, Drosophila*, and mammalian cells) are all examples of small RNA-based gene regulation systems.

In plants, during RNAi mechanism, silencing initiates with the enzyme Dicer and dsRNA is processed to convert the silencing trigger to ~22-nucleotide, small interfering RNAs (siRNAs). The antisense strand of siRNA become specific to endonuclease-protein complex, RNA-induced silencing complex (RISC), which then targets the homologous RNA and degrade it at specific site that results in the knock-down of protein expression. RNAi technology may thus be a substitute of complex molecular techniques because of containing several benefits: its specificity and sequence-based gene silencing. Plants can also control viral diseases by RNAi and reveal resistance when having proper anti-sense or hairpin RNAi constructs. In plants, specifically to achieve pathogen resistance, hairpin (hp) dsRNA including small hairpin RNA (shRNA), self-complementary hpRNA, and intron-spliced hpRNA can be formed in vivo using inverse repeat sequences from viral genomes. Among these, PTGS with the highest efficiency was elicited by the method involving self-complementary hairpin RNAs separated by an intron. High resistance against viruses has been observed in plants even in the presence of inverted repeats of dsRNA-induced PTGS (IR-PTGS).

Meanwhile, a variety of different RNAi constructs to be used as silencing construct to be used according to the various aspects and embodiments of the present disclosure are available to the skilled person (Younis et al., Int J Biol Sci. 2014; 10(10): 1150-1158). Several methods to induce RNAi, RNAi vectors, in vitro dicing and synthetic molecules are reported. Mechanistically, introduction of short pieces of double stranded RNA (dsRNA) and small or short interfering RNA (siRNA) into the cytosol, may initiate the pathway culminating targeted degradation of the specific cellular mRNA, i.e., the target mRNA of the gene transcript to be silenced according to the present invention. Another RNAi molecule are micro RNAs or miRNAs. In spite of similarity in size (20-24 nt), miRNA differ from siRNA in precursor structures, pathway of biogenesis, and modes of action. Artificial miRNAs are known to the skilled person. Both, miRNAs and siRNAs are known to be important regulators of gene expression in plants.

In another embodiment, an RNAi and self-cleaving hammerhead ribozyme may be used to achieve a desired modulation, also on a DNA level (Li Z., Rana T. M. Therapeutic targeting of microRNAs: current status and future challenges. Nat Rev Drug Discov. 2014; 13(8):622-638.). These reagents allow for targeted control of gene expression by promoting the removal of specific mRNAs from the cytoplasm. The hammerhead ribozyme (HHR), first seen in tobacco ringspot virus satellite RNA, is an example of small nucleolytic RNA molecules capable of self-cleavage (i.e., the name ribozymes). Other autocatalytic (self-cleaving type) small RNA molecules are twister, twister sister, pistol, and hatchet ribozyme. HHRs are composed of a conserved central sequence with three radiating helical domains. Natural HHRs are not true ribozymes as they are only capable of carrying out a single self-cleavage reaction. Synthetic HHRs have been engineered to overcome this by separating the HHR into two components: ribozyme (the part of the HHR which remains unchanged) and substrate (the target sequence that will be cleaved). Another class of suitable modulators for the purpose of the present disclosure are riboswitches. Riboswitches are RNA elements that modulate mRNA expression through binding of a ligand, which is typically a small organic molecule or ion, to its aptamer domain. In one embodiment, the use of a riboswitch might be of interest to modify CPL3 expression in a tightly controlled manner. Meanwhile, a variety of ribozymes and riboswitches types including DNAzymes and temperature-sensitive ribozymes is available to the skilled person (Guha T K, Wai A, Hausner G. Programmable Genome Editing Tools and their Regulation for Efficient Genome Engineering. Comput Struct Biotechnol J. 2017; 15:146-160. Published 2017 Jan. 12. doi:10.1016/j.csbj.2016.12.006).

The silencing construct may thus be an RNAi silencing construct. The silencing construct may be presented as vector for expression in a cell of interest, or the silencing construct can be prepared ex vivo to be added to a cell, material, tissue, organ or whole organism of interest. In one embodiment, the silencing construct may be operatively linked to a constitutively active promoter. In another embodiment, the silencing construct may be operatively linked to an inducible promoter to control expression of the construct depending on an inducer. Controlled expression of the silencing construct can allow targeted regulation of expression levels of a target protein of interest to be silenced in a temporal (e.g., only during a certain phase of plant development) and/or spatial (e.g., certain plant organs, tissues, cells, or special compartments/organelles) manner. In particular, due to the fact that the target sequences to be silenced play a critical role in plant immunity, it may have significant advantages to restrict silencing in a tempo-spatial and dose dependent way to avoid severe negative effects of the knock-out of plant immunity effectors like CPL proteins due to their highly relevant roles in defence and development.

In a preferred embodiment, a silencing construct of the present invention may be introduced in a transient manner which additionally guarantees that no genetic material is introduced into a plant or plant cell in an inheritable way.

In yet another embodiment, the silencing construct or the RNAi molecule does not share substantial sequence identity with other genomic regions in the genome of the plant cell, tissue, organ, whole plant, or plant material according to the present disclosure is to be understood as a molecule designed in silico based on the information of a sequence to be silenced in combination with the information of the genome to be modified so that the RNAi molecule does not comprise long stretches of identity to other regions in the genome other than the region to be modulated to avoid off-target effects. Usually, the identity to the sequence to be silenced will thus be very high, i.e., at least 90%, 91%, 92%, 93%, 94%, and more preferably at least 95%, 96%, 97%, 98% or even higher than 99%. The substantial identity to other genomic regions in the genome of the plant cell, tissue, organ, whole plant, or plant material will usually be below 25 bp, preferably below 20 bp, 19 bp, 18 bp, 17 bp, 16 bp, more preferably below 15 bp, 14 bp, 13 bp, 12 bp, 11 bp and most preferably below 10 bp of contiguous stretches aligning with another region of a genome of interest.

In another embodiment, a plant having pathogen resistance may be obtained by modification of the native regulatory sequence(s), wherein the modification may be a transient or stable modification of a regulatory sequence, preferably wherein (i) the modification is introduced by a site-directed DNA modifying enzyme, or wherein (ii) a modified site-directed DNA modifying enzyme mediates the modification, preferably the inhibition, of a regulatory sequence, or wherein (iii) the modification is introduced by random mutagenesis, preferably wherein the random mutagenesis is selected from chemical-induced mutatgenesis or irradiation-induced mutagenesis. Depending on the plant to be modified, both site-directed and random mutagenesis, or a combination thereof, can represent suitable options.

According to the present disclosure, at least one site-directed DNA or RNA modifying enzyme (SDE), or a sequence encoding the same, or a complex comprising the same, can be utilized to modify a CPL3 gene, or a regulatory sequence of a CPL3 gene, or a CPL3 encoded RNA sequence, in a targeted way by at least one SDE, or a catalytically active fragment thereof, or a complex comprising a SDE, or a nucleic acid sequence encoding the same. Targeted genome editing has meanwhile become a powerful genetic tool for studying gene function or for modifying genomes in a precise way. Genome editing tools include meganucleases, zinc finger nucleases (ZFNs), transcription activator-like effector nucleases (TALENs), clustered regularly interspaced short palindromic repeat (CRISPR)-associated nuclease Cas9, and targetrons (Guha et al., supra). SDEs and related constructs or tools relevant to achieve a targeted genome editing event in a given genome are known to the skilled person and can be adapted to a target cell of interest. All of the aforementioned tools can achieve precise genetic modifications by inducing targeted DNA double-strand breaks (DSBs). Depending on the cell cycle stage, as well as the presence or absence of a repair template with homologous terminal regions, the DSB may then be repaired by either non-homologous end joining repair system (NHEJ), or the homologous recombination-based double-strand break repair pathway (HDR).

According to the present disclosure, the at least one site-directed DNA modifying enzyme may thus be selected from at least one of a meganuclease, a ZFN, a TALEN, an Argonaute protein, wherein non-limiting examples of Argonaute proteins include *Thermus thermophilius* Argonaute (TtAgo), *Pyrococcus furiosus* Argonaute (PfAgo), *Natronobacterium gregoryi* Argonaute (NgAgo), homologs thereof, or modified versions thereof, RNA-guided nucleases, wherein non-limiting examples of RNA-guided nucleases include the CRISPR associated nucleases, such as CasI, CasIB, Cas2, Cas3, Cas4, Cas5, Cas6, Cas7, Cas8, Cas9 (also known as CsnI and CsxI2), CasIO, CsyI, Csy2, Csy3, Cse1, Cse2, CscI, Csc2, Csa5, Csn2, Csm2, Csm3, Csm4, Csm5, Csm6, Cmr1, Cmr3, Cmr4, Cmr5, Cmr6, CsbI, Csb2, Csb3, CsxI7, CsxI4, CsxIO, CsxI6, CsaX, Csx3, CsxI, CsxI5, CsfI, Csf2, Csf3, Csf4, CpfI, CasX, CasY, Mad7, homologs thereof, or modified versions thereof and engineered RNA-guided nucleases (RGNs), a restriction endonuclease, including FokI or a variant thereof, a recombinase, or two site-specific nicking endonucleases, or a base editor, or any variant or catalytically active fragment of the aforementioned effectors, wherein the at least one site-directed DNA modifying enzyme induces a genome modification such as a double-stranded DNA break (DSB) or single-strand DNA break, or a targeted nucleotide exchange at the target site of a genomic sequence. In some embodiments, breaks or nicks in the target DNA sequence are repaired by the natural processes of homologous recombination (HR) or non-homologous end-joining (NHEJ). In some embodiments, sequence modifications occur at or near the cleaved or nicked sites, which can include deletions or insertions that result in modification of the nucleic acid sequence, or integration of exogenous nucleic acids by homologous recombination or NHEJ.

In one embodiment according to the aspects of the present disclosure directed to the targeted mutation of at least one nucleotide sequence encoding a CPL3 protein, or directed to the modification of a regulatory sequence of at least one CPL3 protein encoding sequence, the at least one site-directed DNA modifying enzyme is a CRISPR-based nuclease, wherein the CRISPR-based nuclease comprises a site-specific DNA binding domain, wherein the at least one CRISPR-based nuclease, or the nucleic acid sequence encoding the same, is selected from the group comprising (a) Cas9, including SpCas9, SaCas9, SaKKH-Cas9, VQR-Cas9, St1Cas9, (b) Cpf1, including AsCpf1, LbCpf1, FnCpf1, (c) CasX, or (d) CasY, or any variant or derivative of the aforementioned CRISPR-based nucleases, optionally wherein the at least one CRISPR-based nuclease comprises a mutation in comparison to the respective wild-type sequence so that the resulting CRISPR-based nuclease is converted to a single-strand specific DNA nickase, or to a DNA binding effector lacking all DNA cleavage ability.

In other embodiments, a CRISPR-Cas13 RNA editing complex may be used to alter the RNA coding potential in a programmable manner which allows a targeted knockdown of endogenous transcripts, preferably CPL3 transcripts, with comparable levels of knockdown as RNAi. Further, Cas13 or dead Cas13 comprising constructs can be used to exchange a RNA base, not only to achieve a transient knock-down. Additionally, RNA editing platforms are available comprising both an RNA knockdown and an RNA editing tool (Cox et al., Science. 2017 Nov. 24; 358(6366): 1019-1027). As reported for RNAi constructs above, the modulation on RNA level may allow a temporally controlled modulation of expression levels and may have advantages over the creation of knock-outs, in particular due to the fact that CPL3 and CPL3 homologs represent central molecules in plant immunity so that a full knock-out or an uncontrolled modulation may result in undesired side effects or even cell death.

Another class of genome editing tools suitable for the various embodiments of the present invention are base editors.

Base editors, including BEs (base editors mediating C to T conversion) and ABEs (adenine base editors mediating A to G conversion), are powerful tools to introduce direct and programmable mutations of all four transitions to the DNA without the need for double-stranded cleavage (Komor et al., Nature, 2016, 533(7603), 420-424; Gaudelli et al., Nature, 2017, 551, 464-471). In general, base editors are composed of at least a DNA targeting module and a catalytic domain that deaminates cytidine or adenine. There are three BE versions described in Komor et al., 2016 (vide supra), namely BE1, BE2 and BE3, with BE3 showing the highest efficiency of targeted C to T conversion, resulting in up to 37% of desired C to T conversion in human cells. BE3 is composed of APOBEC-XTEN-dCas9(A840H)-UGI, where APOBEC1 is a cytidine deaminase, XTEN is 16-residue linker, dCas9(A840H) is a nickase version of Cas9 that nicks the non-edited strand and UGI is an Uracil DNA glycosylase inhibitor. In this system, the BE complex is guided to the target DNA by the sgRNA, where the cytosine is then converted to uracil by cytosine deamination. The UGI inhibits the function of cellular uracil DNA glycosylase, which catalyzes removal of uracil from DNA and initiates base-excision repair (BER). Nicking of the unedited DNA strand helps to resolved the U:G mismatch into desired U:A and T:A products.

ABEs were first developed by Gaudelli et al., 2017 (supra) for converting A-T to G-C. A transfer RNA adenosine deaminase was evolved to operate on DNA, which catalyzes the deamination of adenosine to yield inosine, which is read and replicated as G by polymerases. By fusion of the evolved adenine deaminase and a Cas9 module, ABEs described in Gaudelli et al., 2017 (supra) showed about 50% efficiency in targeted A to G conversion.

All four transitions of DNA (A-T to G-C and C-G to T-A) are possible as long as the base editors can be guided to the target place. Base editors convert C or A at the non-targeted strand of the sgRNA.

According to the present disclosure, the BE may be specifically optimized for use in a plant cell system, including the use of codon-optimized sequences for a plant or plant cell of interest, and further including the use of a plant specific promoters, for example, an ubiquitin promoter, in case the construct is provided as expression cassette.

In one embodiment according to the various aspects of the present invention, the aspect of modulating a nucleotide sequence encoding an endogenous C-terminal domain phosphatase-like 3 (CPL3) protein or a regulatory sequence thereof can be achieved by specifically combining transient and stable modulation techniques, i.e., by combining any one of introducing as alternative (i) one or more mutation(s) of the nucleotide sequence encoding a CPL3 protein, preferably wherein the one or more mutation(s) has/have a dominant negative effect, preferably wherein the one or more mutation(s) cause(s) an alteration of the amino acid sequence of the conserved catalytic domain of the CPL3 protein comprising the DXDXT/V motif; and/or introducing as alternative (ii) one or more silencing construct(s) directed to one or more endogenous nucleotide sequence(s) encoding a CPL3 protein, preferably directed to all endogenous nucleotide sequences encoding a CPL3 protein; and/or introducing as alternative (iii) a modification of the native regulatory sequence(s) of one or more nucleotide sequence(s) encoding an endogenous CPL3 protein, preferably of all native regulatory sequence(s) of the nucleotide sequences encoding an endogenous CPL3 protein, wherein the modification causes a reduced expression rate of the one or more nucleotide sequence(s) encoding an endogenous CPL3 protein.

For example, in one embodiment, one CPL3 allele, or a regulatory sequence thereof, or a RNA transcript thereof, in a polyploid plant may be stably mutated, wherein another CPL3 allele, or a regulatory sequence thereof, may be transiently modified by a silencing construct according to the present invention. Depending on the total amount of different CPL3 alleles present in a germplasm, this strategy can provide the best dosage effect to achieve optimum pathogen resistance, whilst maintaining normal plant growth and development characteristics as mediated by CPL3 alleles or the proteins encoded thereof and the corresponding regulatory sequences.

In another embodiment, different CPL3 alleles, or the regulatory sequences thereof, or a RNA transcript thereof, may be targeted by the same of the above described alternatives (i) to (iii), depending on the plant and their CPL3 genotype to be modified.

Therefore, any of the above alternatives (i) to (iii) may be used alone or in combination, either simultaneously, or subsequently, wherein subsequently may include the subsequent introduction into the same plant or plant cell, but it may also include the subsequent use in different plant or plant cell generations. For example, the first modulation can be achieved in a first plant or plant cell. Next, a progeny of said plant or plant cell may be obtained and the subsequent introduction according to any of the above alternatives (i) to (iii) may then be an introduction into the progeny plant or plant cell.

In certain embodiments, fusion molecules comprising one or more of the modulation tools according to alternatives (i) to (iii) may be used.

For certain applications, transient and/or non-transgenic methods and modes of introduction of the various constructs according to the present disclosure may be preferred.

In one embodiment according to the various aspects of the present invention, the modification or mutation may be performed by oligonucleotide directed mutagenesis (ODM), chemical mutagenesis, e.g., TILLING, for example, by applying an efficient amount of a mutagenic agent, preferably ethylmethane sulfonate, N-ethyl-N-nitrosourea, or by radiation.

TILLING, initially a functional genomics tool in model plants, has been extended to many plant species and become of paramount importance to reverse genetics in crops species. A major recent change to TILLING has been the application of next-generation sequencing (NGS) to the process, which permits multiplexing of gene targets and genomes. NGS will ultimately lead to TILLING becoming an in silico procedure. Because it is readily applicable to most plants, it remains a dominant non-transgenic method for obtaining mutations in known genes and thus represents a readily available method for non-transgenic approaches according to the methods of the present invention. As it is known to the skilled person, TILLING usually comprises the chemical mutagenesis, e.g., using ethyl methanesulfonate (EMS), N-ethyl-N-nitrosourea, or UV light induced modification of a genome of interest, together with a sensitive DNA screening-technique that identifies single base mutations in a target gene, or a regulatory sequence thereof. The skilled person can thus define an efficient amount of a mutagenic agent to obtain a sufficient number of mutagenic events whilst maintaining genomic integrity for a given plant genome of interest.

SSNs and ODM mutagenesis both are suitable techniques for precision genome engineering in plant cells as well and are suitable to induce a modification or mutation according to the various aspects of the present disclosure. As it is known to the skilled person, ODM offers a rapid, precise and non-transgenic breeding alternative for trait improvement in agriculture to address this urgent need. ODM is a precision genome editing technology, which uses oligonucleotides to make targeted edits in plasmid, episomal and chromosomal DNA of bacterial, fungal, mammalian and plant systems.

According to another aspect, a cell, tissue, organ, seed or material of a plant according to the various aspects and embodiments disclosed herein may be obtained or may be used as starting point for obtaining a pathogen resistant plant, cell, tissue, organ, seed or material of a plant.

In a second aspect, a nucleic acid molecule comprising a nucleotide sequence encoding for a C-terminal domain phosphatase-like 3 (CPL3) protein, wherein the nucleotide sequence is selected from the group consisting of: (a) a nucleotide sequence set forth in SEQ ID NOs: 2-10 or a homologous, orthologous or paralogous sequence thereof; (b) nucleotide sequence having at least 80%, at least 85%, at least 90%, at least 92%, at least 94%, at least 95%, at least 96%, at least 97%, at least 98% or at least 99% identity to one of the nucleotide sequences as defined in (a), or (c) a nucleotide sequence encoding for an amino acid sequence set forth in SEQ ID NOs: 11-19; (d) a nucleotide sequence encoding for an amino acid sequence having at least 80%, at least 85%, at least 90%, at least 92%, at least 94%, at least 95%, at least 96%, at least 97%, at least 98% or at least 99% identity to one of the sequences set forth in SEQ ID NOs: 11-19, or (e) a nucleotide sequence hybridizing with a nucleotide sequence complementary to the nucleotide sequence as defined in (a)-(d) under stringent conditions, wherein the nucleotide sequence comprises at least one mutation capable of conferring or increasing resistance to a pathogen in plant in which the nucleic acid molecule is expressed, preferably wherein the pathogen may be a hemibiotrophic fungus, more preferably the pathogen is a hemibiotrophic fungus selected from the group consisting of: *Zymoseptoria tritici, Setosphaeria turcica, Fusarium* spp. *Fusarium graminearum, Colletotrichum* spp. such as *Colletotrichum graminicola, Magnaporthe grisea, Magnaporthe oryzae, Phytophthora infestans*, or preferably wherein the pathogen may be a fungus selected from *Cercospora* spp., preferably *Cercospora beticola* or *Cercospora zeae-mayidis*, which may be used to obtain a pathogen resistant plant, cell, tissue, organ, seed or material of a plant.

*Cercospora* is the cause of leaf spot diseases in various plants, but it also causes disease on: alfalfa, asparagus, banana, brassicas, *Cannabis*, carrot, celery, cereals, coffee, cucumber, figs, geraniums, grapes, grasses, hazel, hops, lentil, lettuce, mango, millet, orchids, *papaya*, peanut, pear, peas, peppers, potato, roses, sorghum, soybean, spinach, strawberry, sugar beet, sugarcane (the spots merge into stripes; so the disease is called 'black stripe'), sycamore, tobacco, watermelon, and many wild plants and ornamentals and thus represents a relevant fungal pathogen.

In one embodiment, the mutation may be a mutation of the nucleotide sequence encoding a CPL3 protein, preferably a mutation having a dominant negative effect, preferably wherein the mutation causes an alteration of the amino acid sequence of the conserved catalytic domain of the CPL3 protein comprising the DXDXT/V motif, more preferably a mutation of the nucleotide sequence encoding a CPL3 protein causing the substitution of Asp by Ala at position 928 referenced to SEQ ID NO: 19, at position 944 referenced to SEQ ID NO: 14, at position 949 referenced to SEQ ID NO: 11, at position 944 referenced to SEQ ID NO: 14, at position 949 referenced to SEQ ID NO: 11, at position 953 referenced to SEQ ID NO: 12, at position 910 referenced to SEQ ID NO: 13, at position 890 referenced to SEQ ID NO: 18, at position 938 referenced to SEQ ID NO: 15, at position 929 referenced to SEQ ID NO: 16, at position 938 referenced to SEQ ID NO: 17.

According to the second and all further aspects of the present disclosure, one or more of the same, or one or more different mutation(s) may be effected depending on the amount and nature of CPL3 alleles present in the genome of a target plant of interest. In certain embodiments, more than one mutation may be desired to obtain a phenotype of optimum pathogen resistance without side effects, like, for example, impeded plant growth.

In a further aspect, a method of generating a plant having pathogen resistance or a plant cell, tissue, organ, seed, or plant material thereof, may be used based on the above findings on CPL3 modulation and its effect on pathogen resistance, wherein the method may comprise the steps of: (i) providing one or more silencing construct(s) according to the embodiments disclosed for the first aspect, or one or more sequences encoding the same; (ii) modifying a plant cell, tissue, organ, plant, seed, or plant material by introducing the one or more silencing construct(s) or the sequence encoding the same of (i), into the genome of said plant cell, tissue, organ, plant, seed, or plant material; and (iii) obtaining the modified plant cell, tissue, organ, plant, seed or plant material, (iv) optionally, regenerating a plant from the plant cell, tissue, organ or plant material or growing a seed on a plant obtained in (iii), wherein the plant cell, tissue, organ, plant, seed or plant material obtained in (iii), the plant regenerated in (iv) or the seed grown in (iv) may comprise the introduced one or more silencing construct(s) or the sequence encoding the same and thereby has pathogen resistance.

In a further aspect, the method of generating a plant having pathogen resistance or a plant cell, tissue, organ, seed, or plant material thereof, may comprise the steps of: (i) providing at least one site-directed DNA modifying enzyme, or a sequence encoding the same, and optionally at least one DNA repair template, wherein the at least one site-directed DNA modifying enzyme and optionally the at least one DNA repair template: (a) may be directed or targeted to the nucleotide sequence encoding the CPL3 protein as defined in the first aspect above; or (b) may be directed or targeted to regulatory sequence of at least one CPL3 protein encoding nucleotide sequence as defined in the first aspect above; (ii) introducing the at least one site-directed DNA modifying enzyme or a sequence encoding the same, and optionally the at least one DNA repair template into the plant cell, tissue, organ, plant, or plant material; (iii) mutating or modifying the nucleotide sequence encoding the CPL3 protein or the regulatory sequence thereof in the genome of the plant cell, tissue, organ, plant, or plant material and obtaining a mutant or modified population of plant cells, tissues, organs, plants, or plant materials; (iv) optionally: screening the population for a dominant negative mutation, thereby conferring or increasing pathogen resistance, or screening the population for a mutation or modification in the nucleotide sequence encoding the CPL3 protein or the regulatory sequence thereof; (v) identifying and thereby obtaining a plant cell, tissue, organ, plant, or plant material having pathogen resistance.

In certain embodiments, a functional fragment or truncated or modified version of a site-directed DNA modifying enzyme, or a sequence encoding the same, may be used.

A mutant or modified population of plant cells implies that at least one cell in a population comprises a targeted mutation or modification, wherein different cells in the population may comprise a different set of mutations or modifications in their respective genomes. The skilled person can easily identify the mutations or modifications as obtained by the various methods disclosed herein using common techniques like PCR etc.

In yet a further aspect, the method of generating a plant having pathogen resistance or a plant cell, tissue, organ, seed, or plant material thereof, may comprise a TILLING approach and may thus comprise the steps of: (i) subjecting the plant cell, tissue, organ, plant, or plant material, preferably seeds of a plant, to an efficient amount of a mutagenic agent, preferably ethylmethane sulfonate, N-ethyl-N-nitrosourea, or radiation, (ii) obtaining a mutagenized population of plant cells, tissues, organs, plants, or plant materials, optionally by growing plants from the mutagenized population; (iii) screening the mutagenized population for pathogen resistance, optionally by isolating and analyzing genomic DNA from the plants having pathogen resistance; (iv) identifying and obtaining a modified plant cell, tissue, organ, plant, or plant material having pathogen resistance.

In still another aspect, a method of generating a plant having pathogen resistance or a plant cell, tissue, organ, seed, or plant material thereof, may comprise the steps of: (i) transforming at least one plant cell with at least one nucleic acid molecule according to the second aspect disclosed herein; and (ii) regenerating and thus obtaining a plant cell, tissue, organ, plant, or plant material having pathogen resistance.

Depending on the pathogen and the plant of interest, the skilled person can identify suitable assays to determine whether the modulation according to the present invention is suitable to increase pathogen resistance.

Any screening according to the various aspects and embodiments disclosed herein may, for example, be done by means of molecular biology, for example, using a PCR technique, or using a probe, or by phenotypic screening, for example, relying on a visible and traceable marker.

In a further aspect, the nucleic acid molecule according to the second aspect, or a silencing construct as defined in the first aspect, or the modification of a native regulatory sequence, may be used, alone or in combination, for the generation of a plant cell, tissue, organ, whole plant, or plant material having pathogen resistance, or for conferring or increasing pathogen resistance of in a plant, plant cell, tissue, organ, whole plant, or plant material.

In yet another aspect, a method of increasing pathogen resistance in, or a method of conferring pathogen resistance to a plant, a plant cell, tissue, organ or material may be provided, wherein the method may comprise modulation of a nucleotide sequence encoding an endogenous C-terminal domain phosphatase-like 3 (CPL3) protein or a regulatory sequence thereof, or modulation of the transcription of an endogenous CPL3 protein, wherein modulation is achieved by (i) one or more mutation(s) of the nucleotide sequence encoding a CPL3 protein, preferably wherein the one or more mutation(s) has/have a dominant negative effect, preferably wherein the one or more mutation(s) cause(s) an alteration of the amino acid sequence of the conserved catalytic domain of the CPL3 protein comprising the DXDXT/V motif; and/or (ii) one or more silencing construct(s) directed to one or more endogenous nucleotide sequence(s) encoding a CPL3 protein, preferably directed to all endogenous nucleotide sequences encoding a CPL3 protein; and/or (iii) a modification of the native regulatory sequence(s) of one or more nucleotide sequence(s) encoding an endogenous CPL3 protein, preferably all nucleotide sequences encoding an endogenous CPL3 protein, wherein the modification causes a reduced expression rate of the one or more nucleotide sequence(s) encoding an endogenous CPL3 protein may be provided. The above aspect thus covers three different modes (i) to (iii) for a targeted modulation, which may be used alone or in combination to obtain a pathogen resistant plant. According to this aspect, any one of the alternative modes of modulation according to (i) to (iii) can be used alone or in combination to achieve increased pathogen resistance, or to achieve pathogen resistance in a non-resistant plant.

In certain embodiments, it may be suitable to combine different transient and/or stable modes of modulation to obtain a maximum increase in pathogen resistance not negatively influencing the normal plant growth and development, which may depend on the total number of CPL3 alleles present in a given plant or plant cell of interest.

In yet a further aspect, the findings of the above aspects and embodiments can be favorably used for a method to identify a pathogen resistant plant, plant cell, tissue organ or material. In one embodiment, specific mutations or modifications according to the present disclosure can be used to generate a mutant or modified population of a plant, plant cell, tissue organ or material, or to identify further mutations in a relevant CPL3 gene or a regulatory sequence thereof based on the CPL3 target sequence disclosed herein and its implication for pathogen resistance in a variety of major crop plants. Particularly, mutations in a sequence homologous to the CPL3 genes/alleles or regulatory sequences as disclosed and identified herein can be identified based on the knowledge of relevant mutations and their implications for pathogen resistance in a plant. For example, comparable consensus sequences in CPL3 homologous genes can be identified to identify and thus provide further candidates involved in the modulation, preferably the increase, of pathogen resistance in a plant genome, preferably the genome of a major crop plant.

According to the various aspects and embodiment of the present disclosure, the part of the plant or plant material, or a plant cell to be mutated or modified, may be selected and optionally isolated from the group consisting of leaves, stems, roots, emerged radicles, flowers, flower parts, petals, fruits, pollen, pollen tubes, anther filaments, ovules, embryo sacs, egg cells, ovaries, zygotes, embryos, zygotic embryos, somatic embryos, apical meristems, vascular bundles, pericycles, seeds, roots, and cuttings.

According to the various aspects and embodiments disclosed herein, the plant may be, or may originate from, a plant species selected from the group consisting of: *Hordeum vulgare, Hordeum bulbosum, Sorghum bicolor, Saccharum officinarium, Zea mays, Setaria italica, Oryza minuta, Oriza sativa, Oryza australiensis, Oryza alta, Triticum aestivum, Secale cereale, Malus domestica, Brachypodium distach-yon, Hordeum marinum, Aegilops tauschii, Daucus glochidiatus, Beta vulgaris, Daucus pusillus, Daucus muricatus, Daucus carota, Eucalyptus grandis, Nicotiana sylvestris, Nicotiana tomentosiformis, Nicotiana tabacum, Solanum lycopersicum, Solanum tuberosum, Coffea canephora, Vitis vinifera, Erythrante guttata, Genlisea aurea, Cucumis sativus, Morus notabilis, Arabidopsis arenosa, Arabidopsis lyrata, Arabidopsis thaliana, Crucihimalaya himalaica, Crucihimalaya wallichii, Cardamine flexuosa, Lepidium virginicum, Capsella bursa pastoris, Olmarabidopsis pumila, Arabis hirsute, Brassica napus, Brassica oeleracia, Brassica rapa, Raphanus sativus, Brassica juncea, Brassica nigra, Eruca vesicaria* subsp. *sativa, Citrus sinensis, Jatropha curcas, Populus trichocarpa, Medicago truncatula, Cicer yama-shitae, Cicer bijugum, Cicer arietinum, Cicer reticulatum, Cicer judaicum, Cajanus cajanifolius, Cajanus scarabaeoides, Phaseolus vulgaris, Glycine max, Astragalus sinicus, Lotus japonicas, Torenia foumieri, Allium cepa, Allium fistulosum, Allium sativum,* and *Allium tuberosum.*

The various constructs for modulation of a nucleotide sequence encoding an endogenous C-terminal domain phosphatase-like 3 (CPL3) protein or a regulatory sequence thereof, or by modulation of the transcription of an endogenous CPL3 protein, or for modulating any combination of more than one CPL3 gene or allele, or the regulatory sequence or the transcript thereof, may be introduced into a plant or plant cell, tissue, organ or material by any biological, chemical or physical means. Methods of introducing biomolecules into a plant or plant cell, tissue, organ or plant material are well known in the art.

In one embodiment, a biological vector system in the context of VIGS for *Agrobacterium*-based transformation may include, but is not limited to, e.g., Maize Streak Virus (MSV), Barley Stripe Mosaic Virus (BSMV), Brome Mosaic virus (BMV; accession numbers: RNA 1: X58456; RNA2: X58457; RNA3: X58458), Maize Stripe Virus (MSpV), Maize Rayado Fino virus (MYDV), Maize Yellow Dwarf Virus (MYDV), Maize Dwarf Mosaic Virus (MDMV) as further detailed below under Example 1.

Further vector systems suitable for the present disclosure can generally be selected from positive strand RNA viruses of the family Benyviridae, e.g., Beet necrotic yellow vein virus (accession numbers: RNA 1: NC_003514; RNA2: NC_003515; RNA3: NC_003516; RNA4: NC_003517) or of the family Bromoviridae, e.g., viruses of the genus *Alfalfa mosaic virus* (accession numbers: RNA1: NC_001495; RNA2: NC_002024; RNA3: NC_002025) or of the genus *Bromovirus*, e.g., BMV (supra), or of the genus *Cucumovirus*, e.g., Cucumber mosaic virus (accession numbers: RNA1: NC_002034; RNA2: NC_002035; RNA3: NC_001440), or of the genus *Oleavirus*, dsDNA viruses of the family Caulimoviridae, particularly of the family Badnavirus or Caulimovirus, e.g., different Banana streak viruses (e.g., accession numbers: NC_007002, NC_015507, NC_006955 or NC_003381) or Cauliflower mosaic virus (accession number: NC_001497), or viruses of the genus *Cavemovirus, Petuvirus, Rosadnavirus, Solendovirus, Soymovirus* or *Tungrovirus*, positive strand RNA viruses of the family Closteroviridae, e.g., of the genus *Ampelovirus, Crinivirus*, e.g., Lettuce infectious yellows virus (accession numbers: RNA 1: NC_003617; RNA2: NC_003618) or Tomato chlorosis virus (accession numbers: RNA 1: NC_007340; RNA2: NC_007341), Closterovirus, e.g., Beet yellows virus (accession number: NC_001598), or Velarivirus, single-stranded DNA (+0 viruses of the family Geminiviridae, e.g., viruses of the family Becurtovirus, Begomovirus, e.g., Bean golden yellow mosaic virus, Tobacco curly shoot virus, Tobacco mottle leaf curl virus, Tomato chlorotic mottle virus, Tomato dwarf leaf virus, Tomato golden mosaic virus, Tomato leaf curl virus, Tomato mottle virus, or Tomato yellow spot virus, or Geminiviridae of the genus *Curtovirus*, e.g., Beet curly top virus, or Geminiviridae of the genus *Topocuvirus, Turncurtvirus* or *Mastrevirus*, e.g., Maize streak virus (supra), Tobacco yellow dwarf virus, Wheat dwarf virus, positive strand RNA viruses of the family Luteoviridae, e.g., of the genus *Luteovirus*, e.g., Barley yellow dwarf virus-PAV (accession number: NC_004750), or of the genus *Polerovirus*, e.g., Potato leafroll virus (accession number: NC_001747), single-stranded DNA viruses of the family Nanoviridae, comprising the genus *Nanovirus* or *Babuvirus*, double-stranded RNA viruses of the family Partiviridae, comprising inter alia the families Alphapartitivirus, Betapartitivirus or Deltapartitivirus, viroids of the family Pospiviroidae, positive strand RNA viruses of the family Potyviridae, e.g., comprising the genus *Brambyvirus, Bymovirus, Ipomovirus, Macluravirus, Poacevirus*, e.g., *Triticum* mosaic virus (accession number: NC_012799), or Potyviridae of the genus *Potyvirus*, e.g., Beet mosaic virus (accession number: NC_005304), Maize dwarf mosaic virus (accession number: NC_003377), Potato virus Y (accession number: NC_001616), or *Zea* mosaic virus (accession number: NC_018833), or Potyviridae of the genus *Tritimovirus*, e.g., Brome streak mosaic virus (accession number: NC_003501) or Wheat streak mosaic virus (accession number: NC_001886), single-stranded RNA viruses of the family Pseudoviridae, e.g., of the genus *Pseudovirus*, or *Sirevirus*, double-stranded RNA viruses of the family Reoviridae, e.g., Rice dwarf virus (accession numbers: RNA1: NC_003773; RNA2: NC_003774; RNA3: NC_003772; RNA4: NC_003761; RNAS: NC_003762; RNA6: NC_003763; RNA7: NC_003760; RNAB: NC_003764; RNA9: NC_003765; RNA10: NC_003766; RNA11: NC_003767; RNA 12: NC_003768), positive strand RNA viruses of the family Tombusviridae, e.g., comprising the genus *Alphanecrovirus, Aureusvirus, Betanecrovirus, Carmovirus, Dianthovirus, Gallantivirus, Macanavirus, Machlomovirus, Panicovirus, Tombusvirus, Umbra virus* oder *Zeavirus*, e.g., Maize necrotic streak virus (accession number: NC_007729), or positive strand RNA viruses of the family Virgaviridae, e.g., viruses of the genus *Furovirus, Hordeivirus*, e.g., Barley stripe mosaic virus (accession numbers: RNA1: NC_003469; RNA2: NC_003481; RNA3: NC_003478), or of the genus *Pecluvirus, Pomovirus, Tobamovirus* or *Tobravirus*, e.g., Tobacco rattle virus (accession numbers: RNA1: NC_003805; RNA2: NC_003811), as well as negative strand RNA viruses of the order Mononegavirales, particularly of the family Rhabdoviridae, e.g., Barley yellow striate mosaic virus (accession number: KM213865) or Lettuce necrotic yellows virus (accession number/specimen: NC_007642/AJ867584), positive strand RNA viruses of the order Picornavirales, particularly of the family Secoviridae, e.g., of the genus *Comovirus, Fabavirus, Nepovirus, Cheravirus, Sadwavirus, Sequivirus, Torradovirus*, or *Waikavirus*, positive strand RNA viruses of the order Tymovirales, particularly of the family Alphaflexiviridae, e.g., viruses of the genus *Allexivirus, Lolavirus, Mandarivirus*, or *Potexvirus*, Tymovirales, particularly of the family Betaflexiviridae, e.g., viruses of the genus *Capillovirus, Carla virus, Citrivirus, Foveavirus, Tepovirus*, or *Vitivirus*, positive strand RNA viruses of the order Tymovirales, particularly of the family Tymoviridae, e.g., viruses of the order Macula virus, Marafivirus, or Tymovirus.

In another embodiment, a physical introduction means, e.g., particle bombardment, may be chosen. In yet another embodiment, a chemical introduction means, e.g., a transfection agent, can be used. Any combination of biological, physical and chemical introduction means may be used depending on the bio-molecule(s) or constructs to be introduced, and depending on the plant cell or plant to be modified. In particular, the stability of the bio-molecule to be introduced (e.g., RNA) as well as the compartment to be targeted, or the effect to be achieved (e.g., a systemic spread to be achieved, for example, by a viral vector) should be taken into consideration.

In yet a further embodiment, the methods of the present disclosure, alone or in combination, can thus be used to engineer or select plant cells, tissues, organs, materials or whole plants with enhanced pathogen resistance in particular in maize, sorghum, wheat, sugar beet, soybean and potato plants. The technical application of the present teaching elucidating the role of the central plant immunity player CPL3 is not restricted to fungal diseases but might also be used to develop insect, bacterial, nematode and/or viral resistance in major crop plants due to the fact that the signaling pathways leading to pathogen resistance as disclosed herein are also relevant for a variety of plant pathogens, in particular also including pathogenic or parasitic fungi.

In a further aspect there is provided a method for identifying a plant having pathogen resistance or a plant cell, tissue, organ, seed, or plant material thereof, comprising the steps of: (i) isolating DNA from at least one cell of the plant or of tissue, organ, seed, or plant material thereof, and (ii) detecting at least one nucleic acid molecule as defined in the second aspect above, and optionally (iii) selecting a plant comprising at least one nucleic acid molecule as defined in the second aspect above based on the detection in step (ii), and optionally (iv) breeding progeny having pathogen resistance through crossing of the plant selected in step (iii) with another plant, preferably of the same species, and thereby introducing the at least one nucleic acid molecule detecting in step (ii) in to the genome of the progeny.

The present invention will now be illustrated by reference to the following Examples, which are not construed to limit the scope of the present invention.

EXAMPLES

Example 1A: CPL3 Downregulation in Wheat Results in Increased Resistance Against the Hemibiotrophic Fungal Pathogen *Zymoseptoria tritici*

Two silencing constructs targeting all three homologues of TaCPL3 for virus induced gene silencing (VIGS) experiments in wheat (SEQ ID NO: 21 and 22) were specifically developed. The two silencing constructs TaCPL3_fragA and TaCPL3_fragB were specifically designed for having high homology (>95% identity) to all three TaCPL3 homologues at the same time. At the same time, specific efforts were made to avoid large stretches of homology to other coding regions in the wheat genome to avoid undesired off-target effects. Preferably, no more than 20 bp of contiguous identity should be present to another region in the genome, more preferably as few identities as possible to any off-target region should be present.

For the VIGS experiments the protocol described in Yuan et al. (2011, Plos One, 6(10), e26468) was used. Suitable vector systems for *Agrobacterium* based transformation suitable for the purpose of the present invention are well known in the art and include, but are not limited to, e.g., MSV, BSMV, BMV, MSpV, MYDV, MYDV, or MDMV.

After transformation of *Nicotiana benthamiana* with the viral vectors encoding for the silencing constructs, leaves of wheat cultivar Taifun were subsequently transfected with sap extracted from the transformed *Nicotiana benthamiana* leaves. 14 days after transfection with the different viral constructs encoding the targeting sequences against TaCPL3-A (SEQ ID NO: 5), TaCPL3-B (SEQ ID NO: 6) and TaCPL3-D (SEQ ID NO: 7), the wheat plants were infected with *Zymoseptoria tritici* spore suspension (Millyard et al., 2016. The ubiquitin conjugating enzyme, TaU4 regulates wheat defence against the phytopathogen *Zymoseptoria tritici*. Scientific reports, 6, 35683.). The plants were kept under plastic hoods for 4 days to increase the humidity for optimal *Septoria* infection conditions. 23 days after infection, 2 infected leaves per plant were detached and incubated on agar plates. Under these conditions of high humidity pycnidia form on the leaves that were counted over an area of 2 cm per leaf 10 days after transfer to the agar plates. In addition, spores from five leaves were washed off with 10 mL of water and spores were counted using a hemocytometer. In comparison to wheat plants that were mock-inoculated, untreated or infected with an empty vector control, the wheat plants infected with CPL3-silencing constructs showed a significant reduction of pycnidia and spore count (FIG. 3).

The data demonstrate that silencing of all three CPL3 homologues in wheat leads to increased resistance against the hemibiotrophic fungal pathogen *Zymoseptoria tritici*.

Example 1B: CPL3 Downregulation in Wheat Results in Increased Resistance Against the Fungal Pathogen *Fusarium graminearum*

Two silencing constructs targeting all three homologues of TaCPL3 for virus induced gene silencing (VIGS) experiments in wheat (SEQ ID NO: 21 and 22) were tested to increase the *Fusarium graminearum* resistance of wheat. The VIGS inoculation experiments with the two silencing constructs TaCPL3_fragA and TaCPL3_fragB were done as described for example 1A.

After the onset of wheat heads two spikelets in the middle of each head were inoculated with 25 µl/25.000 spores of *Fusarium graminearum*. 10, 14 and 21 days after inoculation the bleaching of the heads by *F. graminearum* was measured (Table 8; FIG. 7).

TABLE 8

VIGS mediated gene silencing of CPL3A and CPL3B by BSMV resulted in reduced head scab symptoms of *Fusarium graminearum* infected wheat heads of the cultivar Taifun.

| Fusarium head scab symptoms | Empty vector (%) | Silencing control (%) | Untreated (%) | CPL3A (%) | CPL3B (%) |
| --- | --- | --- | --- | --- | --- |
| 10 dpi | | | | | |
| 14 dpi | 30.6 ± 15.9 | 41 ± 21.4 | 52 ± 27.7 | 20 ± 4.1 | 20.6 ± 5.8 |
| 21 dpi | 71.3 ± 25.9 | 75 ± 25.6 | 93 ± 15.7 | 23.8 ± 4.8 | 47.8 ± 23.6 |

In comparison to wheat plants that were infected with the empty vector and a silencing control or were not virus-infected (untreated), the wheat plants infected with CPL3-silencing constructs showed a strong reduction of symptoms (FIG. 8).

The data demonstrate that silencing of all three CPL3 homologues in wheat enhances resistance the *Fusarium* head scab.

Example 2: CPL3 Downregulation in Corn Results in Increased Resistance Against *Setosphaeria turcica*

For testing the effect of CPL3 downregulation on pathogen resistance in the relevant crop plant *Zea mays*, an RNAi silencing construct against ZmCPL3 was developed (FIG. 4 and SEQ ID NO: 24) and stably transformed maize plants of the A188 genotype. The ZmCPL3 silencing sequence (SEQ ID NO: 23) was specifically selected for having perfect homology to the ZmCPL3 gene and, at the same time to avoid large stretches of homology (<20 bp) to other sequences in the maize genome. Transgenic maize plants of the segregating T1 generation as well as the homozygous T2 lines along with the respective azygous sister lines (null-segregants) were tested for resistance against *Setosphaeria turcica* (Northern Corn Leaf Blight) in the greenhouse.

The experiments showed that two independent transgenic lines expressing the ZmCPL3-silencing construct were more resistant to NCLB than the respective null-segregants or the transformation genotype A188 (FIGS. 5 and 6). In the same experiments, plant height and width of the fully emerged forth leaf shortly before infection to determine if ZmCPL3 downregulation affects plant growth was measured. The results showed that there was no difference in plant growth between the ZmCPL3 RNAi transgenic plants and the respective null-segregants (FIG. 5). This finding was not necessarily expected as influencing the central plant immune effector CPL3 (in a knock-out) was reported to be associated with decreased growth and development. The inventors thus also analyzed the expression of ZmCPL3 in the transgenic line by qRT-PCR and were able to confirm that ZmCPL3 expression was reduced by the silencing constructs specifically developed.

These results confirm that downregulation of ZmCPL3 leads to increased resistance against a hemibiotrophic fungus and that downregulation of ZmCPL3 does not cause growth retardation.

Example 2B: Targeted Knock-Out of the Maize CPL3 Gene

The Zm-CPL3 sequence, A188v1_046614, was used for gene knock-out by CRISPR genome editing. In this case it has been looked for an active target site in the predicted Zm-CPL3 open reading frame (ORF) that would generate a targeted double-stranded break in the DNA. The desired outcome was DNA repair at the cut site by the NHEJ pathway leading to random deletion and/or insertions (IN-DELs) that could interrupt the normal coding sequence of the Zm-CLP3 gene. Target site activity was assayed initially by using amplicon deep sequencing and next generation sequencing (NGS—Illumina sequencing) to measure the DNA cutting frequency in maize protoplasts. The NGS data was used to identify and then select an individual target site with adequate activity for use in a maize tissue culture and transformation system for recovery of plants. Maize plants were generated after transformation with the selected target site and CRISPR constructs that demonstrated a variety of INDELs in the Zm-CPL3 gene and are likely to knock-out gene function by interruption of the coding sequence.

The Cas12a CRISPR nucleases, named Cpf1 following their initial discovery, have now been derived from a number of source organisms. In the work for the knock-out of ZmCPL3 we used a related nuclease of the Type V (CPF1-like) Cas family. The nuclease is called MAD7 due to its initial discovery in microbes from Madagascar and was obtained from INSCRIPTA™. The gene was modified for optimal maize codons in order to enhance transcription and expression of the nuclease in transformed maize tissue. Constructs were built that express the MAD7 constitutively from the Bd-Ubi promoter that could be used for both the initial protoplast characterization work as well as corn transformation experiments.

A188 protoplasts were isolated, divided into cells for transfection, and separately transfected using constructs pGEZM008-pGEZM011 that carried expression cassettes designed to constitutively express the CRISPR RNA's (crRNA) m7GEP59-m7GEP65 (Table 9). A separate construct, pGEP837, with the maize optimized MAD7 gene linked to the Bd-Ubi promoter and double 35S promoter driven green fluorescent protein gene was co-transfected with each of the crRNA constructs. In this way, each protoplast sample had the combination of constructs for constitutive expression of MAD7 and a unique crRNA with cutting activity targeted to independent sites in the Zm-CPL3 gene. The fluorescent protein was used to determine the transfection efficiency by counting fluorescent cells using a flow cytometer. FIG. 9 shows data from these experiments and each bar is the result of samples that were replicated 3 times using independent co-transfections. Two target sites stood out as having the highest activity that were targeted by crRNA's m7GEP62 and m7GEP64 and expressed by constructs pGEZM008 and pGEZM010 respectively. Based on the position in the Zm-CPL3 gene, m7GEP62 (pGEZM008) was chosen for advancement into plant transformation work.

TABLE 9

List of Zm-CPL3 crRNA sequences and their corresponding constructs used for both protoplast transfection and plant transformation. CRISPR nuclease activity, MAD7 included, requires a protospacer adjacent motif (PAM) sequence in addition to the protospacer sequence that directs where in the Zm-CPL3 that the double stranded break occurs.

| crRNA Name | PAM Sequence | Protospacer Sequence (Target) | SEQ ID NO: | Construct |
|---|---|---|---|---|
| m7GEP59 | TTTC | CTCGTCCTTGGGCGTGACCGT | 25 | pGEZM005 |
| m7GEP60 | TTTG | GTCACTGCTGCCGGGGCGGG | 26 | pGEZM006 |
| m7GEP61 | TTTC | GCTATGCCTTCAATAGCTTTG | 27 | pGEZM007 |
| m7GEP62 | TTTG | CGTGGTCGCAGGCCGTGCGGA | 28 | pGEZM008 |
| m7GEP63 | TTTG | GACTCCGACGCCCCGGAGAAG | 29 | pGEZM009 |
| m7GEP64 | TTTC | AGGTGTCTGAGAAAACCAGTT | 30 | pGEZM010 |
| m7GEP65 | TTTG | TCAGACACCTGAAACAAAGCC | 31 | pGEZM011 |

Maize (A188) transformation for genome editing was done by using a rapid regeneration protocol based on the RBP2 gene (WO 2019/238909) that promotes de-novo embryogenesis from differentiated recipient cells in immature maize embryos. Particle bombardment was used to introduce pGEMT129, pGEZM008, and pGEMT128 into recipient cells. The construct pGEMT129 has the same constitutive MAD7 gene as pGEP837, but includes the tdTomato gene which is useful in indicating how efficiently the DNA was delivered to embryos by particle bombardment. The RBP2 expression cassette with Bd-EF1 promoter is included in pGEMT128. Plates of maize immature embryos (50 ct) are bombarded 3 times with 0.6 µM gold particles (BioRad) coated by these plasmids and associated using the $CaCl_2$+spermidine protocol. Bombardments were done using the 450 PSI rupture discs in order to try to minimize cell damage. Plants were regenerated using a series of tissue culture medium changes and finally recovered in plastic containers as small, rooted corn plants. The young corn plants were sampled for molecular analysis at this stage.

base calls ambiguous. Table 10 shows the results of the process from 4 independent experiments. In each of these experiments there were 150 immature embryos bombarded and initiated in tissue culture. Regeneration of maize plants varied between 59% and 307% with the latter regenerating

TABLE 10

Transformation and genome editing frequencies of maize A188 immature embryos. Maize plants were generated from immature embryos following pGEP1054 + pGEZM008 particle bombardment. Plant leaf samples were taken and used for DNA extraction followed by PCR amplification around the target sequence. Amplicons were Sanger sequenced to identify the presence of INDEL at the m7GEP62 target site and the results of plants still in medium are indicated in the column labelled Assay 1. Plants were then transplanted to soil and recovered to the greenhouse. Surviving plants were assayed again (Assay 2) for the presence of INDEL.

| Experiment | Imm. Embryo (ct.) | Regeneration (ct.) | Assay 1 (ct.) | Assay 2 (ct.) |
|---|---|---|---|---|
| GEZM054-5 | 150 | 211 (141%) | 7 (3.3%) | 3 (1.4%) |
| GEZM054-6 | 150 | 89 (59%) | 3 (3.3%) | 2 (2.2%) |
| GEZM054-7 | 150 | 460 (307%) | 20 (6.5%) | 10 (2.1%) |
| GEZM054-8 | 150 | 159 (106%) | 7 (4.4%) | 5 (3.1%) |

Maize shoots regenerated from bombarded immature embryos were recovered into Phytatrays™ (Sigma) on medium to promote their growth and development. Containers were maintained in the Conviron growth room under long day lighting regimes and at constant temperature and humidity. Transformed maize tissue usually regenerated 1 plant per event but at a low to moderate frequency multiple plants per event were regenerated. In the case of multiple shoots per event, all of the leaf tips were sampled and pooled as one for DNA extraction. Extracted DNA was used for PCR amplification of the sequence flanking the target site (primers, FIG. 10). A portion of the PCR reactions were run on a gel to visually confirm that the amplicon was present and running at the expected size. The remaining portion of the PCR reaction was cleaned up for primer and reagents using ExoSAP-It reagent and submitted directly for Sanger sequencing. Sequence alignments to an unmodified reference sequence were used to identify the candidates with INDEL because those would demonstrate mixed trace results originating from the type of IN DEL and whether it was present on one or both alleles of the Zm-CPL3 gene. A mixed trace is the region in the sequence trace file where multiple base calls are present in each position making the multiple plants per initiated embryo. The Assay 1 column shows results of the 4 experiments and the frequency of events with detected IN DEL that were available to be advanced to the greenhouse. The column Assay 2 contains the final numbers at the T0 stage and includes the plants that survived the transfer to the greenhouse and then passed a second screen by PCR and Sanger sequencing. These will be the T0 plants most likely to yield T1 progeny with the Zm-CPL3 edits.

Sanger sequence trace files (ABI files) provide an indication of which plants to select for advancement to the greenhouse but they do not offer the resolution to provide the precise sequence at one or both Zm-CPL3 alleles in the DNA sample of the plant genome. There are a variety of methods that could be employed to demonstrate the sequence of each allele including analysis of the T1 progeny following genetic segregation of the alleles. Finally, a variety of new edits has been created (Table 11). Most of the edits were deletions as is typical for MAD7 and Cpf1 nucleases. Many of the edits shown disrupt the open reading frame of the CPL3 gene and thus the gene function will be eliminated or knocked out.

TABLE 11

Amplicon sequencing of selected maize A188 events targeting the CPL3 gene. DNA extracted from T0 plants were PCR amplified for the targeted sites in exon 1 of Zm-CPL3. Analysis resolves the INDEL's represented by the mixed trace and showed a wide variety of edits produced by this genome targeting approach. A subset of the total events generated is shown in the table.

| Experiment | T0 Event Name | Sequence |
|---|---|---|
| na | (A188 reference) | TAGCCCCAGCGGCTTAT\|TCCGCA\|CGGCCTGCGACCACGCAAA |
| GEZM054-5 | GEZM054-T811 | TAGCCCCAGCGGCTT--\|------\|CGGCCTGCGACCACGCAAA |
| GEZM054-5 | GEZM054-T821 | TAGCCCCAGCGGCTTAT\|TCC---\|-GGCCTGCGACCACGCAAA |
| GEZM054-5 | GEZM054-T868 | TAGCCCCAGCGG-----\|------\|-----TGCGACCACGCAAA<br>TAGCCCCAGCGGCTTAT\|TC--CA\|CGGCCTGCGACCACGCAAA |
| GEZM054-6 | GEZM054-T929 | TAGCCCCAGCGGCTT--\|------\|--GCCTGCGACCACGCAAA<br>TAGCCCCAGCGGCTT--\|------\|CGGCCTGCGACCACGCAAA |

TABLE 11-continued

Amplicon sequencing of selected maize A188 events targeting the CPL3 gene. DNA
extracted from T0 plants were PCR amplified for the targeted sites in exon 1 of
Zm-CPL3. Analysis resolves the INDEL's represented by the mixed trace and showed
a wide variety of edits produced by this genome targeting approach. A subset of
the total events generated is shown in the table.

```
Experiment    T0 Event Name    Sequence

GEZM054-6     GEZM054-T941     TAGCCCCAG--------|------|CGGCCTGCGACCACGCAAA

GEZM0054-7    GEZM054-T1207    TAGCCCCAGCGGC----|------|-GGCCTGCGACCACGCAAA
                               TAGCCCCAGCGGCTTAT|TC----|CGGCCTGCGACCACGCAAA

GEZM054-7     GEZM054-T1260    TAGCCC-----------|------|CGGCCTGCGACCACGCAAA
                               TAGCCCCAGCGGCTTAT|TC----|CGGCCTGCGACCACGCAAA

GEZM054-7     GEZM054-T1305    TAGCCCCAGCGGCTTAT|TCC---|--GCCTGCGACCACGCAAA

GEZM054-8     GEZM054-T592     TAGCCCCAGCGGC----|------|-GGCCTGCGACCACGCAAA

GEZM054-8     GEZM054-T602     TAGCCCCAGCGGCTT--|------|--GCCTGCGACCACGCAAA

GEZM054-8     GEZM054-T626     TAGCCCCAGCGGCTTA-|------|----------CCACGCAAA
```

Example 3: CPL3 Downregulation in Dicots, Namely *Beta vulgaris*

To confirm the relevance of the CPL3 gene in sugar beet (*Beta vulgaris*) (SEQ ID NO: 4 and 14) for fungal resistance the inventors intend to search for (knock-out) mutations in this gene by a TILLING approach using EMS or ENU as mutagen. The selected plants will subsequently self-pollinated to create homozygous mutants. The homozygous CPL3 mutants will be analyzed for fungal resistance, for example against *Cercospora beticola*. The resistance assay with sugar beet and *Cercospora beticola* could be performed as described by Schmidt et al. (Plant Mol Biol, (2004). Suppression of phenylalanine ammonia lyase expression in sugar beet by the fungal pathogen *Cercospora beticola* is mediated at the core promoter of the gene. *Plant molecular biology,* 55(6), 835-852.). Without wishing to be bound by theory, it is expected that CPL3 knock-out sugar beet plants will show increased resistance. To test potential side-effects as growth retardation, it is intended to rely on full knock-outs of the respective genes, or a strategy relying on a transient modulation by a silencing construct, or a further strategy relying on the creation and/or provision of a dominant negative CPL3 allele to test the different outcomes on resistance in a targeted way.

Example 4: CPL3 Downregulation—Effect in Pathogen Resistance

Given the central role of CPL3 identified herein, the potential of CPL3 modulation in different target plants was addressed. First, relevant target crop plants of economic and agronomic interest were defined. As a next step, the most severe pathogens from all taxa, in part very specific for certain target plants, were defined. To test whether CPL3 modulation can be advantageous for enhanced pathogen resistance against a variety of pathogens, including viral, bacterial, oomycete, nematode, insect or fungal pathogens, target pathogen types and the correlated diseases will thus be studied in various plant models to define the extent of CPL3 modulation needed and the specific way of CPL3 modulation needed (i.e., on RNA level and/or DNA level or even protein level) to achieve enhanced pathogen resistance by biological rather than chemical means for a several plant pathogens in the respective target plant causing major losses in harvest and crop production.

The invention claimed is:

1. A *Zea mays* plant having pathogen resistance, wherein pathogen resistance is conferred or increased by downregulation of a nucleotide sequence encoding an endogenous C-terminal domain phosphatase-like 3 (CPL3) protein, wherein the downregulation is achieved by one or more silencing construct(s) directed to all endogenous nucleotide sequences encoding the CPL3 protein; wherein the downregulation is an incomplete downregulation of the CPL3 transcript and results in an increased pathogen resistance in the plant as compared to a *Zea mays* plant that do not comprise the one or more silencing constructs, and wherein the nucleotide sequence encoding the CPL3 protein is selected from the group consisting of:
   (a) the nucleotide sequence set forth in SEQ ID NO: 9;
   (b) a nucleotide sequence having at least 95% identity to the sequence set forth in SEQ ID NO: 9;
   (c) a nucleotide sequence encoding the amino acid sequence set forth in SEQ ID NO: 19; and
   (d) a nucleotide sequence encoding the amino acid sequence having at least 95% identity to the sequence set forth in SEQ ID NO: 19.

2. The plant according to claim 1, wherein the pathogen is a hemibiotrophic fungus selected from the group consisting of: *Zymoseptoria tritici, Setosphaeria turcica, Fusarium* spp., *Fusarium graminearum, Colletotrichum* spp. *Magnaporthe grisea, Magnaporthe oryzae, Phytophthora infestans*, or wherein the pathogen is a fungus selected from *Cercospora* spp.

3. The plant according to claim 1, wherein the one or more silencing construct(s) comprise(s):
   I. an RNAi molecule directed against, targeting, or hybridizing with the nucleotide sequence encoding the CPL3 protein, or a polynucleotide sequence encoding said RNAi molecule; or
   II. an RNA-specific CRISPR/Cas system directed against or targeting the nucleotide sequence encoding the CPL3 protein, or a polynucleotide sequence encoding said RNA-specific CRISPR/Cas system,
   wherein the RNAi molecule is the sequence set forth in SEQ ID NO: 23, and
   wherein the RNA-specific CRISPR/Cas system comprises a MAD7 nuclease and a crRNA having one of the sequences set forth in SEQ ID NOs: 25-31.

4. The plant according to claim 3, wherein the RNAi molecule does not share substantial sequence identity with other genomic regions in the genome of the plant.

5. A cell, tissue, organ, or seed of the plant according to claim 1; wherein the cell, tissue, organ or seed comprises the one or more silencing constructs.

6. A method of generating a plant having pathogen resistance, the method comprising the steps of:
   (i) providing one or more silencing construct(s) directed to an endogenous nucleotide sequence encoding a CPL3 protein, wherein the nucleotide sequence encoding the CPL3 protein is selected from the group consisting of:
      (a) the nucleotide sequence set forth in SEQ ID NO: 9;
      (b) a nucleotide sequence having at least 95% identity to the sequence set forth in SEQ ID NO: 9;
      (c) a nucleotide sequence encoding the amino acid sequence set forth in SEQ ID NO: 19; and
      (d) a nucleotide sequence encoding the amino acid sequence having at least 95% identity to the sequence set forth in SEQ ID NO: 19, of SEQ ID NO: 19 or as defined in claim 1, or one or more sequences encoding the same;
   (ii) introducing the one or more silencing construct(s) into a plant cell, tissue, organ, plant, seed, or plant material to obtain transformed plant cell, tissue, organ, plant, seed, or plant material; and
   (iii) optionally, regenerating a plant from the transformed plant cell, tissue, organ or plant material,
   wherein the regenerated plant has pathogen resistance.

* * * * *

SEQUENCE LISTING

<160> NUMBER OF SEQ ID NOS: 48

<210> SEQ ID NO 1
<211> LENGTH: 3726
<212> TYPE: DNA
<213> ORGANISM: Artificial Sequence
<220> FEATURE:
<223> OTHER INFORMATION: cDNA of AtCPL3

<400> SEQUENCE: 1

| | | | | | |
|---|---|---|---|---|---|
| atgcttgtag | ctcgatctgg | ttgttctaga | accctaattc | gaatgggcaa | cgatgaaaac | 60 |
| ttgatggtaa | tggtggatgt | tgaggaaggt | gagattcctg | attctgtcaa | cactgagatt | 120 |
| gaagttaagc | acaagagtac | tactactacg | gccgatgttg | gcggagacgt | cgatgttggg | 180 |
| gttgtggctg | gaggaagagg | aggaggtggt | ggtggttcta | atggcaactc | tagggtttgg | 240 |
| acaatggagg | agttgatttc | tcagtatcct | gcttaccgtc | catatgcgaa | ttcgggttta | 300 |
| tctaatttag | cttgggctcg | agctgtgcag | aacaaacctt | ttaatgaagg | tttggtaatg | 360 |
| gattatgaac | caagagagag | tgataagatt | gtgattgaag | atagtgatga | tgagaaagaa | 420 |
| gaaggtgagt | tggaggaagg | tgaaattgat | ttggtcgaca | atgcttctga | tgacaatttg | 480 |
| gttgagaagg | atactgaatc | tgttgtgttg | ataagtgctg | ataaagttga | agatgatcga | 540 |
| attctaaagg | agagagattt | ggagaagaaa | gtgaaactaa | ttcgtggtgt | tttggagagt | 600 |
| acttcgttgg | tagaagcaca | gaccggattt | gaaggagttt | gttccagaat | attggggcg | 660 |
| ttagagtctt | tgcgagagct | ggtttcagat | aatgatgatt | ttccgaagag | ggatacttta | 720 |
| gttcaattgt | catttgcttc | tcttcaaacc | attaactatg | tgttttgctc | gatgaacaat | 780 |
| atttccaagg | agcgtaataa | ggagactatg | tcaagattgc | tgactcttgt | aaatgaccat | 840 |
| ttttcccaat | ttctctcatt | caaccagaaa | aatgagatag | agaccatgaa | tcaggattta | 900 |
| agccgttctg | ctattgcagt | ttttgctgga | accagcagtg | aagagaatgt | taatcaaatg | 960 |
| actcagccga | gtaatggtga | ttcttttctt | gccaaaaagc | tgacttcaga | aagtacacat | 1020 |
| cgaggagccg | cctacttaag | gagtaggttg | cctatgctgc | ctcttctaga | ccttcataag | 1080 |
| gatcatgatg | cagacagcct | tccgtcgccc | acaagggaaa | caacaccaag | tttacctgta | 1140 |
| aatggtcgcc | atacaatggt | tagaccaggt | tttcccgttg | gtagagagag | ccaaacgact | 1200 |
| gagggtgcca | agtctattc | atatgagagt | gatgcccgta | agcagtttc | tacctaccag | 1260 |
| caaaaatttg | gtcttaattc | agtgtttaag | acagatgacc | ttccaagccc | aaccccatca | 1320 |
| ggagaaccta | atgatggcaa | tggagacgtt | ggtggagagg | tttccagttc | tgttgttaag | 1380 |
| agctcgaacc | cggggagtca | cctaatttat | gggcaagacg | ttcctctgcc | ctccaatttt | 1440 |
| aattctagaa | gcatgcctgt | tgcaaattct | gtttctagca | ctgttccacc | acatcatctg | 1500 |
| tcaattcatg | ctatttctgc | accaactgcc | tctgatcaga | cagtgaaacc | ttctgcaaag | 1560 |
| agtcgagatc | caagactaag | gcttgcgaaa | cctgatgctg | ccaatgtaac | catttattcg | 1620 |
| tactcgtctg | gcgacgctag | aaatctttca | aaagtagagc | tttctgcaga | cttggtgaac | 1680 |
| ccaagaaaac | aaaaagccgc | tgatgaattt | ttaattgatg | ggcctgcatg | gaaaagacaa | 1740 |
| aagagtgata | cggatgcacc | aaaagcagct | ggaactggtg | gctggctaga | ggatacagaa | 1800 |
| tcatcgggac | ttctaaaact | ggaatccaag | cccaggctaa | ttgagaacgg | tgtaacatct | 1860 |
| atgacatcaa | gtgttatgcc | cacgagtgct | gtttctgtga | gccaaaaagt | acggacagct | 1920 |
| tcaactgata | ctgcatcatt | gcaatccctt | ttgaaggata | ttgcagtaaa | tcctacaatg | 1980 |
| ctactgaatc | tcctgaaaat | gggagaaaga | caaaaggtac | ctgaaaaagc | tattcagaaa | 2040 |

| cccatggatc caagaagagc agcacaactc cctggctctt ccgtacaacc aggggtatca | 2100 |
| acaccgctta gtatacctgc atcaaatgct ttagctgcta attcttttaaa ctcaggagta | 2160 |
| cttcaggatt cttcccaaaa cgcccctgca gccgaatctg gaagcattcg catgaaacct | 2220 |
| cgtgatcctc gccgaatcct gcatggaagt actcttcaaa gaacggactc ttcaatggaa | 2280 |
| aagcagacca agtgaatga tccttccact ctaggaacct tgactatgaa gggtaaggca | 2340 |
| gaagatttgg aaacacctcc ccagcttgat ccacggcaaa atattagcca gaatggtacc | 2400 |
| agcaaaatga aaatttcggg tgaacttctc agtgggaaga caccagactt tcaacacaa | 2460 |
| ttcaccaaaa acctgaaaag tattgctgat atggttgtcg tatcacaaca acttggcaat | 2520 |
| cccccagcaa gtatgcattc ggtacagctt aagacggaga gagatgttaa acataatcct | 2580 |
| tcaaatccca atgcccagga tgaggatgtg tcagtttcag cagcatcagt aacggctgca | 2640 |
| gctggtccca ctcgttccat gaacagttgg ggagatgtgg aacacctatt tgaaggatat | 2700 |
| gatgacattc agagagtagc tattcaaaga gagagagttc gtaggttaga ggaacagaat | 2760 |
| aaaatgtttg catctcaaaa gctctctctt gtcttggata tagaccacac ccttctcaat | 2820 |
| tcagctaagt ttaatgaggt tgaatcccgc cacgaggaga tattaagaaa gaaggaagaa | 2880 |
| caagatcgtg agaaaccata tagacatctc tttcgtttcc tgcacatggg aatgtggact | 2940 |
| aaactaagac cagggatttg gaattttttg gagaaggcta gcaagctgta cgagttacat | 3000 |
| ctttacacta tgggaaacaa attgtatgct acagagatgg ccaagctgct tgatcccaaa | 3060 |
| ggggttctat ttaatggacg ggtcatatcg aaaggagatg atggagatcc tcttgatgga | 3120 |
| gacgaacgag tacctaagag caaagattta gaaggagtta tgggtatgga atcgtctgtg | 3180 |
| gtgatcatag atgactctgt ccgagtgtgg cctcaacaca aaatgaattt aatagctgtt | 3240 |
| gaaagatatc tttatttccc ttgtagtaga cggcaatttg ggcttcttgg tccttctctt | 3300 |
| cttgagttag atcgtgatga ggtacctgag gagggcacat tggcatcttc attagcggtt | 3360 |
| attgagaaaa tacatcaaaa tttcttctcg cacacttcat tagatgaagt tgatgtgaga | 3420 |
| aatatttag cttctgagca acgaaagata ttggctggtt gtaggattgt atttagtcgg | 3480 |
| ataatcccag tgggtgaagc caaaccgcac ttgcatcccc tgtggcaaac tgctgagcag | 3540 |
| tttggtgctg tctgcacaac ccaggtggat gaacatgtca ctcatgttgt cacaaattct | 3600 |
| cttggaaccg acaaggtaaa ttgggcacta accagaggta gatttgttgt tcatcctggc | 3660 |
| tgggtggaag catcagcttt tctgtaccag agagcaaatg agaacttata tgccatcaac | 3720 |
| ccgtaa | 3726 |

```
<210> SEQ ID NO 2
<211> LENGTH: 3774
<212> TYPE: DNA
<213> ORGANISM: Artificial Sequence
<220> FEATURE:
<223> OTHER INFORMATION: cDNA of GmCPL3_1 (18g282300.2)

<400> SEQUENCE: 2
```

| atgatttttg gatcgttatt ggattgtgag aaattgggaa aattggagaa gatggggaag | 60 |
| gaggtagagg atgttgaaga gggtgagatt tcggatactg cttcggtgga agagatttca | 120 |
| gcggaggatt tcaataagca agatgttaag gtgttaaata ataacaataa gcccaatgga | 180 |
| agtgatgcta gggtttgggc tgttcatgat ctttactcaa gtaccctac catatgtcgt | 240 |
| ggctatgcat cgggtttgta taaccttgct tgggcacagg ccgtgcagaa caagcctttg | 300 |
| aatgatattt ttgtgatgga agtggactct gatgccaatg ctaacagtaa cagcaacaac | 360 |

```
tccaatcgac tggcctctgt tgctgtgaat cctaaggatg tggtggtggt ggatgtggac    420
aaagaggaag gggagttaga ggagggtgag attgatgccg acgcggaacc tgaaggagaa    480
gcagagagtg ttgtggctgt tcctgttgtt tctgattcag agaagcttga tgatgtgaag    540
agggatgttt ctaattctga gcagcttggt gtgaggggtg ttctggaggg tgttaccgtt    600
gctaatgtgg cggagtcgtt tgctcaaact tgcagtaagc tgcaaaatgc tcttcctgaa    660
gtgctctcta gacctgctga ttctgagagg gatgatctcg ttcgcctgtc atttaacgct    720
actgaagtgg tttattctgt gttttgctcc atggactctt taaaaaagga acagaacaag    780
gatagcatat taagattact ttcttttgtg aaggatcaac aacaggctca attattttct    840
ccagagcata taaagagat ccagggcatg atgactgcaa ttgattattt tggtgcttta    900
gttaatagtg aggctattgg caaggagaaa gaattgcaga ccactgtgca gacccatgag    960
ataaagactc aggaaaatca agctgtagaa gctgctgaat tgatttctta taataagcct   1020
ttgcatagtg acataattgg ggcatcacat gctttaaaat ttggacaaaa tagtattaaa   1080
ggtagagggg ttctgctccc tctgttagac cttcacaagg atcatgatgc tgacagttta   1140
ccatcaccaa cccgagaagc accctcatgc ttccctgtga ataaattact ttccgttgga   1200
gagcctatgg ttagttctgg gtcagcagct gctaagccgg agtctggaaa gatggaactt   1260
gatagtgaag gttctaaatt tcatctctat gaaactgatg ctttgaaagc tgtttccaca   1320
tatcaacaga gtttggtcg aagttccctt tttacaaatg ataaatttcc aagtccaact   1380
ccttcaggtg actgtgagga tgagattgtt gatacaaacg aggaggtctc tagtgcttct   1440
actggtgatt ttttaacaag cactaagcca actcttttgg atctgccacc tgtttctgct   1500
acttccacag ataggtccag cttgcatgga ttcattagtt ctagagttga tgcagcaggt   1560
cctgggtctt tgccagtgaa aagctctgca agaatagag atcctaggct tcgtttcgtt   1620
aattctgatg caagtgccgt ggataaccca tctacattga tacataatat gcctaaagtg   1680
gaatatgctg gaacaacaat ctcaaggaaa caaaaggctg ctgaagaacc ttctttggat   1740
gttactgtat caaaaagaca aaaaagtcca ttggaaaata ctgagcataa tatgagcgaa   1800
gtaagaactg gaattggtgg ttggttggaa gagcatactg ggcctggagc tcagtttata   1860
gagaggaatc atttaatgga caaatttgga cctgaacccc aaaagacttt gaatacagtc   1920
agtagttctt gtactggttc tgataatttc aatgcaacaa gcattagaaa tgagcaggca   1980
ccaattacaa gtagtaatgt gctagcttcc ttacctgctc tattgaaagg tgcagctgta   2040
aatccaacca tgctggttaa cttacttaga atagcagaag cccagaagaa atctgctgat   2100
tctgctacaa atatgctgtt gcatccaaca agctcaaatt cggctatggg aacagactca   2160
actgcgagta ttggttcatc aatggccact ggtcttcttc aaagttctgt tggaatgctt   2220
ccagtttcat cacaatcaac ttccatgaca caaacccttc aagatgattc aggaaagatt   2280
cgcatgaaac cccgtgatcc ccggcgcatt ctccacacta ataatactat ccagaagagt   2340
gggaacttgg ggaatgagca attcaaagcc attgtatccc ccgtgtctaa caaccaggga   2400
actggggaca atgtcaatgc ccagaagctt gagggtaggg tggatagtaa attagtgcct   2460
actcaaccaa gtgcacaacc tgatattgct cgacaattcg cccggaatct gaaaaacatt   2520
gctgatatta tgtctgtttc ccaagaatca tcaactcaca ctcctgttgc tcaaattttt   2580
tcttcagcat ctgttcccct tacttcagat agaggggaac agaaatctgt tgtgtcaaac   2640
tctcagaacc tggaggctgg catggtatca gctcatgaaa cagctgcatc aggtacctgt   2700
cgatcccaga atacatgggg agatgttgag catctttttg aaggttatga tgagcagcag   2760
```

-continued

| | |
|---|---|
| aaggctgcta tacagagaga gagagcaagg agaattgaag aacagaataa aatgtttgct | 2820 |
| gctcgaaaat tgtgccttgt attggatcta gatcacacac tacttaattc tgctaagttt | 2880 |
| gtggaagttg atcctgtgca tgatgagata ttgagaaaga aagaagagca ggaccgtgag | 2940 |
| aaaccacaca gacatctttt tcgctttcct catatgggaa tgtggactaa actcagacca | 3000 |
| ggaatctgga acttcttgga gaaggccagt aagctctatg agctgcatct ttacactatg | 3060 |
| ggaaacaagc tatatgcaac agaaatggca aaggtgcttg atccaaaggg acttttgttt | 3120 |
| gctggaagag ttatctctag aggtgatgat actgattcag ttgatggtga ggagagggct | 3180 |
| cccaaaagca aagatttgga aggcgttttg ggtatggaat catctgttgt aattatagat | 3240 |
| gattctgtga gggtctggcc tcataacaaa ctgaacctga tagtggtgga aaggtataca | 3300 |
| tacttcccct gtagtagacg tcagtttgga ctgcctggcc cttcccttct cgagattgat | 3360 |
| catgatgaga gacctgaagc tggaactctg gcatcctctc tggcagttat tgagaaaata | 3420 |
| catcaaatct tttttgcttc tcgatcctta gaagaagtgg atgtcagaaa tatactagca | 3480 |
| tcagagcaga gaaaaatctt agctggttgt cgcatagtat ttagtagggt atttcctgtt | 3540 |
| ggtgaagcaa atcctcacct tcacccatta tggcagacag ctgaacagtt tggtgctttt | 3600 |
| tgcaccaatc agattgacga acaggttact cacgttgttg caaattcccc tgggactgat | 3660 |
| aaggtgaatt gggctctaaa caacggaaga tttgttgtcc atcctggctg ggtggaagca | 3720 |
| tcagcattgc tttataggag ggcgaatgag caagattttg ccattaaacc ataa | 3774 |

<210> SEQ ID NO 3
<211> LENGTH: 3786
<212> TYPE: DNA
<213> ORGANISM: Artificial Sequence
<220> FEATURE:
<223> OTHER INFORMATION: cDNA of GmCPL3_2 (08g257900.1)

<400> SEQUENCE: 3

| | |
|---|---|
| atggttttg gatcgttatt ggattgtgag gtattgggaa aattggagaa gatggggaag | 60 |
| gaggctgagg atgtggaaga gggtgagatt tcggatactg cttcggtgga agagatttca | 120 |
| gccgaggatt tcaataagca agatgttaag ttgttaaata ataacaataa gcccaatgga | 180 |
| agtgatgcta gggtttgggc tgttcatgat ctttactcaa gtaccctac tatatgtcgc | 240 |
| ggctatgcat cgggcttgta taatcttgct tgggcacagg ccgtgcagaa taagcctttg | 300 |
| aatgatattt ttgtgatgga agtggactct gatgccaatg ctaacagtaa ccgcaacagc | 360 |
| tcccatcgac tggcctctgt tgctgtgaat cctaaggatg tggtggtggt ggatgtggac | 420 |
| aaagaggaag gggagttgga ggagggtgag atcgatgctg atgcggaacc cgaaggagaa | 480 |
| gcagagagtg ttgttgtggc tgtttctgat tctgagaagc ttgatgatgt gaagatggat | 540 |
| gtttctgatt ccgagcagct tggtgcgagg ggtgttctgg agggtgttac cgttgctaat | 600 |
| gtggttgagt cgtttgctca aacttgcagt aagctgcaaa ataccccttcc tgaagtgctc | 660 |
| tctagacctg ctggttctga aaggatgat ctcgttcgct tgtcatttaa tgctactgaa | 720 |
| gtggtttatt ctgtgttttg ctctatggac tcttcggaga agaacagaa caaggatagc | 780 |
| atattaagat tgctttcttt tgtgaaggat caacaacagg ctcaattatt ttctccagag | 840 |
| catgtaaaag agattcaggg catgatgact gcaattgatt ctgttggtgc tttagtaaat | 900 |
| agtgaggcta ttggcaagga gaaagaattg cagaccactg agataaagac tcaagaaaat | 960 |
| tcagctgtag aagtgcagat ccatgagata aagactcagg aaaatcaggc tgtagaagct | 1020 |
| gctgaattga tttcttatag taagcctttg cataggggaca taactgggac atcacaggct | 1080 |

```
ttaaaatttg gacaaaatag tattaaaggc agagggttc tgctccctct gttagacctt    1140
cacaaggatc atgatgcaga cagtttacca tcaccaactc gagaagcacc ttcctgcttc    1200
cctgtgaata agttactttc tgttggagag tctatggtta gatctgggtc agcatctgct    1260
aagatggaac ttgatagtga aggttctaaa tttcatctat atgaaactga tgctttgaaa    1320 gctgttttcca catatcaaca gaagtttggt cgaagttccc ttttttacaaa tgataaattt    1380 ccaagtccaa ctccttcagg tgactgtgaa gatgaggttg ttgatacaaa cgaggaggtc    1440
tctagtgctt ctactggtga ttttttaaca agcactaaac caactctttt ggatcagcca    1500
cctgtttctg ctacttccat ggataggtcc agcatgcatg gattcattag ttctagagtg    1560
gatgcaacag gtcctgggtc tttcccggtg aaaagctctg caaagaatag agatcccagg    1620
cttcgtttca ttaattctga tgcaagtgct gtggataacc tgtctacatt gataaataat    1680
atgtctaaag tggaatattc tggaacaaca atctcaagga acaaaaggc tgctgaagaa    1740 ccttctttgg atgttactgt atcaaaaaga ctaaaaagtt ctttggaaaa tactgagcat    1800
aatatgagcg aagtaagaac tggaagtggt ggttggttgg aagagaatac tgggcctgga    1860
gctcagttga tagagaggaa tcatttaatg gacaaatttg gacccgaagc caaaaagact    1920
ttgaatacag tcagtagttc ctgtactggt tctgataatt tcaatgcaac aagcattaga    1980
aatgagcagg caccaattac agctagtaat gtgctagctt ccttacctgc tctattgaaa    2040
gaagcatctg taaatccaat catgcttgtt aacatactta gattagctga gcccagaag    2100 aaatctgctg attctgctgc aattatgctg ctgcatccaa caagctcaaa tccggcaatg    2160
ggaacagact caacagcgag tattggttca tcaatggcca ctggtcttct tcaaagttct    2220
gttggaatgc ttcctgtttc atcacaatca acttccacgg cacaaaccct acaagatgat    2280
tcaggaaaga ttcgcatgaa accccgtgat ccacggcgca ttctccacac taataatact    2340
atccagaaga gtggggactt ggggaatgag caattcaaag ccattgtatc cctgtgtct    2400 aacaaccaga gaacagggga caatgtcaat gccccgaagc ttagggtag ggtgataat    2460 aaattagtgc ctactcaatc aagtgcacaa cctgatattg ctcgacaatt caccggaat    2520 ctgaaaaaca ttgctgatat tatgtctgtt tcccaagaat catcaactca cactcctgtt    2580
tctcaaaatt tttcttctgc atctgttccg cttacttcag atagagggga acaaaatcc    2640 gttgtgtcaa gctctcagaa cctgcaggct gacatggcat ctgctcacga aacagctgca    2700
tcagttacct ctcgatccca gagtacatgg ggagatgttg agcatctttt tgaaggttat    2760
gacgagcagc agaaggctgc tatacagaga gagagggcca ggaggattga agaacagaat    2820
aaaatgtttg ctgctcggaa attgtgcctt gtattggacc tagaccacac gctacttaat    2880
tctgccaagt ttgtggaagt tgatcctctg cacgatgaga tattgagaaa gaaagaagag    2940
caggaccgtg agaaacctca cagacatctt tttcgctttc ctcatatggg aatgtggact    3000
aaactcagac caggaatctg gaacttcttg gagaaggcta gtaagctcta tgagttgcat    3060
ctttacacta tgggaaacaa gctatatgcg acagaaatgg caaaggtgct tgatccaaag    3120
ggagttttgt ttgctggaag agttatctct agaggtgatg atactgattc agttgatggt    3180
gaggagaggg ttccaaaag caaagatttg gaaggcgttt tgggtatgga atcatctgtt    3240
gtaattatag atgattctgt gagggtctgg cctcataaca aactgaactt gatagtggtg    3300
gaaaggtata catacttccc ctgtagtaga cgtcagtttg gactgcctgg cccttccctt    3360
cttgagattt atcatgatga gagacctgaa gctggaactc tggcatcctc tttgcagtt    3420 attgagaaaa tacaccaaat cttttttgcc tctcaatcct tagaagaagt ggatgtcaga    3480
```

| | |
|---|---|
| aatatacttg catcagaaca gagaaaaatc ttagctggtt gtcgcatagt atttagcagg | 3540 |
| gtatttcctg ttggtgaagc aaatcctcac cttcatccat tgtggcagac agctgaacaa | 3600 |
| tttggtgctg tttgcaccaa ccagattgat gaacaggtta ctcacgtagt tgcaaattcc | 3660 |
| cctgggactg ataaggtgaa ttgggctctt aacaacggaa gatttgttgt ccatcctggc | 3720 |
| tgggtggaag catcagcatt gctgtatagg agggcgaatg agcaagattt tgccattaaa | 3780 |
| ccttaa | 3786 |

```
<210> SEQ ID NO 4
<211> LENGTH: 3759
<212> TYPE: DNA
<213> ORGANISM: Artificial Sequence
<220> FEATURE:
<223> OTHER INFORMATION: cDNA of BvCPL3 (g12062.t1)

<400> SEQUENCE: 4
```

| | |
|---|---|
| atgaaagtat caggtggtga agatggtgaa attccagaat cagacgccat tgttgagatg | 60 |
| aaacatcaat caaagactac gacgacaacg acgacaacga taacatcgga ttcatcgaat | 120 |
| aaaaaagata taacagtta ttggatgaga gatctgtaca agtattcatc gtacagagga | 180 |
| tatggcgctg cgtcaggttt atacaattta gcatgggcgc aagcagtaca gaataagcca | 240 |
| ttgaatgagg tacttgttga gctggatgat aagaaaaaca ataaaaatgc aagtactgat | 300 |
| gatactagtg ttaataagga acaaggtgaa gtacaacaac attgtgttga agtaaagag | 360 |
| gtttttgagg tggttgacag tgagaaagaa gaaggagaat tggaagaagg cgaaatcgat | 420 |
| tttgattctg atgatactgg taataatcat aatagtaatg gtaataaagt tcaggatgat | 480 |
| tttggtggat tggagatgga tgatggtgag ttggagaatc aagtgtcttc tattcgtaaa | 540 |
| gttcttcata atgttactgt tgctgaagct cataaatcat ttgatattgt gtgtgctcga | 600 |
| ttgaggactt ctttggagac gttgagagag ttggttttgc atacatggtt tccttccaaa | 660 |
| gacgcgctca ttcaacaagc ttttgctgca attcagtgtg tatactctgt ttacagttct | 720 |
| atgagcccta ccttaagaga tcagaataag gataggatgt caaggttgct tacttttgtc | 780 |
| atggaccta gttctgttct ttttacaccg gaacagagga agaggtgga gggtatgatt | 840 |
| acctctgtta acccccgat tgttccagtg aaacccaagt cgagggacag gcaggaagaa | 900 |
| ttgcctgtta cagagaaggc tatcctcacc gattctaata cattgactgt gaatactggt | 960 |
| gacaataagt cagacttatt gaagaaagtg ggacccgaat tgtctgttta tcagtcggaa | 1020 |
| aaaaagaaca ctgacatttt atcagaagca atgagacatt ttccgtctag cttaaaggtc | 1080 |
| agaagcagtt tcggccctct gcttgatctc cataaagttc atgatgaaga cagccttcca | 1140 |
| tctcctacca gcaagacaat gccttccttg cctttctttg aaacggctcc tcctcgagta | 1200 |
| gtgcatggtt tgcagaaatc tggtgtgcac ccttatgaaa ctgaagcagt gaaagctgtg | 1260 |
| tcaagctacc aacaaagatt tggtcggagt acattcttag caacggacat gcttcccagt | 1320 |
| ccaactcctt ctgaagatgg caatgaagga ggagctgatg actctaatga agaggtttct | 1380 |
| agttctaatg cctatactaa tgttgttagt aggacaacaa attcctctgt agtgccacaa | 1440 |
| ccagttgttt cttctgctgc ttatacaagt agttcaacca tgcaaggggt gatcagtggt | 1500 |
| actagtgctg agagttctag tgtcgggtct tctccttcac tgcgagcctc tgcaaagagc | 1560 |
| cgagatccta ggcttcggca tcttaatcct aattttggct cgttagacct tagttttgt | 1620 |
| ccgtctccta tggttcccag ttcagcatct aaattggagc gctaggggga aattatgaaa | 1680 |
| tcaaagaaga ccaaggcact tgagggcgc cttctggatg gtcctactgc aagagacca | 1740 |

-continued

```
agaaatggcc tggaaactga agatatgtcc atgaatgcaa atcaagtaaa aactctccag    1800
ggaagtactc gaatggagac ttctagttct agtattttgg gaccacagtc ttccagcaga    1860
ggactcttgg gcccagctat tgatcctcgg aaaccaggaa gtggtaccgt ttcctccggg    1920
attactacaa acaatcctag catggcagta aataaaacgg caaagccctc aatgaatgtc    1980
agtggttctc cgtccttgca gtcactgttg aaagacattg cagggaatcc aggagcatgg    2040
atgaatatta ttaaggagca gaacaaatcc agtgaacctt acaaagtgt gtcacattca     2100
atgaactcaa attcaatatt aggagcagca ccctctgcta ttgctgttcc acctatatca    2160
tctggggtgg gacagacaag tgcaggattg cttcaggtcc cttctccgaa agtggtcacg    2220
agctcacagg atgattcggc aaaacttcgc atgaaacccc gtgaccctcg tcgtgccctg    2280
catgccaata tggcccaaag gactggcagt tctgtgccag aacagcctaa ggtaaatgga    2340
gtacacaaca caacaacaca aggactccag agaaatatca atgctcaaag atatgttaat    2400
ggaacgagtc caagtgctgc gtcatctcag accccaatcc tacctgatat aactaagcaa    2460
tttacaaaga acttgaaaaa cattgctgac attatttctt ccccacaaac gtcaagtata    2520
cagtctccgc tagcagtaag ttctttgtcg gcgcaagcta attcggatac gacaagtatt    2580
agttctggtg gacaagcaag ttgtagttct ggtggacccg tgattactgg taatcagcgt    2640
actgtgtctg cattgaggcc cgaagaagtt gtctcgggcc gtccacaatc acagaacaat    2700
tggggagatg ttgagcatct cttttgacgga tatgatgatc agcaaaaggc agctattcaa    2760
caagagagag ctagaaggct tgatgagcag aacaaaatgt ttgctgatcg caagttgtgt    2820
cttgtgctgg atctgatca cacgcttctt aattcagcaa agttttcaga ggtagatcct    2880
gtgcatgatg aaattctgag gaagaaagag gaacaagatc gtgaaaagcc tcgacgacat    2940
ctctttcgtt ttccacatat ggcaatgtgg acaaaattac gacctggtat ttggaatttc    3000
ttagagaagg ctagtaagct ttttgaactg catctctata ccatggggaa caagttgtat    3060
gccactgaaa tggcaaaagt gcttgatcca aagggaactc tatttgctgg acgagttatc    3120
tcacggggtg atgatgggga tcctattgat ggtgatgaga gggtaccgaa gagcaaggat    3180
ttagagggtg ttatgggtat ggaatcttct gttgtaataa tagatgattc tgctagagtt    3240
tggccacata acaagctaaa cttgatagtc gtggaaaggt atacttactt tccttgtagt    3300
aggaaacaat ttgggctccc aggaccttca cttcttgaga ttgatcatga tgagagacca    3360
gaagagggaa ctctggcatc ttctttggca gtcattgaga aaatacacca aaacttttc    3420
tctcacaagt cccttgatga tgtggatgtg agaaatatat gggagctga gcagcggaag    3480
attcttgctg gttgccgaat cttgtttagc agggttttcc ctgttgggga agctaatccc    3540
catttacacc cactttggca gacggcagag cagtttggtg ctgtgtgcac caatcagcta    3600
gatgaacaag ttacccacgt agtggcaaat tctttaggga ctgacaaggt taattgggct    3660
ctgtcaacta aaagatttgt tgtacaccct agctgggttg aagcttctgc attgctttac    3720
agaagggtta atgagcaaga ctttgccatc aaaacttga                          3759
```

```
<210> SEQ ID NO 5
<211> LENGTH: 3759
<212> TYPE: DNA
<213> ORGANISM: Artificial Sequence
<220> FEATURE:
<223> OTHER INFORMATION: cDNA of TACPL3-A

<400> SEQUENCE: 5
```

```
atgcgcgtga ctctcacgcc caaggacgag gattggctgg tcgtgctgat gacgagggag    60
```

```
cgcccgcggt cggcggtggt cgcgcctggg ggggacgtct tcaccgccgg tggcggcggg    120
gagacgtccg atgggactc ctcagagtcg ctggaagaaa ttagtgccgc cgactttaag    180
gagtcgtcca gtggcaccgc tgctccgtcg gcgtcgtcgc agagatctag ggtttggatg    240
gggtacacca tgtcccggag ttatgcaccg gcgttccaca gctttgcttg ggcgcaagct    300
gtgcagaaca agcctctcgt tccgcggcct gctgccgacg aggacgaggt agagcacctc    360
gtcgacacct cggacgagga aaggaagag ggcgagattg aggaggggga ggccgtacag    420
tccacttccc ctccaattaa gcagcctgag accatcgact tggactctga tgcgcaggac    480
aagtcagagt cagtggacat ggagcagacc cgtttggccg ttgaggcggc tgatgagctg    540
gattttgacc agcgcgtggg gagtatactg gaggagcttg agaggctttc cattgaggaa    600
gctgagaagt catttgaggc ttcgtgtgcc cgcctgcggt cttgctttga gagccttaag    660
ccgctgttcc cagagagcgg tagcccgatg cctatgcttg atgctcttgt gcaacaggct    720
tttgttggaa tcgacaccat caccactgta gctaattcat atgcgatgcc gaagagggag    780
cagaacaaga acatgctgtt gaagctgctg tttcacataa agaacagata ttcagacatg    840
ctggcactca accagcgaga tgagctcgat agtcgtgtga cacagttagt ttttgtagat    900
ggagaagaca atgccggttc caattgtagc accaaaacag tgaatgtggt tgttccatct    960
ggacaggttc catcagatag actgccagtc gagtcaggag cagcaaatcc acctaggggc   1020 tctagttttcc ccagctggga gataccggcg aataatagaa ttgttagccc cttgttggac   1080
cttcatgcag attatgacga gaacagctta ccctcaccca cccgagttag tgccccacct   1140
tttcctgtgc caaagcccat tgggtttgga gtatttccaa tggcacctga cagatatttt   1200
tcggcagaaa gaattgatcc ttcaaaaaat tttctttatc catgtgtgaa tgatgcgcta   1260
aaggatgttt cctcgtaccg acagaagtat ggcccgacgt ctacctttgc aagtgatgat   1320
cttccaagcc caaccccatc tgatgatggg gataaatctg gagacaaaga aggtgatata   1380
tttggtgaag tttcaagctt ttcagcttct aataagtctg ctccgccaag tgggaatctg   1440
atgcctgctt cccgacctag tgcagttatc agcagcaatg acagttttgc aggtggtcct   1500
ccaggttatg ctaaacaaat tgaacagtct gtttcaggac ccagccatgc tcttaagcct   1560
tcagctaaaa gtagagatcc aaggctcagg ttttttgaacc gtgattctgg tggtactgca   1620
gatgcaaata tacatgtaaa tttggcagag ccaaatgctt ccaaagatgg gaccttgggg   1680
ggtgttgtat cagataatag ccggaagcac aaggcaactg gccaacctct catggatgaa   1740
accgtgttaa aaagagctag ggagagtact gggagtccca gagacattct ggtaccacct   1800
ggtagagatg gaagtaacat cagctcctat tcaggtgaca gggttcaatc aaataagcat   1860
acagggcttg aaactaagac agccaggaat cctagtatta ggaccagtag tcaacttatt   1920
agcaatgtaa gtagtatccc agacagtact ggaactctcc aagcctccca acctaattca   1980
gttccacaga ccagtgcagc tcctattgtt tcattgcctg cagtgttaaa ggacattgct   2040
gtgaacccga ctgtgctcat gcattggatt caaatggaac atcagaagag gtccgcatca   2100
gagcctcagc ctgcttcagg tatcatctct agtggcatga tcaataatgt cactgctggg   2160
atggttatac cacctggcaa tgctctgaag accgcagaag ttgcacacat tccttcttat   2220
aggccacaag caacatcgca aacagcctct gtgaattcac aaaatgaccc tggagtaata   2280
cgtatgaagg cgcgtgatcc ccgtcgtgtc ctccacaata acacatcaca gaagaacgat   2340
actctgaact ctgatcaagc caaaagcaat ggtatcgccc tgccggcctt ccaggacagc   2400
aaagacaatt tgattaaccg tcaacaactg gcagagcaac ttcagactac tgtgttgcca   2460
```

| | |
|---|---|
| tctcaaccag tctcattatc cagcattgct cgacagtcca ccatgagcgc gagtaaggtc | 2520 |
| gatcctgtct ctaattcaca gttagctgct tcatcactca ttgctcctca agaaagttta | 2580 |
| gtcagcgtaa ataggggcaga tccaagagta gctgctggac agaatgattc caataatgct | 2640 |
| gccccctgcta caacacttgg taccaggcca ccagctaacc agtggggtga tcttgatgat | 2700 |
| ctccttaacg gttatgatga ccagcagaag gctctcatac agaaggaaag ggcaagacgg | 2760 |
| atcatggaac agcacacgat gttttcatcg aggaaacttt gtttagtgct tgatttggat | 2820 |
| cacactctcc tcaattctgc gaagtttata gaagtggatc ctattcatga agagattttg | 2880 |
| cggaagaaag aggaacaaga ctgggaaagg tcagagcggc atctgttccg attccatcat | 2940 |
| atgcaaatgt ggactaaact aagaccagga atatggaatt ttctcgagaa ggcgagcaag | 3000 |
| ctttacgagt tacatctgta cacgatgggg aacaagctgt atgctactga gatggctaag | 3060 |
| gttcttgatc ctagtggaac cctgtttgca gggagagtaa tctcaagggg tggtgatggt | 3120 |
| atctcaagag gtggtgacgg tgatacattt gacagcgatg accgtgtacc aaaaagtaaa | 3180 |
| gatcttgatg gggtattggg gatggaatct gcagtagtga tcatcgatga ctctgtgaga | 3240 |
| gtctggcccc acaacaaaaa caatatgatt gttgtagaga gatacaccta tttcccttgc | 3300 |
| agcagacggc aatttggcct tcctggacca tcacttcttg aaattgatcg tgatgaaagg | 3360 |
| cctgaggatg gcactcttgc ttcttcgttg gcggttattg ggcgcattca tcaaaacttc | 3420 |
| ttttctcatc ccaacctcaa tgatgctgat gtgcgcagca tactatcatc tgagcagcgg | 3480 |
| aggatccttg ccggctgccg tattgtcttt agccggattt tccctgttgg agaggctaac | 3540 |
| ccccacttgc atcctctctg gcagactgca gagcagttcg gtgcagtgtg cacgaaccag | 3600 |
| attgacgatc gggttactca tgttgtcgcc aactcactag gaaccgacaa ggtgaattgg | 3660 |
| gcactacaaa caggcagatt cgtcgttcat ccaggatggg tagaagcttc agcacttcta | 3720 |
| taccggcgtg ccaatgaaca cgattttgca gtaaaataa | 3759 |

<210> SEQ ID NO 6
<211> LENGTH: 3732
<212> TYPE: DNA
<213> ORGANISM: Artificial Sequence
<220> FEATURE:
<223> OTHER INFORMATION: cDNA of TACPL3-B

<400> SEQUENCE: 6

| | |
|---|---|
| atgcgcgtga cgctcacgcc caaggacgag gattggctgg tcgagctgat gacgagggag | 60 |
| cgcccgcggt cggcggtggt cgcgcctggg ggggacgtct tcaccgccag tggcggcggg | 120 |
| gagacgtctg atggggactc ctcagagtcg ctggaagaaa ttagtgccgc cgactttaag | 180 |
| gagtcgtcca gtggcaccgc cgctgcgtcg cgtcgtcgc agagatctag gtttggatg | 240 |
| ggatacacca tgtcccggag ttatgcgccg gcgttccaca gctttgcttg ggcgcaggct | 300 |
| gtgcagaaca agcctctcgt tccgcggcct gccgacgagg acgaagtaga gcatctcgtg | 360 |
| gacgcctcgg aggaggagaa ggaagagggc gagattgagg aggggaggc cgtacagtcc | 420 |
| acttcccctc caattaagca gcctgaggcc atcgacttgg actctgatgc gcaggacaag | 480 |
| tcagagtcag tggccatgga gcagaccccct ttggccgtcg aggcggctga tgagctggat | 540 |
| tttgaccagc gcgtggggag tatactggag gagcttgaga ggctttccat tgaggaagct | 600 |
| gagaagtcat ttgagggttc gtgtgtccgc ctgcggtctt gttttgagag ccttaagccg | 660 |
| ctgttcccag agagcggtag cccgatgcct atgcttgatg ctcttgtgca acaggctttt | 720 |
| gttggaatcg acaccatcac cactgtagct aattcatatg cgatgccgaa gagggagcag | 780 |

```
aacaagaaca tgctgttgaa gctgctgttt cacataaaga acagatattc agacatgctg    840
gcactcaacc agcgagatga gcttgatagt cgtgtgagac agttagtttt tgtagatgga    900
gaagaccatg ccggttccaa ttgtagctcc aaaacagtga atttggttgt tccatctgga    960
caggttccat cagatagact gccagtcgag tcaggagcag caaatccact tgggggctct   1020
agtttcccta gctgggagat accggcgaat aatagaatgg ttagccccTt gttggacctt   1080
catgcagatt atgacgagaa cagcttaccc tcacccaccc gagatagtgc accaccTttt   1140
cctgtgccaa agcccattgg atttggatta tttccaatgg cacctgacag atatttttcg   1200
gcggaaagag ttgatccttc gaaaaaagtt ctgtatccat gtgtaatga tgcgctaaag    1260 gatgtttcct cgtaccgaca gaagtatggc cagacatcta ccttcgcaag tgatgatctt   1320
ccaagcccaa ccccatctga tgatggtgat aaatctggag acaaagaagg tgatatattt   1380
ggtgaagttt caagcttttc agcttctaat ctgatacctg cctcccgacc tagtgcagtt   1440
atcagcagca atgacagttt tgcaggtggt cctccaggct atgctaaaca aattgaacag   1500
tctgtttcag acccagcca tgctcttaag ccttcagcta aaagtagaga tccaaggctc    1560
aggtttttga accgtgattc tggtggtact gcagatgcaa atagacatgt aaatttggca   1620
gagccaaatg cttccaaaga tgggaccttg ggggtgttg tatcagataa tagccggaag    1680
cacaaggcaa ctggccaacc tctcacggat gaaaccgtgt taaaagagc tagggagagt    1740 actgggaatc cagagacat gcaggtacca cctggtagag atgaagtaa cattagctcc     1800 tattcaggta cagggttca atcaaatcag cataaagggc ttgaaactaa ggcagccggg    1860
aatcctagta ttaggaccag cagtcaactt attagcaatg taagtagtat cccagacagt   1920
actggaactc tccaagcctc ccaacctaat tcagttccac agaccagtgc agctcctatt   1980
gtttcattgc ctgcagtgtt aaaggacatt gctgtgaacc cgactgtgct catgcattgg   2040
attcaaatgg aacatcagaa gtggtcagca tcagagcctc agcctgcttc aggtatcatc   2100
tctagtggca tgatcaataa tgtcactgct gggatggtta taccacctgg caatgctccg   2160
aagaccgcag aagttgcaca cattccttct tataggccac aagcaacatc gcaaacagcc   2220
tctgtgaatt cacaaaatga ccctggagta atacgtatga aggcccgtga tccccgtcgt   2280
gtcctccaca ataacacatc acagaagaac gatactccga actctgatca agccaaaagc   2340
aatggaatcg ccctgccggc cttccaggac agcaaagaca atttgattaa ccgtgaacaa   2400
ctggcagagc aacttcagac tactgtgttg ccatctcaac cagtctcatt atccagcatt   2460
gctcgacagt ccaccatgag cgcgagtaag gtggatcctg tctctaattc acagttagct   2520
gcttcatcgc tcattgctcc tcaagaaact ttagtcagcg taaatagggc agatccaaga   2580
gtagctgctg gacagaatga ttccaatgat gctgccctg ctacaacact tggtaccagg    2640
ccaccagcta accagtgggg tgatcttgat gatctcctca acggttatga tgaccagcag   2700
aaggctctca tacagaagga aagggcaaga cggatcatgg aacagcacac gatgttttca   2760
tcgaggaaac tttgtttagt gcttgatttg gatcacactc tcctcaattc tgctaagttt   2820
atagaagtgg atcctattca tgaagagatt ttgcggaaga agaggaaca agaccgggaa    2880 aggtcagagc ggcatctgtt ccgattccat catatgcaaa tgtggactaa actaagacca   2940
ggaatatgga atttttctcga gaaggcgagc aagctttatg agttacatct gtacacgatg   3000
gggaacaagc tgtatgctac tgagatggct aaggttcttg atcctagtgg aaccctgttt   3060
gcagggagag tcatctcaag aggtggtgat ggcatctcaa gaggtggtga tggtgataca   3120
tttgacagcg atgaccgtgt accaaaaagt aaagatcttg atggggtatt ggggatggaa   3180
```

```
tctgcagtag tgatcatcga cgactctgtg agagtctggc cccacaacaa aaacaatatg   3240
attgttgtag agagatacac ttatttcccc tgcagcagac ggcaatttgg ccttcctgga   3300
ccatcacttc ttgaaattga tcgtgatgaa aggccggagg atggcactct tgcttcttcg   3360
ttggcggtta ttgggcgcat tcatcaaaac ttcttttccc atcccaacct caatgatgct   3420
gatgtgcgca gcatactatc atctgagcag cggaggatcc ttgcgggctg ccgtattgtc   3480
tttagccgga ttttcctgt tggagaggct aaccccact tgcatcctct ctggcagact    3540
gcagagcagt tcggtgcagt gtgcacgaac cagattgacg atcgggttac tcatgttgtt   3600
gccaactcac taggaaccga caaggtgaat tgggcactac aaacaggcag attcgtcgtt   3660
cacccaggat gggtagaagc ttcagcactt ctataccggc gtgccaatga acacgatttt   3720
gcagtaaaat aa                                                      3732

<210> SEQ ID NO 7
<211> LENGTH: 3759
<212> TYPE: DNA
<213> ORGANISM: Artificial Sequence
<220> FEATURE:
<223> OTHER INFORMATION: cDNA of TACPL3-D

<400> SEQUENCE: 7
atgcgcgtga cgctcacgcc caaggacgag gattggctgg tcgtgctgat gacgagggag    60
cgcccgcggt cggcggtggt cgcgcctggg ggggacgtct tcaccgccgg tggcggcggg   120
gagacgtccg atggggactc ctcagagtcg ctggaagaaa ttagtgccgc cgactttaag   180
gagtcgtcca gtggcaccgc cgctgcgtcg gcgtcggcgc agagatctag gtttggatg    240 ggatacacca tgtccaggag ttatgcgccg gcgttccaca gctttgcttg gcgcaggct    300 gtgcagaaca agcctctcgt tccgcggcct gttgccgacg aggacgaggt agagcacctc   360
gtcgacgcct cggacgagga aaggaagag gcgagattg aggagggga ggccgtacag     420 tccacttccc ctccaattaa gcagcctgag accatcgact tggactctga tgcgcaggac   480
aagtcagagt cagtggccat ggagcagacc cctttggcct tcgaggcagc tgatgagctg   540
gattttgacc agcgcgtggg gagtatactg gaggagcttg agaggctttc cattgaggaa   600
gctgagaagt catttgaggg ttcgtgtgcc cgcctgcggt cttgctttga gagccttaag   660
ccgctgttcc cagagagcgg tagcccgatg cctatgcttg atgctcttgt caacaggct    720 tttgttggaa tcgacaccat caccactgta gctaattcat atgcgatgcc gaagagggag   780
cagaacaaga acatgctctt gaagctgttg tttcacataa agaacagata ttcagacatg   840
ctggcactca gccagcgaga tgagctcgat agtcgtgtga cagttagt ttttgtagat     900 ggagaagaca atgccggttc caattgtagc accaaaacag tgaatgtggt tgttcaatct   960
ggacaggttc catcagatag actgccagtc gagtcaggag cagcaaatcc acttaggggc  1020 tctagttttcc ctagctggga gataccggcg aataatagaa tggttagccc cttgttggac  1080
cttcatgcag attatgacga gaacagctta ccctcaccca cccgagatag tgcaccacct  1140
tttcctgtgc caaagcccat tggatttgga gtatttccaa tggcacctga cagatatttt  1200
ttggcggaaa gagttgatcc ttcaaaaaaa gttctgtata catgtgtgaa tgatgcgcta  1260
aaggatgttt cctcgtaccg acagaagtat ggccagacat ctacctttgc aagtgatgat  1320
cttccaagcc caaccccatc tgatgatggg ataaatctg agacaaaga aggtgatata    1380 tttggtgaag tttcaagctt ttcagcttct aataagtctg ctccgccaag tgggaatctg  1440
atacctgcct cccgacctag tgcagttatc agcagcaatg acagttttgc aggtggtcct  1500
```

```
ccaggctatg ctaaacaaat tgaacagtct gtttcaggac ccagccatgc tcttaagcct    1560
tcagctaaaa gtagagatcc aaggctcagg tttttgaacc gtgattctgg tggtactgca    1620
gatgcaaata gacatgtaaa ttttgcagag ccaaatgctt ccaaagatgg gaccttgggg    1680
ggtgttgtat cagataatag ccggaagcac aaggcaactg ccaacctct cacgggtgaa     1740 accgtgttaa aaagagctag ggagagtact gggaatccca gagacatgca ggtaccacct    1800
agtagagatg gaagtaacat tagctcctat tcaggtgaca gggttcaatc aaatcagcat    1860
aaagggcttg aaactaaggc agccgggaat cctagtatta ggaccagtag tcaacttatt    1920
agcaacgtaa gtagtatccc agacagtact ggaactctcc aagcctccca gcctaattca    1980
gttccacaga ccagtgcagc tcctattgtt tcattgcccg cagtgttaaa ggacatcgct    2040
gtgaacccga ctgtgctcat gcattggatt caaatggaac atcagaagag gtcagcatca    2100
gagcctcagc ctgcttcagg tattatctct agtggcatga tcaataatgt cactgctggg    2160
atggttatac cacctggcaa tgctctgaag accgcagaag ttgcacacat tccttcttat    2220
aggccacaag caacatcgca aacagcctct gtgaattcac aaaatgaccc tggagtaata    2280
cgtatgaagg cccgtgatcc ccgtcgtgtc ctccacaata acacatcaca gaagaacgat    2340
actccgaact ctgatcaagc caaaagcaat ggaatcaccc tgccggcctt ccaggacagc    2400
aaagacaatt tgattaaccg tgaacaactg gcagagcaac ttcagactac tgtgttgcca    2460
tctcaaccag tctcattatc cagcattgct ggacagtcca ccatgagcgc gagtaaggtg    2520
gatcctgtct ctaattcaca gttagctgct tcatcactca ttgctcctca agaaacttta    2580
gtcagcgtaa atagggcaga tccaagagta gctgctggac agaatgattc caatgatgct    2640 gccccctgcta caacacttgg taccaggcca ccagctaacc agtggggtga tcttgatgat    2700
ctcctcaacg ttatgatga ccagcagaag gctctcatac agaaggaaag ggcaagacgg    2760
atcatggaac agcacacgat gttttcatcg aggaaacttt gtttagtgct tgatttggat    2820
cacactctcc tcaattctgc gaagtttata gaagtggatc ctattcatga agagattttg    2880
cggaagaaag aggaacaaga ccgggaaagg tcagagcggc atctgttccg attccatcat    2940
atgcaaatgt ggactaaaact aagaccagga atatggaatt ttctcgagaa ggcgagcaag    3000
ctttacgagt tacatctgta cacgatgggg aacaagctgt atgctactga gatggctaag    3060
gttcttgatc ctagtggaac cctgtttgca gggagagtca tctcaagagg tggtgatggc    3120
atctcaagag gtggtgatgg tgatacattt gacagcgatg accgtgtacc aaaaagtaaa    3180
gatcttgatg gggttttggg gatggaatct gcagtagtga tcatcgacga ttctgtgaga    3240
gtctggcccc acaacaaaaa caatatgatt gttgtagaga gatacaccta tttcccctgc    3300
agcagacggc aatttggcct tcctggacca tcacttcttg aaattgatcg tgatgaaagg    3360
ccggaggatg gcactcttgc ttcttcgttg gcggttattg ggcgcattca tcaaaacttc    3420
ttttctcatc ccaacctcaa tgatgctgat gtgcgcagca tactatcatc tgagcagcgg    3480
aggatccttg ccgctgccg tattgtcttt agccggattt tccctgttgg agaggctaac    3540
ccccacttgc atcctctctg gcagactgca gagcagttcg gtgcagtgtg cacgaaccag    3600
attgacgatc aggttactca tgtcgttgcc aactcactag gaaccgacaa ggtgaattgg    3660
gcactacaaa caggcagatt cgtcgttcac ccaggatggg tagaagcttc agcacttcta    3720
taccggcgtg ccaatgaaca cgattttgca gtaaaataa                           3759
```

<210> SEQ ID NO 8
<211> LENGTH: 3594
<212> TYPE: DNA
<213> ORGANISM: Artificial Sequence
<220> FEATURE:
<223> OTHER INFORMATION: cDNA of SbCPL3 (Sb05g019010.1)

<400> SEQUENCE: 8

| | | | | | | |
|---|---|---|---|---|---|---|
| atggcgcggg | agcggccgcg | gtccacggtg | gttgcggcgg | gcggagattt | ggtcactgct | 60 |
| cccggcggcg | gcgaggggtc | ggatggggac | tcggcgggt | cgatagagga | gatttcagct | 120 |
| gacgacttca | ggaaggactc | gtcgtcggcg | ttgggcggcc | ccgccgccgc | ggcggctgcg | 180 |
| gggcagagat | ctaggtcttg | ggtgggtccg | cccgccgtgg | gttacatggc | gcggaacttt | 240 |
| gggcacgcct | tcaacagctt | cgcgtggtcg | caggccgtgc | ggaacaagcc | gctggggtta | 300 |
| cagccgccgc | ctgcctcgga | cgaggacgag | gtggagcatg | ccgtggacgc | gtccgacggg | 360 |
| gagaaggagg | agggcgagat | tgaggagggg | gaggctgtgg | aggccgaggc | atcgcctgcc | 420 |
| cgcgcacagc | ctgagaccat | cgacttggac | gcggacgcgg | acgcgctgga | gaagtcagag | 480 |
| tcgctggctg | gtgctgtgcc | tgcctctgct | gctgaggaag | aggaggtgaa | ccttgatcag | 540 |
| cgtgtcggca | gtatactgga | ggagcttgag | atggtctcca | ttgaggaagc | cgagaagtct | 600 |
| tttgagggtg | catgtggacg | actgcatacc | tgctttgaga | acctgaagcc | gctgttccag | 660 |
| gaactggaga | cgggagccc | gatggctata | cttgaacccc | tcatgcagca | ggcgttcatt | 720 |
| ggaattgaca | cactcaccac | tgtggcgatt | tcgtataact | tgccgaggag | tgagcagaat | 780 |
| aagacaacgc | ttttgaagtc | gttgttccac | ataaagaaca | gatattcaga | catgctgact | 840 |
| cccgagcagc | gagacgagtt | ggacagccgc | gtgaggaagt | tagttttttgg | agaaaaagac | 900 |
| aatgtcagtg | acccaagtac | aagtagtggc | accaatgcga | taaatgtttt | ggctccatct | 960 |
| gggcaggtct | catcctcagg | aggactgcca | tttgaatcag | gtgcagcaaa | tccatttagt | 1020 |
| agcttgccga | ggttggaagt | acctgccaaa | aggattagtc | ccttgttgga | tcttcatgca | 1080 |
| gattatgatg | aaaacagctt | accatcgcca | accagggata | atgcaccgcc | ttttcctgtg | 1140 |
| ccaaagccta | ttggttttgg | agcatttcca | atggtgcctg | agaaattatc | tttcccagaa | 1200 |
| agagttgagc | ctgcaaagaa | ttcgttatat | ccatccttaa | atgatcctct | gaaggctgtc | 1260 |
| tcctcatatc | agcagaagta | tgggcagaaa | tctgtatttc | caagtgatga | tctgccaagt | 1320 |
| ccaactccat | ctggtgatga | gggtaaatct | gcagataaag | gtggtgacat | atttagtgag | 1380 |
| gtttccagct | tccctgttcc | aaagagtatt | gcattgccaa | gtacaagcca | gatgcctgct | 1440 |
| tctcaaccta | gcacagtcag | cagcagtggt | attagttatg | catctggtcc | acctggtttt | 1500 |
| gctaaacaaa | ttgagcagcc | ggttgcaggt | ccaaatcacg | caataaaggc | agcatcgaaa | 1560 |
| agtagagatc | caaggctcag | gtttttgaac | cgtgattctg | ctggtgctac | agatgtgaat | 1620 |
| cggcgcgcaa | attttcaga | actgaaggat | gggaacttgg | gtggagcgtc | agttggtaac | 1680 |
| cgtaaacaca | aagcaattga | tgatcctcag | gtggatgaaa | atgtgttaaa | agatttagg | 1740 |
| ggcggaactg | caaatccgag | agacttgcaa | cctacaggga | atcctaatca | gcttatgaac | 1800 |
| attagggctc | ctacaaatag | tagcggtatc | aatatgaaaa | ctttgcagcc | ccctcaaact | 1860 |
| actgctccac | atgtcagtgc | agctcctgct | gtcccagtgc | cttctatgtt | gttaaaggac | 1920 |
| attgctgtga | acccaacatt | gcttatgcat | ttgatccaaa | tggaacatca | aaagaagtca | 1980 |
| gcatcagaaa | ctcagggtgg | catgtctagt | gggatgagca | caatggaat | tgcaggcatg | 2040 |
| gttttcacac | ctggcaatgc | tccaaagacc | acagaagctg | cacaagtccc | ctctgttagg | 2100 |

-continued

```
ccacaggttc cagcgcagac accttctttg aactcacaaa atgatggtgg aatccttcgc    2160
atgaagcccc gtgatccacg acgcatccta cacaataacg tagcacagaa atctgatgca    2220
atggtcttgg agcaagtgaa actaatggaa attacccagc cagactctca gggcaccaag    2280
gaccagacta gttcaatgcc ttctcaacca actttgccat ctagcgttgc aaggccattc    2340
acaaacacaa acatgttga tcctgtctct aattcacagt tagctgctac agctataatg     2400
gctcctacac aacaagcttt gggcagcata aataaggtgg atccaagact agcagttgaa    2460
cagaatgggc aaaatgctga tgcaacaaca actgatgctt ctgcaacaga acttgaagct    2520
acacagcctg ttagcccatg gggtaatctt gatcatctcc ttgatggata tgatgataag    2580
caaaaagctc tgatacagaa ggaaagggca agacgaataa cggaacagca caaaatgttc    2640
tcagcgcgaa agctatgcct ggtgcttgat ttggatcaca cccttcttaa ttctgcaaag    2700
tttatagaag tggaacccat tcatgaagag atgttacgga agaaagagga gcaagacagg    2760
actttgccag aacgtcatct ctaccgtttt catcatatga atatgtggac gaagttgagg    2820
ccaggaatat ggaactttct tgagaaggct agtaacctat tcgagttgca tttgtacact    2880
atgggaaaca aactgtatgc tactgagatg gccaaggttc ttgatcctac tggaaccttg    2940
tttgctggac gagtcatatc aagaggtgat gatggcgatc cctttgacag tgatgagcga    3000
gtgccgaaaa gtaaagattt ggatggggta ctgggtatgg aatctgcagt cgtgatcata    3060
gatgattctg taagagtctg gcctcataac aggcacaatt tgatagttgt agaaagatac    3120
acctatttcc cctgcagcag acgtcaattt ggccttcctg gaccatcact tttagagatt    3180
gacagagacg agaggcctga ggatggtacc cttgcttctt cacttgcggt cattgagaga    3240
atccaccaca atttcttttc acatcctaac ctcaatgagg ctgatgtgcg gagcatacta    3300
gcatctgagc agcgaaggat ccttgctggt tgtcgtattg tctttagccg ggttttccca    3360
gttggcgacg ccagccccca cttgcatcct ctgtggcaga ctgcagagca gtttggtgcg    3420
gtctgcacaa acctggttga tgatcgggtt actcatgttg ttgccaactc ccctgggaca    3480
gacaaggtga attgggcatt atccaaaggc aaatttgtgg tgcatccagg atgggtagaa    3540
gcttcagccc tgttgtaccg gcgcgccaac gaacatgact ttgcagtcaa ataa          3594
```

<210> SEQ ID NO 9
<211> LENGTH: 3705
<212> TYPE: DNA
<213> ORGANISM: Artificial Sequence
<220> FEATURE:
<223> OTHER INFORMATION: cDNA of ZmCPL3

<400> SEQUENCE: 9

```
atgcgcgtga cggtcacgcc caaggacgag gaaaggctgg ttgacttgat ggcgcgcgag     60
cagccgcggt cggcggtggt tgcggcgggc ggagatttgg tcactgctgc cggggcggg    120 ggcgagggt cggataggga ctcttcgggg tccataaggg agattacggc tgacgacttc    180
aagaaggact cgtcgtcggc gttgggcggc gcggcgcgc cggcggggcc gagatctagg    240
tcttgggtgg ccccgcccgc cgtgggttac atggcccgga actttcgcta tgccttcaat    300
agctttgcgt ggtcgcaggc cgtgcggaat aagccgctgg ggctacaacc gcctgcccca    360
gacgacgacg aggtggagca cgccgtggac gtctccgacg gagagaagga gagggcgag    420 attgaggagg gggaggctgt ggaggccttg gcctcgcctg ctcctgcgca gcctgagacc    480
atcgatttgg actccgacgc cccggagaag tcagagtcgg tggctatcga tggaagtgcc    540
agtgttgtgc ctgtcccagc tgctgaggaa gaggaggtga accttgatca gcgtgtgggg    600
```

```
agtatactgg aggagctcga gatggtctcc attgaggaag ctgagaagtc gttcgagggt    660
gcatgcgcac gactgcatac ctgcttcgag aacctgaagc ctctgttcca ggaactggag    720
aacgggagcc cgatggctat ccttgaaccc ctcatgcagc aggcgtttat tggaattgac    780
acactcacca ctgtggcgaa tttgtataac ttgccgagga gggagcagaa taagacaaca    840
cttttgaagt tgttgttcca cataaaaaac agatattcgg acatgctgac gcctgagcag    900
cgagaagaga tggacagccg cgtgaggaag ttagttttg gagagaaaga caatgtcagt     960
gacccaagta ccagttgtgg caccagtgcg ataaatgttt cagctccatc tgggcaggtt   1020
tcaaacacag gaggactgcc atttgaatca ggtgcagcaa atctatttag tagcttgcca   1080
aggttggaag tacctgccaa aaggaatagt cccttgttga atcttcatgc agattatgat   1140
gagaacagct taccctcgcc aacccgggac aatgcaccgc cttttcctgc gctaaagcct   1200
attggttttg gagcatttcc aatggtacct gagaaactat cttcctaga cagagttgag    1260
cctacaaaga attcgttata tccaccctta aatgatcctc tgaaggctgt ctcttcctat   1320
cagcagaagt atgggcagaa atctgtatat ccaagtgatg atctaccaag tccaactcca   1380
tctggtgatg agggtaaacc tgcagataaa ggtggtgata tatttagtga tgtttccagc   1440
ttccctgttc caaagagtat tgtattacca agtacaagtc agatgcctgc ttctcaacct   1500
agcacagtca gcagcagcag tattagttat gcttcaagta caagtcagat ggctgcttct   1560
caacctatca cagtcagcag tagcggtatt agttatgcgt ctggtccacc tggttttgct   1620
aaacaaattg agcagtcgac tgcaggtccg aatcatgcaa taaaggcagc atccaaaagt   1680
agagatccga ggctcagatt tttgaaccgt gattctgctg gtgctacaga tgtaaattgg   1740
cgtgcaaatt tttcagaact gaaggatggg aacttgggtg gagtttcagt tggtaaccgt   1800
aaacagaaag cagttgatga tcctcaggtg gatgacaatg cgttaaaaag atttagggc    1860
ggaattgcga atcagagaga catgcagcct acggggaacc ccaatcagct tatgaacatc   1920
agggctccta cacatagtag cagtatcaat atgaaaactt tgcaacctcc tcaaactact   1980
gctccacatg tcagtgcggc tcctgctgtc ccattgcctc ctatgttgtt aaaggacatt   2040
gctgtgaacc cagcattgct tatgcatttg atccaaatgg aacatcaaaa gaagtcagca   2100
tcagaaagtc agggtggcat gtctagtggg atgaccaaca atggaattgc aggcatggtt   2160
ttcacacctg gcaatgctcc gaagatcaca gaagctgcac aagtcccatc tgttaggcca   2220
caggttccag tgcagacacc tcctttgaac tcacaaaatg atggtggaat cgttcgcatg   2280
aagccccgtg atccacggcg catcctacac aataacatag cacagaaatc tgatgcaatg   2340
agcttggagc aagtgaaaaa taatggaact acacagccag actctcaggg caccaaggac   2400
cagactactc cagtgccttc tcaaccagcc ttgccgtcta gcattgcaag gccattcagc   2460
agcgcaaaac atgttgatcc tgtctctaat tcacagttag ctgctacagc tattatggct   2520
ccgacacaag ctttgagtag cgtaaataag gtggatccaa gactagcagt tgaacagaat   2580
ggacaaaatg ctgatgcaac aacaaatggt gcttctgcaa caacacttga agctacacag   2640
cctgttagtc catggggtga tgttgatcat ctccttgatg gatatgatga ccagcaaaag   2700
gctctgatac agaaggaaag ggcaagacga ataacagaac aacacaaaat gttctcagca   2760
cggaagctat gcttggtgct tgatttggat cacacccttc ttaattctgc aaagtttata   2820
gaagtggaac caattcatga agagatgtta cggaagaaag aggagcaaga caggactttg   2880
cctgaacgtc atctctaccg ttttcatcat atgaatatgt ggacgaagct gaggccagga   2940
atatggaact tcttcagaa ggctagtaac ctgtttgagt tgcatttata cactatggga   3000
```

| | |
|---|---:|
| aacaaactgt atgctactga gatggccaag gttcttgatc ctactgggac cttgttcgct | 3060 |
| ggacgagtca tatcaagagg tgatgatggt gatcctttg acagtgatga acgagtgcca | 3120 |
| aaaagtaaag atctggatgg ggtactgggt atggaatctg cagttgtgat catagatgat | 3180 |
| tctgtaagag tctggcctca taacaggcac aatttgatag ttgtagagag atacacctat | 3240 |
| ttcccctgca gcaggcgtca atttggcctt cctggaccat cacttctaga gattgacaga | 3300 |
| gatgagaggc ctgaggatgg tacccttgct tcttcacttg cggtcattga gagaatccac | 3360 |
| cacaattttt tttcacatcc taacctcaat gaggctgacg tgcggagcat actagcatct | 3420 |
| gagcagcgaa ggatacttac tggttgccgt attgtcttta gccgggtttt cccggttgga | 3480 |
| gacgccagcc ctcacttgca tcctctgtgg cagactgcag aacagtttgg tgcagtctgc | 3540 |
| acaaacctgg ttgatgatcg ggtcactcat attgttgcaa actcccctgg acagacaag | 3600 |
| gtgaattggg cattatccaa aggcaaattc gtagtgcatc caggggtaga agcttcagct | 3660 |
| ctgttgtacc ggcgcgccaa cgaacatgac tttgcagtca aataa | 3705 |

<210> SEQ ID NO 10
<211> LENGTH: 3657
<212> TYPE: DNA
<213> ORGANISM: Artificial Sequence
<220> FEATURE:
<223> OTHER INFORMATION: cDNA of StCPL3 (PGSC0003DMT400052897)

<400> SEQUENCE: 10

| | |
|---|---:|
| atggaagaat gtaatcgagt tgaagatgta gaggagggtg agatctcaga ttcggcttca | 60 |
| gttgaagaaa taagtgagga tgcgttcaat aggcaagacc cacctactac tactaagatt | 120 |
| aagattgcga gtaatgaaaa tcaaaatcaa aattcgacga cgacgactag ggtttggacg | 180 |
| atgagagatg catataaata tccaatttct agggattatg ctagaggttt gtataacctg | 240 |
| gcttgggctc aggctgtgca gaataagcct ttagacgaac tattcgtcat gactagtgac | 300 |
| aattccaacc agtgtgctaa tgctaatgct aatgttgaat ccaaggtcat cattgatgtg | 360 |
| gatgtggatg acgatgctaa agaggaagga gagttggagg aaggcgagat cgacttggat | 420 |
| gccgctgacc tagttctaaa ttttggaaag gaggccaatt tcgttaggga caacttcag | 480 |
| agtgttactc tagacgaaac ccacaaatcc ttttctatgg tttgttccaa attgcaaact | 540 |
| tcattactgg ccttggggga actagctctt tctcaagaca agaatgacat tcttattcaa | 600 |
| ctctttatga ctgcactccg aaccattaat tctgtttttt actccatgaa ccaggatcag | 660 |
| aagcaacaaa acacagatat tctatctagg ttgcttttc atgcaaagac acaattacct | 720 |
| gctcttttgt cttctgagca gttaaaagag gtggatgctg tgattctctc tattaaccag | 780 |
| tcagctgttt tctcaaatac tcaagacaat gacaaggtca atgggatcaa agttgttgaa | 840 |
| ctgttagata agaaggtttc tcataaatcc tctgaaaatg caaatcagga ttttactgct | 900 |
| gtaaacaagt atgatttagg tgctgtatct atcaaatctt caggcctgaa ggaacagagt | 960 |
| gtgtcatttg aatctgtaaa accaggatta gccaattcta aagctaaagg ttatccatt | 1020 |
| cctttgctag acctccataa ggaccatgat gaagatactc ttccgtcgcc tacacgagag | 1080 |
| attggaccac agttccctgt tgcaaaagct acacaggctc atggaatggt gaaactggac | 1140 |
| ttgcctattt ttgcgggttc tcttgagaaa gggaattctt tattgcatcc ttatgaaact | 1200 |
| gatgccctta agctgtttc ctcttatcaa caaaaatttg gtcgaagttc ccttttttgtt | 1260 |
| agtgaaaacc ttccaagtcc aactccgtct gaagagggtg atagtggcaa agggacatt | 1320 |
| ggtggggagg tcaccagtct tgatgttgta cataatgcta gccatctgaa tgaatctagc | 1380 |

-continued

| | |
|---|---|
| atggggcaac caatattgtc ttctgttccc cagaccaata ttcttgatgg acaaggactg | 1440 |
| ggaactgctc ggactgcaga tcctctgagt tttctgccaa atccttcttt gcgatcttct | 1500 |
| acagcaaaaa gtagagatcc cagactcaga ctggcaacca cgatgcagt tgctcagaac | 1560 |
| acgaataaaa atatcttgcc tatcccagac attgatttga aattggaggc ttctttagag | 1620 |
| atgattggtt caaaaaagca gaagacagta gacctaccag tctttggtgc tccattgccg | 1680 |
| aaaagacaaa gaagtgaaca gactgattca atcattgtga gtgatgtgcg tccttcgact | 1740 |
| ggaaatggtg gttggttaga ggatagaggg actgctgggt tgccaattac gagtagtaac | 1800 |
| tgtgctacag atagcagtga caatgatatt aggaaattgg agcaagtaac agctactatc | 1860 |
| gctactatac ctagtgtcat agttaatgct gctgagaact ttccagtgac tggcattagc | 1920 |
| acgtcaacaa ctttgcattc tttgttaaaa gatatagcta taaatccatc gatatggatg | 1980 |
| aatataatca agatggaaca gcagaaatct gctgatgctt ctagaactac tacagcacaa | 2040 |
| gcttcaagtt ctaaatctat tcttggagca gttccatcaa cggatgcaat agctcccaga | 2100 |
| tcttctgcta ttggccagag atcagtagga atacttcaga ctcctacaca cacagcatca | 2160 |
| gcggatgaag tggctatagt ccgcatgaaa cctcgtgacc ctcggcgtgt tcttcataat | 2220 |
| actgcagttc taaaggggtgg taatgttgga tcagatcaat gtaaaactgg tgtagcaggc | 2280 |
| acacacgcaa cgataagcaa tcttggtttc caaagtcaag aggaccagtt ggataggaag | 2340 |
| tcagctgtga ctcttccgac tacaccacca gacattgctc gccaattcac caaaaatttg | 2400 |
| aaaaatattg ctgacatgat ctctgtttca ccatccacat cactgtctgc tgcttctcaa | 2460 |
| actcagacac aatgcctaca atctcatcag agtagatcgg aaggtaagga agcagtttct | 2520 |
| gaaccaagtg aacgggtgaa tgatgctggc ttagcttctg aaaaaggttc tcctggttca | 2580 |
| ttgcaaccac agatctcttg gggagatgtt gagcatctat ttgaggggta cagcgaccaa | 2640 |
| cagagagctg atatccagag agaaagggct aggaggcttg aggaacagaa aaaaatgttt | 2700 |
| tctgttcgga agctctgtct cgtcttggac ttggaccata ctcttctgaa ttcagcaaag | 2760 |
| tttgttgaaa tcgacccagt tcatgaagag atattgagga gaaagagga acaagaccgt | 2820 |
| gaaaagccgt gtaggcacct attccggttt ccacacatgg gaatgtggac caagttacgg | 2880 |
| cctgggattt ggaatttctt ggaaaaggct agcaatcttt ttgagctgca tctctatacc | 2940 |
| atgggtaaca agctatatgc cacggagatg gccaaattgc tagatccaaa aggggatctg | 3000 |
| tttgctggac gagtgatctc caggggtgac gatgggagatc catttgatgg ggatgaaagg | 3060 |
| gttcctaaga gtaaggactt ggaggggggtt ttgggcatgg agtcagctgt tgtgattatt | 3120 |
| gatgattctg tgagagtctg gccacataac aagctaaatt tgattgttgt agagaggtat | 3180 |
| atttactttc cttgcagtag acggcaattt ggtctccctg gtccttctct tcttgagatt | 3240 |
| gatcatgatg aaagaccaga agatgggaca ttggcctctt gtttggggt tattcaaaga | 3300 |
| atacatcaga attttttcgc acatcggtcc atagatgaag ctgatgttag gaacatttta | 3360 |
| gcgacagaac aaaaaaagat tctggcaggt tgccgtattg tcttcagcag agtgttccct | 3420 |
| gttggtgaag ccaatcctca tttgcatcct ctgtggcaga cagctgaaca gtttggtgct | 3480 |
| gtctgcacta gtcaaattga tgatcaggtt acccatgtgg ttgcaaattc tcttgggacg | 3540 |
| gataaggtta ttgggcact ttccaccgga cgatttgttg ttcatcctgg ctgggtggag | 3600 |
| gcatcagctt tactttatcg gagggcaaat gagcatgatt ttgctattaa atcttaa | 3657 |

<210> SEQ ID NO 11
<211> LENGTH: 1257
<212> TYPE: PRT
<213> ORGANISM: Glycine max

<400> SEQUENCE: 11

```
Met Ile Phe Gly Ser Leu Leu Asp Cys Glu Lys Leu Gly Lys Leu Glu
1               5                   10                  15

Lys Met Gly Lys Glu Val Glu Asp Val Glu Glu Gly Glu Ile Ser Asp
            20                  25                  30

Thr Ala Ser Val Glu Glu Ile Ser Ala Glu Asp Phe Asn Lys Gln Asp
        35                  40                  45

Val Lys Val Leu Asn Asn Asn Lys Pro Asn Gly Ser Asp Ala Arg
50                  55                  60

Val Trp Ala Val His Asp Leu Tyr Ser Lys Tyr Pro Thr Ile Cys Arg
65                  70                  75                  80

Gly Tyr Ala Ser Gly Leu Tyr Asn Leu Ala Trp Ala Gln Ala Val Gln
                85                  90                  95

Asn Lys Pro Leu Asn Asp Ile Phe Val Met Glu Val Asp Ser Asp Ala
            100                 105                 110

Asn Ala Asn Ser Asn Ser Asn Asn Ser Asn Arg Leu Ala Ser Val Ala
        115                 120                 125

Val Asn Pro Lys Asp Val Val Val Asp Val Asp Lys Glu Glu Gly
130                 135                 140

Glu Leu Glu Glu Gly Glu Ile Asp Ala Asp Ala Glu Pro Glu Gly Glu
145                 150                 155                 160

Ala Glu Ser Val Val Ala Val Pro Val Val Ser Asp Ser Glu Lys Leu
                165                 170                 175

Asp Asp Val Lys Arg Asp Val Ser Asn Ser Glu Gln Leu Gly Val Arg
            180                 185                 190

Gly Val Leu Glu Gly Val Thr Val Ala Asn Val Ala Glu Ser Phe Ala
        195                 200                 205

Gln Thr Cys Ser Lys Leu Gln Asn Ala Leu Pro Glu Val Leu Ser Arg
    210                 215                 220

Pro Ala Asp Ser Glu Arg Asp Asp Leu Val Arg Leu Ser Phe Asn Ala
225                 230                 235                 240

Thr Glu Val Val Tyr Ser Val Phe Cys Ser Met Asp Ser Leu Lys Lys
                245                 250                 255

Glu Gln Asn Lys Asp Ser Ile Leu Arg Leu Leu Ser Phe Val Lys Asp
            260                 265                 270

Gln Gln Gln Ala Gln Leu Phe Ser Pro Glu His Ile Lys Glu Ile Gln
        275                 280                 285

Gly Met Met Thr Ala Ile Asp Tyr Phe Gly Ala Leu Val Asn Ser Glu
    290                 295                 300

Ala Ile Gly Lys Glu Lys Glu Leu Gln Thr Thr Val Gln Thr His Glu
305                 310                 315                 320

Ile Lys Thr Gln Glu Asn Gln Ala Val Glu Ala Ala Glu Leu Ile Ser
                325                 330                 335

Tyr Asn Lys Pro Leu His Ser Asp Ile Ile Gly Ala Ser His Ala Leu
            340                 345                 350

Lys Phe Gly Gln Asn Ser Ile Lys Gly Arg Gly Val Leu Leu Pro Leu
        355                 360                 365

Leu Asp Leu His Lys Asp His Asp Ala Asp Ser Leu Pro Ser Pro Thr
    370                 375                 380
```

-continued

```
Arg Glu Ala Pro Ser Cys Phe Pro Val Asn Lys Leu Leu Ser Val Gly
385                 390                 395                 400
Glu Pro Met Val Ser Ser Gly Ser Ala Ala Lys Pro Glu Ser Gly
            405                 410                 415
Lys Met Glu Leu Asp Ser Glu Gly Ser Lys Phe His Leu Tyr Glu Thr
            420                 425                 430
Asp Ala Leu Lys Ala Val Ser Thr Tyr Gln Gln Lys Phe Gly Arg Ser
            435                 440                 445
Ser Leu Phe Thr Asn Asp Lys Phe Pro Ser Pro Thr Pro Ser Gly Asp
    450                 455                 460
Cys Glu Asp Glu Ile Val Asp Thr Asn Glu Glu Val Ser Ser Ala Ser
465                 470                 475                 480
Thr Gly Asp Phe Leu Thr Ser Thr Lys Pro Thr Leu Leu Asp Leu Pro
            485                 490                 495
Pro Val Ser Ala Thr Ser Thr Asp Arg Ser Ser Leu His Gly Phe Ile
            500                 505                 510
Ser Ser Arg Val Asp Ala Ala Gly Pro Gly Ser Leu Pro Val Lys Ser
            515                 520                 525
Ser Ala Lys Asn Arg Asp Pro Arg Leu Arg Phe Val Asn Ser Asp Ala
            530                 535                 540
Ser Ala Val Asp Asn Pro Ser Thr Leu Ile His Asn Met Pro Lys Val
545                 550                 555                 560
Glu Tyr Ala Gly Thr Thr Ile Ser Arg Lys Gln Lys Ala Ala Glu Glu
            565                 570                 575
Pro Ser Leu Asp Val Thr Val Ser Lys Arg Gln Lys Ser Pro Leu Glu
            580                 585                 590
Asn Thr Glu His Asn Met Ser Glu Val Arg Thr Gly Ile Gly Gly Trp
            595                 600                 605
Leu Glu Glu His Thr Gly Pro Gly Ala Gln Phe Ile Glu Arg Asn His
            610                 615                 620
Leu Met Asp Lys Phe Gly Pro Glu Pro Gln Lys Thr Leu Asn Thr Val
625                 630                 635                 640
Ser Ser Ser Cys Thr Gly Ser Asp Asn Phe Asn Ala Thr Ser Ile Arg
            645                 650                 655
Asn Glu Gln Ala Pro Ile Thr Ser Ser Asn Val Leu Ala Ser Leu Pro
            660                 665                 670
Ala Leu Leu Lys Gly Ala Ala Val Asn Pro Thr Met Leu Val Asn Leu
            675                 680                 685
Leu Arg Ile Ala Glu Ala Gln Lys Lys Ser Ala Asp Ser Ala Thr Asn
            690                 695                 700
Met Leu Leu His Pro Thr Ser Ser Asn Ser Ala Met Gly Thr Asp Ser
705                 710                 715                 720
Thr Ala Ser Ile Gly Ser Ser Met Ala Thr Gly Leu Leu Gln Ser Ser
            725                 730                 735
Val Gly Met Leu Pro Val Ser Ser Gln Ser Thr Ser Met Thr Gln Thr
            740                 745                 750
Leu Gln Asp Asp Ser Gly Lys Ile Arg Met Lys Pro Arg Asp Pro Arg
            755                 760                 765
Arg Ile Leu His Thr Asn Asn Thr Ile Gln Lys Ser Gly Asn Leu Gly
            770                 775                 780
Asn Glu Gln Phe Lys Ala Ile Val Ser Pro Val Ser Asn Asn Gln Gly
785                 790                 795                 800
```

```
Thr Gly Asp Asn Val Asn Ala Gln Lys Leu Glu Gly Arg Val Asp Ser
                805                 810                 815

Lys Leu Val Pro Thr Gln Pro Ser Ala Gln Pro Asp Ile Ala Arg Gln
                820                 825                 830

Phe Ala Arg Asn Leu Lys Asn Ile Ala Asp Ile Met Ser Val Ser Gln
                835                 840                 845

Glu Ser Ser Thr His Thr Pro Val Ala Gln Ile Phe Ser Ser Ala Ser
    850                 855                 860

Val Pro Leu Thr Ser Asp Arg Gly Glu Gln Lys Ser Val Val Ser Asn
865                 870                 875                 880

Ser Gln Asn Leu Glu Ala Gly Met Val Ser Ala His Glu Thr Ala Ala
                885                 890                 895

Ser Gly Thr Cys Arg Ser Gln Asn Thr Trp Gly Asp Val Glu His Leu
                900                 905                 910

Phe Glu Gly Tyr Asp Glu Gln Gln Lys Ala Ala Ile Gln Arg Glu Arg
                915                 920                 925

Ala Arg Arg Ile Glu Glu Gln Asn Lys Met Phe Ala Ala Arg Lys Leu
                930                 935                 940

Cys Leu Val Leu Asp Leu Asp His Thr Leu Leu Asn Ser Ala Lys Phe
945                 950                 955                 960

Val Glu Val Asp Pro Val His Asp Glu Ile Leu Arg Lys Lys Glu Glu
                965                 970                 975

Gln Asp Arg Glu Lys Pro His Arg His Leu Phe Arg Phe Pro His Met
                980                 985                 990

Gly Met Trp Thr Lys Leu Arg Pro Gly Ile Trp Asn Phe Leu Glu Lys
                995                 1000                1005

Ala Ser  Lys Leu Tyr Glu Leu  His Leu Tyr Thr Met  Gly Asn Lys
    1010                1015                1020

Leu Tyr  Ala Thr Glu Met Ala  Lys Val Leu Asp Pro  Lys Gly Leu
    1025                1030                1035

Leu Phe  Ala Gly Arg Val Ile  Ser Arg Gly Asp Asp  Thr Asp Ser
    1040                1045                1050

Val Asp  Gly Glu Glu Arg Ala  Pro Lys Ser Lys Asp  Leu Glu Gly
    1055                1060                1065

Val Leu  Gly Met Glu Ser Ser  Val Val Ile Ile Asp  Asp Ser Val
    1070                1075                1080

Arg Val  Trp Pro His Asn Lys  Leu Asn Leu Ile Val  Val Glu Arg
    1085                1090                1095

Tyr Thr  Tyr Phe Pro Cys Ser  Arg Arg Gln Phe Gly  Leu Pro Gly
    1100                1105                1110

Pro Ser  Leu Leu Glu Ile Asp  His Asp Glu Arg Pro  Glu Ala Gly
    1115                1120                1125

Thr Leu  Ala Ser Ser Leu Ala  Val Ile Glu Lys Ile  His Gln Ile
    1130                1135                1140

Phe Phe  Ala Ser Arg Ser Leu  Glu Glu Val Asp Val  Arg Asn Ile
    1145                1150                1155

Leu Ala  Ser Glu Gln Arg Lys  Ile Leu Ala Gly Cys  Arg Ile Val
    1160                1165                1170

Phe Ser  Arg Val Phe Pro Val  Gly Glu Ala Asn Pro  His Leu His
    1175                1180                1185

Pro Leu  Trp Gln Thr Ala Glu  Gln Phe Gly Ala Phe  Cys Thr Asn
    1190                1195                1200
```

```
Gln Ile Asp Glu Gln Val Thr His Val Val Ala Asn Ser Pro Gly
    1205                1210                1215

Thr Asp Lys Val Asn Trp Ala Leu Asn Asn Gly Arg Phe Val Val
    1220                1225                1230

His Pro Gly Trp Val Glu Ala Ser Ala Leu Leu Tyr Arg Arg Ala
    1235                1240                1245

Asn Glu Gln Asp Phe Ala Ile Lys Pro
    1250                1255

<210> SEQ ID NO 12
<211> LENGTH: 1261
<212> TYPE: PRT
<213> ORGANISM: Glycine max

<400> SEQUENCE: 12

Met Val Phe Gly Ser Leu Leu Asp Cys Glu Val Leu Gly Lys Leu Glu
1               5                   10                  15

Lys Met Gly Lys Glu Ala Glu Asp Val Glu Gly Glu Ile Ser Asp
            20                  25                  30

Thr Ala Ser Val Glu Glu Ile Ser Ala Glu Asp Phe Asn Lys Gln Asp
        35                  40                  45

Val Lys Leu Leu Asn Asn Asn Lys Pro Asn Gly Ser Asp Ala Arg
50                  55                  60

Val Trp Ala Val His Asp Leu Tyr Ser Lys Tyr Pro Thr Ile Cys Arg
65                  70                  75                  80

Gly Tyr Ala Ser Gly Leu Tyr Asn Leu Ala Trp Ala Gln Ala Val Gln
            85                  90                  95

Asn Lys Pro Leu Asn Asp Ile Phe Val Met Glu Val Asp Ser Asp Ala
            100                 105                 110

Asn Ala Asn Ser Asn Arg Asn Ser Ser His Arg Leu Ala Ser Val Ala
        115                 120                 125

Val Asn Pro Lys Asp Val Val Val Asp Val Asp Lys Glu Glu Gly
130                 135                 140

Glu Leu Glu Glu Gly Glu Ile Asp Ala Asp Ala Glu Pro Gly Gly Glu
145                 150                 155                 160

Ala Glu Ser Val Val Val Ala Val Ser Asp Ser Lys Leu Asp Asp
            165                 170                 175

Val Lys Met Asp Val Ser Asp Ser Glu Gln Leu Gly Ala Arg Gly Val
            180                 185                 190

Leu Glu Gly Val Thr Val Ala Asn Val Val Glu Ser Phe Ala Gln Thr
        195                 200                 205

Cys Ser Lys Leu Gln Asn Thr Leu Pro Glu Val Leu Ser Arg Pro Ala
210                 215                 220

Gly Ser Glu Lys Asp Asp Leu Val Arg Leu Ser Phe Asn Ala Thr Glu
225                 230                 235                 240

Val Val Tyr Ser Val Phe Cys Ser Met Asp Ser Ser Glu Lys Glu Gln
            245                 250                 255

Asn Lys Asp Ser Ile Leu Arg Leu Leu Ser Phe Val Lys Asp Gln Gln
            260                 265                 270

Gln Ala Gln Leu Phe Ser Pro Glu His Val Lys Glu Ile Gln Gly Met
        275                 280                 285

Met Thr Ala Ile Asp Ser Val Gly Ala Leu Val Asn Ser Glu Ala Ile
    290                 295                 300

Gly Lys Glu Lys Glu Leu Gln Thr Thr Glu Ile Lys Thr Gln Glu Asn
305                 310                 315                 320
```

-continued

Ser Ala Val Glu Val Gln Ile His Glu Ile Lys Thr Gln Glu Asn Gln
              325                 330                 335

Ala Val Glu Ala Ala Glu Leu Ile Ser Tyr Ser Lys Pro Leu His Arg
              340                 345                 350

Asp Ile Thr Gly Thr Ser Gln Ala Leu Lys Phe Gly Gln Asn Ser Ile
              355                 360                 365

Lys Gly Arg Gly Val Leu Leu Pro Leu Leu Asp Leu His Lys Asp His
370                 375                 380

Asp Ala Asp Ser Leu Pro Ser Pro Thr Arg Glu Ala Pro Ser Cys Phe
385                 390                 395                 400

Pro Val Asn Lys Leu Leu Ser Val Gly Glu Ser Met Val Arg Ser Gly
              405                 410                 415

Ser Ala Ser Ala Lys Met Glu Leu Asp Ser Glu Gly Ser Lys Phe His
              420                 425                 430

Leu Tyr Glu Thr Asp Ala Leu Lys Ala Val Ser Thr Tyr Gln Gln Lys
              435                 440                 445

Phe Gly Arg Ser Ser Leu Phe Thr Asn Asp Lys Phe Pro Ser Pro Thr
450                 455                 460

Pro Ser Gly Asp Cys Glu Asp Glu Val Val Asp Thr Asn Glu Glu Val
465                 470                 475                 480

Ser Ser Ala Ser Thr Gly Asp Phe Leu Thr Ser Thr Lys Pro Thr Leu
              485                 490                 495

Leu Asp Gln Pro Pro Val Ser Ala Thr Ser Met Asp Arg Ser Ser Met
              500                 505                 510

His Gly Phe Ile Ser Ser Arg Val Asp Ala Thr Gly Pro Gly Ser Phe
              515                 520                 525

Pro Val Lys Ser Ser Ala Lys Asn Arg Asp Pro Arg Leu Arg Phe Ile
530                 535                 540

Asn Ser Asp Ala Ser Ala Val Asp Asn Leu Ser Thr Leu Ile Asn Asn
545                 550                 555                 560

Met Ser Lys Val Glu Tyr Ser Gly Thr Thr Ile Ser Arg Lys Gln Lys
              565                 570                 575

Ala Ala Glu Glu Pro Ser Leu Asp Val Thr Val Ser Lys Arg Leu Lys
              580                 585                 590

Ser Ser Leu Glu Asn Thr Glu His Asn Met Ser Glu Val Arg Thr Gly
              595                 600                 605

Ser Gly Gly Trp Leu Glu Glu Asn Thr Gly Pro Gly Ala Gln Leu Ile
              610                 615                 620

Glu Arg Asn His Leu Met Asp Lys Phe Gly Pro Glu Ala Lys Lys Thr
625                 630                 635                 640

Leu Asn Thr Val Ser Ser Ser Cys Thr Gly Ser Asp Asn Phe Asn Ala
              645                 650                 655

Thr Ser Ile Arg Asn Glu Gln Ala Pro Ile Thr Ala Ser Asn Val Leu
              660                 665                 670

Ala Ser Leu Pro Ala Leu Leu Lys Glu Ala Ser Val Asn Pro Ile Met
              675                 680                 685

Leu Val Asn Ile Leu Arg Leu Ala Glu Ala Gln Lys Lys Ser Ala Asp
690                 695                 700

Ser Ala Ala Ile Met Leu Leu His Pro Thr Ser Ser Asn Pro Ala Met
705                 710                 715                 720

Gly Thr Asp Ser Thr Ala Ser Ile Gly Ser Ser Met Ala Thr Gly Leu
              725                 730                 735

```
Leu Gln Ser Ser Val Gly Met Leu Pro Val Ser Ser Gln Ser Thr Ser
        740                 745                 750

Thr Ala Gln Thr Leu Gln Asp Asp Ser Gly Lys Ile Arg Met Lys Pro
        755                 760                 765

Arg Asp Pro Arg Arg Ile Leu His Thr Asn Asn Thr Ile Gln Lys Ser
        770                 775                 780

Gly Asp Leu Gly Asn Glu Gln Phe Lys Ala Ile Val Ser Pro Val Ser
785                 790                 795                 800

Asn Asn Gln Arg Thr Gly Asp Asn Val Asn Ala Pro Lys Leu Glu Gly
                805                 810                 815

Arg Val Asp Asn Lys Leu Val Pro Thr Gln Ser Ser Ala Gln Pro Asp
                820                 825                 830

Ile Ala Arg Gln Phe Thr Arg Asn Leu Lys Asn Ile Ala Asp Ile Met
                835                 840                 845

Ser Val Ser Gln Glu Ser Ser Thr His Thr Pro Val Ser Gln Asn Phe
        850                 855                 860

Ser Ser Ala Ser Val Pro Leu Thr Ser Asp Arg Gly Glu Gln Lys Ser
865                 870                 875                 880

Val Val Ser Ser Gln Asn Leu Gln Ala Asp Met Ala Ser Ala His
                885                 890                 895

Glu Thr Ala Ala Ser Val Thr Ser Arg Ser Gln Ser Thr Trp Gly Asp
                900                 905                 910

Val Glu His Leu Phe Glu Gly Tyr Asp Glu Gln Lys Ala Ala Ile
        915                 920                 925

Gln Arg Glu Arg Ala Arg Arg Ile Glu Glu Gln Asn Lys Met Phe Ala
        930                 935                 940

Ala Arg Lys Leu Cys Leu Val Leu Asp Leu Asp His Thr Leu Leu Asn
945                 950                 955                 960

Ser Ala Lys Phe Val Glu Val Asp Pro Leu His Asp Glu Ile Leu Arg
                965                 970                 975

Lys Lys Glu Glu Gln Asp Arg Glu Lys Pro His Arg His Leu Phe Arg
                980                 985                 990

Phe Pro His Met Gly Met Trp Thr Lys Leu Arg Pro Gly Ile Trp Asn
        995                 1000                1005

Phe Leu Glu Lys Ala Ser Lys Leu Tyr Glu Leu His Leu Tyr Thr
        1010                1015                1020

Met Gly Asn Lys Leu Tyr Ala Thr Glu Met Ala Lys Val Leu Asp
        1025                1030                1035

Pro Lys Gly Val Leu Phe Ala Gly Arg Val Ile Ser Arg Gly Asp
        1040                1045                1050

Asp Thr Asp Ser Val Asp Gly Glu Glu Arg Val Pro Lys Ser Lys
        1055                1060                1065

Asp Leu Glu Gly Val Leu Gly Met Glu Ser Ser Val Val Ile Ile
        1070                1075                1080

Asp Asp Ser Val Arg Val Trp Pro His Asn Lys Leu Asn Leu Ile
        1085                1090                1095

Val Val Glu Arg Tyr Thr Tyr Phe Pro Cys Ser Arg Arg Gln Phe
        1100                1105                1110

Gly Leu Pro Gly Pro Ser Leu Leu Glu Ile Asp His Asp Glu Arg
        1115                1120                1125

Pro Glu Ala Gly Thr Leu Ala Ser Ser Leu Ala Val Ile Glu Lys
        1130                1135                1140
```

```
Ile His Gln Ile Phe Phe Ala Ser Gln Ser Leu Glu Val Asp
    1145                1150                1155

Val Arg Asn Ile Leu Ala Ser Glu Gln Arg Lys Ile Leu Ala Gly
1160                1165                1170

Cys Arg Ile Val Phe Ser Arg Val Phe Pro Val Gly Glu Ala Asn
    1175                1180                1185

Pro His Leu His Pro Leu Trp Gln Thr Ala Glu Gln Phe Gly Ala
    1190                1195                1200

Val Cys Thr Asn Gln Ile Asp Glu Gln Val Thr His Val Val Ala
    1205                1210                1215

Asn Ser Pro Gly Thr Asp Lys Val Asn Trp Ala Leu Asn Asn Gly
    1220                1225                1230

Arg Phe Val Val His Pro Gly Trp Val Glu Ala Ser Ala Leu Leu
    1235                1240                1245

Tyr Arg Arg Ala Asn Glu Gln Asp Phe Ala Ile Lys Pro
    1250                1255                1260

<210> SEQ ID NO 13
<211> LENGTH: 1218
<212> TYPE: PRT
<213> ORGANISM: Solanum tuberosum

<400> SEQUENCE: 13

Met Glu Glu Cys Asn Arg Val Glu Asp Val Glu Gly Glu Ile Ser
1               5                   10                  15

Asp Ser Ala Ser Val Glu Glu Ile Ser Glu Asp Ala Phe Asn Arg Gln
            20                  25                  30

Asp Pro Pro Thr Thr Thr Lys Ile Lys Ile Ala Ser Asn Glu Asn Gln
        35                  40                  45

Asn Gln Asn Ser Thr Thr Thr Thr Arg Val Trp Thr Met Arg Asp Ala
    50                  55                  60

Tyr Lys Tyr Pro Ile Ser Arg Asp Tyr Ala Arg Gly Leu Tyr Asn Leu
65                  70                  75                  80

Ala Trp Ala Gln Ala Val Gln Asn Lys Pro Leu Asp Glu Leu Phe Val
                85                  90                  95

Met Thr Ser Asp Asn Ser Asn Gln Cys Ala Asn Ala Asn Ala Asn Val
            100                 105                 110

Glu Ser Lys Val Ile Ile Asp Val Asp Val Asp Asp Ala Lys Glu
        115                 120                 125

Glu Gly Glu Leu Glu Glu Gly Glu Ile Asp Leu Asp Ala Ala Asp Leu
    130                 135                 140

Val Leu Asn Phe Gly Lys Glu Ala Asn Phe Val Arg Glu Gln Leu Gln
145                 150                 155                 160

Ser Val Thr Leu Asp Glu Thr His Lys Ser Phe Ser Met Val Cys Ser
                165                 170                 175

Lys Leu Gln Thr Ser Leu Leu Ala Leu Gly Glu Leu Ala Leu Ser Gln
            180                 185                 190

Asp Lys Asn Asp Ile Leu Ile Gln Leu Phe Met Thr Ala Leu Arg Thr
        195                 200                 205

Ile Asn Ser Val Phe Tyr Ser Met Asn Gln Asp Lys Gln Gln Asn
    210                 215                 220

Thr Asp Ile Leu Ser Arg Leu Leu Phe His Ala Lys Thr Gln Leu Pro
225                 230                 235                 240

Ala Leu Leu Ser Ser Glu Gln Leu Lys Glu Val Asp Ala Val Ile Leu
                245                 250                 255
```

```
Ser Ile Asn Gln Ser Ala Val Phe Ser Asn Thr Gln Asp Asn Asp Lys
            260                 265                 270

Val Asn Gly Ile Lys Val Val Glu Leu Leu Asp Lys Lys Val Ser His
        275                 280                 285

Lys Ser Ser Glu Asn Ala Asn Gln Asp Phe Thr Ala Val Asn Lys Tyr
            290                 295                 300

Asp Leu Gly Ala Val Ser Ile Lys Ser Ser Gly Leu Lys Glu Gln Ser
305                 310                 315                 320

Val Ser Phe Glu Ser Val Lys Pro Gly Leu Ala Asn Ser Lys Ala Lys
                325                 330                 335

Gly Leu Ser Ile Pro Leu Leu Asp Leu His Lys Asp His Asp Glu Asp
            340                 345                 350

Thr Leu Pro Ser Pro Thr Arg Glu Ile Gly Pro Gln Phe Pro Val Ala
            355                 360                 365

Lys Ala Thr Gln Ala His Gly Met Val Lys Leu Asp Leu Pro Ile Phe
        370                 375                 380

Ala Gly Ser Leu Glu Lys Gly Asn Ser Leu Leu His Pro Tyr Glu Thr
385                 390                 395                 400

Asp Ala Leu Lys Ala Val Ser Ser Tyr Gln Gln Lys Phe Gly Arg Ser
                405                 410                 415

Ser Leu Phe Val Ser Glu Asn Leu Pro Ser Pro Thr Pro Ser Glu Glu
            420                 425                 430

Gly Asp Ser Gly Lys Gly Asp Ile Gly Gly Glu Val Thr Ser Leu Asp
            435                 440                 445

Val Val His Asn Ala Ser His Leu Asn Glu Ser Ser Met Gly Gln Pro
    450                 455                 460

Ile Leu Ser Ser Val Pro Gln Thr Asn Ile Leu Asp Gly Gln Gly Leu
465                 470                 475                 480

Gly Thr Ala Arg Thr Ala Asp Pro Leu Ser Phe Leu Pro Asn Pro Ser
                485                 490                 495

Leu Arg Ser Ser Thr Ala Lys Ser Arg Asp Pro Arg Leu Arg Leu Ala
            500                 505                 510

Thr Ser Asp Ala Val Ala Gln Asn Thr Asn Lys Asn Ile Leu Pro Ile
    515                 520                 525

Pro Asp Ile Asp Leu Lys Leu Glu Ala Ser Leu Glu Met Ile Gly Ser
530                 535                 540

Lys Lys Gln Lys Thr Val Asp Leu Pro Val Phe Gly Ala Pro Leu Pro
545                 550                 555                 560

Lys Arg Gln Arg Ser Glu Gln Thr Asp Ser Ile Ile Val Ser Asp Val
                565                 570                 575

Arg Pro Ser Thr Gly Asn Gly Gly Trp Leu Glu Asp Arg Gly Thr Ala
            580                 585                 590

Gly Leu Pro Ile Thr Ser Ser Asn Cys Ala Thr Asp Ser Ser Asp Asn
            595                 600                 605

Asp Ile Arg Lys Leu Glu Gln Val Thr Ala Thr Ile Ala Thr Ile Pro
610                 615                 620

Ser Val Ile Val Asn Ala Ala Glu Asn Phe Pro Val Thr Gly Ile Ser
625                 630                 635                 640

Thr Ser Thr Thr Leu His Ser Leu Leu Lys Asp Ile Ala Ile Asn Pro
            645                 650                 655

Ser Ile Trp Met Asn Ile Ile Lys Met Glu Gln Gln Lys Ser Ala Asp
            660                 665                 670
```

```
Ala Ser Arg Thr Thr Thr Ala Gln Ala Ser Ser Ser Lys Ser Ile Leu
            675                 680                 685

Gly Ala Val Pro Ser Thr Asp Ala Ile Ala Pro Arg Ser Ser Ala Ile
690                 695                 700

Gly Gln Arg Ser Val Gly Ile Leu Gln Thr Pro Thr His Thr Ala Ser
705                 710                 715                 720

Ala Asp Glu Val Ala Ile Val Arg Met Lys Pro Arg Asp Pro Arg Arg
                725                 730                 735

Val Leu His Asn Thr Ala Val Leu Lys Gly Asn Val Gly Ser Asp
            740                 745                 750

Gln Cys Lys Thr Gly Val Ala Gly Thr His Ala Thr Ile Ser Asn Leu
        755                 760                 765

Gly Phe Gln Ser Gln Glu Asp Gln Leu Asp Arg Lys Ser Ala Val Thr
770                 775                 780

Leu Ser Thr Thr Pro Pro Asp Ile Ala Arg Gln Phe Thr Lys Asn Leu
785                 790                 795                 800

Lys Asn Ile Ala Asp Met Ile Ser Val Ser Pro Ser Thr Ser Leu Ser
                805                 810                 815

Ala Ala Ser Gln Thr Gln Thr Gln Cys Leu Gln Ser His Gln Ser Arg
            820                 825                 830

Ser Glu Gly Lys Glu Ala Val Ser Glu Pro Ser Glu Arg Val Asn Asp
        835                 840                 845

Ala Gly Leu Ala Ser Glu Lys Gly Ser Pro Gly Ser Leu Gln Pro Gln
    850                 855                 860

Ile Ser Trp Gly Asp Val Glu His Leu Phe Glu Gly Tyr Ser Asp Gln
865                 870                 875                 880

Gln Arg Ala Asp Ile Gln Arg Glu Arg Ala Arg Arg Leu Glu Glu Gln
                885                 890                 895

Lys Lys Met Phe Ser Val Arg Lys Leu Cys Leu Val Leu Asp Leu Asp
            900                 905                 910

His Thr Leu Leu Asn Ser Ala Lys Phe Val Glu Ile Asp Pro Val His
        915                 920                 925

Glu Glu Ile Leu Arg Lys Lys Glu Glu Gln Asp Arg Glu Lys Pro Cys
930                 935                 940

Arg His Leu Phe Arg Phe Pro His Met Gly Met Trp Thr Lys Leu Arg
945                 950                 955                 960

Pro Gly Ile Trp Asn Phe Leu Glu Lys Ala Ser Asn Leu Phe Glu Leu
                965                 970                 975

His Leu Tyr Thr Met Gly Asn Lys Leu Tyr Ala Thr Glu Met Ala Lys
            980                 985                 990

Leu Leu Asp Pro Lys Gly Asp Leu Phe Ala Gly Arg Val Ile Ser Arg
        995                 1000                1005

Gly Asp Asp Gly Asp Pro Phe Asp Gly Asp Glu Arg Val Pro Lys
    1010                1015                1020

Ser Lys Asp Leu Glu Gly Val Leu Gly Met Glu Ser Ala Val Val
    1025                1030                1035

Ile Ile Asp Asp Ser Val Arg Val Trp Pro His Asn Lys Leu Asn
    1040                1045                1050

Leu Ile Val Val Glu Arg Tyr Ile Tyr Phe Pro Cys Ser Arg Arg
    1055                1060                1065

Gln Phe Gly Leu Pro Gly Pro Ser Leu Leu Glu Ile Asp His Asp
    1070                1075                1080
```

```
Glu Arg Pro Glu Asp Gly Thr Leu Ala Ser Cys Leu Gly Val Ile
    1085                1090                1095

Gln Arg Ile His Gln Asn Phe Phe Ala His Arg Ser Ile Asp Glu
    1100                1105                1110

Ala Asp Val Arg Asn Ile Leu Ala Thr Glu Gln Lys Lys Ile Leu
    1115                1120                1125

Ala Gly Cys Arg Ile Val Phe Ser Arg Val Phe Pro Val Gly Glu
    1130                1135                1140

Ala Asn Pro His Leu His Pro Leu Trp Gln Thr Ala Glu Gln Phe
    1145                1150                1155

Gly Ala Val Cys Thr Ser Gln Ile Asp Asp Gln Val Thr His Val
    1160                1165                1170

Val Ala Asn Ser Leu Gly Thr Asp Lys Val Asn Trp Ala Leu Ser
    1175                1180                1185

Thr Gly Arg Phe Val Val His Pro Gly Trp Val Glu Ala Ser Ala
    1190                1195                1200

Leu Leu Tyr Arg Arg Ala Asn Glu His Asp Phe Ala Ile Lys Ser
    1205                1210                1215

<210> SEQ ID NO 14
<211> LENGTH: 1252
<212> TYPE: PRT
<213> ORGANISM: Beta vulgaris

<400> SEQUENCE: 14

Met Lys Val Ser Gly Gly Glu Asp Gly Glu Ile Pro Glu Ser Asp Ala
1               5                   10                  15

Ile Val Glu Met Lys His Gln Ser Lys Thr Thr Thr Thr Thr Thr Thr
            20                  25                  30

Thr Ile Thr Ser Asp Ser Ser Asn Lys Lys Asp Asn Asn Ser Tyr Trp
        35                  40                  45

Met Arg Asp Leu Tyr Lys Tyr Ser Ser Tyr Arg Gly Tyr Gly Ala Ala
    50                  55                  60

Ser Gly Leu Tyr Asn Leu Ala Trp Ala Gln Ala Val Gln Asn Lys Pro
65                  70                  75                  80

Leu Asn Glu Val Leu Val Glu Leu Asp Asp Lys Lys Asn Asn Lys Asn
                85                  90                  95

Ala Ser Thr Asp Asp Thr Ser Val Asn Lys Glu Gln Gly Glu Val Gln
            100                 105                 110

Gln His Cys Val Glu Ser Lys Glu Val Phe Glu Val Val Asp Ser Glu
        115                 120                 125

Lys Glu Glu Gly Glu Leu Glu Glu Gly Glu Ile Asp Phe Asp Ser Asp
    130                 135                 140

Asp Thr Gly Asn Asn His Asn Ser Asn Gly Asn Lys Val Gln Asp Asp
145                 150                 155                 160

Phe Gly Gly Leu Glu Met Asp Asp Gly Glu Leu Glu Asn Gln Val Ser
                165                 170                 175

Ser Ile Arg Lys Val Leu His Asn Val Thr Val Ala Glu Ala His Lys
            180                 185                 190

Ser Phe Asp Ile Val Cys Ala Arg Leu Arg Thr Ser Leu Glu Thr Leu
        195                 200                 205

Arg Glu Leu Val Leu His Thr Trp Phe Pro Ser Lys Asp Ala Leu Ile
    210                 215                 220

Gln Gln Ala Phe Ala Ala Ile Gln Cys Val Tyr Ser Val Tyr Ser Ser
225                 230                 235                 240
```

```
Met Ser Pro Thr Leu Arg Asp Gln Asn Lys Asp Arg Met Ser Arg Leu
                245                 250                 255

Leu Thr Phe Val Met Asp Leu Ser Ser Val Leu Phe Thr Pro Glu Gln
            260                 265                 270

Arg Lys Glu Val Glu Gly Met Ile Thr Ser Val Asn Pro Pro Ile Val
        275                 280                 285

Pro Val Lys Pro Lys Ser Arg Asp Arg Gln Glu Leu Pro Val Thr
    290                 295                 300

Glu Lys Ala Ile Leu Thr Asp Ser Asn Thr Leu Thr Val Asn Thr Gly
305                 310                 315                 320

Asp Asn Lys Ser Asp Leu Leu Lys Lys Val Gly Pro Glu Leu Ser Val
                325                 330                 335

Tyr Gln Ser Glu Lys Lys Asn Thr Asp Ile Leu Ser Glu Ala Met Arg
            340                 345                 350

His Phe Pro Ser Ser Leu Lys Val Arg Ser Ser Phe Gly Pro Leu Leu
        355                 360                 365

Asp Leu His Lys Val His Asp Glu Asp Ser Leu Pro Ser Pro Thr Ser
    370                 375                 380

Lys Thr Met Pro Ser Leu Pro Phe Phe Glu Thr Ala Pro Pro Arg Val
385                 390                 395                 400

Val His Gly Leu Gln Lys Ser Gly Val His Pro Tyr Glu Thr Glu Ala
                405                 410                 415

Val Lys Ala Val Ser Ser Tyr Gln Gln Arg Phe Gly Arg Ser Thr Phe
            420                 425                 430

Leu Ala Thr Asp Met Leu Pro Ser Pro Thr Pro Ser Glu Asp Gly Asn
        435                 440                 445

Glu Gly Gly Ala Asp Asp Ser Asn Glu Glu Val Ser Ser Asn Ala
450                 455                 460

Tyr Thr Asn Val Val Ser Arg Thr Thr Asn Ser Ser Val Val Pro Gln
465                 470                 475                 480

Pro Val Val Ser Ser Ala Ala Tyr Thr Ser Ser Thr Met Gln Gly
                485                 490                 495

Val Ile Ser Gly Thr Ser Ala Glu Ser Ser Ser Val Gly Ser Ser Pro
            500                 505                 510

Ser Leu Arg Ala Ser Ala Lys Ser Arg Asp Pro Arg Leu Arg His Leu
        515                 520                 525

Asn Pro Asn Phe Gly Ser Leu Asp Leu Ser Phe Cys Pro Ser Pro Met
    530                 535                 540

Val Pro Ser Ser Ala Ser Lys Leu Glu Pro Leu Gly Glu Ile Met Lys
545                 550                 555                 560

Ser Lys Lys Thr Lys Ala Leu Glu Gly Arg Leu Leu Asp Gly Pro Thr
                565                 570                 575

Ala Lys Arg Pro Arg Asn Gly Leu Glu Thr Glu Asp Met Ser Met Asn
            580                 585                 590

Ala Asn Gln Val Lys Thr Leu Gln Gly Ser Thr Arg Met Glu Thr Ser
        595                 600                 605

Ser Ser Ser Ile Leu Gly Pro Gln Ser Ser Arg Gly Leu Leu Gly
    610                 615                 620

Pro Ala Ile Asp Pro Arg Lys Pro Gly Ser Gly Thr Val Ser Ser Gly
625                 630                 635                 640

Ile Thr Thr Asn Asn Pro Ser Met Ala Val Asn Lys Thr Ala Lys Pro
                645                 650                 655
```

```
Ser Met Asn Val Ser Gly Ser Pro Ser Leu Gln Ser Leu Leu Lys Asp
            660                 665                 670

Ile Ala Gly Asn Pro Gly Ala Trp Met Asn Ile Ile Lys Glu Gln Asn
        675                 680                 685

Lys Ser Ser Glu Pro Leu Gln Ser Val Ser His Ser Met Asn Ser Asn
    690                 695                 700

Ser Ile Leu Gly Ala Ala Pro Ser Ala Ile Ala Val Pro Pro Ile Ser
705                 710                 715                 720

Ser Gly Val Gly Gln Thr Ser Ala Gly Leu Leu Gln Val Pro Ser Pro
            725                 730                 735

Lys Val Val Thr Ser Ser Gln Asp Asp Ser Ala Lys Leu Arg Met Lys
            740                 745                 750

Pro Arg Asp Pro Arg Arg Ala Leu His Ala Asn Met Ala Gln Arg Thr
            755                 760                 765

Gly Ser Ser Val Pro Glu Gln Pro Lys Val Asn Gly Val His Asn Thr
        770                 775                 780

Thr Thr Gln Gly Leu Gln Glu Asn Ile Asn Ala Gln Arg Tyr Val Asn
785                 790                 795                 800

Gly Thr Ser Pro Ser Ala Ala Ser Ser Gln Thr Pro Ile Leu Pro Asp
            805                 810                 815

Ile Thr Lys Gln Phe Thr Lys Asn Leu Lys Asn Ile Ala Asp Ile Ile
            820                 825                 830

Ser Ser Pro Gln Thr Ser Ser Ile Gln Ser Pro Leu Ala Val Ser Ser
        835                 840                 845

Leu Ser Ala Gln Ala Asn Ser Asp Thr Thr Ser Ile Ser Ser Gly Gly
    850                 855                 860

Gln Ala Ser Cys Ser Ser Gly Gly Pro Val Ile Thr Gly Asn Gln Arg
865                 870                 875                 880

Thr Val Ser Ala Leu Arg Pro Glu Glu Val Val Ser Gly Arg Pro Gln
            885                 890                 895

Ser Gln Asn Asn Trp Gly Asp Val Glu His Leu Phe Asp Gly Tyr Asp
            900                 905                 910

Asp Gln Gln Lys Ala Ala Ile Gln Gln Glu Arg Ala Arg Arg Leu Asp
            915                 920                 925

Glu Gln Asn Lys Met Phe Ala Asp Arg Lys Leu Cys Leu Val Leu Asp
        930                 935                 940

Leu Asp His Thr Leu Leu Asn Ser Ala Lys Phe Ser Glu Val Asp Pro
945                 950                 955                 960

Val His Asp Glu Ile Leu Arg Lys Lys Glu Glu Gln Asp Arg Glu Lys
            965                 970                 975

Pro Arg Arg His Leu Phe Arg Phe Pro His Met Ala Met Trp Thr Lys
            980                 985                 990

Leu Arg Pro Gly Ile Trp Asn Phe Leu Glu Lys Ala Ser Lys Leu Phe
        995                 1000                1005

Glu Leu His Leu Tyr Thr Met Gly Asn Lys Leu Tyr Ala Thr Glu
    1010                1015                1020

Met Ala Lys Val Leu Asp Pro Lys Gly Thr Leu Phe Ala Gly Arg
    1025                1030                1035

Val Ile Ser Arg Gly Asp Asp Gly Asp Pro Ile Asp Gly Asp Glu
    1040                1045                1050

Arg Val Pro Lys Ser Lys Asp Leu Glu Gly Val Met Gly Met Glu
    1055                1060                1065
```

-continued

```
Ser Ser Val Val Ile Ile Asp Asp Ser Ala Arg Val Trp Pro His
    1070                1075                1080

Asn Lys Leu Asn Leu Ile Val Val Glu Arg Tyr Thr Tyr Phe Pro
    1085                1090                1095

Cys Ser Arg Lys Gln Phe Gly Leu Pro Gly Pro Ser Leu Leu Glu
    1100                1105                1110

Ile Asp His Asp Glu Arg Pro Glu Glu Gly Thr Leu Ala Ser Ser
    1115                1120                1125

Leu Ala Val Ile Glu Lys Ile His Gln Asn Phe Phe Ser His Lys
    1130                1135                1140

Ser Leu Asp Asp Val Asp Val Arg Asn Ile Leu Gly Ala Glu Gln
    1145                1150                1155

Arg Lys Ile Leu Ala Gly Cys Arg Ile Leu Phe Ser Arg Val Phe
    1160                1165                1170

Pro Val Gly Glu Ala Asn Pro His Leu His Pro Leu Trp Gln Thr
    1175                1180                1185

Ala Glu Gln Phe Gly Ala Val Cys Thr Asn Gln Leu Asp Glu Gln
    1190                1195                1200

Val Thr His Val Val Ala Asn Ser Leu Gly Thr Asp Lys Val Asn
    1205                1210                1215

Trp Ala Leu Ser Thr Lys Arg Phe Val Val His Pro Ser Trp Val
    1220                1225                1230

Glu Ala Ser Ala Leu Leu Tyr Arg Arg Val Asn Glu Gln Asp Phe
    1235                1240                1245

Ala Ile Lys Thr
    1250

<210> SEQ ID NO 15
<211> LENGTH: 1252
<212> TYPE: PRT
<213> ORGANISM: Triticum aestivum

<400> SEQUENCE: 15

Met Arg Val Thr Leu Thr Pro Lys Asp Glu Asp Trp Leu Val Val Leu
1               5                   10                  15

Met Thr Arg Glu Arg Pro Arg Ser Ala Val Val Ala Pro Gly Gly Asp
                20                  25                  30

Val Phe Thr Ala Gly Gly Gly Glu Thr Ser Asp Gly Asp Ser Ser
            35                  40                  45

Glu Ser Leu Glu Glu Ile Ser Ala Ala Asp Phe Lys Glu Ser Ser Ser
    50                  55                  60

Gly Thr Ala Ala Pro Ser Ala Ser Ser Gln Arg Ser Arg Val Trp Met
65                  70                  75                  80

Gly Tyr Thr Met Ser Arg Ser Tyr Ala Pro Ala Phe His Ser Phe Ala
                85                  90                  95

Trp Ala Gln Ala Val Gln Asn Lys Pro Leu Val Pro Arg Pro Ala Ala
            100                 105                 110

Asp Glu Asp Glu Val Glu His Leu Val Asp Thr Ser Asp Glu Glu Lys
        115                 120                 125

Glu Glu Gly Glu Ile Glu Glu Gly Glu Ala Val Gln Ser Thr Ser Pro
    130                 135                 140

Pro Ile Lys Gln Pro Glu Thr Ile Asp Leu Asp Ser Asp Ala Gln Asp
145                 150                 155                 160

Lys Ser Glu Ser Val Asp Met Glu Gln Thr Arg Leu Ala Val Glu Ala
                165                 170                 175
```

```
Ala Asp Glu Leu Asp Phe Asp Gln Arg Val Gly Ser Ile Leu Glu Glu
            180                 185                 190

Leu Glu Arg Leu Ser Ile Glu Glu Ala Glu Lys Ser Phe Glu Ala Ser
        195                 200                 205

Cys Ala Arg Leu Arg Ser Cys Phe Glu Ser Leu Lys Pro Leu Phe Pro
210                 215                 220

Glu Ser Gly Ser Pro Met Pro Met Leu Asp Ala Leu Val Gln Gln Ala
225                 230                 235                 240

Phe Val Gly Ile Asp Thr Ile Thr Thr Val Ala Asn Ser Tyr Ala Met
                    245                 250                 255

Pro Lys Arg Glu Gln Asn Lys Asn Met Leu Leu Lys Leu Leu Phe His
                260                 265                 270

Ile Lys Asn Arg Tyr Ser Asp Met Leu Ala Leu Asn Gln Arg Asp Glu
            275                 280                 285

Leu Asp Ser Arg Val Arg Gln Leu Val Phe Val Asp Gly Glu Asp Asn
        290                 295                 300

Ala Gly Ser Asn Cys Ser Thr Lys Thr Val Asn Val Val Pro Ser
305                 310                 315                 320

Gly Gln Val Pro Ser Asp Arg Leu Pro Val Glu Ser Gly Ala Ala Asn
                    325                 330                 335

Pro Pro Arg Gly Ser Ser Phe Pro Ser Trp Glu Ile Pro Ala Asn Asn
                340                 345                 350

Arg Ile Val Ser Pro Leu Leu Asp Leu His Ala Asp Tyr Asp Glu Asn
            355                 360                 365

Ser Leu Pro Ser Pro Thr Arg Val Ser Ala Pro Pro Phe Pro Val Pro
        370                 375                 380

Lys Pro Ile Gly Phe Gly Val Phe Pro Met Ala Pro Asp Arg Tyr Phe
385                 390                 395                 400

Ser Ala Glu Arg Ile Asp Pro Ser Lys Asn Phe Leu Tyr Pro Cys Val
                    405                 410                 415

Asn Asp Ala Leu Lys Asp Val Ser Ser Tyr Arg Gln Lys Tyr Gly Pro
                420                 425                 430

Thr Ser Thr Phe Ala Ser Asp Asp Leu Pro Ser Pro Thr Pro Ser Asp
            435                 440                 445

Asp Gly Asp Lys Ser Gly Asp Lys Glu Gly Asp Ile Phe Gly Glu Val
        450                 455                 460

Ser Ser Phe Ser Ala Ser Asn Lys Ser Ala Pro Pro Ser Gly Asn Leu
465                 470                 475                 480

Met Pro Ala Ser Arg Pro Ser Ala Val Ile Ser Ser Asn Asp Ser Phe
                    485                 490                 495

Ala Gly Gly Pro Pro Gly Tyr Ala Lys Gln Ile Glu Gln Ser Val Ser
                500                 505                 510

Gly Pro Ser His Ala Leu Lys Pro Ser Ala Lys Ser Arg Asp Pro Arg
            515                 520                 525

Leu Arg Phe Leu Asn Arg Asp Ser Gly Gly Thr Ala Asp Ala Asn Ile
        530                 535                 540

His Val Asn Leu Ala Glu Pro Asn Ala Ser Lys Asp Gly Thr Leu Gly
545                 550                 555                 560

Gly Val Val Ser Asp Asn Ser Arg Lys His Lys Ala Thr Gly Gln Pro
                    565                 570                 575

Leu Met Asp Glu Thr Val Leu Lys Arg Ala Arg Glu Ser Thr Gly Ser
                580                 585                 590
```

```
Pro Arg Asp Ile Leu Val Pro Pro Gly Arg Asp Gly Ser Asn Ile Ser
            595                 600                 605

Ser Tyr Ser Gly Asp Arg Val Gln Ser Asn Lys His Thr Gly Leu Glu
    610                 615                 620

Thr Lys Thr Ala Arg Asn Pro Ser Ile Arg Thr Ser Ser Gln Leu Ile
625                 630                 635                 640

Ser Asn Val Ser Ser Ile Pro Asp Ser Thr Gly Thr Leu Gln Ala Ser
                645                 650                 655

Gln Pro Asn Ser Val Pro Gln Thr Ser Ala Ala Pro Ile Val Ser Leu
            660                 665                 670

Pro Ala Val Leu Lys Asp Ile Ala Val Asn Pro Thr Val Leu Met His
        675                 680                 685

Trp Ile Gln Met Glu His Gln Lys Arg Ser Ala Ser Glu Pro Gln Pro
    690                 695                 700

Ala Ser Gly Ile Ile Ser Ser Gly Met Ile Asn Asn Val Thr Ala Gly
705                 710                 715                 720

Met Val Ile Pro Pro Gly Asn Ala Leu Lys Thr Ala Glu Val Ala His
                725                 730                 735

Ile Pro Ser Tyr Arg Pro Gln Ala Thr Ser Gln Thr Ala Ser Val Asn
            740                 745                 750

Ser Gln Asn Asp Pro Gly Val Ile Arg Met Lys Ala Arg Asp Pro Arg
        755                 760                 765

Arg Val Leu His Asn Asn Thr Ser Gln Lys Asn Asp Thr Leu Asn Ser
    770                 775                 780

Asp Gln Ala Lys Ser Asn Gly Ile Ala Leu Pro Ala Phe Gln Asp Ser
785                 790                 795                 800

Lys Asp Asn Leu Ile Asn Arg Gln Gln Leu Ala Glu Gln Leu Gln Thr
                805                 810                 815

Thr Val Leu Pro Ser Gln Pro Val Ser Leu Ser Ser Ile Ala Arg Gln
            820                 825                 830

Ser Thr Met Ser Ala Ser Lys Val Asp Pro Val Ser Asn Ser Gln Leu
        835                 840                 845

Ala Ala Ser Ser Leu Ile Ala Pro Gln Glu Ser Leu Val Ser Val Asn
    850                 855                 860

Arg Ala Asp Pro Arg Val Ala Ala Gly Gln Asn Asp Ser Asn Asn Ala
865                 870                 875                 880

Ala Pro Ala Thr Thr Leu Gly Thr Arg Pro Pro Ala Asn Gln Trp Gly
                885                 890                 895

Asp Leu Asp Asp Leu Leu Asn Gly Tyr Asp Asp Gln Gln Lys Ala Leu
            900                 905                 910

Ile Gln Lys Glu Arg Ala Arg Arg Ile Met Glu Gln Thr Met Phe
        915                 920                 925

Ser Ser Arg Lys Leu Cys Leu Val Leu Asp Leu Asp His Thr Leu Leu
    930                 935                 940

Asn Ser Ala Lys Phe Ile Glu Val Asp Pro Ile His Glu Glu Ile Leu
945                 950                 955                 960

Arg Lys Lys Glu Glu Gln Asp Trp Glu Arg Ser Glu Arg His Leu Phe
                965                 970                 975

Arg Phe His His Met Gln Met Trp Thr Lys Leu Arg Pro Gly Ile Trp
            980                 985                 990

Asn Phe Leu Glu Lys Ala Ser Lys  Leu Tyr Glu Leu His  Leu Tyr Thr
        995                 1000                1005
```

-continued

Met Gly Asn Lys Leu Tyr Ala Thr Glu Met Ala Lys Val Leu Asp
    1010                1015                1020

Pro Ser Gly Thr Leu Phe Ala Gly Arg Val Ile Ser Arg Gly Gly
    1025                1030                1035

Asp Gly Ile Ser Arg Gly Gly Asp Gly Asp Thr Phe Asp Ser Asp
    1040                1045                1050

Asp Arg Val Pro Lys Ser Lys Asp Leu Asp Gly Val Leu Gly Met
    1055                1060                1065

Glu Ser Ala Val Val Ile Ile Asp Asp Ser Val Arg Val Trp Pro
    1070                1075                1080

His Asn Lys Asn Asn Met Ile Val Val Glu Arg Tyr Thr Tyr Phe
    1085                1090                1095

Pro Cys Ser Arg Arg Gln Phe Gly Leu Pro Gly Pro Ser Leu Leu
    1100                1105                1110

Glu Ile Asp Arg Asp Glu Arg Pro Glu Asp Gly Thr Leu Ala Ser
    1115                1120                1125

Ser Leu Ala Val Ile Gly Arg Ile His Gln Asn Phe Phe Ser His
    1130                1135                1140

Pro Asn Leu Asn Asp Ala Asp Val Arg Ser Ile Leu Ser Ser Glu
    1145                1150                1155

Gln Arg Arg Ile Leu Ala Gly Cys Arg Ile Val Phe Ser Arg Ile
    1160                1165                1170

Phe Pro Val Gly Glu Ala Asn Pro His Leu His Pro Leu Trp Gln
    1175                1180                1185

Thr Ala Glu Gln Phe Gly Ala Val Cys Thr Asn Gln Ile Asp Asp
    1190                1195                1200

Arg Val Thr His Val Val Ala Asn Ser Leu Gly Thr Asp Lys Val
    1205                1210                1215

Asn Trp Ala Leu Gln Thr Gly Arg Phe Val Val His Pro Gly Trp
    1220                1225                1230

Val Glu Ala Ser Ala Leu Leu Tyr Arg Arg Ala Asn Glu His Asp
    1235                1240                1245

Phe Ala Val Lys
    1250

<210> SEQ ID NO 16
<211> LENGTH: 1243
<212> TYPE: PRT
<213> ORGANISM: Triticum aestivum

<400> SEQUENCE: 16

Met Arg Val Thr Leu Thr Pro Lys Asp Glu Asp Trp Leu Val Glu Leu
1               5                   10                  15

Met Thr Arg Glu Arg Pro Arg Ser Ala Val Val Ala Pro Gly Gly Asp
                20                  25                  30

Val Phe Thr Ala Ser Gly Gly Gly Glu Thr Ser Asp Gly Asp Ser Ser
            35                  40                  45

Glu Ser Leu Glu Glu Ile Ser Ala Ala Asp Phe Lys Glu Ser Ser Ser
        50                  55                  60

Gly Thr Ala Ala Ala Ser Ala Ser Ser Gln Arg Ser Arg Val Trp Met
65                  70                  75                  80

Gly Tyr Thr Met Ser Arg Ser Tyr Ala Pro Ala Phe His Ser Phe Ala
                85                  90                  95

Trp Ala Gln Ala Val Gln Asn Lys Pro Leu Val Pro Arg Pro Ala Asp
                100                 105                 110

```
Glu Asp Glu Val Glu His Leu Val Asp Ala Ser Glu Glu Lys Glu
            115                 120                 125

Glu Gly Glu Ile Glu Gly Glu Ala Val Gln Ser Thr Ser Pro Pro
            130                 135                 140

Ile Lys Gln Pro Glu Ala Ile Asp Leu Asp Ser Asp Ala Gln Asp Lys
145                 150                 155                 160

Ser Glu Ser Val Ala Met Glu Gln Thr Pro Leu Ala Val Glu Ala Ala
                165                 170                 175

Asp Glu Leu Asp Phe Asp Gln Arg Val Gly Ser Ile Leu Glu Glu Leu
                180                 185                 190

Glu Arg Leu Ser Ile Glu Glu Ala Glu Lys Ser Phe Glu Gly Ser Cys
            195                 200                 205

Val Arg Leu Arg Ser Cys Phe Glu Ser Leu Lys Pro Leu Phe Pro Glu
            210                 215                 220

Ser Gly Ser Pro Met Pro Met Leu Asp Ala Leu Val Gln Gln Ala Phe
225                 230                 235                 240

Val Gly Ile Asp Thr Ile Thr Thr Val Ala Asn Ser Tyr Ala Met Pro
                245                 250                 255

Lys Arg Glu Gln Asn Lys Asn Met Leu Leu Lys Leu Leu Phe His Ile
            260                 265                 270

Lys Asn Arg Tyr Ser Asp Met Leu Ala Leu Asn Gln Arg Asp Glu Leu
            275                 280                 285

Asp Ser Arg Val Arg Gln Leu Val Phe Val Asp Gly Glu Asp His Ala
            290                 295                 300

Gly Ser Asn Cys Ser Ser Lys Thr Val Asn Leu Val Val Pro Ser Gly
305                 310                 315                 320

Gln Val Pro Ser Asp Arg Leu Pro Val Glu Ser Gly Ala Ala Asn Pro
                325                 330                 335

Leu Gly Gly Ser Ser Phe Pro Ser Trp Glu Ile Pro Ala Asn Asn Arg
            340                 345                 350

Met Val Ser Pro Leu Leu Asp Leu His Ala Asp Tyr Asp Glu Asn Ser
            355                 360                 365

Leu Pro Ser Pro Thr Arg Asp Ser Ala Pro Pro Phe Pro Val Pro Lys
            370                 375                 380

Pro Ile Gly Phe Gly Leu Phe Pro Met Ala Pro Asp Arg Tyr Phe Ser
385                 390                 395                 400

Ala Glu Arg Val Asp Pro Ser Lys Lys Val Leu Tyr Pro Cys Val Asn
                405                 410                 415

Asp Ala Leu Lys Asp Val Ser Ser Tyr Arg Gln Lys Tyr Gly Gln Thr
                420                 425                 430

Ser Thr Phe Ala Ser Asp Asp Leu Pro Ser Pro Thr Pro Ser Asp Asp
            435                 440                 445

Gly Asp Lys Ser Gly Asp Lys Glu Gly Asp Ile Phe Gly Glu Val Ser
            450                 455                 460

Ser Phe Ser Ala Ser Asn Leu Ile Pro Ala Ser Arg Pro Ser Ala Val
465                 470                 475                 480

Ile Ser Ser Asn Asp Ser Phe Ala Gly Gly Pro Pro Gly Tyr Ala Lys
                485                 490                 495

Gln Ile Glu Gln Ser Val Ser Gly Pro Ser His Ala Leu Lys Pro Ser
            500                 505                 510

Ala Lys Ser Arg Asp Pro Arg Leu Arg Phe Leu Asn Arg Asp Ser Gly
            515                 520                 525
```

```
Gly Thr Ala Asp Ala Asn Arg His Val Asn Leu Ala Glu Pro Asn Ala
            530                 535                 540

Ser Lys Asp Gly Thr Leu Gly Val Val Ser Asp Asn Ser Arg Lys
545                 550                 555                 560

His Lys Ala Thr Gly Gln Pro Leu Thr Asp Glu Thr Val Leu Lys Arg
                565                 570                 575

Ala Arg Glu Ser Thr Gly Asn Pro Arg Asp Met Gln Val Pro Pro Gly
            580                 585                 590

Arg Asp Gly Ser Asn Ile Ser Ser Tyr Ser Gly Asn Arg Val Gln Ser
                595                 600                 605

Asn Gln His Lys Gly Leu Glu Thr Lys Ala Ala Gly Asn Pro Ser Ile
            610                 615                 620

Arg Thr Ser Ser Gln Leu Ile Ser Asn Val Ser Ser Ile Pro Asp Ser
625                 630                 635                 640

Thr Gly Thr Leu Gln Ala Ser Gln Pro Asn Ser Val Pro Gln Thr Ser
                645                 650                 655

Ala Ala Pro Ile Val Ser Leu Pro Ala Val Leu Lys Asp Ile Ala Val
                660                 665                 670

Asn Pro Thr Val Leu Met His Trp Ile Gln Met Glu His Gln Lys Trp
            675                 680                 685

Ser Ala Ser Glu Pro Gln Pro Ala Ser Gly Ile Ile Ser Ser Gly Met
690                 695                 700

Ile Asn Asn Val Thr Ala Gly Met Val Ile Pro Pro Gly Asn Ala Pro
705                 710                 715                 720

Lys Thr Ala Glu Val Ala His Ile Pro Ser Tyr Arg Pro Gln Ala Thr
                725                 730                 735

Ser Gln Thr Ala Ser Val Asn Ser Gln Asn Asp Pro Gly Val Ile Arg
            740                 745                 750

Met Lys Ala Arg Asp Pro Arg Arg Val Leu His Asn Asn Thr Ser Gln
                755                 760                 765

Lys Asn Asp Thr Pro Asn Ser Asp Gln Ala Lys Ser Asn Gly Ile Ala
770                 775                 780

Leu Pro Ala Phe Gln Asp Ser Lys Asp Asn Leu Ile Asn Arg Glu Gln
785                 790                 795                 800

Leu Ala Glu Gln Leu Gln Thr Thr Val Leu Pro Ser Gln Pro Val Ser
            805                 810                 815

Leu Ser Ser Ile Ala Arg Gln Ser Thr Met Ser Ala Ser Lys Val Asp
                820                 825                 830

Pro Val Ser Asn Ser Gln Leu Ala Ala Ser Ser Leu Ile Ala Pro Gln
                835                 840                 845

Glu Thr Leu Val Ser Val Asn Arg Ala Asp Pro Arg Val Ala Ala Gly
            850                 855                 860

Gln Asn Asp Ser Asn Asp Ala Ala Pro Ala Thr Thr Leu Gly Thr Arg
865                 870                 875                 880

Pro Pro Ala Asn Gln Trp Gly Asp Leu Asp Asp Leu Leu Asn Gly Tyr
                885                 890                 895

Asp Asp Gln Gln Lys Ala Leu Ile Gln Lys Glu Arg Ala Arg Arg Ile
            900                 905                 910

Met Glu Gln His Thr Met Phe Ser Ser Arg Lys Leu Cys Leu Val Leu
            915                 920                 925

Asp Leu Asp His Thr Leu Leu Asn Ser Ala Lys Phe Ile Glu Val Asp
            930                 935                 940
```

```
Pro Ile His Glu Glu Ile Leu Arg Lys Lys Glu Gln Asp Arg Glu
945                 950                 955                 960

Arg Ser Glu Arg His Leu Phe Arg Phe His Met Gln Met Trp Thr
                965                 970                 975

Lys Leu Arg Pro Gly Ile Trp Asn Phe Leu Glu Lys Ala Ser Lys Leu
            980                 985                 990

Tyr Glu Leu His Leu Tyr Thr Met Gly Asn Lys Leu Tyr Ala Thr Glu
        995                 1000                1005

Met Ala Lys Val Leu Asp Pro Ser Gly Thr Leu Phe Ala Gly Arg
    1010                1015                1020

Val Ile Ser Arg Gly Gly Asp Gly Ile Ser Arg Gly Gly Asp Gly
    1025                1030                1035

Asp Thr Phe Asp Ser Asp Arg Val Pro Lys Ser Lys Asp Leu
    1040                1045                1050

Asp Gly Val Leu Gly Met Glu Ser Ala Val Val Ile Ile Asp Asp
    1055                1060                1065

Ser Val Arg Val Trp Pro His Asn Lys Asn Asn Met Ile Val Val
    1070                1075                1080

Glu Arg Tyr Thr Tyr Phe Pro Cys Ser Arg Arg Gln Phe Gly Leu
    1085                1090                1095

Pro Gly Pro Ser Leu Leu Glu Ile Asp Arg Asp Glu Arg Pro Glu
    1100                1105                1110

Asp Gly Thr Leu Ala Ser Ser Leu Ala Val Ile Gly Arg Ile His
    1115                1120                1125

Gln Asn Phe Phe Ser His Pro Asn Leu Asn Asp Ala Asp Val Arg
    1130                1135                1140

Ser Ile Leu Ser Ser Glu Gln Arg Arg Ile Leu Ala Gly Cys Arg
    1145                1150                1155

Ile Val Phe Ser Arg Ile Phe Pro Val Gly Glu Ala Asn Pro His
    1160                1165                1170

Leu His Pro Leu Trp Gln Thr Ala Glu Gln Phe Gly Ala Val Cys
    1175                1180                1185

Thr Asn Gln Ile Asp Asp Arg Val Thr His Val Val Ala Asn Ser
    1190                1195                1200

Leu Gly Thr Asp Lys Val Asn Trp Ala Leu Gln Thr Gly Arg Phe
    1205                1210                1215

Val Val His Pro Gly Trp Val Glu Ala Ser Ala Leu Leu Tyr Arg
    1220                1225                1230

Arg Ala Asn Glu His Asp Phe Ala Val Lys
    1235                1240

<210> SEQ ID NO 17
<211> LENGTH: 1252
<212> TYPE: PRT
<213> ORGANISM: Triticum aestivum

<400> SEQUENCE: 17

Met Arg Val Thr Leu Thr Pro Lys Asp Glu Asp Trp Leu Val Val Leu
1               5                   10                  15

Met Thr Arg Glu Arg Pro Arg Ser Ala Val Val Ala Pro Gly Gly Asp
            20                  25                  30

Val Phe Thr Ala Gly Gly Gly Gly Glu Thr Ser Asp Gly Asp Ser Ser
        35                  40                  45

Glu Ser Leu Glu Glu Ile Ser Ala Ala Asp Phe Lys Glu Ser Ser Ser
    50                  55                  60
```

```
Gly Thr Ala Ala Ala Ser Ala Ser Ala Gln Arg Ser Arg Val Trp Met
 65                  70                  75                  80

Gly Tyr Thr Met Ser Arg Ser Tyr Ala Pro Ala Phe His Ser Phe Ala
             85                  90                  95

Trp Ala Gln Ala Val Gln Asn Lys Pro Leu Val Pro Arg Pro Val Ala
            100                 105                 110

Asp Glu Asp Glu Val Glu His Leu Val Asp Ala Ser Asp Glu Glu Lys
        115                 120                 125

Glu Glu Gly Glu Ile Glu Gly Glu Ala Val Gln Ser Thr Ser Pro
    130                 135                 140

Pro Ile Lys Gln Pro Glu Thr Ile Asp Leu Asp Ser Asp Ala Gln Asp
145                 150                 155                 160

Lys Ser Glu Ser Val Ala Met Glu Gln Thr Pro Leu Ala Phe Glu Ala
                165                 170                 175

Ala Asp Glu Leu Asp Phe Asp Gln Arg Val Gly Ser Ile Leu Glu Glu
            180                 185                 190

Leu Glu Arg Leu Ser Ile Glu Glu Ala Glu Lys Ser Phe Glu Gly Ser
        195                 200                 205

Cys Ala Arg Leu Arg Ser Cys Phe Glu Ser Leu Lys Pro Leu Phe Pro
210                 215                 220

Glu Ser Gly Ser Pro Met Pro Met Leu Asp Ala Leu Val Gln Gln Ala
225                 230                 235                 240

Phe Val Gly Ile Asp Thr Ile Thr Thr Val Ala Asn Ser Tyr Ala Met
                245                 250                 255

Pro Lys Arg Glu Gln Asn Lys Asn Met Leu Leu Lys Leu Leu Phe His
            260                 265                 270

Ile Lys Asn Arg Tyr Ser Asp Met Leu Ala Leu Ser Gln Arg Asp Glu
        275                 280                 285

Leu Asp Ser Arg Val Arg Gln Leu Val Phe Val Asp Gly Glu Asp Asn
    290                 295                 300

Ala Gly Ser Asn Cys Ser Thr Lys Thr Val Asn Val Val Gln Ser
305                 310                 315                 320

Gly Gln Val Pro Ser Asp Arg Leu Pro Val Glu Ser Gly Ala Ala Asn
                325                 330                 335

Pro Leu Arg Gly Ser Ser Phe Pro Ser Trp Glu Ile Pro Ala Asn Asn
            340                 345                 350

Arg Met Val Ser Pro Leu Leu Asp Leu His Ala Asp Tyr Asp Glu Asn
        355                 360                 365

Ser Leu Pro Ser Pro Thr Arg Asp Ser Ala Pro Pro Phe Pro Val Pro
    370                 375                 380

Lys Pro Ile Gly Phe Gly Val Phe Pro Met Ala Pro Asp Arg Tyr Phe
385                 390                 395                 400

Leu Ala Glu Arg Val Asp Pro Ser Lys Lys Val Leu Tyr Thr Cys Val
                405                 410                 415

Asn Asp Ala Leu Lys Asp Val Ser Ser Tyr Arg Gln Lys Tyr Gly Gln
            420                 425                 430

Thr Ser Thr Phe Ala Ser Asp Asp Leu Pro Ser Pro Thr Pro Ser Asp
        435                 440                 445

Asp Gly Asp Lys Ser Gly Asp Lys Glu Gly Asp Ile Phe Gly Glu Val
    450                 455                 460

Ser Ser Phe Ser Ala Ser Asn Lys Ser Ala Pro Pro Ser Gly Asn Leu
465                 470                 475                 480
```

```
Ile Pro Ala Ser Arg Pro Ser Ala Val Ile Ser Ser Asn Asp Ser Phe
                485                 490                 495

Ala Gly Gly Pro Pro Gly Tyr Ala Lys Gln Ile Glu Gln Ser Val Ser
            500                 505                 510

Gly Pro Ser His Ala Leu Lys Pro Ser Ala Lys Ser Arg Asp Pro Arg
            515                 520                 525

Leu Arg Phe Leu Asn Arg Asp Ser Gly Gly Thr Ala Asp Ala Asn Arg
530                 535                 540

His Val Asn Phe Ala Glu Pro Asn Ala Ser Lys Asp Gly Thr Leu Gly
545                 550                 555                 560

Gly Val Val Ser Asp Asn Ser Arg Lys His Lys Ala Thr Gly Gln Pro
                565                 570                 575

Leu Thr Gly Glu Thr Val Leu Lys Arg Ala Arg Glu Ser Thr Gly Asn
            580                 585                 590

Pro Arg Asp Met Gln Val Pro Pro Ser Arg Asp Gly Ser Asn Ile Ser
        595                 600                 605

Ser Tyr Ser Gly Asp Arg Val Gln Ser Asn Gln His Lys Gly Leu Glu
    610                 615                 620

Thr Lys Ala Ala Gly Asn Pro Ser Ile Arg Thr Ser Ser Gln Leu Ile
625                 630                 635                 640

Ser Asn Val Ser Ser Ile Pro Asp Ser Thr Gly Thr Leu Gln Ala Ser
                645                 650                 655

Gln Pro Asn Ser Val Pro Gln Thr Ser Ala Ala Pro Ile Val Ser Leu
            660                 665                 670

Pro Ala Val Leu Lys Asp Ile Ala Val Asn Pro Thr Val Leu Met His
            675                 680                 685

Trp Ile Gln Met Glu His Gln Lys Arg Ser Ala Ser Glu Pro Gln Pro
            690                 695                 700

Ala Ser Gly Ile Ile Ser Ser Gly Met Ile Asn Asn Val Thr Ala Gly
705                 710                 715                 720

Met Val Ile Pro Pro Gly Asn Ala Leu Lys Thr Ala Glu Val Ala His
                725                 730                 735

Ile Pro Ser Tyr Arg Pro Gln Ala Thr Ser Gln Thr Ala Ser Val Asn
            740                 745                 750

Ser Gln Asn Asp Pro Gly Val Ile Arg Met Lys Ala Arg Asp Pro Arg
        755                 760                 765

Arg Val Leu His Asn Asn Thr Ser Gln Lys Asn Asp Thr Pro Asn Ser
    770                 775                 780

Asp Gln Ala Lys Ser Asn Gly Ile Thr Leu Pro Ala Phe Gln Asp Ser
785                 790                 795                 800

Lys Asp Asn Leu Ile Asn Arg Glu Gln Leu Ala Glu Gln Leu Gln Thr
                805                 810                 815

Thr Val Leu Pro Ser Gln Pro Val Ser Leu Ser Ser Ile Ala Gly Gln
            820                 825                 830

Ser Thr Met Ser Ala Ser Lys Val Asp Pro Val Ser Asn Ser Gln Leu
        835                 840                 845

Ala Ala Ser Ser Leu Ile Ala Pro Gln Glu Thr Leu Val Ser Val Asn
    850                 855                 860

Arg Ala Asp Pro Arg Val Ala Ala Gly Gln Asn Asp Ser Asn Asp Ala
865                 870                 875                 880

Ala Pro Ala Thr Thr Leu Gly Thr Arg Pro Pro Ala Asn Gln Trp Gly
                885                 890                 895
```

```
Asp Leu Asp Leu Leu Asn Gly Tyr Asp Asp Gln Gln Lys Ala Leu
            900                 905                 910

Ile Gln Lys Glu Arg Ala Arg Arg Ile Met Glu Gln His Thr Met Phe
        915                 920                 925

Ser Ser Arg Lys Leu Cys Leu Val Leu Asp Leu Asp His Thr Leu Leu
    930                 935                 940

Asn Ser Ala Lys Phe Ile Glu Val Asp Pro Ile His Glu Ile Leu
945                 950                 955                 960

Arg Lys Lys Glu Glu Gln Asp Arg Glu Arg Ser Glu Arg His Leu Phe
                965                 970                 975

Arg Phe His His Met Gln Met Trp Thr Lys Leu Arg Pro Gly Ile Trp
                980                 985                 990

Asn Phe Leu Glu Lys Ala Ser Lys Leu Tyr Glu Leu His Leu Tyr Thr
        995                 1000                1005

Met Gly Asn Lys Leu Tyr Ala Thr Glu Met Ala Lys Val Leu Asp
    1010                1015                1020

Pro Ser Gly Thr Leu Phe Ala Gly Arg Val Ile Ser Arg Gly Gly
    1025                1030                1035

Asp Gly Ile Ser Arg Gly Gly Asp Gly Asp Thr Phe Asp Ser Asp
    1040                1045                1050

Asp Arg Val Pro Lys Ser Lys Asp Leu Asp Gly Val Leu Gly Met
    1055                1060                1065

Glu Ser Ala Val Val Ile Ile Asp Asp Ser Val Arg Val Trp Pro
    1070                1075                1080

His Asn Lys Asn Asn Met Ile Val Val Glu Arg Tyr Thr Tyr Phe
    1085                1090                1095

Pro Cys Ser Arg Arg Gln Phe Gly Leu Pro Gly Pro Ser Leu Leu
    1100                1105                1110

Glu Ile Asp Arg Asp Glu Arg Pro Glu Asp Gly Thr Leu Ala Ser
    1115                1120                1125

Ser Leu Ala Val Ile Gly Arg Ile His Gln Asn Phe Phe Ser His
    1130                1135                1140

Pro Asn Leu Asn Asp Ala Asp Val Arg Ser Ile Leu Ser Ser Glu
    1145                1150                1155

Gln Arg Arg Ile Leu Ala Gly Cys Arg Ile Val Phe Ser Arg Ile
    1160                1165                1170

Phe Pro Val Gly Glu Ala Asn Pro His Leu His Pro Leu Trp Gln
    1175                1180                1185

Thr Ala Glu Gln Phe Gly Ala Val Cys Thr Asn Gln Ile Asp Asp
    1190                1195                1200

Gln Val Thr His Val Val Ala Asn Ser Leu Gly Thr Asp Lys Val
    1205                1210                1215

Asn Trp Ala Leu Gln Thr Gly Arg Phe Val Val His Pro Gly Trp
    1220                1225                1230

Val Glu Ala Ser Ala Leu Leu Tyr Arg Arg Ala Asn Glu His Asp
    1235                1240                1245

Phe Ala Val Lys
    1250

<210> SEQ ID NO 18
<211> LENGTH: 1197
<212> TYPE: PRT
<213> ORGANISM: Sorghum bicolor
```

```
<400> SEQUENCE: 18

Met Ala Arg Glu Arg Pro Arg Ser Thr Val Ala Ala Gly Gly Asp
1               5                   10                  15

Leu Val Thr Ala Pro Gly Gly Glu Gly Ser Asp Gly Asp Ser Ala
            20                  25                  30

Gly Ser Ile Glu Glu Ile Ser Ala Asp Asp Phe Arg Lys Asp Ser Ser
        35                  40                  45

Ser Ala Leu Gly Gly Pro Ala Ala Ala Ala Ala Gly Gln Arg Ser
    50                  55                  60

Arg Ser Trp Val Gly Pro Pro Ala Val Gly Tyr Met Ala Arg Asn Phe
65                  70                  75                  80

Gly His Ala Phe Asn Ser Phe Ala Trp Ser Gln Ala Val Arg Asn Lys
                85                  90                  95

Pro Leu Gly Leu Gln Pro Pro Ala Ser Asp Glu Asp Glu Val Glu
            100                 105                 110

His Ala Val Asp Ala Ser Asp Gly Glu Lys Glu Glu Gly Glu Ile Glu
            115                 120                 125

Glu Gly Glu Ala Val Glu Ala Glu Ala Ser Pro Ala Arg Ala Gln Pro
    130                 135                 140

Glu Thr Ile Asp Leu Asp Ala Asp Ala Asp Ala Leu Glu Lys Ser Glu
145                 150                 155                 160

Ser Leu Ala Gly Ala Val Pro Ala Ser Ala Ala Glu Glu Glu Val
            165                 170                 175

Asn Leu Asp Gln Arg Val Gly Ser Ile Leu Glu Glu Leu Glu Met Val
            180                 185                 190

Ser Ile Glu Glu Ala Glu Lys Ser Phe Glu Gly Ala Cys Gly Arg Leu
    195                 200                 205

His Thr Cys Phe Glu Asn Leu Lys Pro Leu Phe Gln Glu Leu Glu Asn
            210                 215                 220

Gly Ser Pro Met Ala Ile Leu Glu Pro Leu Met Gln Gln Ala Phe Ile
225                 230                 235                 240

Gly Ile Asp Thr Leu Thr Thr Val Ala Ile Ser Tyr Asn Leu Pro Arg
                245                 250                 255

Ser Glu Gln Asn Lys Thr Thr Leu Leu Lys Ser Leu Phe His Ile Lys
            260                 265                 270

Asn Arg Tyr Ser Asp Met Leu Thr Pro Glu Gln Arg Asp Glu Leu Asp
    275                 280                 285

Ser Arg Val Arg Lys Leu Val Phe Gly Glu Lys Asp Asn Val Ser Asp
290                 295                 300

Pro Ser Thr Ser Ser Gly Thr Asn Ala Ile Asn Val Leu Ala Pro Ser
305                 310                 315                 320

Gly Gln Val Ser Ser Gly Gly Leu Pro Phe Glu Ser Gly Ala Ala
            325                 330                 335

Asn Pro Phe Ser Ser Leu Pro Arg Leu Glu Val Pro Ala Lys Arg Ile
            340                 345                 350

Ser Pro Leu Leu Asp Leu His Ala Asp Tyr Asp Glu Asn Ser Leu Pro
            355                 360                 365

Ser Pro Thr Arg Asp Asn Ala Pro Pro Phe Val Pro Lys Pro Ile
            370                 375                 380

Gly Phe Gly Ala Phe Pro Met Val Pro Glu Lys Leu Ser Phe Pro Glu
385                 390                 395                 400

Arg Val Glu Pro Ala Lys Asn Ser Leu Tyr Pro Ser Leu Asn Asp Pro
            405                 410                 415
```

```
-continued

Leu Lys Ala Val Ser Ser Tyr Gln Gln Lys Tyr Gly Gln Lys Ser Val
                420                 425                 430

Phe Pro Ser Asp Asp Leu Pro Ser Pro Thr Pro Ser Gly Asp Glu Gly
            435                 440                 445

Lys Ser Ala Asp Lys Gly Gly Asp Ile Phe Ser Glu Val Ser Ser Phe
450                 455                 460

Pro Val Pro Lys Ser Ile Ala Leu Pro Ser Thr Ser Gln Met Pro Ala
465                 470                 475                 480

Ser Gln Pro Ser Thr Val Ser Ser Gly Ile Ser Tyr Ala Ser Gly
                485                 490                 495

Pro Pro Gly Phe Ala Lys Gln Ile Glu Gln Pro Val Ala Gly Pro Asn
            500                 505                 510

His Ala Ile Lys Ala Ala Ser Lys Ser Arg Asp Pro Arg Leu Arg Phe
            515                 520                 525

Leu Asn Arg Asp Ser Ala Gly Ala Thr Asp Val Asn Arg Arg Ala Asn
530                 535                 540

Phe Ser Glu Leu Lys Asp Gly Asn Leu Gly Gly Ala Ser Val Gly Asn
545                 550                 555                 560

Arg Lys His Lys Ala Ile Asp Asp Pro Gln Val Asp Glu Asn Val Leu
                565                 570                 575

Lys Arg Phe Arg Gly Gly Thr Ala Asn Pro Arg Asp Leu Gln Pro Thr
            580                 585                 590

Gly Asn Pro Asn Gln Leu Met Asn Ile Arg Ala Pro Thr Asn Ser Ser
            595                 600                 605

Gly Ile Asn Met Lys Thr Leu Gln Pro Pro Gln Thr Thr Ala Pro His
            610                 615                 620

Val Ser Ala Ala Pro Ala Val Pro Val Pro Ser Met Leu Leu Lys Asp
625                 630                 635                 640

Ile Ala Val Asn Pro Thr Leu Leu Met His Leu Ile Gln Met Glu His
                645                 650                 655

Gln Lys Lys Ser Ala Ser Glu Thr Gln Gly Gly Met Ser Ser Gly Met
            660                 665                 670

Ser Asn Asn Gly Ile Ala Gly Met Val Phe Thr Pro Gly Asn Ala Pro
            675                 680                 685

Lys Thr Thr Glu Ala Ala Gln Val Pro Ser Val Arg Pro Gln Val Pro
690                 695                 700

Ala Gln Thr Pro Ser Leu Asn Ser Gln Asn Asp Gly Gly Ile Leu Arg
705                 710                 715                 720

Met Lys Pro Arg Asp Pro Arg Arg Ile Leu His Asn Asn Val Ala Gln
                725                 730                 735

Lys Ser Asp Ala Met Val Leu Glu Gln Val Lys Thr Asn Gly Ile Thr
            740                 745                 750

Gln Pro Asp Ser Gln Gly Thr Lys Asp Gln Thr Ser Ser Met Pro Ser
            755                 760                 765

Gln Pro Thr Leu Pro Ser Ser Val Ala Arg Pro Phe Thr Asn Thr Lys
            770                 775                 780

His Val Asp Pro Val Ser Asn Ser Gln Leu Ala Ala Thr Ala Ile Met
785                 790                 795                 800

Ala Pro Thr Gln Gln Ala Leu Gly Ser Ile Asn Lys Val Asp Pro Arg
                805                 810                 815

Leu Ala Val Glu Gln Asn Gly Gln Asn Ala Asp Ala Thr Thr Thr Asp
            820                 825                 830
```

Ala Ser Ala Thr Glu Leu Glu Ala Thr Gln Pro Val Ser Pro Trp Gly
835                 840                 845

Asn Leu Asp His Leu Leu Asp Gly Tyr Asp Asp Lys Gln Lys Ala Leu
850                 855                 860

Ile Gln Lys Glu Arg Ala Arg Arg Ile Thr Glu Gln His Lys Met Phe
865                 870                 875                 880

Ser Ala Arg Lys Leu Cys Leu Val Leu Asp Leu Asp His Thr Leu Leu
                885                 890                 895

Asn Ser Ala Lys Phe Ile Glu Val Glu Pro Ile His Glu Glu Met Leu
            900                 905                 910

Arg Lys Lys Glu Glu Gln Asp Arg Thr Leu Pro Glu Arg His Leu Tyr
        915                 920                 925

Arg Phe His His Met Asn Met Trp Thr Lys Leu Arg Pro Gly Ile Trp
    930                 935                 940

Asn Phe Leu Glu Lys Ala Ser Asn Leu Phe Glu Leu His Leu Tyr Thr
945                 950                 955                 960

Met Gly Asn Lys Leu Tyr Ala Thr Glu Met Ala Lys Val Leu Asp Pro
                965                 970                 975

Thr Gly Thr Leu Phe Ala Gly Arg Val Ile Ser Arg Gly Asp Asp Gly
            980                 985                 990

Asp Pro Phe Asp Ser Asp Glu Arg  Val Pro Lys Ser Lys  Asp Leu Asp
        995                 1000                1005

Gly Val  Leu Gly Met Glu Ser  Ala Val Val Ile  Asp Asp Ser
    1010                1015                1020

Val Arg  Val Trp Pro His Asn  Arg His Asn Leu Ile  Val Val Glu
    1025                1030                1035

Arg Tyr  Thr Tyr Phe Pro Cys  Ser Arg Arg Gln Phe  Gly Leu Pro
    1040                1045                1050

Gly Pro  Ser Leu Leu Glu Ile  Asp Arg Asp Glu Arg  Pro Glu Asp
    1055                1060                1065

Gly Thr  Leu Ala Ser Ser Leu  Ala Val Ile Glu Arg  Ile His His
    1070                1075                1080

Asn Phe  Phe Ser His Pro Asn  Leu Asn Glu Ala Asp  Val Arg Ser
    1085                1090                1095

Ile Leu  Ala Ser Glu Gln Arg  Arg Ile Leu Ala Gly  Cys Arg Ile
    1100                1105                1110

Val Phe  Ser Arg Val Phe Pro  Val Gly Asp Ala Ser  Pro His Leu
    1115                1120                1125

His Pro  Leu Trp Gln Thr Ala  Glu Gln Phe Gly Ala  Val Cys Thr
    1130                1135                1140

Asn Leu  Val Asp Asp Arg Val  Thr His Val Val Ala  Asn Ser Pro
    1145                1150                1155

Gly Thr  Asp Lys Val Asn Trp  Ala Leu Ser Lys Gly  Lys Phe Val
    1160                1165                1170

Val His  Pro Gly Trp Val Glu  Ala Ser Ala Leu Leu  Tyr Arg Arg
    1175                1180                1185

Ala Asn  Glu His Asp Phe Ala  Val Lys
    1190                1195

<210> SEQ ID NO 19
<211> LENGTH: 1234
<212> TYPE: PRT
<213> ORGANISM: Zea mays

<400> SEQUENCE: 19

Met Arg Val Thr Val Thr Pro Lys Asp Glu Arg Leu Val Asp Leu
1               5                   10                  15

Met Ala Arg Glu Gln Pro Arg Ser Ala Val Val Ala Ala Gly Gly Asp
            20                  25                  30

Leu Val Thr Ala Ala Gly Gly Gly Gly Gly Ser Asp Arg Asp Ser
        35                  40                  45

Ser Gly Ser Ile Glu Glu Ile Thr Ala Asp Asp Phe Lys Lys Asp Ser
    50                  55                  60

Ser Ser Ala Leu Gly Gly Ala Ala Ala Ala Gly Pro Arg Ser Arg
65                  70                  75                  80

Ser Trp Val Ala Pro Pro Ala Val Gly Tyr Met Ala Arg Asn Phe Arg
                85                  90                  95

Tyr Ala Phe Asn Ser Phe Ala Trp Ser Gln Ala Val Arg Asn Lys Pro
            100                 105                 110

Leu Gly Leu Gln Pro Pro Ala Pro Asp Asp Asp Glu Val Glu His Ala
        115                 120                 125

Val Asp Val Ser Asp Gly Glu Lys Glu Glu Gly Glu Ile Glu Glu Gly
    130                 135                 140

Glu Ala Val Glu Ala Leu Ala Ser Pro Ala Pro Ala Gln Pro Glu Thr
145                 150                 155                 160

Ile Asp Leu Asp Ser Asp Ala Pro Glu Lys Ser Glu Ser Val Ala Ile
                165                 170                 175

Asp Gly Ser Ala Ser Val Val Pro Val Pro Ala Ala Glu Glu Glu Glu
            180                 185                 190

Val Asn Leu Asp Gln Arg Val Gly Ser Ile Leu Glu Glu Leu Glu Met
        195                 200                 205

Val Ser Ile Glu Glu Ala Glu Lys Ser Phe Glu Gly Ala Cys Ala Arg
    210                 215                 220

Leu His Thr Cys Phe Glu Asn Leu Lys Pro Leu Phe Gln Glu Leu Glu
225                 230                 235                 240

Asn Gly Ser Pro Met Ala Ile Leu Glu Pro Leu Met Gln Gln Ala Phe
                245                 250                 255

Ile Gly Ile Asp Thr Leu Thr Thr Val Ala Asn Leu Tyr Asn Leu Pro
            260                 265                 270

Arg Arg Glu Gln Asn Lys Thr Thr Leu Leu Lys Leu Leu Phe His Ile
        275                 280                 285

Lys Asn Arg Tyr Ser Asp Met Leu Thr Pro Glu Gln Arg Glu Glu Met
    290                 295                 300

Asp Ser Arg Val Arg Lys Leu Val Phe Gly Glu Lys Asp Asn Val Ser
305                 310                 315                 320

Asp Pro Ser Thr Ser Cys Gly Thr Ser Ala Ile Asn Val Ser Ala Pro
                325                 330                 335

Ser Gly Gln Val Ser Asn Thr Gly Gly Leu Pro Phe Glu Ser Gly Ala
            340                 345                 350

Ala Asn Leu Phe Ser Ser Leu Pro Arg Leu Glu Val Pro Ala Lys Arg
        355                 360                 365

Asn Ser Pro Leu Leu Asn Leu His Ala Asp Tyr Asp Glu Asn Ser Leu
    370                 375                 380

Pro Ser Pro Thr Arg Asp Asn Ala Pro Pro Phe Pro Ala Leu Lys Pro
385                 390                 395                 400

Ile Gly Phe Gly Ala Phe Pro Met Val Pro Glu Lys Leu Ser Phe Leu
                405                 410                 415

-continued

```
Asp Arg Val Glu Pro Thr Lys Asn Ser Leu Tyr Pro Pro Leu Asn Asp
            420                 425                 430
Pro Leu Lys Ala Val Ser Ser Tyr Gln Gln Lys Tyr Gly Gln Lys Ser
        435                 440                 445
Val Tyr Pro Ser Asp Asp Leu Pro Ser Pro Thr Pro Ser Gly Asp Glu
    450                 455                 460
Gly Lys Pro Ala Asp Lys Gly Gly Asp Ile Phe Ser Asp Val Ser Ser
465                 470                 475                 480
Phe Pro Val Pro Lys Ser Ile Val Leu Pro Ser Thr Ser Gln Met Pro
                485                 490                 495
Ala Ser Gln Pro Ser Thr Val Ser Ser Ser Ser Ile Ser Tyr Ala Ser
            500                 505                 510
Ser Thr Ser Gln Met Ala Ala Ser Gln Pro Ile Thr Val Ser Ser Ser
        515                 520                 525
Gly Ile Ser Tyr Ala Ser Gly Pro Pro Gly Phe Ala Lys Gln Ile Glu
    530                 535                 540
Gln Ser Thr Ala Gly Pro Asn His Ala Ile Lys Ala Ala Ser Lys Ser
545                 550                 555                 560
Arg Asp Pro Arg Leu Arg Phe Leu Asn Arg Asp Ser Ala Gly Ala Thr
                565                 570                 575
Asp Val Asn Trp Arg Ala Asn Phe Ser Glu Leu Lys Asp Gly Asn Leu
            580                 585                 590
Gly Gly Val Ser Val Gly Asn Arg Lys Gln Lys Ala Val Asp Asp Pro
        595                 600                 605
Gln Val Asp Asp Asn Ala Leu Lys Arg Phe Arg Gly Gly Ile Ala Asn
    610                 615                 620
Gln Arg Asp Met Gln Pro Thr Gly Asn Pro Asn Gln Leu Met Asn Ile
625                 630                 635                 640
Arg Ala Pro Thr His Ser Ser Ser Ile Asn Met Lys Thr Leu Gln Pro
                645                 650                 655
Pro Gln Thr Thr Ala Pro His Val Ser Ala Ala Pro Ala Val Pro Leu
            660                 665                 670
Pro Pro Met Leu Leu Lys Asp Ile Ala Val Asn Pro Ala Leu Leu Met
        675                 680                 685
His Leu Ile Gln Met Glu His Gln Lys Lys Ser Ala Ser Glu Ser Gln
    690                 695                 700
Gly Gly Met Ser Ser Gly Met Thr Asn Asn Gly Ile Ala Gly Met Val
705                 710                 715                 720
Phe Thr Pro Gly Asn Ala Pro Lys Ile Thr Glu Ala Ala Gln Val Pro
                725                 730                 735
Ser Val Arg Pro Gln Val Pro Val Gln Thr Pro Leu Asn Ser Gln
            740                 745                 750
Asn Asp Gly Gly Ile Val Arg Met Lys Pro Arg Asp Pro Arg Arg Ile
        755                 760                 765
Leu His Asn Asn Ile Ala Gln Lys Ser Asp Ala Met Ser Leu Glu Gln
    770                 775                 780
Val Lys Asn Asn Gly Thr Thr Gln Pro Asp Ser Gln Gly Thr Lys Asp
785                 790                 795                 800
Gln Thr Thr Pro Val Pro Ser Gln Pro Ala Leu Pro Ser Ser Ile Ala
                805                 810                 815
Arg Pro Phe Ser Ser Ala Lys His Val Asp Pro Val Ser Asn Ser Gln
            820                 825                 830
```

```
Leu Ala Ala Thr Ala Ile Met Ala Pro Thr Gln Ala Leu Ser Ser Val
            835                 840                 845

Asn Lys Val Asp Pro Arg Leu Ala Val Glu Gln Asn Gly Gln Asn Ala
850                 855                 860

Asp Ala Thr Thr Asn Gly Ala Ser Ala Thr Thr Leu Glu Ala Thr Gln
865                 870                 875                 880

Pro Val Ser Pro Trp Gly Asp Val Asp His Leu Leu Asp Gly Tyr Asp
                885                 890                 895

Asp Gln Gln Lys Ala Leu Ile Gln Lys Glu Arg Ala Arg Arg Ile Thr
            900                 905                 910

Glu Gln His Lys Met Phe Ser Ala Arg Lys Leu Cys Leu Val Leu Asp
            915                 920                 925

Leu Asp His Thr Leu Leu Asn Ser Ala Lys Phe Ile Glu Val Glu Pro
        930                 935                 940

Ile His Glu Glu Met Leu Arg Lys Lys Glu Glu Gln Asp Arg Thr Leu
945                 950                 955                 960

Pro Glu Arg His Leu Tyr Arg Phe His His Met Asn Met Trp Thr Lys
                965                 970                 975

Leu Arg Pro Gly Ile Trp Asn Phe Leu Gln Lys Ala Ser Asn Leu Phe
            980                 985                 990

Glu Leu His Leu Tyr Thr Met Gly Asn Lys Leu Tyr Ala Thr Glu Met
        995                 1000                1005

Ala Lys Val Leu Asp Pro Thr Gly Thr Leu Phe Ala Gly Arg Val
        1010                1015                1020

Ile Ser Arg Gly Asp Asp Gly Asp Pro Phe Asp Ser Asp Glu Arg
        1025                1030                1035

Val Pro Lys Ser Lys Asp Leu Asp Gly Val Leu Gly Met Glu Ser
        1040                1045                1050

Ala Val Val Ile Ile Asp Asp Ser Val Arg Val Trp Pro His Asn
        1055                1060                1065

Arg His Asn Leu Ile Val Val Glu Arg Tyr Thr Tyr Phe Pro Cys
        1070                1075                1080

Ser Arg Arg Gln Phe Gly Leu Pro Gly Pro Ser Leu Leu Glu Ile
        1085                1090                1095

Asp Arg Asp Glu Arg Pro Glu Asp Gly Thr Leu Ala Ser Ser Leu
        1100                1105                1110

Ala Val Ile Glu Arg Ile His His Asn Phe Phe Ser His Pro Asn
        1115                1120                1125

Leu Asn Glu Ala Asp Val Arg Ser Ile Leu Ala Ser Glu Gln Arg
        1130                1135                1140

Arg Ile Leu Thr Gly Cys Arg Ile Val Phe Ser Arg Val Phe Pro
        1145                1150                1155

Val Gly Asp Ala Ser Pro His Leu His Pro Leu Trp Gln Thr Ala
        1160                1165                1170

Glu Gln Phe Gly Ala Val Cys Thr Asn Leu Val Asp Asp Arg Val
        1175                1180                1185

Thr His Ile Val Ala Asn Ser Pro Gly Thr Asp Lys Val Asn Trp
        1190                1195                1200

Ala Leu Ser Lys Gly Lys Phe Val Val His Pro Gly Val Glu Ala
        1205                1210                1215

Ser Ala Leu Leu Tyr Arg Arg Ala Asn Glu His Asp Phe Ala Val
        1220                1225                1230

Lys
```

```
<210> SEQ ID NO 20
<211> LENGTH: 1241
<212> TYPE: PRT
<213> ORGANISM: Arabidopsis thaliana

<400> SEQUENCE: 20

Met Leu Val Ala Arg Ser Gly Cys Ser Arg Thr Leu Ile Arg Met Gly
1               5                   10                  15

Asn Asp Glu Asn Leu Met Val Met Val Asp Val Glu Glu Gly Glu Ile
            20                  25                  30

Pro Asp Ser Val Asn Thr Glu Ile Glu Val Lys His Lys Ser Thr Thr
        35                  40                  45

Thr Thr Ala Asp Val Gly Asp Val Asp Val Gly Val Val Ala Gly
    50                  55                  60

Gly Arg Gly Gly Gly Gly Gly Ser Asn Gly Asn Ser Arg Val Trp
65                  70                  75                  80

Thr Met Glu Glu Leu Ile Ser Gln Tyr Pro Ala Tyr Arg Pro Tyr Ala
                85                  90                  95

Asn Ser Gly Leu Ser Asn Leu Ala Trp Ala Arg Ala Val Gln Asn Lys
            100                 105                 110

Pro Phe Asn Glu Gly Leu Val Met Asp Tyr Glu Pro Arg Glu Ser Asp
        115                 120                 125

Lys Ile Val Ile Glu Asp Ser Asp Glu Lys Glu Glu Gly Glu Leu
130                 135                 140

Glu Glu Gly Glu Ile Asp Leu Val Asp Asn Ala Ser Asp Asp Asn Leu
145                 150                 155                 160

Val Glu Lys Asp Thr Glu Ser Val Val Leu Ile Ser Ala Asp Lys Val
                165                 170                 175

Glu Asp Asp Arg Ile Leu Lys Glu Arg Asp Leu Glu Lys Lys Val Lys
            180                 185                 190

Leu Ile Arg Gly Val Leu Glu Ser Thr Ser Leu Val Glu Ala Gln Thr
        195                 200                 205

Gly Phe Glu Gly Val Cys Ser Arg Ile Leu Gly Ala Leu Glu Ser Leu
210                 215                 220

Arg Glu Leu Val Ser Asp Asn Asp Phe Pro Lys Arg Asp Thr Leu
225                 230                 235                 240

Val Gln Leu Ser Phe Ala Ser Leu Gln Thr Ile Asn Tyr Val Phe Cys
                245                 250                 255

Ser Met Asn Asn Ile Ser Lys Glu Arg Asn Lys Glu Thr Met Ser Arg
            260                 265                 270

Leu Leu Thr Leu Val Asn Asp His Phe Ser Gln Phe Leu Ser Phe Asn
        275                 280                 285

Gln Lys Asn Glu Ile Glu Thr Met Asn Gln Asp Leu Ser Arg Ser Ala
    290                 295                 300

Ile Ala Val Phe Ala Gly Thr Ser Ser Glu Glu Asn Val Asn Gln Met
305                 310                 315                 320

Thr Gln Pro Ser Asn Gly Asp Ser Phe Leu Ala Lys Lys Leu Thr Ser
                325                 330                 335

Glu Ser Thr His Arg Gly Ala Ala Tyr Leu Arg Ser Arg Leu Pro Met
            340                 345                 350

Leu Pro Leu Leu Asp Leu His Lys Asp His Asp Ala Asp Ser Leu Pro
        355                 360                 365

Ser Pro Thr Arg Glu Thr Thr Pro Ser Leu Pro Val Asn Gly Arg His
    370                 375                 380
```

```
Thr Met Val Arg Pro Gly Phe Pro Val Gly Arg Glu Ser Gln Thr Thr
385                 390                 395                 400

Glu Gly Ala Lys Val Tyr Ser Tyr Glu Ser Asp Ala Arg Lys Ala Val
            405                 410                 415

Ser Thr Tyr Gln Gln Lys Phe Gly Leu Asn Ser Val Phe Lys Thr Asp
            420                 425                 430

Asp Leu Pro Ser Pro Thr Pro Ser Gly Glu Pro Asn Asp Gly Asn Gly
            435                 440                 445

Asp Val Gly Gly Glu Val Ser Ser Val Val Lys Ser Ser Asn Pro
        450                 455                 460

Gly Ser His Leu Ile Tyr Gly Gln Asp Val Pro Leu Pro Ser Asn Phe
465                 470                 475                 480

Asn Ser Arg Ser Met Pro Val Ala Asn Ser Val Ser Ser Thr Val Pro
            485                 490                 495

Pro His His Leu Ser Ile His Ala Ile Ser Ala Pro Thr Ala Ser Asp
            500                 505                 510

Gln Thr Val Lys Pro Ser Ala Lys Ser Arg Asp Pro Arg Leu Arg Leu
            515                 520                 525

Ala Lys Pro Asp Ala Ala Asn Val Thr Ile Tyr Ser Tyr Ser Ser Gly
530                 535                 540

Asp Ala Arg Asn Leu Ser Lys Val Glu Leu Ser Ala Asp Leu Val Asn
545                 550                 555                 560

Pro Arg Lys Gln Lys Ala Ala Asp Glu Phe Leu Ile Asp Gly Pro Ala
            565                 570                 575

Trp Lys Arg Gln Lys Ser Asp Thr Asp Ala Pro Lys Ala Ala Gly Thr
            580                 585                 590

Gly Gly Trp Leu Glu Asp Thr Glu Ser Ser Gly Leu Leu Lys Leu Glu
            595                 600                 605

Ser Lys Pro Arg Leu Ile Glu Asn Gly Val Thr Ser Met Thr Ser Ser
            610                 615                 620

Val Met Pro Thr Ser Ala Val Ser Val Ser Gln Lys Val Arg Thr Ala
625                 630                 635                 640

Ser Thr Asp Thr Ala Ser Leu Gln Ser Leu Leu Lys Asp Ile Ala Val
            645                 650                 655

Asn Pro Thr Met Leu Leu Asn Leu Leu Lys Met Gly Glu Arg Gln Lys
            660                 665                 670

Val Pro Glu Lys Ala Ile Gln Lys Pro Met Asp Pro Arg Arg Ala Ala
            675                 680                 685

Gln Leu Pro Gly Ser Ser Val Gln Pro Gly Val Ser Thr Pro Leu Ser
            690                 695                 700

Ile Pro Ala Ser Asn Ala Leu Ala Ala Asn Ser Leu Asn Ser Gly Val
705                 710                 715                 720

Leu Gln Asp Ser Ser Gln Asn Ala Pro Ala Ala Glu Ser Gly Ser Ile
            725                 730                 735

Arg Met Lys Pro Arg Asp Pro Arg Arg Ile Leu His Gly Ser Thr Leu
            740                 745                 750

Gln Arg Thr Asp Ser Ser Met Glu Lys Gln Thr Lys Val Asn Asp Pro
            755                 760                 765

Ser Thr Leu Gly Thr Leu Thr Met Lys Gly Lys Ala Glu Asp Leu Glu
            770                 775                 780

Thr Pro Pro Gln Leu Asp Pro Arg Gln Asn Ile Ser Gln Asn Gly Thr
785                 790                 795                 800
```

-continued

```
Ser Lys Met Lys Ile Ser Gly Glu Leu Leu Ser Gly Lys Thr Pro Asp
            805                 810                 815

Phe Ser Thr Gln Phe Thr Lys Asn Leu Lys Ser Ile Ala Asp Met Val
            820                 825                 830

Val Val Ser Gln Gln Leu Gly Asn Pro Pro Ala Ser Met His Ser Val
            835                 840                 845

Gln Leu Lys Thr Glu Arg Asp Val Lys His Asn Pro Ser Asn Pro Asn
850                 855                 860

Ala Gln Asp Glu Asp Val Ser Val Ser Ala Ala Ser Val Thr Ala Ala
865                 870                 875                 880

Ala Gly Pro Thr Arg Ser Met Asn Ser Trp Gly Asp Val Glu His Leu
            885                 890                 895

Phe Glu Gly Tyr Asp Asp Ile Gln Arg Val Ala Ile Gln Arg Glu Arg
            900                 905                 910

Val Arg Arg Leu Glu Glu Gln Asn Lys Met Phe Ala Ser Gln Lys Leu
            915                 920                 925

Ser Leu Val Leu Asp Ile Asp His Thr Leu Leu Asn Ser Ala Lys Phe
930                 935                 940

Asn Glu Val Glu Ser Arg His Glu Glu Ile Leu Arg Lys Lys Glu Glu
945                 950                 955                 960

Gln Asp Arg Glu Lys Pro Tyr Arg His Leu Phe Arg Phe Leu His Met
            965                 970                 975

Gly Met Trp Thr Lys Leu Arg Pro Gly Ile Trp Asn Phe Leu Glu Lys
            980                 985                 990

Ala Ser Lys Leu Tyr Glu Leu His Leu Tyr Thr Met Gly Asn Lys Leu
            995                 1000                1005

Tyr Ala Thr Glu Met Ala Lys Leu Leu Asp Pro Lys Gly Val Leu
            1010                1015                1020

Phe Asn Gly Arg Val Ile Ser Lys Gly Asp Asp Gly Asp Pro Leu
            1025                1030                1035

Asp Gly Asp Glu Arg Val Pro Lys Ser Lys Asp Leu Glu Gly Val
            1040                1045                1050

Met Gly Met Glu Ser Ser Val Val Ile Ile Asp Asp Ser Val Arg
            1055                1060                1065

Val Trp Pro Gln His Lys Met Asn Leu Ile Ala Val Glu Arg Tyr
            1070                1075                1080

Leu Tyr Phe Pro Cys Ser Arg Arg Gln Phe Gly Leu Leu Gly Pro
            1085                1090                1095

Ser Leu Leu Glu Leu Asp Arg Asp Glu Val Pro Glu Glu Gly Thr
            1100                1105                1110

Leu Ala Ser Ser Leu Ala Val Ile Glu Lys Ile His Gln Asn Phe
            1115                1120                1125

Phe Ser His Thr Ser Leu Asp Glu Val Asp Val Arg Asn Ile Leu
            1130                1135                1140

Ala Ser Glu Gln Arg Lys Ile Leu Ala Gly Cys Arg Ile Val Phe
            1145                1150                1155

Ser Arg Ile Ile Pro Val Gly Glu Ala Lys Pro His Leu His Pro
            1160                1165                1170

Leu Trp Gln Thr Ala Glu Gln Phe Gly Ala Val Cys Thr Thr Gln
            1175                1180                1185

Val Asp Glu His Val Thr His Val Val Thr Asn Ser Leu Gly Thr
            1190                1195                1200
```

```
Asp Lys Val Asn Trp Ala Leu Thr Arg Gly Arg Phe Val Val His
    1205                1210                1215

Pro Gly Trp Val Glu Ala Ser Ala Phe Leu Tyr Gln Arg Ala Asn
    1220                1225                1230

Glu Asn Leu Tyr Ala Ile Asn Pro
    1235                1240

<210> SEQ ID NO 21
<211> LENGTH: 206
<212> TYPE: DNA
<213> ORGANISM: Artificial Sequence
<220> FEATURE:
<223> OTHER INFORMATION: silencing constructs TaCPL3_fragA

<400> SEQUENCE: 21
gaaccgtgat tctggtggta ctgcagatgc aaatagacat gtaaatttgg cagagccaaa      60
tgcttccaaa gatgggacct tgggggggtgt tgtatcagat aatagccgga agcacaaggc    120
aactggccaa cctctcacgg atgaaaccgt gttaaaaaga gctagggaga gtactgggaa    180
tcccagagac atgcaggtac caccta                                          206

<210> SEQ ID NO 22
<211> LENGTH: 201
<212> TYPE: DNA
<213> ORGANISM: Artificial Sequence
<220> FEATURE:
<223> OTHER INFORMATION: silencing constructs TaCPL3_fragB

<400> SEQUENCE: 22
agcttctaat ctgataccct cctcccgacc tagtgcagtt atcagcagca atgacagttt      60
tgcaggtggt cctccaggct atgctaaaca aattgaacag tctgtttcag acccagcca    120 tgctcttaag ccttcagcta aaagtagaga tccaaggctc aggttttga accgtgattc    180 tggtggtact gcagatgcaa a                                              201

<210> SEQ ID NO 23
<211> LENGTH: 201
<212> TYPE: DNA
<213> ORGANISM: Zea mays

<400> SEQUENCE: 23
gaaggctgtc tcttcctatc agcagaagta tgggcagaaa tctgtatatc caagtgatga      60
tctaccaagt ccaactccat ctggtgatga gggtaaacct gcagataaag gtggtgatat    120
atttagtgat gtttccagct tccctgttcc aaagagtatt gtattaccaa gtacaagtca    180
gatgcctgct tctcaaccta g                                              201

<210> SEQ ID NO 24
<211> LENGTH: 12867
<212> TYPE: DNA
<213> ORGANISM: Artificial Sequence
<220> FEATURE:
<223> OTHER INFORMATION: p7U-70Subiintron-ZmCPL3_RNAi

<400> SEQUENCE: 24
aaaaggatct aggtgaagat cctttttgat aatctcatga ccaaaatccc ttaacgtgag      60
ttttcgttcc actgagcgtc agaccccgta gaaaagatca aggatcttct tgagatcct    120 ttttttctgc gcgtaatctg ctgcttgcaa acaaaaaaac caccgctacc agcggtggtt    180
tgtttgccgg atcaagagct accaactctt tttccgaagg taactggctt cagcagagcg    240
```

```
cagataccaa atactgttct tctagtgtag ccgtagttag gccaccactt caagaactct    300
gtagcaccgc ctacatacct cgctctgcta atcctgttac cagtggctgc tgccagtggc    360
gataagtcgt gtcttaccgg gttggactca agacgatagt taccggataa ggcgcagcgg    420
tcgggctgaa cgggggggttc gtgcacacag cccagcttgg agcgaacgac ctacaccgaa    480
ctgagatacc tacagcgtga gctatgagaa agcgccacgc ttcccgaagg gagaaaggcg    540
gacaggtatc cggtaagcgg cagggtcgga acaggagagc gcacgaggga gcttccaggg    600
ggaaacgcct ggtatcttta tagtcctgtc gggtttcgcc acctctgact tgagcgtcga    660
tttttgtgat gctcgtcagg ggggcggagc ctatggaaaa acgccagcaa cgcggccttt    720
ttacggttcc tggccttttg ctggcctttt gctcacatgt tctttcctgc gttatcccct    780
gattctgtgg ataaccgatt accgcctttg agtgagctga taccgctcgc cgcagccgaa    840
cgaccgagcg cagcgagtca gtgagcgagg aagcggaaga gcgcctgatg cggtattttc    900
tccttacgca tctgtgcggt atttcacacc gcatatggtg cactctcagt acaatctgct    960
ctgatgccgc atagttaagc cagtatacac tccgctatcg ctacgtgact gggtcatggc    1020
tgcgccccga cacccgccaa cacccgctga cgcgccctga cgggcttgtc tgctcccggc    1080
atccgcttac agacaagctg tgaccgtctc cgggagctgc atgtgtcaga ggttttcacc    1140
gtcatcaccg aaacgcgcga ggcaggggta cgtcgaggtc gatccaaccc ctccgctgct    1200
atagtgcagt cggcttctga cgttcagtgc agccgtcttc tgaaaacgac atgtcgcaca    1260
agtcctaagt tacgcgacag gctgccgccc tgccctttc ctggcgtttt cttgtcgcgt    1320
gttttagtcg cataaagtag aatacttgcg actagaaccg gagacattac gccatgaaca    1380
agagcgccgc cgctggcctg ctgggctatg cccgcgtcag caccgacgac caggacttga    1440
ccaaccaacg ggccgaactg cacgcggccg gctgcaccaa gctgttttcc gagaagatca    1500
ccggcaccag gcgcgaccgc ccggagctgg ccaggatgct tgaccaccta cgccctggcg    1560
acgttgtgac agtgaccagg ctagaccgcc tggcccgcag cacccgcgac ctactggaca    1620
ttgccgagcg catccaggag gccggcgcgg gcctgcgtag cctggcagag ccgtgggccg    1680
acaccaccac gccggccggc cgcatggtgt tgaccgtgtt cgccggcatt gccgagttcg    1740
agcgttccct aatcatcgac cgcacccgga gcggcgcga ggccgccaag gcgcgaggcg    1800
tgaagtttgg cccccgccct accctcaccc cggcacagat cgcgcacgcc cgcgagctga    1860
tcgaccagga aggccgcacc gtgaaagagg cggctgcact gcttggcgtg catcgctcga    1920
ccctgtaccg cgcacttgag cgcagcgagg aagtgacgcc caccgaggcc aggcggcgcg    1980
gtgccttccg tgaggacgca ttgaccgagg ccgacgccct ggcggccgcc gagaatgaac    2040
gccaagagga acaagcatga aaccgcacca ggacggccag gacgaaccgt ttttcattac    2100
cgaagagatc gaggcggaga tgatcgcggc cgggtacgtg ttcgagccgc ccgcgcacgt    2160
ctcaaccgtg cggctgcatg aaatcctggc cggtttgtct gatgccaagc tcgcggcctg    2220
gccggcgagc ttggccgctg aagaaaccga gcgccgccgt ctaaaaggt gatgtgtatt    2280 tgagtaaaac agcttgcgtc atgcggtcgc tgcgtatatg atgcgatgag taaataaaca    2340
aatacgcaag gggaacgcat gaaggttatc gctgtactta accagaaagg cgggtcaggc    2400
aagacgacca tcgcaaccca tctagcccgc gccctgcaac tcgccggggc cgatgttctg    2460
ttagtcgatt ccgatcccca gggcagtgcc cgcgattggg cggccgtgcg gaagatcaa    2520 ccgctaaccg ttgtcggcat cgaccgcccg acgattgacc gcgacgtgaa ggccatcggc    2580
cggcgcgact tcgtagtgat cgacggagcg ccccaggcgg cggacttggc tgtgtccgcg    2640
```

```
atcaaggcag ccgacttcgt gctgattccg gtgcagccaa gcccttacga catatgggcc     2700
accgccgacc tggtggagct ggttaagcag cgcattgagg tcacggatgg aaggctacaa     2760
gcggcctttg tcgtgtcgcg ggcgatcaaa ggcacgcgca tcggcggtga ggttgccgag     2820
gcgctggccg ggtacgagct gcccattctt gagtcccgta tcacgcagcg cgtgagctac     2880
ccaggcactg ccgccgccgg cacaaccgtt cttgaatcag aacccgaggg cgacgctgcc     2940
cgcgaggtcc aggcgctggc cgctgaaatt aaatcaaaac tcatttgagt taatgaggta     3000
aagagaaaat gagcaaaagc acaaacacgc taagtgccgg ccgtccgagc gcacgcagca     3060
gcaaggctgc aacgttggcc agcctggcag acacgccagc catgaagcgg gtcaactttc     3120
agttgccggc ggaggatcac accaagctga agatgtacgc ggtacgccaa ggcaagacca     3180
ttaccgagct gctatctgaa tacatcgcgc agctaccaga gtaaatgagc aaatgaataa     3240
atgagtagat gaattttagc ggctaaagga ggcggcatgg aaaatcaaga caaccaggc      3300
accgacgccg tggaatgccc catgtgtgga ggaacgggcg gttggccagg cgtaagcggc     3360
tgggttgtct gccggccctg caatggcact ggaacccca  agcccgagga tcggcgtga     3420
gcggtcgcaa accatccggc ccggtacaaa tcggcgcggc gctgggtgat gacctggtgg     3480
agaagttgaa ggcggcgcag gccgcccagc ggcaacgcat cgaggcagaa gcacgccccg     3540
gtgaatcgtg gcaagcggcc gctgatcgaa tccgcaaaga atcccggcaa ccgccggcag     3600
ccggtgcgcc gtcgattagg aagccgccca agggcgacga gcaaccagat tttttcgttc     3660
cgatgctcta tgacgtgggc acccgcgata gtcgcagcat catggacgtg ccgtttttcc     3720
gtctgtcgaa gcgtgaccga cgagctggcg aggtgatccg ctacgagctt ccagacgggc     3780
acgtagaggt ttccgcaggg ccggccggca tggcgagtgt gtgggattac gacctggtac     3840
tgatggcggt ttcccatcta accgaatcca tgaaccgata ccgggaaggg aagggagaca     3900
agcccggccg cgtgttccgt ccacacgttg cggacgtact caagttctgc cggcgagccg     3960
atggcggaaa gcagaaagac gacctggtag aaacctgcat tcggttaaac accacgcacg     4020
ttgccatgca gcgtacgaag aaggccaaga acggccgcct ggtgacggta tccgagggtg     4080
aagccttgat tagccgctac aagatcgtaa agagcgaaac cggcggccg  gagtacatcg     4140
agatcgagct agctgattgg atgtaccgcg agatcacaga aggcaagaac ccggacgtgc     4200
tgacggttca ccccgattac ttttttgatcg atcccggcat cggccgtttt ctctaccgcc     4260
tggcacgccg cgccgcaggc aaggcagaag ccagatggtt gttcaagacg atctacgaac     4320
gcagtggcag cgccggagag ttcaagaagt tctgtttcac cgtgcgcaag ctgatcgggt     4380
caaatgacct gccggagtac gatttgaagg aggaggcggg gcaggctggc ccgatcctag     4440
tcatgcgcta ccgcaacctg atcgagggcg aagcatccgc cggttcctaa tgtacggagc     4500
agatgctagg gcaaattgcc ctagcagggg aaaaggtcg  aaaaggtctg tttcctgtgg     4560
atagcacgta cattgggaac ccaaagccgt acattgggaa ccggaacccg tacattggga     4620
acccaaagcc gtacattggg aaccggtcac acatgtaagt gactgatata aaagagaaaa     4680
aaggcgattt ttccgcctaa aactctttaa aacttattaa aactcttaaa acccgcctgg     4740
cctgtgcata actgtctggc cagcgcacag ccgaagagct gcaaaaagcg cctacccttc     4800
ggtcgctgcg ctccctacgc cccgccgctt cgcgtcggcc tatcgcggcc gctggccgct     4860
caaaaatggc tggcctacgg ccaggcaatc taccagggcg cggacaagcc gcgccgtcgc     4920
cactcgaccg ccggcgccca catcaaggca ccggtgggta tgcctgacga tgcgtgcaga     4980
ccgaaacctt gcgctcgttc gccagccagg acagaaatgc ctcgacttcg ctgctgccca     5040
```

```
aggttgccgg gtgacgcaca ccgtggaaac ggatgaaggc acgaacccag tggacataag   5100
cctgttcggt tcgtaagctg taatgcaagt agcgtatgcg ctcacgcaac tggtccagaa   5160
ccttgaccga acgcagcggt ggtaacggcg cagtggcggt tttcatggct tgttatgact   5220 gttttttttgg ggtacagtct atgcctcggg catccaagca gcaagcgcgt tacgccgtgg   5280
gtcgatgttt gatgttatgg agcagcaacg atgttacgca gcagggcagt cgccctaaaa   5340
caaagttaaa catcatgagg gaagcggtga tcgccgaagt atcgactcaa ctatcagagg   5400
tagttggcgt catcgagcgc catctcgaac cgacgttgct ggccgtacat ttgtacggct   5460
ccgcagtgga tggcggcctg aagccacaca gtgatattga tttgctggtt acggtgaccg   5520
taaggcttga tgaaacaacg cggcgagctt tgatcaacga ccttttggaa acttcggctt   5580
cccctggaga gagcgagatt ctccgcgctg tagaagtcac cattgttgtg cacgacgaca   5640
tcattccgtg gcgttatcca gctaagcgcg aactgcaatt tggagaatgg cagcgcaatg   5700
acattcttgc aggtatcttc gagccagcca cgatcgacat tgatctggct atcttgctga   5760
caaaagcaag agaacatagc gttgccttgg taggtccagc ggcggaggaa ctctttgatc   5820
cggttcctga acaggatcta tttgaggcgc taaatgaaac cttaacgcta tggaactcgc   5880
cgcccgactg ggctggcgat gagcgaaatg tagtgcttac gttgtcccgc atttggtaca   5940
gcgcagtaac cggcaaaatc gcgccgaagg atgtcgctgc cgactgggca atggagcgcc   6000
tgccggccca gtatcagccc gtcatacttg aagctagaca ggcttatctt ggacaagaag   6060
aagatcgctt ggcctcgcgc gcagatcagt tggaagaatt tgtccactac gtgaaggcg   6120 agatcaccaa ggtagtcggc aaataatgtc taacaattcg ttcaagccga cgccgcttcg   6180
cggcgcggct taactcaagc gttagatgca ctaagcacat aattgctcac agccaaacta   6240
tcaggtcaag tctgctttta ttatttttaa gcgtgcataa taagccctac acaaattggg   6300
agatatatca tgaaaggctg gcttttttctt gttatcgcaa tagttggcga agtaatcgca   6360
acatagcttg cttggtcgtt ccgcgtgaac gtcggctcga ttgtacctgc gttcaaatac   6420
tttgcgatcg tgttgcgcgc ctgcccggtg cgtcggctga tctcacggat cgactgcttc   6480
tctcgcaacg ccatccgacg gatgatgttt aaaagtccca tgtggatcac tccgttgccc   6540
cgtcgctcac cgtgttgggg ggaaggtgca catggctcag ttctcaatgg aaattatctg   6600
cctaaccggc tcagttctgc gtagaaacca acatgcaagc tccaccgggt gcaaagcggc   6660
agcggcggca ggatatattc aattgtaaat ggcttcatgt ccgggaaatc tacatggatc   6720
agcaatgagt atgatggtca atatggagaa aagaaagag taattaccaa ttttttttca   6780
attcaaaaat gtagatgtcc gcagcgttat tataaaatga agtacatttt tgataaaacg   6840
acaaattacg atccgtcgta tttataggcg aaagcaataa acaaattatt ctaattcgga   6900
aatctttatt tcgacgtgtc tacattcacg tccaaatggg ggcttagatg agaaacttca   6960
cgatcggctc tagtagtctg cagtgcagcg tgacccggtc gtgcccctct ctagagataa   7020
tgagcattgc atgtctaagt tataaaaaat taccacatat ttttttgtc acacttgttt   7080 gaagtgcagt ttatctatct ttatacatat atttaaactt tactctacga ataatataat   7140
ctatagtact acaataatat cagtgtttta gagaatcata taaatgaaca gttagacatg   7200
gtctaaagga caattgagta ttttgacaac aggactctac agttttatct ttttagtgtg   7260
catgtgttct cctttttttt tgcaaatagc ttcacctata taatacttca tccatttttat   7320 tagtacatcc atttagggtt tagggttaat ggttttata gactaatttt tttagtacat   7380
ctattttatt ctatttttagc ctctaaatta agaaaactaa aactctattt tagtttttttt   7440
```

```
atttaataat ttagatataa aatagaataa aataaagtga ctaaaaatta aacaaataCC    7500
ctttaagaaa ttaaaaaaac taaggaaaca tttttcttgt ttcgagtaga taatgccagc    7560
ctgttaaacg ccgtcgatcg acgagtctaa cggacaccaa ccagcgaacc agcagcgtcg    7620
cgtcgggcca agcgaagcag acggcacggc atctctgtcg ctgcctctgg acccctctcg    7680
agagttccgc tccaccgttg gacttgctcc gctgtcggca tccagaaatt gcgtggcgga    7740
gcggcagacg tgagccggca cggcaggcgg cctcctcctc ctctcacggc accggcagct    7800
acggggggatt cctttcccac cgctccttcg cttcccttc ctcgcccgcc gtaataaata    7860
gacaccccct ccacaccctc ttccccaac ctcgtgttgt tcggagcgca cacacacaca    7920
accagatctc ccccaaatcc acccgtcggc acctccgctt caaggtacgc cgctcgtcct    7980
cccccccccc ccctctctac cttctctaga tcggcgttcc ggtccatggt tagggcccgg    8040
tagttctact tctgttcatg tttgtgttag atccgtgttt gtgttagatc cgtgctgcta    8100
gcgttcgtac acggatgcga cctgtacgtc agacacgttc tgattgctaa cttgccagtg    8160
tttctctttg gggaatcctg ggatggctct agccgttccg cagacgggat cgatctagga    8220
taggtataca tgttgatgtg ggttttactg atgcatatac atgatggcat atgcagcatc    8280
tattcatatg ctctaacctt gagtacctat ctattataat aaacaagtat gttttataat    8340
tattttgatc ttgatatact tggatgatgg catatgcagc agctatatgt ggattttttt    8400
agccctgcct tcatacgcta tttatttgct tggtactgtt tcttttgtcg atgctcaccc    8460
tgttgtttgg tgttacttct gcaggtcgag tggccaccat gggcccagaa cgacgcccgg    8520
ccgacatccg ccgtgccacc gaggcggaca tgccggcggt ctgcaccatc gtcaaccact    8580
acatcgagac aagcacggtc aacttccgta ccgagccgca ggaaccgcag gagtggacgg    8640
acgacctcgt ccgtctgcgg gagcgctatc cctggctcgt cgccgaggtg gacggcgagg    8700
tcgccggcat cgcctacgcg ggcccctgga aggcacgcaa cgcctacgac tggacggccg    8760
agtcgaccgt gtacgtctcc ccccgccacc agcggacggg actgggctcc acgtctcaca    8820
cccacctgct gaagtccctg gaggcacagg gcttcaagag cgtggtcgct gtcatcgggc    8880
tgcccaacga cccgagcgtg cgcatgcacg aggcgctcgg atatgccccc gcggcatgc    8940
tgcgggcggc cggcttcaag cacgggaact ggcatgacgt gggtttctgg cagctggact    9000
tcagcctgcc ggtaccgccc cgtccggtcc tgcccgtcac cgagatctga gatcacgcgt    9060
tctagtccgc aaaaatcacc agtctctctc tacaaatcta tctctctcta ttttctcca    9120
gaataatgtg tgagtagttc ccagataagg gaattagggt tcttataggg tttcgctcat    9180
gtgttgagca tataagaaac ccttagtatg tatttgtatt tgtaaaatac ttctatcaat    9240
aaaatttcta attcctaaaa ccaaaatcca gtgacctgca ggcatgcaag ctgatccact    9300
agaggccatg gcggccgcgt cgagcgatct agtaacatag atgacaccgc gcgcgataat    9360
ttatcctagt ttgcgcgcta tattttgttt tctatcgcgt attaaatgta taattgcggg    9420
actctaatca taaaaaccca tctcataaat aacgtcatgc attacatgtt aattattaca    9480
tgcttaacgt aattcaacag aaattatatg ataatcatcg caagaccggc aacaggattc    9540
aatcttaaga aactttattg ccaaatgttt gaacgatcgg ggaaattcga gtcgacacgc    9600
gtaagcttga attcctgcag cccggggggat tggaaggctg tctcttccta tcagcagaag    9660
tatgggcaga aatctgtata tccaagtgat gatctaccaa gtccaactcc atctggtgat    9720
gagggtaaac ctgcagataa aggtggtgat atatttagtg atgtttccag cttccctgtt    9780
ccaaagagta ttgtattacc aagtacaagt cagatgcctg cttctcaacc tagcgagagg    9840
```

```
tatggatagt gtatcttcat actgcatttg tttaatttga aaatggttat ctagttgcct    9900
aacaaaatat agctgggata tcatataaca catgtgcagg tgacatggaa aaaaatgcct    9960
attttttctat gcactaacta ttcatcatgt gacatacttc cccaaaaaac taaataagcc  10020
aaattttcca gcttccgagt cctgaaaaag agtagtgtac ctgatacaat ttatagagtt  10080
ttttttttcga aagaaggga tggccctcat agatagagta ctaactaaaa gtctacttttt 10140
accaattttca ggcctcgcta ggttgagaag caggcatctg acttgtactt ggtaatacaa  10200
tactctttgg aacagggaag ctggaaacat cactaaatat atcaccacct ttatctgcag  10260
gtttacccctc atcaccagat ggagttggac ttggtagatc atcacttgga tatacagatt  10320
tctgcccata cttctgctga taggaagaga cagccttcca atccccgggt acctctagac  10380
ttgtacagct cgtccatgcc gtacaggaac aggtggtggc ggccctcgga gcgacctgca  10440
gaagtaacac caaacaacag ggtgagcatc gacaaaagaa acagtaccaa gcaaataaat  10500
agcgtatgaa ggcagggcta aaaaaatcca catatagctg ctgcatatgc catcatccaa  10560
gtatatcaag atcaaaataa ttataaaaca tacttgttta ttataataga taggtactca  10620
aggttagagc atatgaatag atgctgcata tgccatcatg tatatgcatc agtaaaaccc  10680
acatcaacat gtataccctat cctagatcga tatttccatc catcttaaac tcgtaactat  10740
gaagatgtat gacacacaca tacagttcca aaattaataa atacaccagg tagtttgaaa  10800
cagtattcta ctccgatcta gaacgaatga acgaccgccc aaccacacca catcatcaca  10860
accaagcgaa caaaaagcat ctctgtatat gcatcagtaa aacccgcatc aacatgtata  10920
cctatcctag atcgatattt ccatccatca tcttcaattc gtaactatga atatgtatgg  10980
cacacacata cagatccaaa attaataaat ccaccaggta gtttgaaaca gaattctact  11040
ccgatctaga acgaccgccc aaccagacca catcatcaca accaagacaa aaaaaagcat  11100
gaaaagatga cccgacaaac aagtgcacgg catatattga aataaaggaa aagggcaaac  11160
caaaccctat gcaacgaaac aaaaaaaaatc atgaaatcga tcccgtctgc ggaacggcta  11220
gagccatccc aggattcccc aaagagaaac actggcaagt tagcaatcag aacgtgtctg  11280
acgtacaggt cgcatccgtg tacgaacgct agcagcacgg atctaacaca acacggatc   11340
taacacaaac atgaacagaa gtagaactac cgggccctaa ccatggaccg gaacgccgat  11400
ctagagaagg tagagagggg ggggggggga ggacgagcgg cgtaccttga gcggaggtg   11460
ccgacgggtg gatttggggg agatccacta gttctagagc ggccgccacc gcggtggaat  11520
tctcgaggtc ctctccaaat gaaatgaact tccttatata gaggaagggt cttgcgaagg  11580
atagtgggat tgtgcgtcat cccttacgtc agtggagata tcacatcaat ccacttgctt  11640
tgaagacgtg gttggaacgt cttcttttt cacgatgttc ctcgtgggtg ggggtccatc   11700
tttgggacca ctgtcggtag aggcatcttg aacgatagcc tttcctttat cgcaatgatg  11760
gcatttgtag aagccatctt ccttttctac tgtcctttcg atgaagtgac agatagctgg  11820
gcaatggaat ccgaggaggt ttcccgatat tacccttgt tgaaaagtct caatagccct    11880
ctggtcttct gagactgtat ctttgatatt cttggagtag acgagagtgt cgtgctccac  11940
catgtatcac atcaatccac ttgctttgaa gacgtggttg gaacgtcttc ttttccacg   12000
atgttcctcg tgggtggggg tccatctttg ggaccactgt cggtagaggc atcttgaacg  12060
atagcctttc ctttatcgca atgatggcat ttgtagaagc catcttcctt ttctactgtc  12120
ctttcgatga agtgacagat agctgggcaa tggaatccga ggaggtttcc cgatattacc  12180
ctttgttgaa aagtctcaat agccctctgg tcttctgaac ctgcatagta aggccttaag  12240
```

-continued

| | |
|---|---|
| ggccagatct tgggcccggt acccgatcag attgtcgttt cccgccttcg gtttaaacta | 12300 |
| tcagtgtttg acaggatata ttggcgggta aacctaagag aaaagagcgt ttattagaat | 12360 |
| aatcggatat ttaaaagggc gtgaaaaggt ttatccgttc gtccatttgt atgtgcatgc | 12420 |
| caaccacagg gttcccctcg ggagtgcttg gcattccgtg cgataatgac ttctgttcaa | 12480 |
| ccacccaaac gtcggaaagc ctgacgacgg agcagcattc caaaaagatc ccttggctcg | 12540 |
| tctgggtcgg ctagaaggtc gagtgggctg ctgtggcttg atccctcaac gcggtcgcgg | 12600 |
| acgtagcgca gcgccgaaaa atcctcgatc gcaaatccga cgctgtcgaa aagcgtgatc | 12660 |
| tgcttgtcgc tctttcggcc gacgtcctgg ccagtcatca cgcgccaaag ttccgtcaca | 12720 |
| ggatgatctc gcgcgagttg ctggatctcg ccttcaatcc gggtctgtgg cgggaactcc | 12780 |
| acgaaaatat ccgaacgcag caagatatcg cggtgcatct cggtcttgcc tgggcagtcg | 12840 |
| ccgccgacgc cgttgatgtg gacgccg | 12867 |

<210> SEQ ID NO 25
<211> LENGTH: 21
<212> TYPE: DNA
<213> ORGANISM: Artificial Sequence
<220> FEATURE:
<223> OTHER INFORMATION: M7GEP59

<400> SEQUENCE: 25
ctcgtccttg ggcgtgaccg t                                         21

<210> SEQ ID NO 26
<211> LENGTH: 21
<212> TYPE: DNA
<213> ORGANISM: Artificial Sequence
<220> FEATURE:
<223> OTHER INFORMATION: m7GEP60

<400> SEQUENCE: 26
gtcactgctg ccgggggcgg g                                         21

<210> SEQ ID NO 27
<211> LENGTH: 21
<212> TYPE: DNA
<213> ORGANISM: Artificial Sequence
<220> FEATURE:
<223> OTHER INFORMATION: m7GEP61

<400> SEQUENCE: 27
gctatgcctt caatagcttt g                                         21

<210> SEQ ID NO 28
<211> LENGTH: 21
<212> TYPE: DNA
<213> ORGANISM: Artificial Sequence
<220> FEATURE:
<223> OTHER INFORMATION: m7GEP62

<400> SEQUENCE: 28
cgtggtcgca ggccgtgcgg a                                         21

<210> SEQ ID NO 29
<211> LENGTH: 21
<212> TYPE: DNA
<213> ORGANISM: Artificial Sequence
<220> FEATURE:
<223> OTHER INFORMATION: m7GEP63

```
<400> SEQUENCE: 29
gactccgacg ccccggagaa g                                              21

<210> SEQ ID NO 30
<211> LENGTH: 21
<212> TYPE: DNA
<213> ORGANISM: Artificial Sequence
<220> FEATURE:
<223> OTHER INFORMATION: m7GEP64

<400> SEQUENCE: 30
aggtgtctga gaaaccagt t                                               21

<210> SEQ ID NO 31
<211> LENGTH: 21
<212> TYPE: DNA
<213> ORGANISM: Artificial Sequence
<220> FEATURE:
<223> OTHER INFORMATION: m7GEP65

<400> SEQUENCE: 31
tcagacacct gaaacaaagc c                                              21

<210> SEQ ID NO 32
<211> LENGTH: 42
<212> TYPE: DNA
<213> ORGANISM: Zea mays

<400> SEQUENCE: 32
tagccccagc ggcttattcc gcacggcctg cgaccacgca aa                       42

<210> SEQ ID NO 33
<211> LENGTH: 34
<212> TYPE: DNA
<213> ORGANISM: Artificial Sequence
<220> FEATURE:
<223> OTHER INFORMATION: Event GEZM054-T811

<400> SEQUENCE: 33
tagccccagc ggcttcggcc tgcgaccacg caaa                                34

<210> SEQ ID NO 34
<211> LENGTH: 38
<212> TYPE: DNA
<213> ORGANISM: Artificial Sequence
<220> FEATURE:
<223> OTHER INFORMATION: Event GEZM054-T821

<400> SEQUENCE: 34
tagccccagc ggcttattcc ggcctgcgac cacgcaaa                            38

<210> SEQ ID NO 35
<211> LENGTH: 26
<212> TYPE: DNA
<213> ORGANISM: Artificial Sequence
<220> FEATURE:
<223> OTHER INFORMATION: Event GEZM054-T868

<400> SEQUENCE: 35
tagccccagc ggtgcgacca cgcaaa                                         26

<210> SEQ ID NO 36
<211> LENGTH: 40
<212> TYPE: DNA
<213> ORGANISM: Artificial Sequence
```

```
<220> FEATURE:
<223> OTHER INFORMATION: Event GEZM054-T868

<400> SEQUENCE: 36
tagccccagc ggcttattcc acggcctgcg accacgcaaa                               40

<210> SEQ ID NO 37
<211> LENGTH: 32
<212> TYPE: DNA
<213> ORGANISM: Artificial Sequence
<220> FEATURE:
<223> OTHER INFORMATION: Event GEZM054-T929

<400> SEQUENCE: 37
tagccccagc ggcttgcctg cgaccacgca aa                                       32

<210> SEQ ID NO 38
<211> LENGTH: 34
<212> TYPE: DNA
<213> ORGANISM: Artificial Sequence
<220> FEATURE:
<223> OTHER INFORMATION: Event GEZM054-T929

<400> SEQUENCE: 38
tagccccagc ggcttcggcc tgcgaccacg caaa                                     34

<210> SEQ ID NO 39
<211> LENGTH: 28
<212> TYPE: DNA
<213> ORGANISM: Artificial Sequence
<220> FEATURE:
<223> OTHER INFORMATION: Event GEZM054-T941

<400> SEQUENCE: 39
tagccccagc ggcctgcgac cacgcaaa                                            28

<210> SEQ ID NO 40
<211> LENGTH: 31
<212> TYPE: DNA
<213> ORGANISM: Artificial Sequence
<220> FEATURE:
<223> OTHER INFORMATION: Event GEZM054-T1207

<400> SEQUENCE: 40
tagccccagc ggcggcctgc gaccacgcaa a                                        31

<210> SEQ ID NO 41
<211> LENGTH: 38
<212> TYPE: DNA
<213> ORGANISM: Artificial Sequence
<220> FEATURE:
<223> OTHER INFORMATION: Event GEZM054-T1207

<400> SEQUENCE: 41
tagccccagc ggcttattcc ggcctgcgac cacgcaaa                                 38

<210> SEQ ID NO 42
<211> LENGTH: 25
<212> TYPE: DNA
<213> ORGANISM: Artificial Sequence
<220> FEATURE:
<223> OTHER INFORMATION: Event GEZM054-T1260

<400> SEQUENCE: 42
tagccccggc ctgcgaccac gcaaa                                               25
```

```
<210> SEQ ID NO 43
<211> LENGTH: 38
<212> TYPE: DNA
<213> ORGANISM: Artificial Sequence
<220> FEATURE:
<223> OTHER INFORMATION: Event GEZM054-T1260

<400> SEQUENCE: 43
tagccccagc ggcttattcc ggcctgcgac cacgcaaa                              38

<210> SEQ ID NO 44
<211> LENGTH: 37
<212> TYPE: DNA
<213> ORGANISM: Artificial Sequence
<220> FEATURE:
<223> OTHER INFORMATION: Event GEZM054-T1305

<400> SEQUENCE: 44
tagccccagc ggcttattcc gcctgcgacc acgcaaa                               37

<210> SEQ ID NO 45
<211> LENGTH: 31
<212> TYPE: DNA
<213> ORGANISM: Artificial Sequence
<220> FEATURE:
<223> OTHER INFORMATION: Event GEZM054-T592

<400> SEQUENCE: 45
tagccccagc ggcggcctgc gaccacgcaa a                                     31

<210> SEQ ID NO 46
<211> LENGTH: 32
<212> TYPE: DNA
<213> ORGANISM: Artificial Sequence
<220> FEATURE:
<223> OTHER INFORMATION: Event GEZM054-T602

<400> SEQUENCE: 46
tagccccagc ggcttgcctg cgaccacgca aa                                    32

<210> SEQ ID NO 47
<211> LENGTH: 25
<212> TYPE: DNA
<213> ORGANISM: Artificial Sequence
<220> FEATURE:
<223> OTHER INFORMATION: Event GEZM054-T626

<400> SEQUENCE: 47
tagccccagc ggcttaccac gcaaa                                            25

<210> SEQ ID NO 48
<211> LENGTH: 998
<212> TYPE: DNA
<213> ORGANISM: Zea mays

<400> SEQUENCE: 48
atcctctctt ttcttcgccc aaatctcgcg tgctgcctcc gtcctgcccc cagcgcgtgc      60
gctccgatcc gccgggtttc agcgctgcgg ctgtcgattt acgcgatttg tctggcagaa     120
tacagttcag agcctcgagc gctgcagatc gaggacctgg tcgtcggatt cgggcgccgc     180 ggtgagacc taggcgccgg agttttttgtg acggagtttt ggcgtggttg gtggaggggg     240
ggaggaagga gcggtctcat atgcgcgtga cggtcacgcc caaggacgag gaaaggctgg     300
ttgacttgat ggcgcgcgag cagccgcggt cggcggtggt tgcggcgggc ggagatttgg     360
```

```
                                                            -continued tcactgctgc cggggcggg ggcgaggggt cggataggga ctcttcgggg tccatagagg       420
agattacggc tgacgacttc aagaaggact cgtcgtcggc gttgggcggc gcggcggcgg     480
cggcggggcc gagatctagg tcttgggtgg ccccgcccgc cgtgggttac atggcccgga     540
actttcgcta tgccttcaat agctttgcgt ggtcgcaggc cgtgcggaat aagccgctgg     600
ggctacaacc gcctgcccca gacgacgacg aggtggagca cgccgtggac gtctccgacg     660
gacagaagga agagggcgag attgaggagg gggaggctgt ggaggccttc gcctcgcctg     720
ctcctgcgca gcctgagacc atcgatttgg actccgacgc cccggagaag tcagagtcgg     780
tggctatcga tggaagtgcc agtgttgtgc ctgtcccagc tgctgaggaa gaggaggtga     840
accttgatca gcgtgtgggg agtatactgg aggagctcga gatggtctcc attgaggaag     900
ctgagaagta tatgggcata tgcttcatgt ttttccttga acaaaggctt tgtttcaggt     960
gtctgagaaa accagttgta accgctgcca tgttgcag                             998
```